United States Patent
Brousmiche et al.

(10) Patent No.: US 11,352,325 B2
(45) Date of Patent: Jun. 7, 2022

(54) RAPID FLUORESCENCE TAGGING OF GLYCANS AND OTHER BIOMOLECULES WITH ENHANCED MS SIGNALS

(71) Applicant: Waters Technologies Corporation, Milford, MA (US)

(72) Inventors: Darryl W. Brousmiche, Grafton, MA (US); Matthew A. Lauber, North Smithfield, RI (US)

(73) Assignee: Waters Technologies Corporation, Milford, MA (US)

( * ) Notice: Subject to any disclaimer, the term of this patent is extended or adjusted under 35 U.S.C. 154(b) by 1060 days.

(21) Appl. No.: 15/005,619

(22) Filed: Jan. 25, 2016

(65) Prior Publication Data
US 2016/0139136 A1    May 19, 2016

Related U.S. Application Data

(63) Continuation-in-part of application No. 14/458,760, filed on Aug. 13, 2014, which is a
(Continued)

(51) Int. Cl.
*G01N 33/00* (2006.01)
*C07D 207/46* (2006.01)
(Continued)

(52) U.S. Cl.
CPC ......... *C07D 207/46* (2013.01); *C07D 401/12* (2013.01); *C07D 405/12* (2013.01);
(Continued)

(58) Field of Classification Search
CPC .................................................. C07D 207/46
(Continued)

(56) References Cited

U.S. PATENT DOCUMENTS

| 2,016,962 A | 10/1935 | Flint et al. |
| 4,003,912 A | 1/1977 | Franz |

(Continued)

FOREIGN PATENT DOCUMENTS

| CA | 2475011 | 7/2004 |
| CN | 1973047 A | 5/2007 |

(Continued)

OTHER PUBLICATIONS

Jean-Michel Chezal, et al. "Evaluation of Radiolabeled (Hetero) Aromatic Analogues of N-(2-diethylaminoethyl)-4-iodobenzamide for Imaging and Targeted Radionuclide Therapy of Melanoma" J. Med. Chem. 2008, 51, 3133-3144.

(Continued)

*Primary Examiner* — Elizabeth A Robinson
*Assistant Examiner* — Emily R. Berkeley
(74) *Attorney, Agent, or Firm* — Womble Bond Dickinson (US) LLP; Deborah M. Vernon

(57) ABSTRACT

Reagents comprising MS active, fluorescent molecules with an activated functionality for reaction with amines useful in tagging biomolecules such as N-glycans and uses thereof are taught and described. In particular embodiments, the MS active, fluorescent molecules are of the compound of the Formula III (Continued)

or of the Formula IV

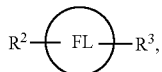

where $R^1$, $R^2$ and $R^3$ are defined herein.

7 Claims, 2 Drawing Sheets

Related U.S. Application Data continuation-in-part of application No. 14/193,418, filed on Feb. 28, 2014, now Pat. No. 9,772,333, which is a continuation of application No. PCT/US2012/057996, filed on Sep. 28, 2012, said application No. 14/458,760 is a continuation-in-part of application No. 14/342,131, filed as application No. PCT/US2012/057996 on Sep. 28, 2012.

(60) Provisional application No. 61/540,306, filed on Sep. 28, 2011.

(51) Int. Cl.
*G01N 33/533* (2006.01)
*C07D 401/12* (2006.01)
*C07D 405/12* (2006.01)
*C07D 491/22* (2006.01)

(52) U.S. Cl.
CPC .......... *C07D 491/22* (2013.01); *G01N 33/533* (2013.01); *G01N 2400/00* (2013.01); *G01N 2400/12* (2013.01); *G01N 2458/15* (2013.01); *G01N 2458/20* (2013.01)

(58) Field of Classification Search
USPC .......................................................... 436/89
See application file for complete search history.

(56) References Cited

U.S. PATENT DOCUMENTS

| | | | |
|---|---|---|---|
| 4,138,398 A | 2/1979 | Richter et al. |
| 5,296,599 A | 3/1994 | Cohen et al. |
| 6,245,478 B1 | 6/2001 | Uetani et al. |
| 6,632,629 B2 | 10/2003 | Yang et al. |
| 7,148,069 B2 | 12/2006 | Miyano et al. |
| 7,494,815 B2 | 2/2009 | Shimbo et al. |
| 8,124,792 B2 | 2/2012 | Baginski |
| 8,445,292 B2 | 5/2013 | Baginski |
| 9,658,234 B2 | 5/2017 | Miyano et al. |
| 2001/0026929 A1 | 10/2001 | Yang et al. |
| 2005/0079624 A1 | 4/2005 | Miyano et al. |
| 2005/0158708 A1 | 7/2005 | Alroy et al. |
| 2006/0004220 A1 | 1/2006 | Hamprecht et al. |
| 2006/0035304 A1 | 2/2006 | Lebrilla et al. |
| 2006/0286673 A1 | 12/2006 | Miyano et al. |
| 2008/0241856 A1 | 10/2008 | Wong et al. |
| 2008/0315084 A1 | 12/2008 | Yamada et al. |
| 2009/0258437 A1 | 10/2009 | Baginski |
| 2011/0171736 A1 | 6/2011 | Agnew et al. |
| 2012/0107942 A1 | 5/2012 | Baginski |
| 2012/0165370 A1 | 6/2012 | Tang et al. |
| 2014/0178912 A1 | 6/2014 | Liu et al. |
| 2014/0179011 A1 | 6/2014 | Brousmiche et al. |
| 2014/0200148 A1 | 7/2014 | Slade |
| 2014/0350263 A1 | 11/2014 | Brousmiche et al. |
| 2015/0346194 A1 | 12/2015 | Magnelli et al. |

FOREIGN PATENT DOCUMENTS

| | | |
|---|---|---|
| CN | 103842818 A | 6/2014 |
| CN | 103877748 A | 6/2014 |
| CN | 104024849 A | 9/2014 |
| EP | 0671401 | 9/1995 |
| EP | 0533200 | 12/2001 |
| EP | 1750126 | 12/2005 |
| EP | 1475632 | 5/2013 |
| JP | S60186502 A | 9/1985 |
| JP | 10306075 | 11/1998 |
| JP | 11080107 | 3/1999 |
| JP | 2000510854 A | 8/2000 |
| JP | 2006523305 A | 9/2006 |
| JP | 2008539413 A | 11/2008 |
| JP | 2012512234 A | 5/2012 |
| JP | 2015091953 A | 5/2015 |
| WO | 2003069328 | 8/2003 |
| WO | 2004027388 | 4/2004 |
| WO | 2004086050 A2 | 10/2004 |
| WO | 2005116629 | 12/2005 |
| WO | 2006114663 A1 | 11/2006 |
| WO | 2007069591 | 6/2007 |
| WO | 2009070233 | 6/2009 |
| WO | 2009100155 | 8/2009 |
| WO | 2011038873 A1 | 4/2011 |
| WO | 2011146594 | 11/2011 |
| WO | 2013025527 A1 | 2/2013 |
| WO | 2013049622 A1 | 4/2013 |
| WO | 2013084236 A1 | 6/2013 |
| WO | 2016069764 A1 | 5/2016 |

OTHER PUBLICATIONS

International Search Report and Written Opinion, dated Apr. 27, 2017 PCT/US 2017/014790, 7 pages.

Mazzocchi and Schuda. "A Photochemical Route to Pyrrolo [1,4] Benzodiazepine Antitumor Antibiotics" Heterocycles, vol. 23, No. 7, 1985, 1603-1606.

Darren L. Holmes, et al. "Solid-Phase Synthesis of Artificial beta-Sheets" J. Am. Chem. Soc. 1997, 119, 7665-7669.

Extended European Search Report and Written Opinion dated Feb. 2, 2016, regarding EP15180680.9, 7 pages.

EP Communication with extended search report, EP Application No. 15180680.9, dated Feb. 2, 2016.

Response to EP Communication, EP Application No. 15180680.9, dated Sep. 2, 2016.

Liu, Hongji, et.al.; "Homogeneous Fluorescent Derivatization of Large Proteins"; Journal of Chromatography A, 927 (2001) pp. 77-89.

Ullmer, Roman, et.al.; "Derivatization by 6-aminoquinolyl-N-hydroxysuccinimidyl Carbamate for Enhancing the Ionization Yield of Small Peptides and Glycopeptides in Matrix-Assisted Laser Desorption/Ionization and Electrospray Ionization Mass Spectrometry"; Rapid Communications in Mass Spectrometry (2006) pp. 1469-1479.

Hossler et al., Optimal and Consistent Protein Glycosylation in Mammalian Cell Culture, Glycobiology 2009; 19:936-49.

Anumula et al., High Resolution and High Sensitivity Methods for Oligosaccharide Mapping and Characterization by Normal Phase High Performance Liquid Chromatography Following Derivatization with Highly Fluorescent Anthranilic Acid, Glycobiology 1998; 8:685-94.

Marino et al., A Systematic Approach to Protein Glycosylation Analysis: A Path Through the Maze, Nature Chemical Biology 2010; 6:713-23.

Suzuki et al., Comparison of the Sensitivities of Various Derivatives of Oligosaccharides in LC/MS with Fast Atom Bombardment and Electrospray Ionization Interfaces, Anal Chem 1996; 68:2073-83.

Harvey, Identification of Protein-Bound Carbohydrates by Mass Spectrometry, Proteomics 2001, 1:311-28.

Yu et al., A Rapid Sample Preparation Method for Mass Spectrometric Characterization of N-linked Glycans, Rapid Comm Mass Spectrometry 2005; 19:331-36.

(56) References Cited

OTHER PUBLICATIONS

Klapoetke et al., The Evaluation of a Novel Approach for the Profiling and Identification of N-linked Glycans With a Procainamide Tag by HPLC With Fluorescent and Mass Spectrometric Detection, J. Pharmaceutical and Biomedical Anal 2010; 53:315-24.
Nimura et al., Activated Carbamate Reagent as Derivatizing Agent for Amino Compounds in High-Performance Liquid Chromatography, Anal Chem 1986; 58:2372-75.
Takeda et al., Convenient Methods for Syntheses of Active Carbamates, Ureas and Nitrosoureas Using N,N'-Disuccinimido Carbonate (DSC), Tetrahedron Lett 1983; 24:4569-72.
Wada et al., Comparison of the Methods For Profiling Glycoprotein Glycans—HUPO Human Disease Glycomics/Proteome Initiative Multi-Institutional Study, Glycobiology 2007; 17:411-22.
Wuhrer et al., Nano-Scale Liquid Chromatography—Mass Spectrometry of 2-Aminobenzamide-Labeled Oligosaccharides at Low Femtomole Sensitivity, Int J Mass Spectrom 2004; 232:51-57.
Heinze-Krauss et al., Structure-Based Design of β-Lactamase Inhibitors. 1. Synthesis and Evaluation of Bridged Monobactams, J Med Chem 1998; 41:3961-71.
Isbell et al., Effect of pH in the Mutarotation and Hydrolysis of Glycosylamines, JACS 1950; 72:1043-4.
Tarentino et al., 2-Iminothiolane: A Reagent for the Introduction of Sylphydryl Groups into Oligosaccharides Derived from Asparagine-Linked Glycans, Glycobiology 1993; 3:279-85.
Saurina et al., Chromatographic Determination of Amino Acids by Pre-Column Derivatization Using 1,2-Napthoquinone-4-Sulfonate As Reagent, J Chromatogr A 1996; 740:21-30.
Piepponen et al., Rapid and Sensitive Step Gradient Assays of Glutamate, Glycine, Taurine and γ-Aminobutyric Acid by High-Performance Liquid Chromatography—Fluorescence Detection with o-Phthalaldehyde-Mercaptoethanol Derivatization With an Emphasis on Microdialysis Samples, J Chromatogr B 2001; 757:277-83.
Black et al., Simple, Rapid, and Highly Efficient Separation of Amino Acid Phenylthiohydantoins by Reversed-Phase High-Performance Liquid Chromatography, Anal Biochem 1982; 121:281-85.
Casoli et al., Use of High-Performance Liquid Chromatography For the Determination of Amino Acids in Sparkling Wines, Am J Enol Vitic 1982; 33:135-39.
Liu et al., Determination of Submicromolar Concentrations of Neurotransmitter Amino Acids by Fluorescence Detection Using a Modification of the 6-Aminoquinolyl-N-Hydroxysuccinimidyl Carbamate Method for Amino Acid Analysis, J Chromatogr A 1998; 828:383-95.
Park et al., Regioselective Covalent Modification of Hemoglobin in Search of Antisickling Agents, J Med Chem 2003; 46:936-53.
Saurina et al., Determination of Amino Acids by Ion-Pair Liquid Chromatography With Post-Column Derivatization Using 1,2-Naphthoquinone-4-Sulfonate, J Chromatogr A 1994; 676:311-19.
Schmidt et al., Amino Acid Profiling of Protein Hydrolysates Using Liquid Chromatography and Fluorescence Detection, J Liq Chromatogr 1979; 2:1031-45.
Van Wandelen et al., Using Quaternary High-Performance Liquid Chromatography Eluent Systems for Separating 6-Aminoquinolyl-N-Hydroxysuccinimidyl Carbamate-Derivatized Amino Acid Mixtures, J Chromatogr A 1997; 763:11-22.
Wei et al., Study on N-Hydroxyphthalimide as Blocking Agent for Isocyanates, J Appl Polym Sci 2002; 84:1346-52.
Kurita et al., Synthesis and Properties of Polyurethanes Derived from bis-N-Hydroxyimides and Diisocyanates, J Polym Sci 1979; 17:1619-29.
International Search Report and Written Opinion of the International Searching Authority, PCT/US12/57996, dated Jan. 31, 2013.
Vasilevich et al., Conversion of O-Succinimidyl Carbamates to N-(O-Carbamoyl)-Succinmonoamides and Ureas: Effects of N-Substituents and Reaction Conditions on the Reaction Pathway, Tetrahedron Lett 2002; 43:6649-52.
Guichard et al,. Preparation of O-Succinimidyl-2-(tert-Butoxycarbonylamino)ethylcarbamate Derivatives from Beta-Amino Acids. Application to the Synthesis of Urea-Containing Pseudopeptides and Oligoureas, J Org Chem 1999; 64:8702-5.
Cooper et al., LC-MS/MS Analysis of AccQ-Tag Derivatised Amino Acids, Micromass Application Brief, Sep. 200 and Jun. 2000.
Cohen, Compositional Protein Analysis Using 6-Aminoquinolyl-N-Hydroxysuccinimidyl Carbamate, a Novel Derivatization Reagent, Techniques in Prot Chem IV 1993; 289-298.
De Antonis et al., High-Performance Liquid Chromatographic Analysis of Synthetic Peptides Using Derivatization with 6-Aminoquinolyl-N-Hydroxysuccinimidyl Carbamate, Anal Biochem 1994; 223:191-7.
Liu et al., Femtomole Peptide Mapping by Derivatization, High-Performance Liquid Chromatography, and Fluorescence Detection, Anal Biochem 2001; 294:7-18.
Cohen et al., Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography, Anal Biochem 1993; 211:279-87.
Higashi et al., Derivatization of Neutral Steroids to Enhance Their Detection Characteristics in Liquid Chromatography—Mass Spectrometry, Anal Bioanal Chem 2004; 378:875-882.
Hochleitner et al., Determination of the Stoichiometry of Protein Complexes Using Liquid Chromatography with Fluorescence and Mass Spectrometric Detection of Fluorescently Labeled Proteolytic Peptides, Proteomics 2004; 4:669-676.
Schmeer et al., Compositional Analysis of the Phenylthiocarbamyl Amino Acids by Liquid Chromatography—Atmospheric Pressure Ionization Mass Spectrometry with Particular Attention to the Cyst(e)ine Derivatives, J of Chromatography 1995; 691:285-99.
Martinez-Force et al., Separation of O-Phthalaldehyde Derivatives of Amino Acids of the Internal Pool of Yeast by Reverse-Phase Liquid Chromatography, Biotech Tech 1991; 5(3):209-14.
Block, The Use of 6-Aminoquinolyl-N-Hydroxy Succinimidyl Carbamate Derivatives for HPLC/MS Analysis of Amino Acids, AMD35 Waters Alliance LC/MS System 2000.
Cooper et al., LC-MS/MS Analysis of AccQ-Tag Derivatised Amino Acids, Micromass UK Limited 2000.
Block et al., Abstract 2050P: HPLC-MS Analysis of Amino Acids, Pittsburgh Conference, Mar. 1999.
Block et al., Poster 2050P: HPLC/MS Analysis of Amino Acids: The Use of 6-Aminoquinolyl-N-Hydroxy-Succinimidyl Carbamate Derivatives, Pittsburgh Conference, Mar. 1999.
Cooper et al., LC-MS-MS Analysis of Amino Acids Using AccQ-Tag derivatisation, Application Brief AB25, Micromass June and Sep. 2000.
Block, Presentation: LC/MS Application Notes: The Use of 6-Aminoquinolyl N Hydroxy Succinimidyl Carbamate Derivatives for HPLC/MS Analysis of Amino Acids, Pittsburgh Conference, Mar. 1999.
Chromatography Forum: LC-MS & GC-MS Archives: AAA LC-MS, http://www.lcresources.com/discus/messages/5135/3143.html?MondayApril1420030826pm Jan.-Apr. 2003.
Kimzey, Michael et al., Development of an Instant Glycan Labeling Dye for High Throughput Analysis by Mass Spectrometry, Prozyme Advancing Glycosciences, May 13, 2015.
International Preliminary Report on Patentability, PCT/US2012/057996, dated Apr. 1, 2014.
Extended European Search Report, EP12836127.6, dated Aug. 26, 2014.
Kinzel, Olaf et al., Identification of MK-5710 ((8aS)-8a-methyl-1,3-dioxo-2-[(1S,2R)-2-phenylcyclo-propyl]-N-(1-phenyl-1H-pyrazol-5-yl)hexahydro-imidazo[1,5-a]pyrazine-7(1H)-carboxamide), a Potent Smoothened Antagonist for Use in Hedgehog Pathway Dependent Malignancies, Part 2, Bioogranic and Medicinal Chemistry Letters, vol. 21, 2011, pp. 4429-4435.
Supplementary European Search Report, EP12836127.6 dated Sep. 12, 2014 and Response dated Mar. 19, 2015.
Supplementary European Search Report, EP12836127.6 dated Sep. 12, 2014, 2 pages.
Ahn J., et al., "Separation of 2-aminobenzamide labeled glycans using hydrophilic interaction chromatography columns packed with 1.7 μm sorbent," Journal of Chromatography B, 878: 403-8, 2010.

(56) References Cited

OTHER PUBLICATIONS

Campbell M. P., et al., "GlycoBase and autoGU: tools for HPLC-based glycan analysis," Bioinformatics, 24 (9): 1214-1216, 2008.

Guile G R., et al., "A Rapid High-Resolution High-Performance Liquid Chromatographic Method for Separating Glycan Mixtures and Analyzing Oligosaccharide Profiles," Analytical Biochemistry, 240: 210-226, 1996.

Yu Y. Q., "N-linked Glycan Characterization and Profiling: Combining the Power of Accurate Mass, Reference Glucose Units, and UNIFI Software for Confident Glycan Assignments," Waters, Application Note, 2013.

Dextran Calibration Ladder Standard. Waters. 2012.

Dextran Calibration Ladder. Waters. Product Solution. 2013.

International Search Report and Written Opinion, dated Feb. 2, 2016, PCT/US15/60326. 4 pages.

Harvey, D., "Identification of protein-bound carbohydrates by mass spectrometry," Proteomics, 1:318-319, 2001.

Communication of a notice of opposition for EP Patent No. 2761296 mailed Jun. 5, 2018.

Response to notice of opposition for EP Patent No. 2761296 filed Oct. 19, 2018.

Briggs, J. B., et al., "An analytical system for the characterization of highly heterogeneous mixtures of N-linked oligosaccharides," Analytical Biochemistry, 389:40-51, Jan. 15, 2009.

Higuchi, K., et al., "Chemistry of Succinimido Esters IV*1. A Facile Preparation of N-Succinimidyl Carboxylates Using N, N-Disuccinimidyl Carbonate", Oil Chemistry, 36(1):16-20 (1987).

EP12836127.6 Opposition Communication Jul. 23, 2019.,10 pages.

Expert Declaration by Prof. Ulf Diederichsen dated Jul. 23, 2019, 7 pp.

Fu-Chuan, Li, et al., "Studies on Fluorescent Labeling of Marine Sulfated Polysaccharide 911", Chemical Journal of Chinese Universities, 23(9):1704-1708 (2002).

RAPID FLUORESCENCE TAGGING OF GLYCANS AND OTHER BIOMOLECULES WITH ENHANCED MS SIGNALS

CROSS REFERENCE TO RELATED APPLICATIONS

This application is a continuation-in-part of U.S. patent application Ser. No. 14/458,760, filed Aug. 13, 2014, which is a continuation-in-part of U.S. patent application Ser. No. 14/193,418, filed Feb. 28, 2014, which is a continuation of International Application No. PCT/US2012/057996, filed Sep. 28, 2012, which claims the benefit of Provisional Application No. 61/540,306, filed Sep. 28, 2011, and also a continuation-in-part of U.S. patent application Ser. No. 14/342,131, filed Feb. 28, 2014 which is the National Stage of International Application No. PCT/US2012/057996, filed Sep. 28, 2012, which claims the benefit of Provisional Application No. 61/540,306.

STATEMENT REGARDING FEDERALLY SPONSORED RESEARCH OR DEVELOPMENT

None.

THE NAMES OF PARTIES TO A JOINT RESEARCH AGREEMENT

None.

BACKGROUND OF THE INVENTION

Fluorescent labeling of N-glycans is beneficial to detecting glycans because it improves both sensitivity and selectivity of the detection as well as the chromatographic behavior of glycans. Amino acid analysis is a fundamental process in protein research and is of particular importance to clinical chemists and pharmaceutical manufacturers when glycosylation profiling of proteins must be monitored to ensure consistency of a therapeutic product. Upon derivation with a reagent having a fluorescent moiety, the functional group of the compound can only be estimated. Mass spectrometry ("MS") is then required to identify the specific compound.

Analysis by MS has reached a high degree of development with respect to glycan and amino acid analysis and proteomics. However, the necessary reaction time to functionalize most amines is slow. The current state of the art utilizes tagging molecules that either (1) react quickly and have good fluorescence signal, but poor MS signal or (2) react very slowly and give good MS/fluorescence signals. A combination of MS and fluorescence detection is desirable, however, because fluorescence detection is very useful tool in determining quantitatively how much is present. On the other hand, MS is used to determine what the molecular makeup is.

A need exists, therefore, for molecules with that rapidly react with biomolecules and provide strong mass spectrometry and fluorescence signals.

SUMMARY OF THE INVENTION

Described herein are MS active compounds useful in rapid fluorescence tagging of glycans such as N-linked glycans and other bio-molecules including, but not limited to, proteins, peptides and amino acids. These MS active, fluorescent compounds have three functional components: (a) a tertiary amino group or other MS active atom; (b) a highly fluorescent moiety, and (c) a functional group that rapidly reacts with amines, such as an isocynanate or succidimidylcarbamate. The reactive functional group provides rapid tagging of desired bio-molecules, and the fluorescent moiety provides for a strong fluorescent signal. The tertiary amino group substituent provides a strong MS signal. Furthermore, it is envisioned that there is no specific connectivity between the rapidly reacting functional group, the fluorescent moiety or the tertiary amino group as any group can be attached to the other.

In particular, the invention relates to compounds of the various formulas described herein. Each compound can act as a reagent for rapid fluorescence tagging of biomolecules and enhanced MS signaling. For example, the MS active, rapid fluorescence tagging compounds can be of the structural Formula I:

wherein

FL is

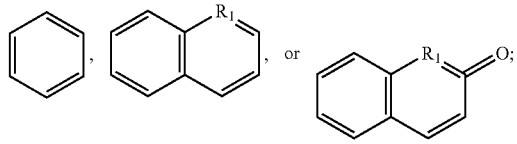

$R^1$ is O or N;

$R^2$ is

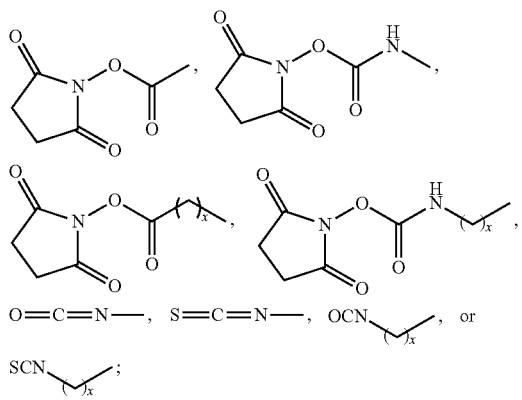

$R^3$ is

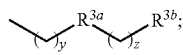

$R^{3a}$ is selected from ester, amide, amine, ether, urea, carbamate, carbonate, thiol, thiourea, thiocarbamate, alkyl or carbonyl;

$R^{3b}$ is

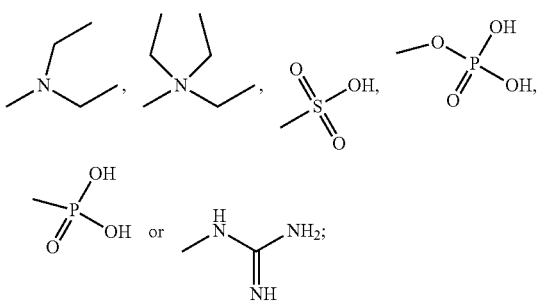

x=0-12;
y=0-12;
z=1-12;
and salts or solvates thereof.

The MS active, rapid fluorescence tagging compounds can also be of the structural Formula II:

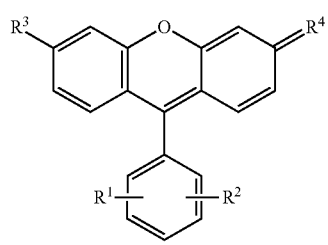

wherein
$R^1$ is

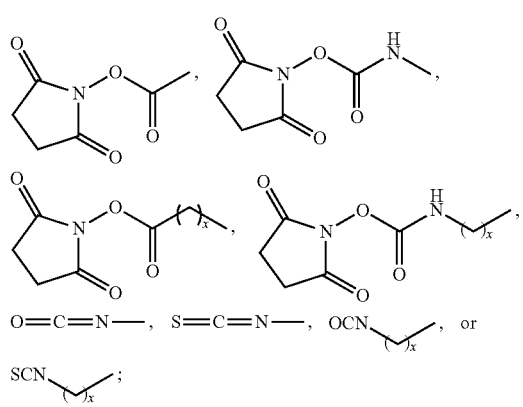

$R^2$ is

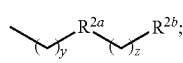

$R^{2a}$ is selected from ester, amide, amine, ether, urea, carbamate, carbonate, thiol, thiourea, thiocarbamate, alkyl or carbonyl;

$R^{2b}$ is

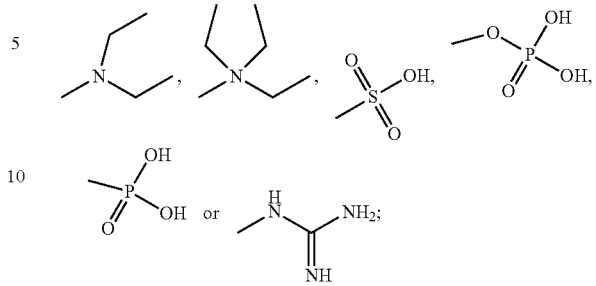

$R^3$ is

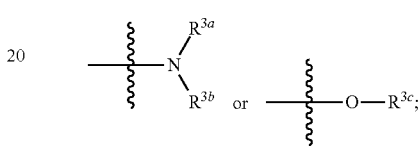

$R^4$ is

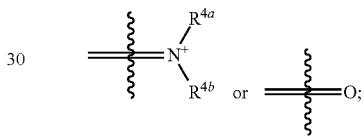

$R^{3a}$, $R^{3b}$, $R^{3c}$, $R^{4a}$ and $R^{4b}$ are independently selected from H, optionally substituted alkyl;
x=0-12;
y=0-24;
z=1-12;
and salts or solvates thereof.

The compounds of the formulas described herein may have optical centers and therefore may occur in different enantiomeric and diastereomeric configurations. The invention described herein includes all enantiomers, diastereomers and other stereoisomers of such compounds of each formula, as well as racemic compounds and racemic mixtures and other mixtures of stereoisomers thereof.

DETAILED DESCRIPTION

Figure 1:
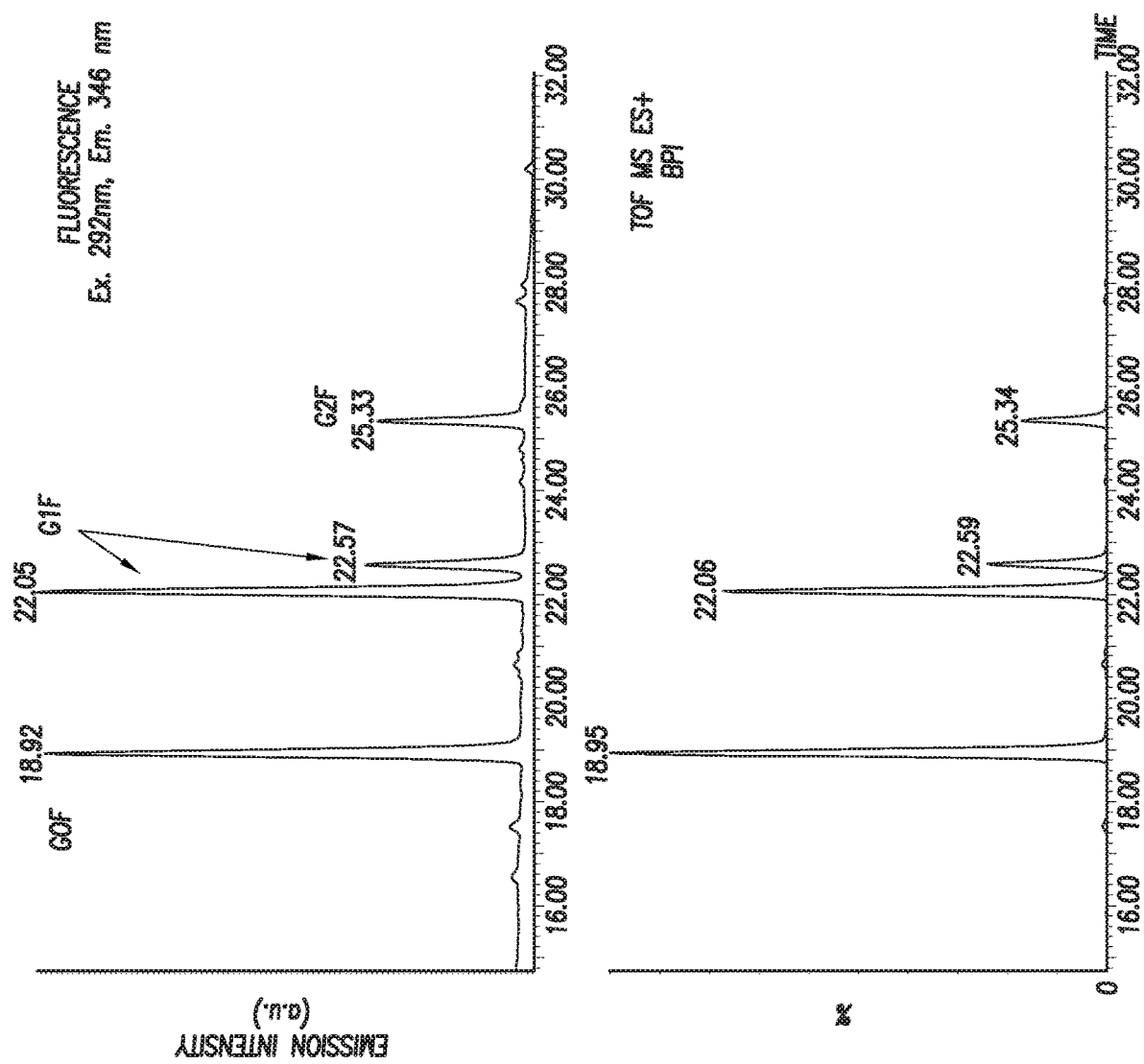
FIG. 1 shows the fluorescence and MS detection of the glycans G0F, G1F, and G2F released from 0.8 µg Herceptin IgG labeled with 2,5-dioxopyrrolidin-1-yl (4-((2-(diethylamino)ethyl)carbamoyl)phenyl)carbamate.

Novel compounds useful in the rapid fluorescence tagging of glycans such as N-linked glycans and other bio-molecules including, but not limited to, proteins, peptides and amino acids and with enhanced MS signaling are provided herein. These compounds are used to analyze glycans and/or other biomolecules in a sample. To analyze the biomolecule, the molecule is rapidly labeled with a compound described herein and then subjected to liquid chromatography, mass spectrometry, and fluorescence detection.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein without changing or effecting the fluorescent or mass spec properties of the molecule. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene ($-CH_2-$).

The term "alkylamino," as used herein may be a mono- or dialkylated groups (also referred to "dialkylamino") such as, for example, N-methylamino, N-ethylamino, N,N-dimethylamino, N,N-ethylmethylamino and the like and combination, refers to $-NRR'$, wherein R is independently selected from the group consisting of hydrogen and alkyl, and R' is alkyl, any of which may themselves be optionally substituted and the dialkyamino group can further comprise a spacer (sometimes referred to as a linker or linker group). A molecular spacer or simply a "spacer" in chemistry is any flexible part of a molecule that provides a connection between two other parts of a molecule The term "parent molecular moiety" as used herein means and includes phenyl, quinoline, coumarin or rhodamine.

The term "amino," as used herein, alone or in combination, refers to $-NRR'$, wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The terms "benzo" and "benz," as used herein, alone or in combination, refer to the divalent radical $C_6H_4=$derived from benzene. Examples include benzothiophene and benzimidazole.

The term "carbamate," as used herein, alone or in combination, refers to an ester of carbamic acid ($-NHCOO-$) which may be attached to the parent molecular moiety from either the nitrogen or acid end, and which may be optionally substituted as defined herein.

The term "O-carbamyl" as used herein, alone or in combination, refers to a $-OC(O)NRR'$, group—with R and R' as defined herein.

The term "N-carbamyl" as used herein, alone or in combination, refers to a $ROC(O)NR'-$ group, with R and R' as defined herein.

The term "carbonyl," as used herein, when alone includes formyl [$-C(O)H$] and in combination is a $-C(O)-$ group.

The term "carboxy," as used herein, refers to $-C(O)OH$ or the corresponding "carboxylate" anion, such as is in a carboxylic acid salt. An "O-carboxy" group refers to a RC(O)O— group, where R is as defined herein. A "C-carboxy" group refers to a $-C(O)OR$ groups where R is as defined herein.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene ($-CFH-$), difluoromethylene ($-CF_2-$), chloromethylene ($-CHCl-$) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, $-CH_2-NH-OCH_3$.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The terms "OCN" and "SCN" mean O=C=N—, isocyanate, and S=C=N—, thioisocyanate, respectively The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecular moiety or may occupy a position in a chain of elements from either end as written. Thus, by way of example only, an unsymmetrical group such as —C(O)N (R)— may be attached to the parent molecular moiety at either the carbon or the nitrogen.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position. The development and production of therapeutic proteins is becoming the fastest-growing segment of the pharmaceutical industry. The efficacy, stability and protein secretion of these large molecule drugs depend on their Post Translational Modifications ("PTMs"). Glycosylation is the most complex and common PTM and plays a vital role in the safety and efficacy of many therapeutic proteins such as recombinant antibodies. Several studies have shown the correlation between glycosylation variations caused by cell line selection and changes in culture medium parameters. Patrick Hossler et al., *Optimal and Consistent Protein Glycosylation in Mammalian Cell Culture,* 19 GLYCOBIOLOGY 926 (2009). These variations can have a profound effect on the biological activities of the mAb drugs, which leads to changes in drug potency in the final product. Regulatory agencies require monitoring of batch-to-batch recombinant antibody drug production quality and mandate detailed assessment of the protein glycosylation micro-heterogeneity and consistency.

The compounds described herein may also form hydrogen bonds with other compounds. A hydrogen bond is an electromagnetic attractive interaction between polar molecules, where hydrogen is bonded to an electronegative atom such as nitrogen or oxygen. The hydrogen bond represents a strong dipole-dipole attraction. These hydrogen-bond attractions can occur between molecules (intermolecular) or within different parts of a single molecule (intramolecular). When a hydrogen atom is attached to an electronegative atom, it is considered a hydrogen bond donor. The electronegative atom is considered a hydrogen bond acceptor, whether it is bonded to a hydrogen atom or not. While many possible hydrogen bonds can exist between two compounds, an exemplary bonding of a compound with another could take one of many forms, including, but not limited to, for example the following:

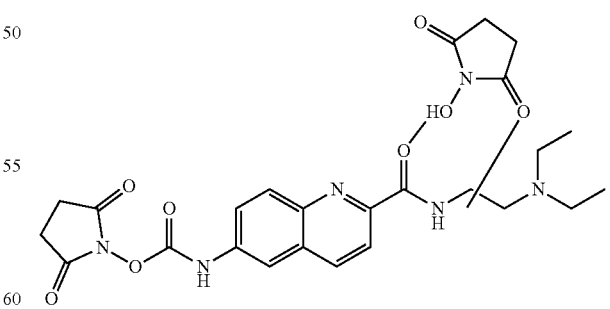

A general representation for hydrogen bonded compounds is provided immediately below:

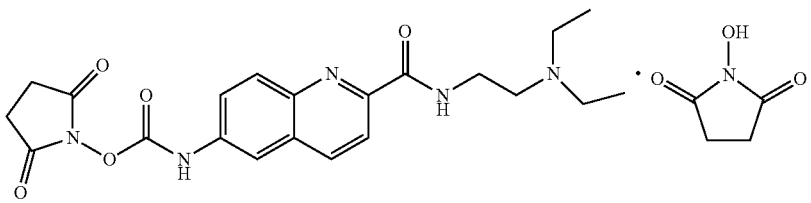

where the dot represents a first compound hydrogen bonded to a second compound, but not the exact bonding between such compounds, and hydrogen bonds could be formed at different positions within compounds.

Asymmetric centers exist in the compounds presented herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Hence, the compounds described herein can also be in the form of a salt or solvate, in particular acid addition salts. Through a reaction with either organic or inorganic acids, compounds presented herein or groups of compounds can form a salt. For example, in acid-base neutralization, an acid and a base react to form water and a salt. Basically, to react together, there must be the transfer of protons between acids and bases. Also, different acids can produce different ions. For example, an Arrhenius acid produces hydronium ions when it dissociates in water. Similarly, a Bronsted-Lowry acid is a proton donor that donates hydrogen ions to the base. Hence, proton acceptors and proton donors are the basis for the reaction and are referred to sometimes as a conjugate base or a conjugate acid. A conjugate pair refers to acids and bases with common features, where there is an equal loss/gain of protons between the pairs. For example $NH_4^+$ is the conjugate acid to the base $NH_3$ because $NH_3$ gains a hydrogen ion to form $NH_4^+$ as $H_2O$ donates a hydrogen ion to form $OH^-$, the conjugate base. On the other hand, under a different theory, a Lewis acid accepts an electron pair and a Lewis base donates an electron pair donor. Accordingly, the proton $H^+$ can be an electron pair acceptor. Moreover, a compound can be both, a Lewis acid and a Lewis base, depending on the reaction. For example, methyl iodide can behave as both, a Lewis acid and a Lewis base, where the methyl group is donated to form a salt.

Examples of acids which can be employed to form a salt of any of the compounds provided herein include inorganic acids and organic acids as well known to those skilled in the art such as, but not limited to, N-hydroxysuccinimide, hydrochloric, hydrofluoric, hydroiodic, hydrobromic, sulfuric, hydrosulfuric, thiosulfuric, hydrocyanic, phosphoric, phosphorous, hydrochlorous, chlorous, nitrous, nitric, chloric, perchloric, sulfurous, oxalic, maleic, succinic, and citric. Salts may also be formed by coordination of the compounds with an alkali metal or alkaline earth ion. In addition, other acids can form a salt including, but not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic a cid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, isobutyric acid, lactic acid (DL), lactobionic acid, lauric acid, maleic acid, malic acid (−L), malonic acid, mandelic acid (DL), methanesulfonic acid, naphthalene-1,5, disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), undecylenic acid.

For the compounds described herein, the counterion can be the conjugate base formed after reacting a compound or groups of compounds with an acid. In other words, counterion holds the opposite charge to that of the compound or compounds it is associated with. Thus, with respect to possible salts of the compounds herein having a conjugate acid of $NH_4^+$, the counterion represents the anionic part of the salt. In addition, it can be possible to have four organic substituents on the nitrogen. These species are not amines but are quaternary ammonium cations having a charged nitrogen center. Quaternary ammonium salts can exist with many kinds of anions.

Hence, counterions of a salt compound described herein can include, but are not limited to, any of the following common anions and oxoanions: N-hydroxysuccinimidyl, hydride ($H^-$), fluoride ($F^-$), chloride ($Cl^-$), bromide ($Br^-$), iodide ($I^-$), oxide ($O^{2-}$), hydroxide ($OH^-$), peroxide ($O_2^{2-}$), sulfide ($S^{2-}$), hydrogen sulfide ($HS^-$), selenide ($Se^{2-}$), nitride ($N^{3-}$), azide ($Ni_3^-$), phosphide ($P^{3-}$), arsinide ($As^{3-}$), carbide ($C^{4-}$), cyanide ($CN^-$), hypochlorite ($ClO_1^-$), chlorite ($ClO_2^-$), chlorate ($ClO_3^-$), perchlorate ($ClO_4^-$), sulfite ($SO_3^{2-}$), sulfate ($SO_4^{2-}$), hydrogen sulfate ($HSO_4^-$), thiosulfate ($S_2O_3^{2-}$), nitrite ($NO_2^-$), nitrate ($NO_3^-$), phosphite ($PO_3^{2-}$), phosphate ($PO_4^{3-}$), (mono)hydrogen phosphate ($HPO_4^{2-}$), dihydrogen phosphate ($H2PO_4^-$), carbonate ($CO_3^{2-}$), hydrogen carbonate ($HCO_3^-$), oxalate ($C_2O_4^{2-}$), cyanate ($NCO^-$), isocyanate ($OCN^-$), thiocyanate ($SCN^-$), chromate ($CrO_4^{2-}$), dichromate ($Cr_2O_7^{2-}$), permanganate ($MnO_4^-$).

The MS active, rapid fluorescence tagging compounds can also be of the Formula III:

wherein $R^1$ is

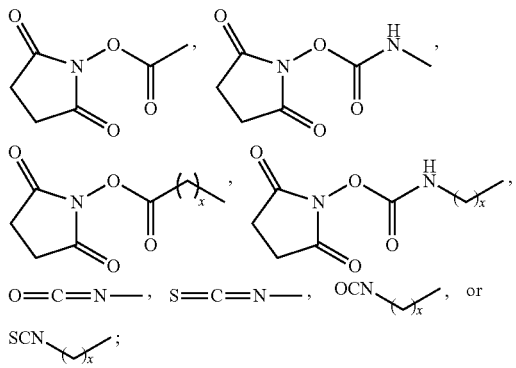

$R^2$ is

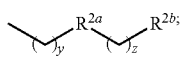

$R^{2a}$ is selected from ester, amide, amine, ether, urea, carbamate, carbonate, thiol, thiourea, thiocarbamate, alkyl or carbonyl;

$R^{2b}$ is

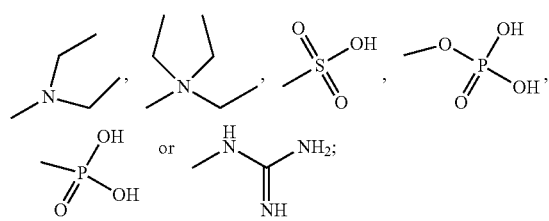

x=0-12;
y=0-12;
z=1-12; and
salts or solvates thereof.

The MS active, rapid fluorescence tagging compounds can be of the Formula IV:

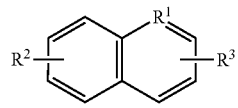

wherein
$R^1$ is C or N;
$R^2$ is

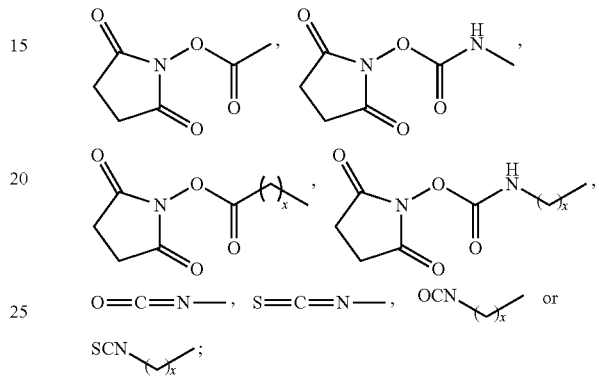

$R^3$ is

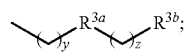

$R^{3a}$ is selected from ester, amide, amine, ether, urea, carbamate, carbonate, thiol, thiourea, thiocarbamate, alkyl or carbonyl;

$R^{3b}$ is

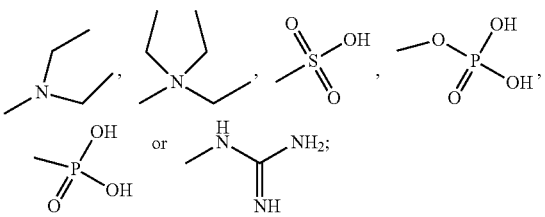

x=0-12;
y=0-12;
z=1-12; and
salts or solvates thereof.

The MS active, rapid fluorescence tagging compounds can be of the Formula V:

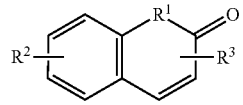

wherein
R¹ is NH; NR where R is alkyl, or O;
R² is

[structures: NHS-acetate, NHS-carbamate, NHS-(CH₂)ₓ-ester, NHS-(CH₂)ₓ-carbamate]

O=C=N—, S=C=N—, OCN−(CH₂)ₓ− or

SCN−(CH₂)ₓ−;

R³ is

[structure: −(CH₂)ᵧ−R³ᵃ−(CH₂)_z−R³ᵇ]

R³ᵃ is selected from ester, amide, amine, ether, urea, carbamate, carbonate, thiol, thiourea, thiocarbamate, alkyl or carbonyl;
R³ᵇ is

[structures: −N(Et)₂ / −NMe(Et), −SO₂OH, −O−P(O)(OH)₂, −P(O)(OH)₂, or −NH−C(=NH)NH₂]

x=0-12;
y=0-12;
z=1-12; and
salts or solvates thereof.

In addition, provided herein are compounds of the structural Formula VI:

[structure of xanthene/rhodamine-like core with R³, R⁴ on the xanthene and R¹, R² on the pendant phenyl]

wherein
R¹ is

[structures: NHS-acetate, NHS-carbamate,]

-continued

[structures: NHS-(CH₂)ₓ-ester, NHS-(CH₂)ₓ-carbamate,]

O=C=N—, S=C=N—, OCN−(CH₂)ₓ− or

SCN−(CH₂)ₓ−;

R² is

[structure: −(CH₂)ᵧ−R²ᵃ−(CH₂)_z−R²ᵇ]

R²ᵃ is selected from ester, amide, amine, ether, urea, carbamate, carbonate, thiol, thiourea, thiocarbamate, alkyl or carbonyl;
R²ᵇ is

[structures: −N(Et)₂ / −NMe(Et), −SO₂OH, −O−P(O)(OH)₂, −P(O)(OH)₂, or −NH−C(=NH)NH₂]

R³ is

[structures: −N(R³ᵃ)(R³ᵇ) or −O−R³ᶜ]

R⁴ is

[structures: =N⁺(R⁴ᵃ)(R⁴ᵇ) or =O]

$R^{3a}$, $R^{3b}$, $R^{3c}$, $R^{4a}$ and $R^{4b}$ are independently selected from H, optionally substituted alkyl;
x=0-12;
y=0-24;
z=1-12;
and salts or solvates thereof.

The MS active, rapid fluorescence tagging compounds can be of the Formula VII:

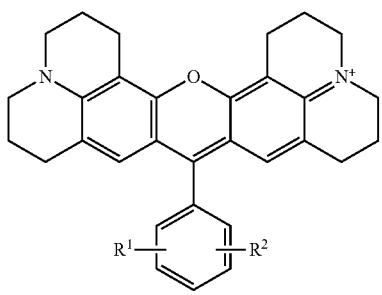

wherein

R¹ is

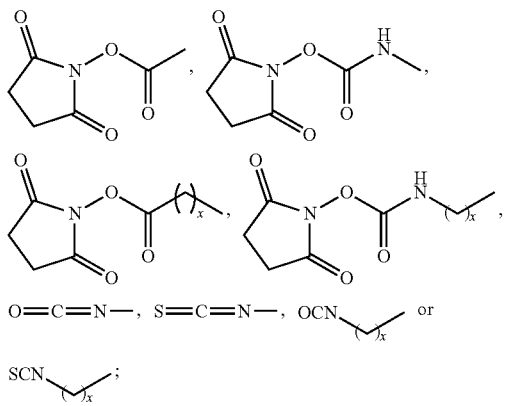

O=C=N—, S=C=N—, OCN—(CH₂)ₓ— or

SCN—(CH₂)ₓ—;

R² is

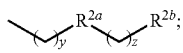

R²ᵃ is selected from ester, amide, amine, ether, urea, carbamate, carbonate, thiol, thiourea, thiocarbamate, alkyl or carbonyl;

R²ᵇ is

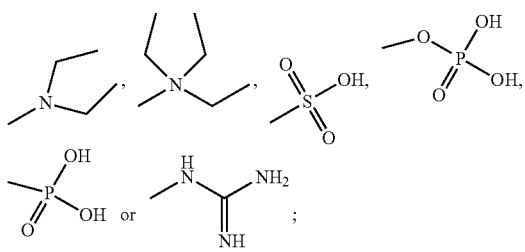

x=0-12;
y=0-24;
z=1-12;

and salts or solvates thereof.

The MS active, rapid fluorescence tagging compounds can also be of the Formula VIII:

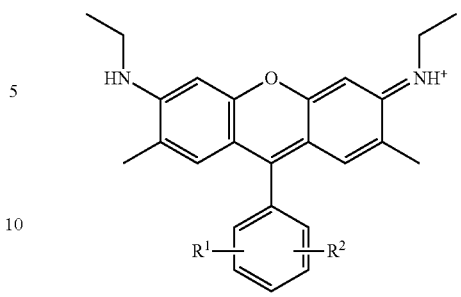

wherein

R¹ is

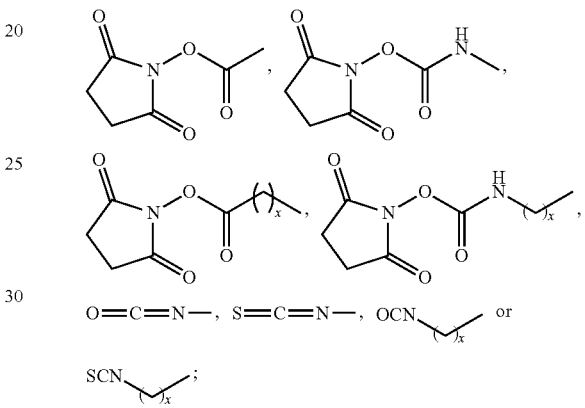

O=C=N—, S=C=N—, OCN—(CH₂)ₓ— or

SCN—(CH₂)ₓ—;

R² is

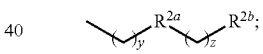

R²ᵃ is selected from ester, amide, amine, ether, urea, carbamate, carbonate, thiol, thiourea, thiocarbamate, alkyl or carbonyl;

R²ᵇ is

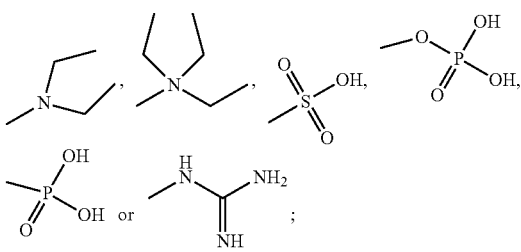

x=0-12;
y=0-24; and
z=1-12;

and salts or solvates thereof.

The MS active, rapid fluorescence tagging compounds can also be of the Formula IX:

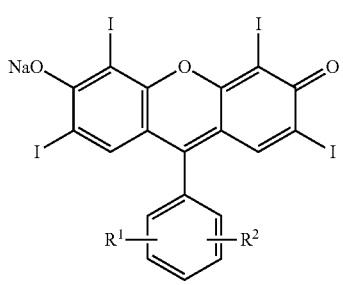

wherein
R¹ is

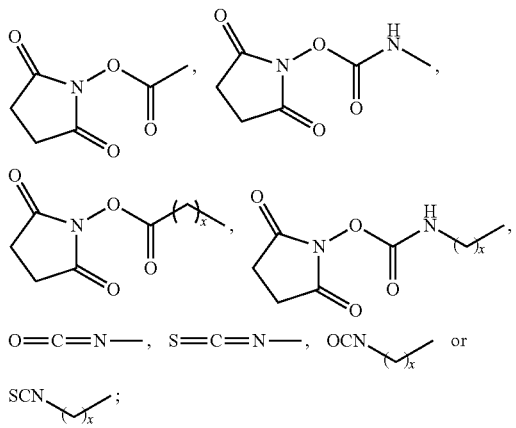

$O{=}C{=}N{-}$, $S{=}C{=}N{-}$, OCN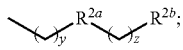 or

SCN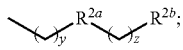;

R² is

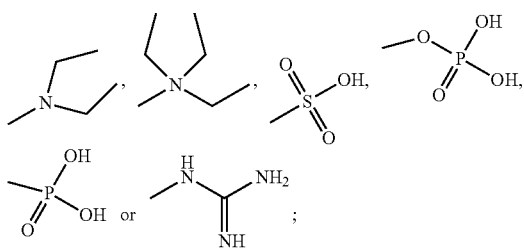

$R^{2a}$ is selected from ester, amide, amine, ether, urea, carbamate, carbonate, thiol, thiourea, thiocarbamate, alkyl or carbonyl;

$R^{2b}$ is

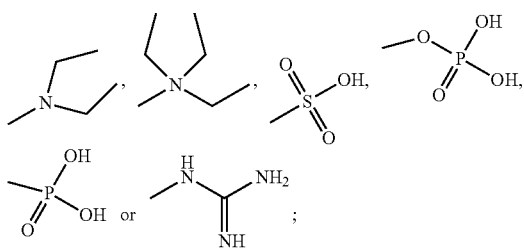

x=0-12;
y=0-24;
z=1-12;
and salts or solvates thereof.

The MS active, rapid fluorescence tagging compounds can also be of the Formula X:

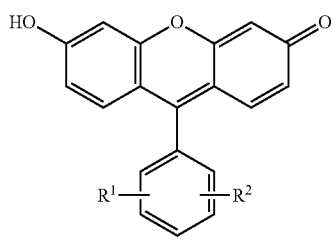

wherein
R¹ is

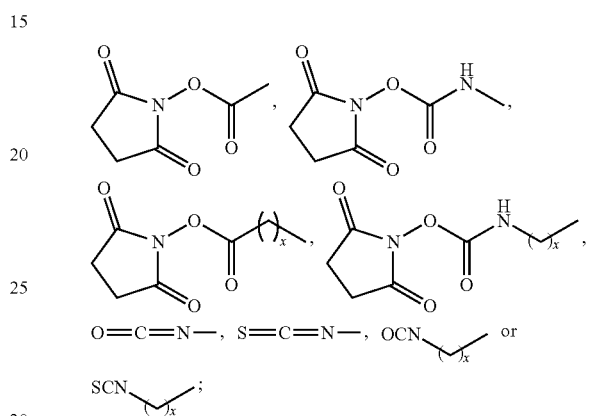

$O{=}C{=}N{-}$, $S{=}C{=}N{-}$, OCN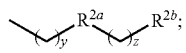 or

SCN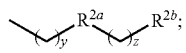;

R² is

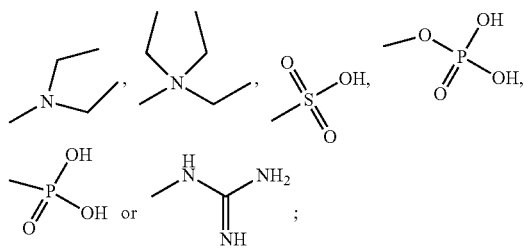

$R^{2a}$ is selected from ester, amide, amine, ether, urea, carbamate, carbonate, thiol, thiourea, thiocarbamate, alkyl or carbonyl;

$R^{2b}$ is

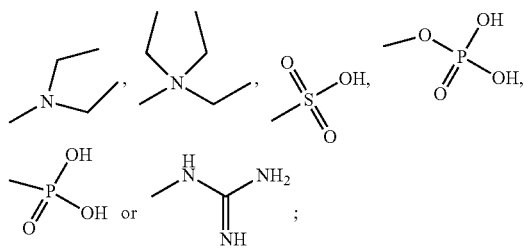

x=0-12;
y=0-24;
z=1-12;
and salts or solvates thereof.

In addition provided below are exemplary compounds of the structural Formulas I, II, III, IV, V, VI, VII, VIII, IX or X which can be useful for rapid fluorescent labeling of glycans and subsequent analysis by means of liquid chromatography and mass spectrometry. It is further envisioned that the Formula I through Formula X could be optionally substituted with any group that does not substantially reduce the fluorescence of the compound.

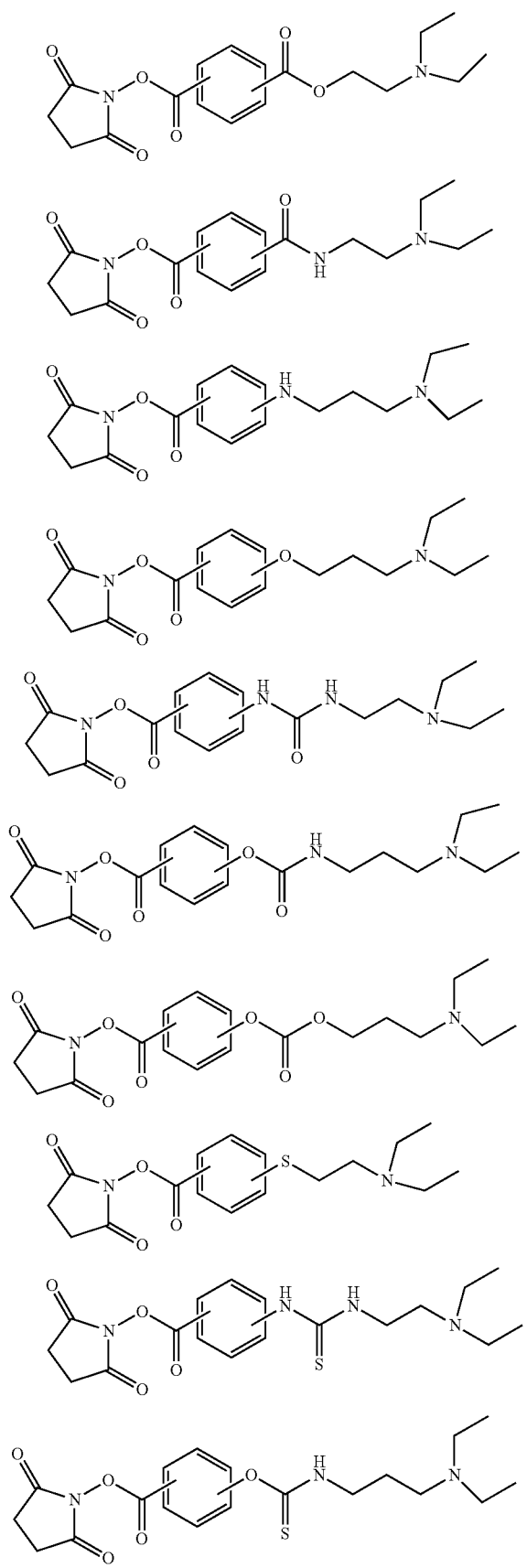
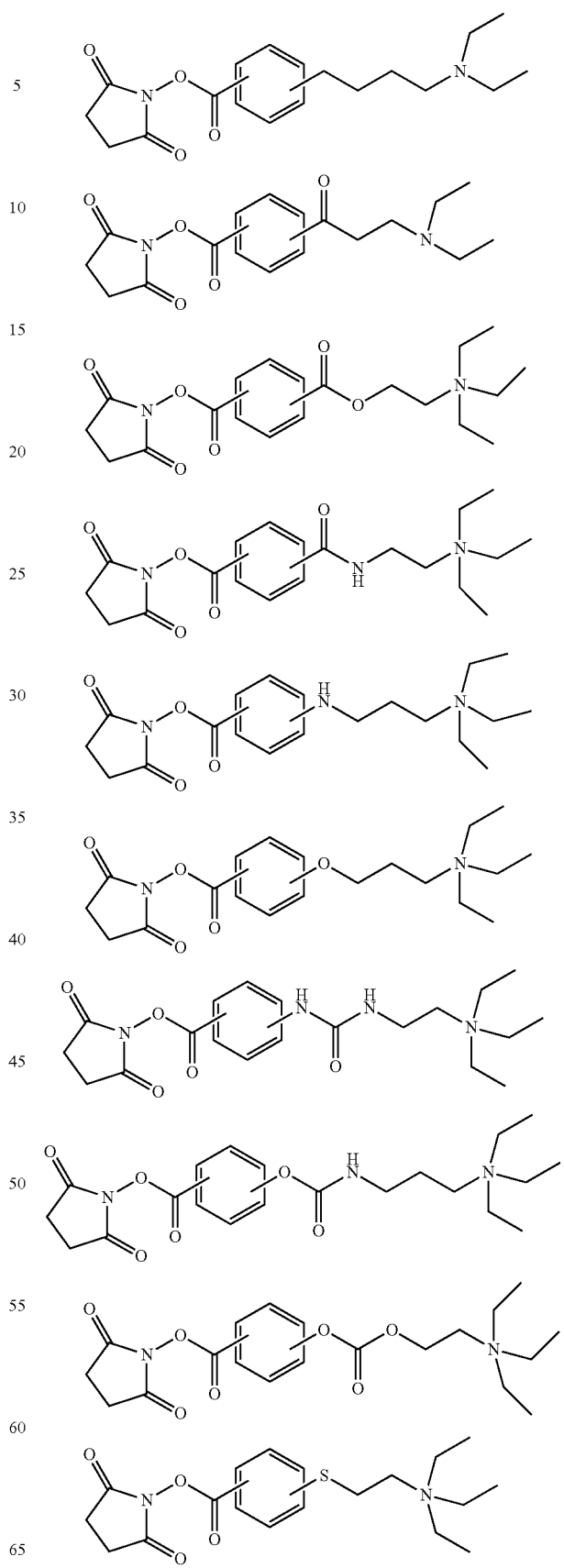

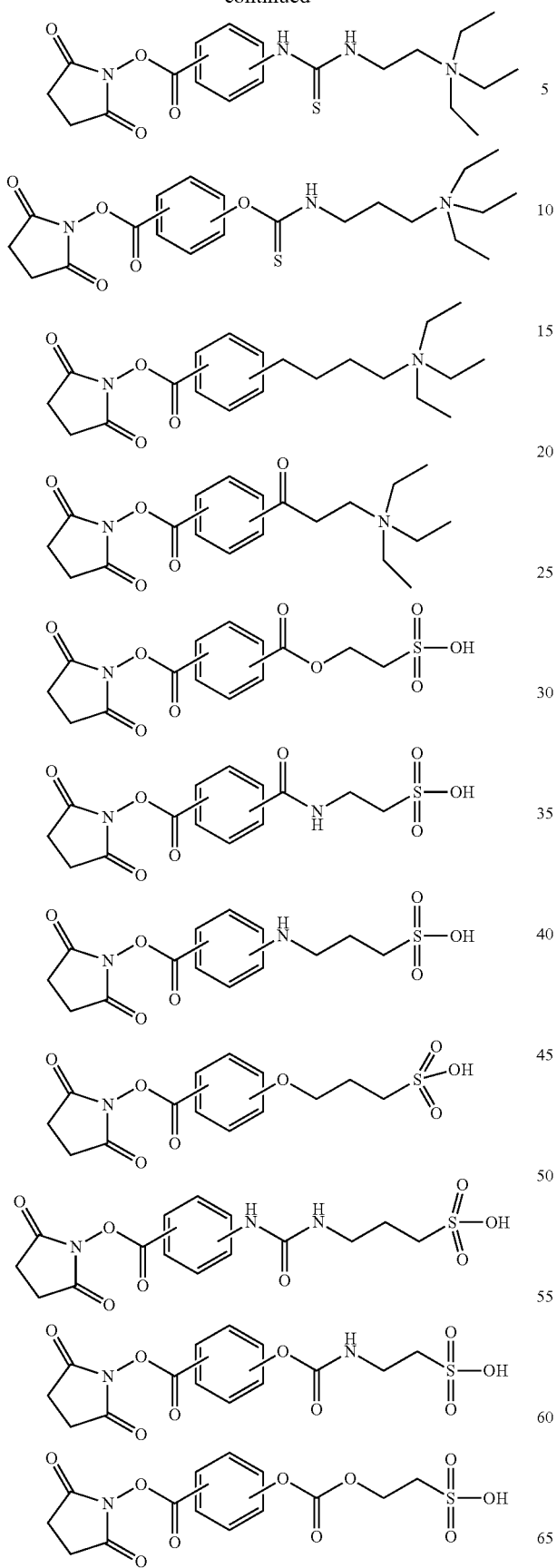
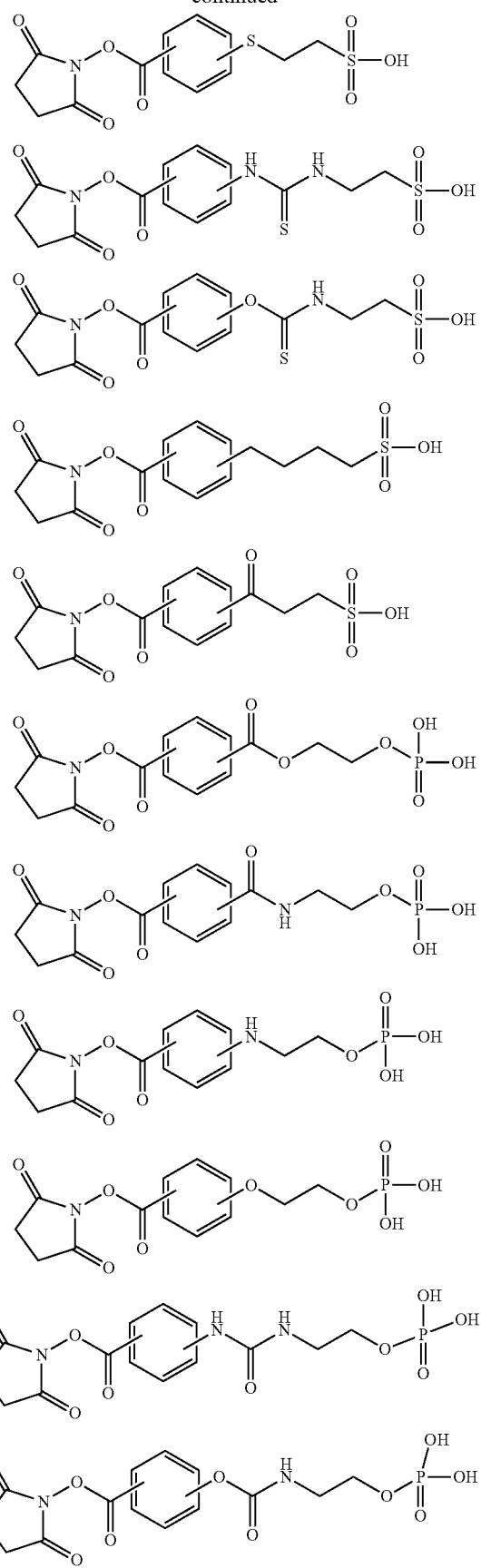

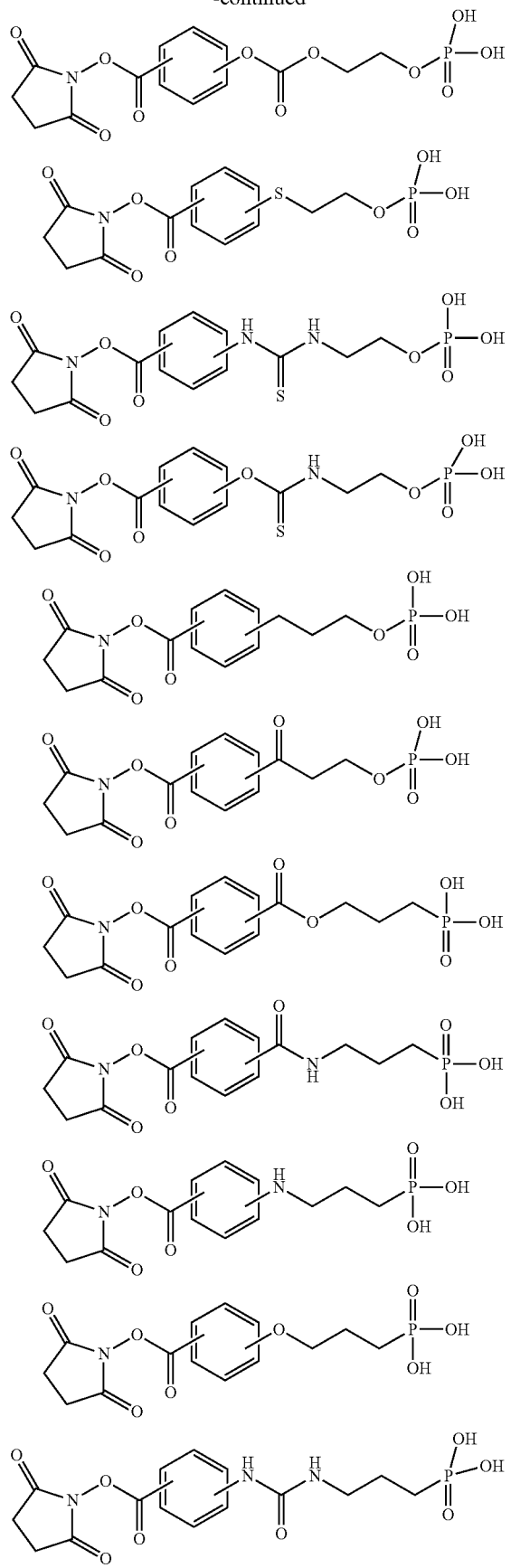
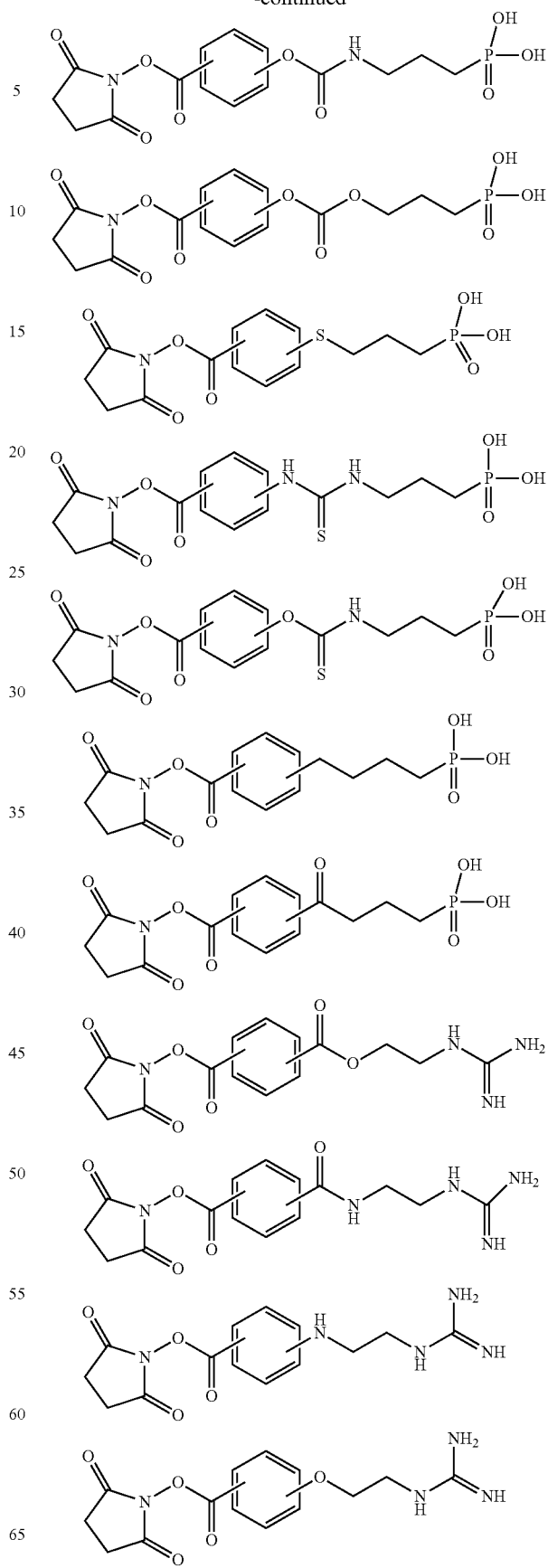

25
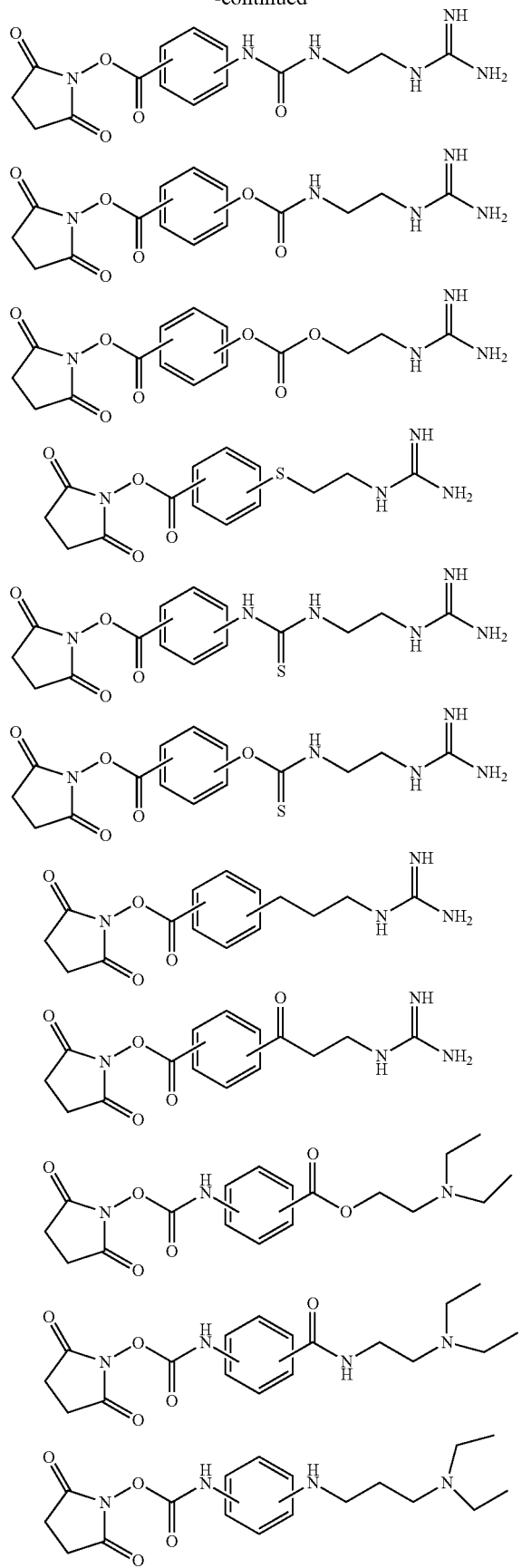
26
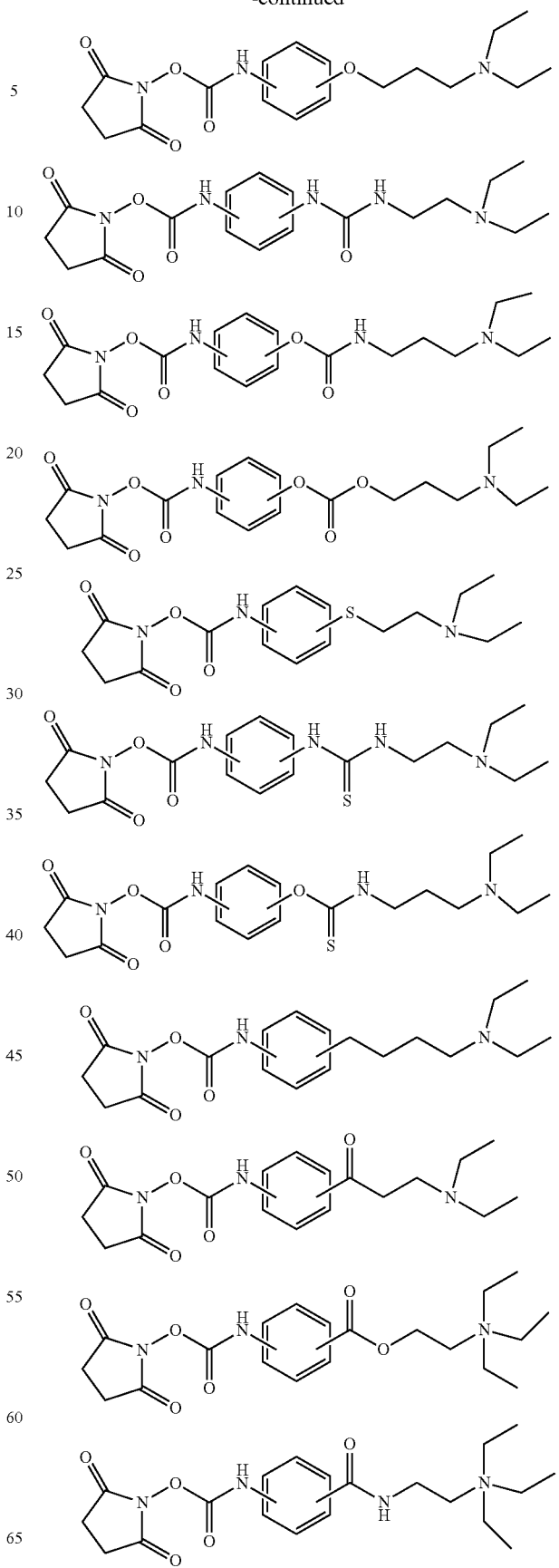

27
-continued
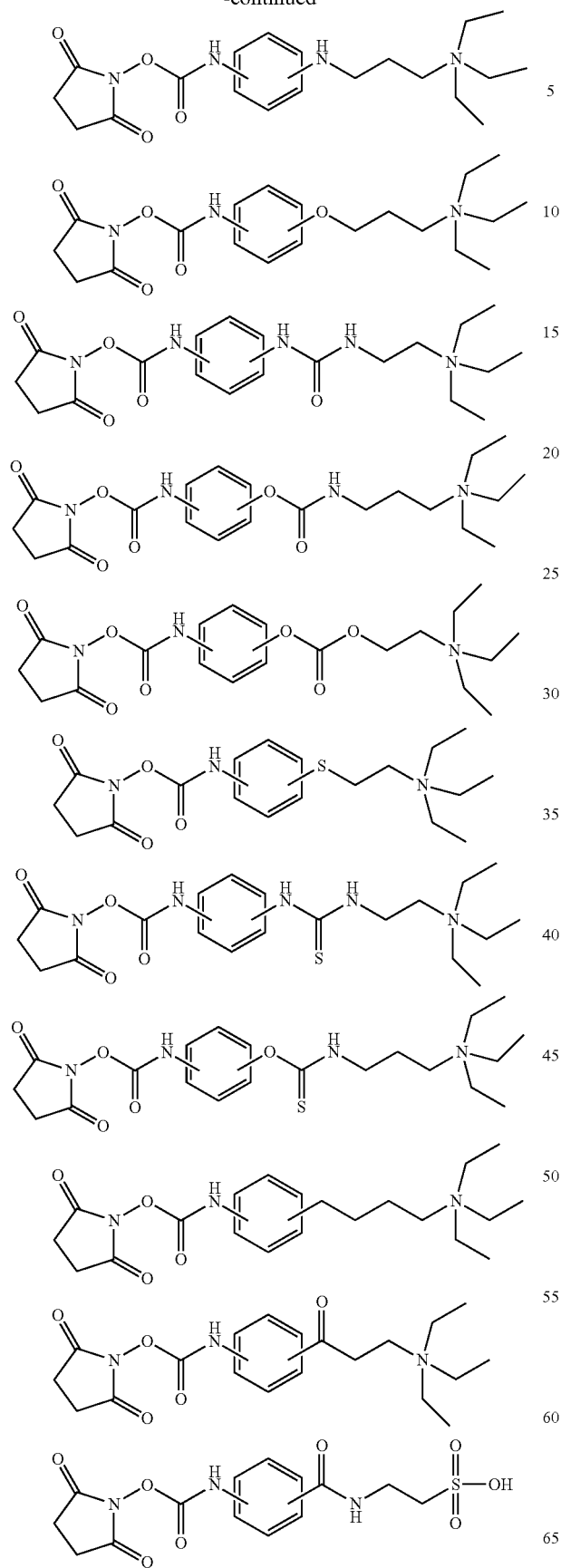
28
-continued
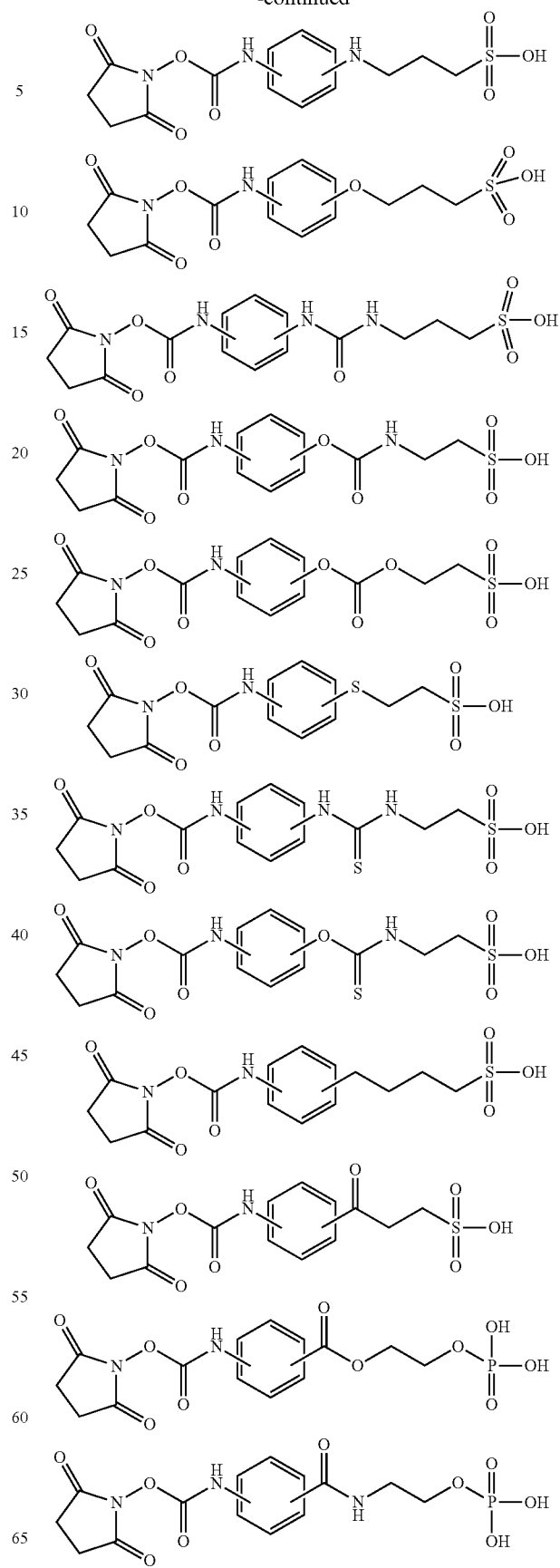

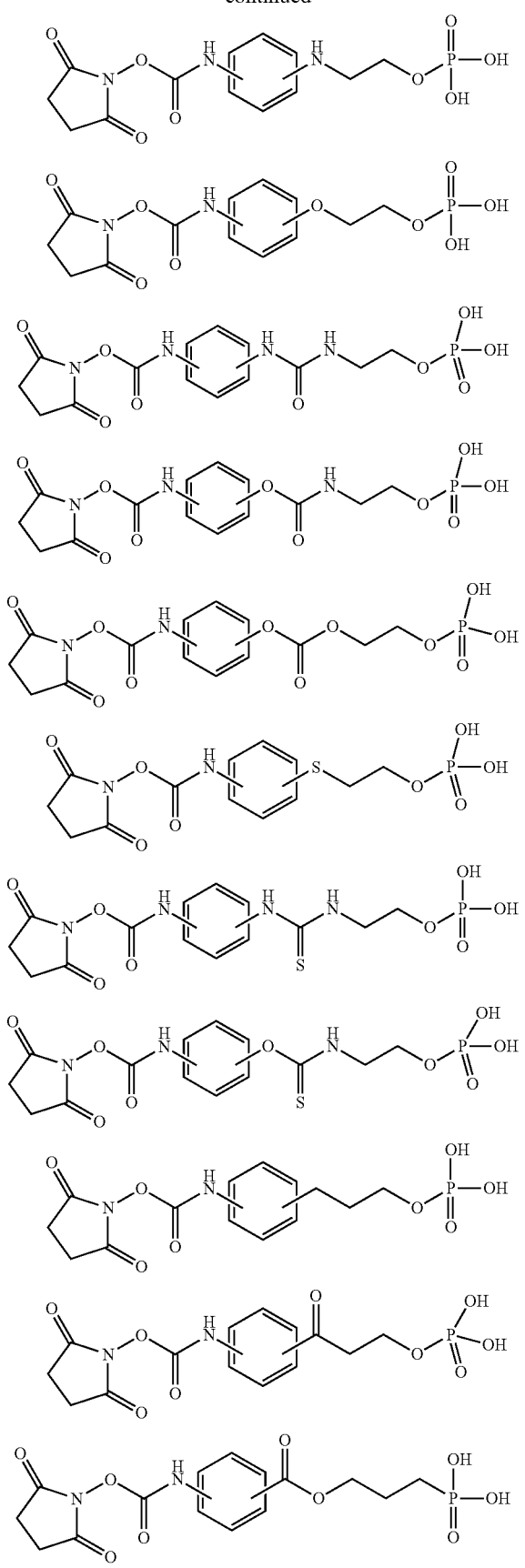
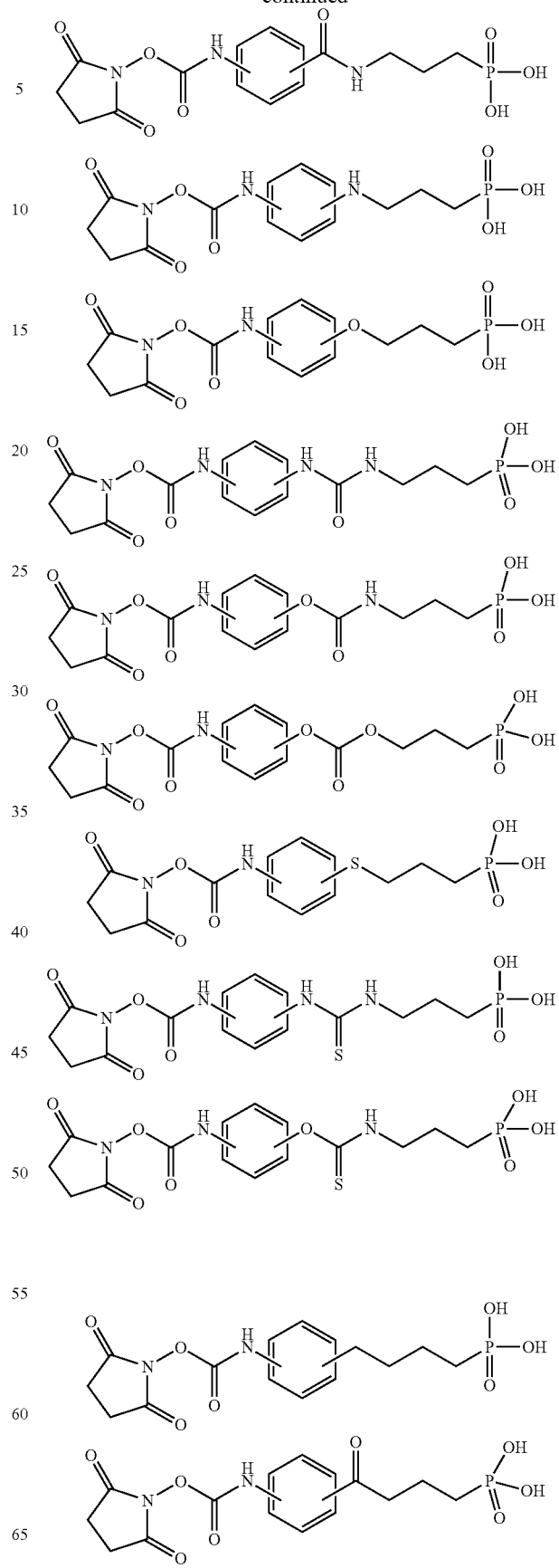

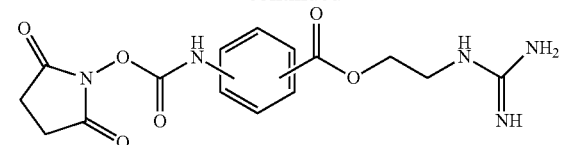
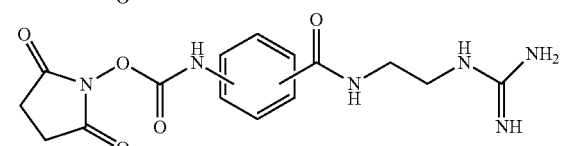
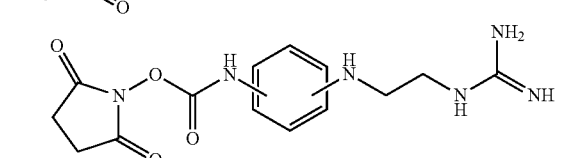

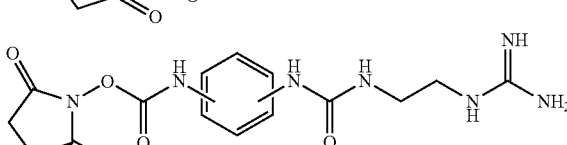
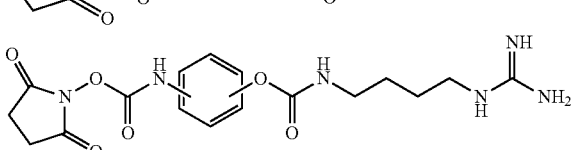
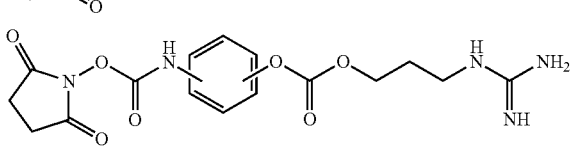
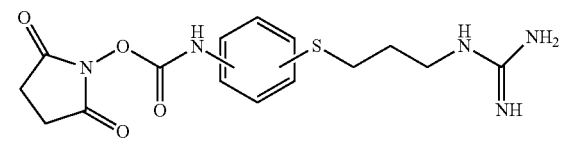
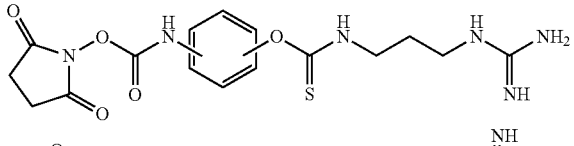
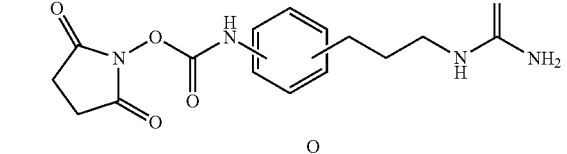
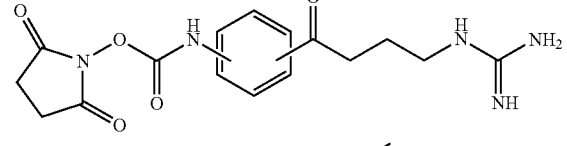
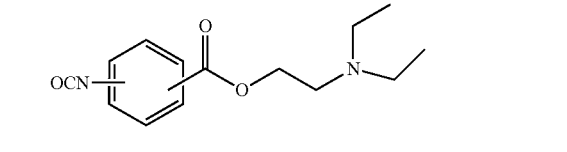
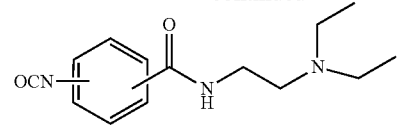
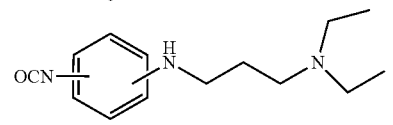
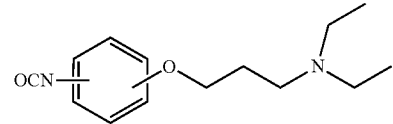
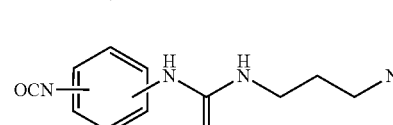
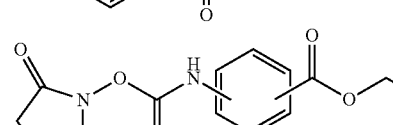
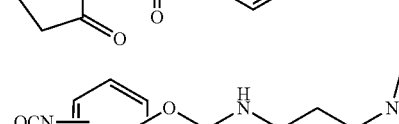
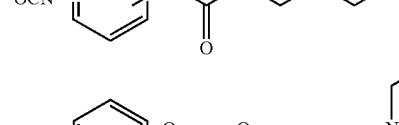
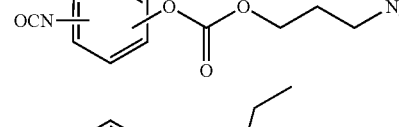
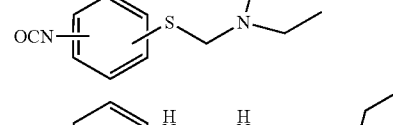
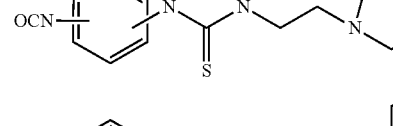
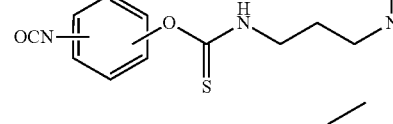
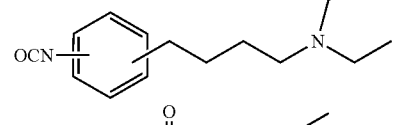
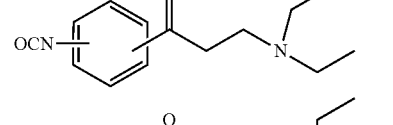

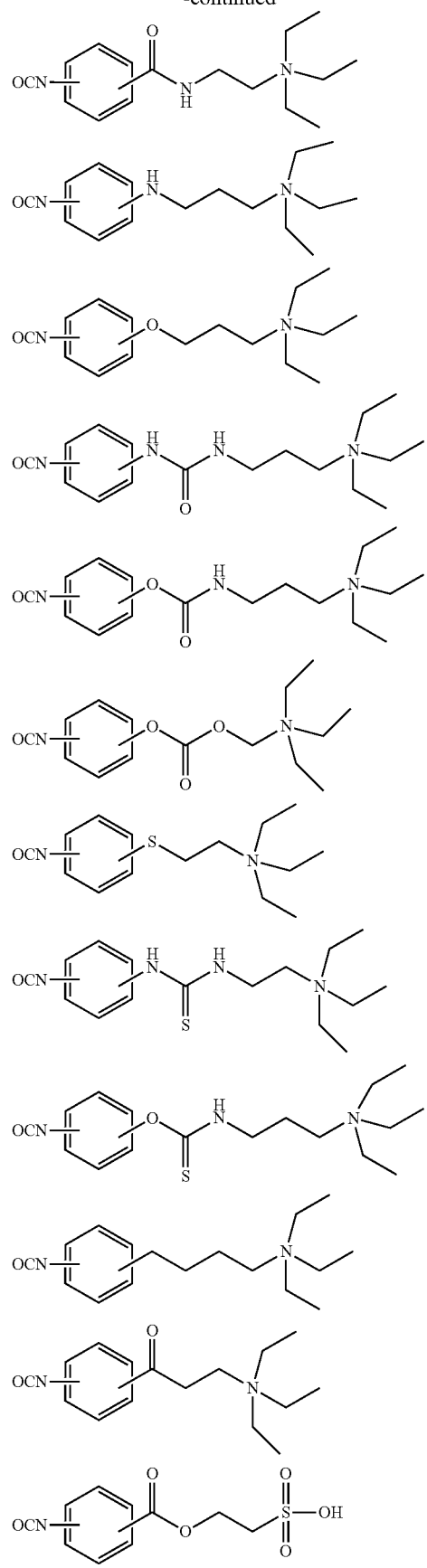
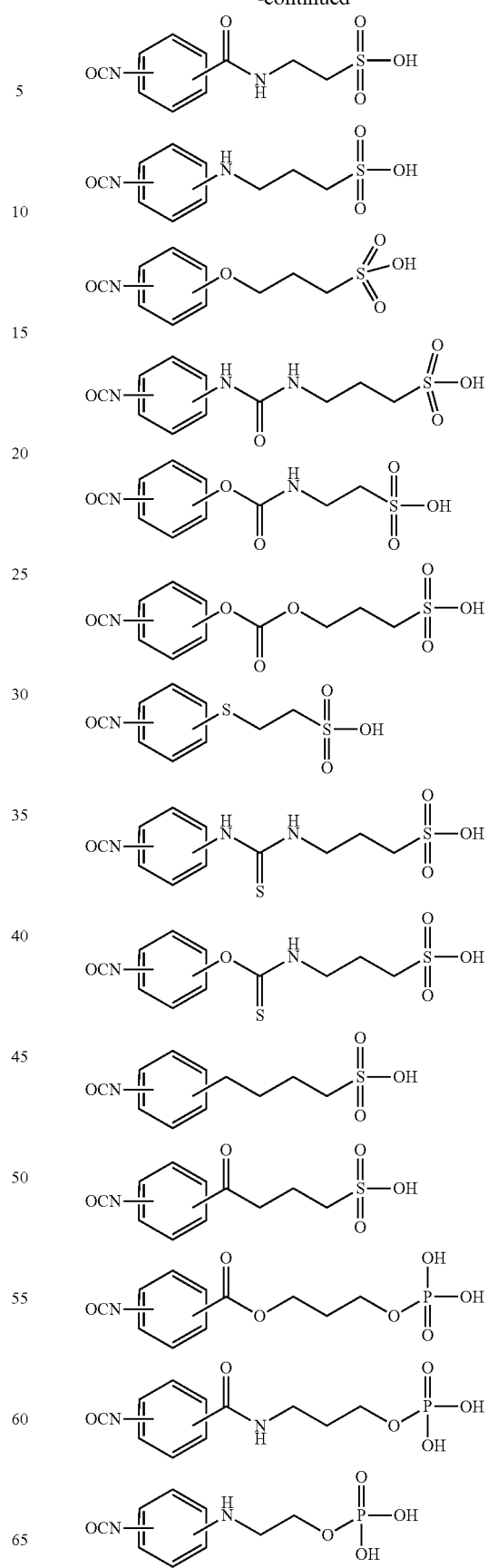

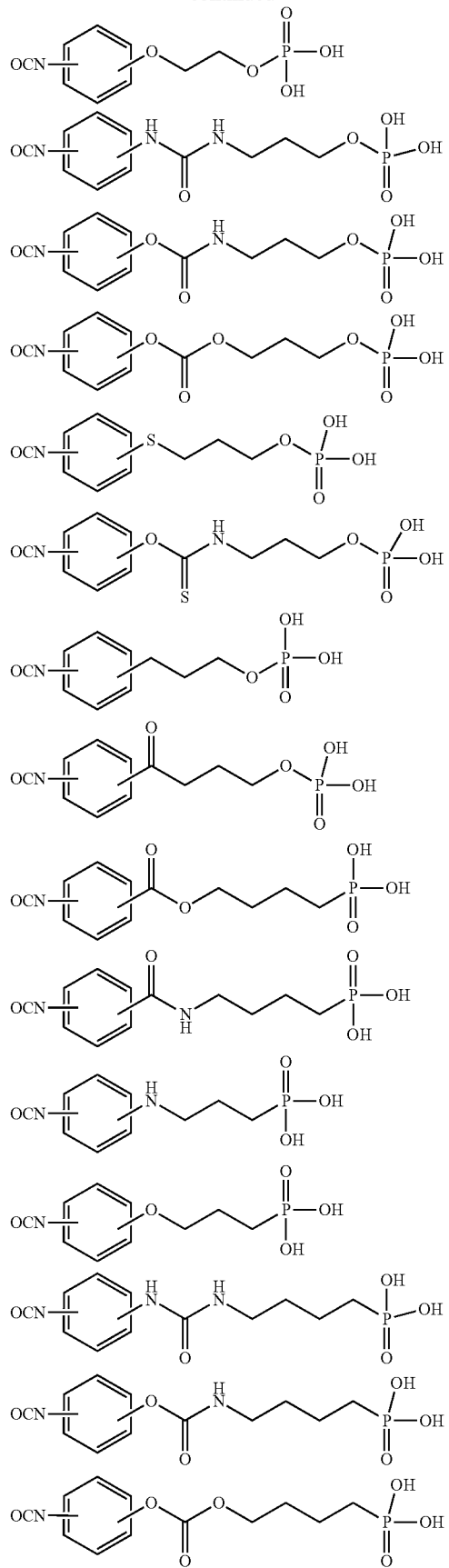
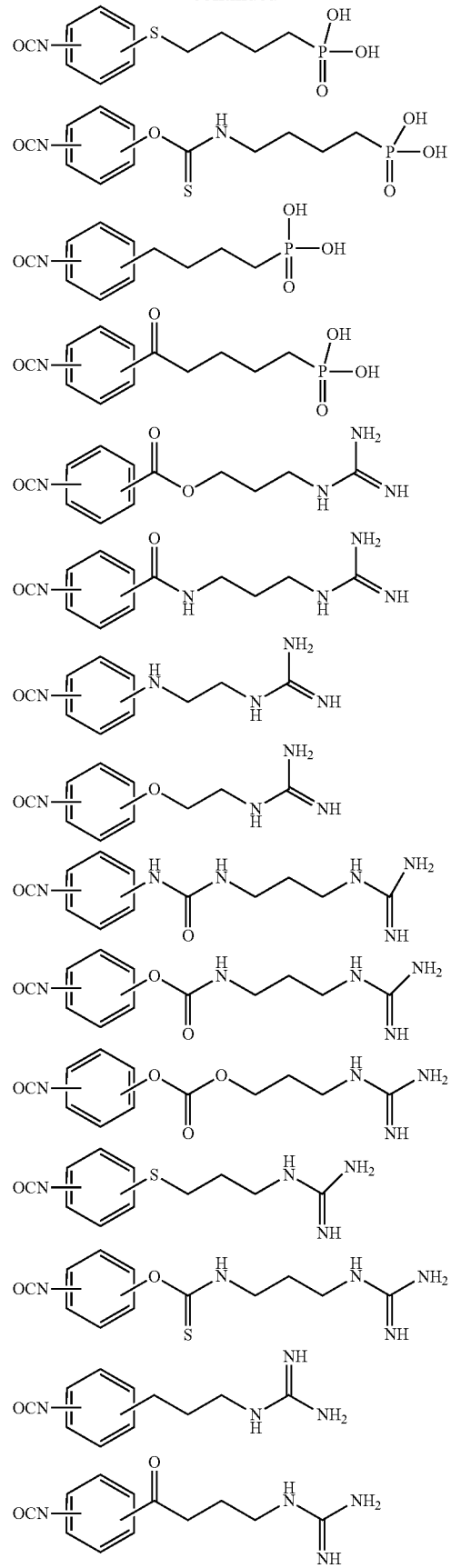

-continued
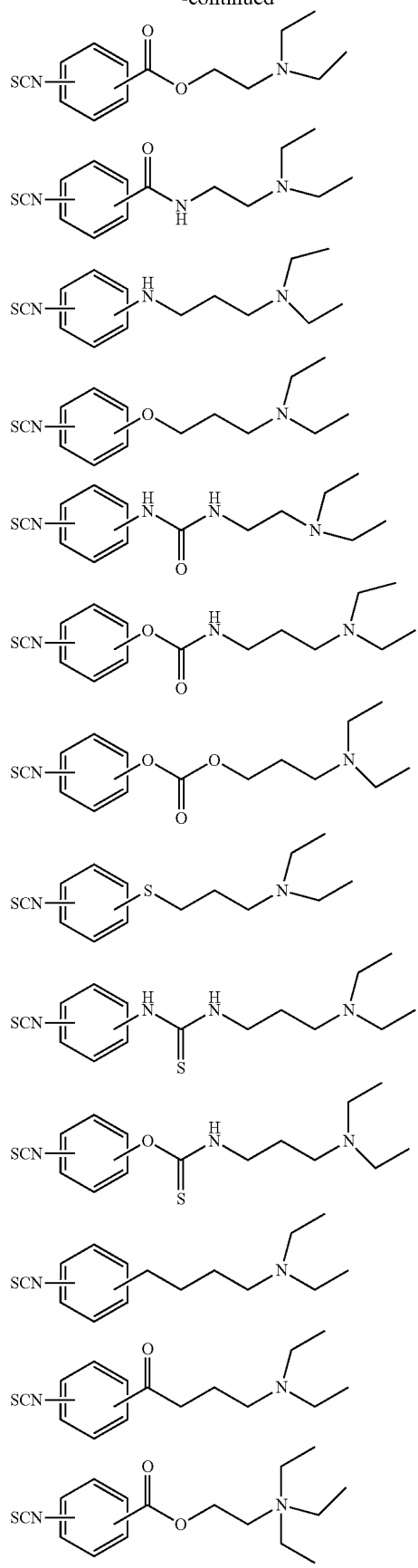
-continued
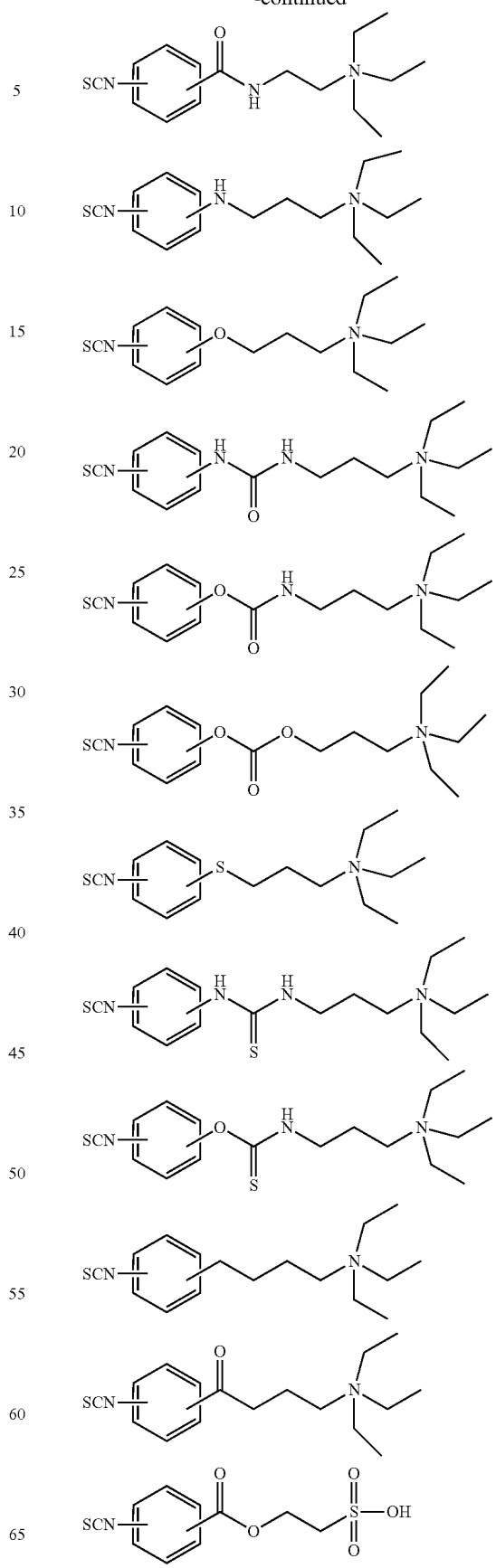

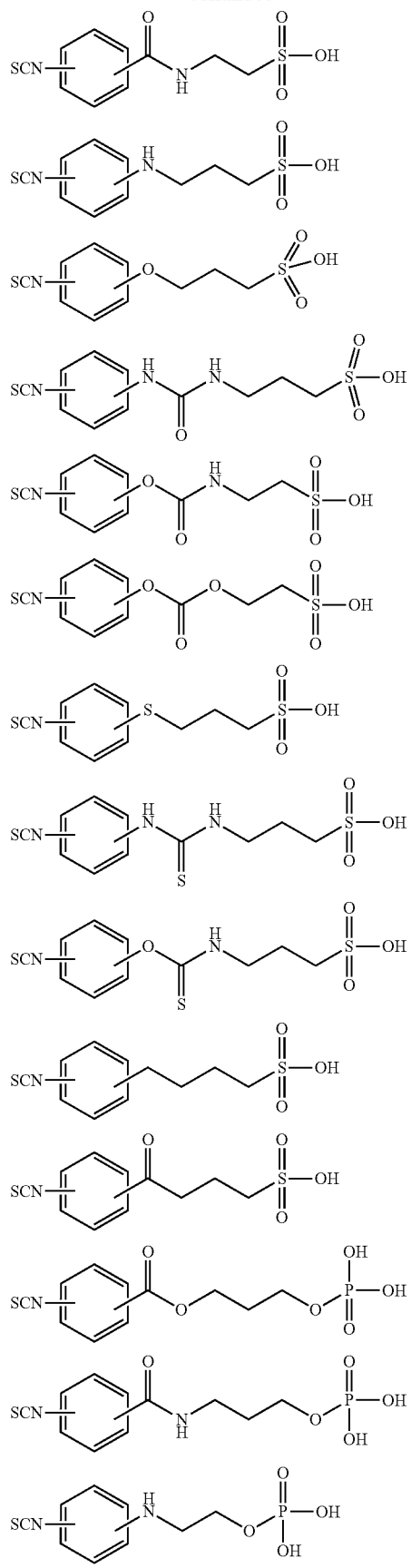
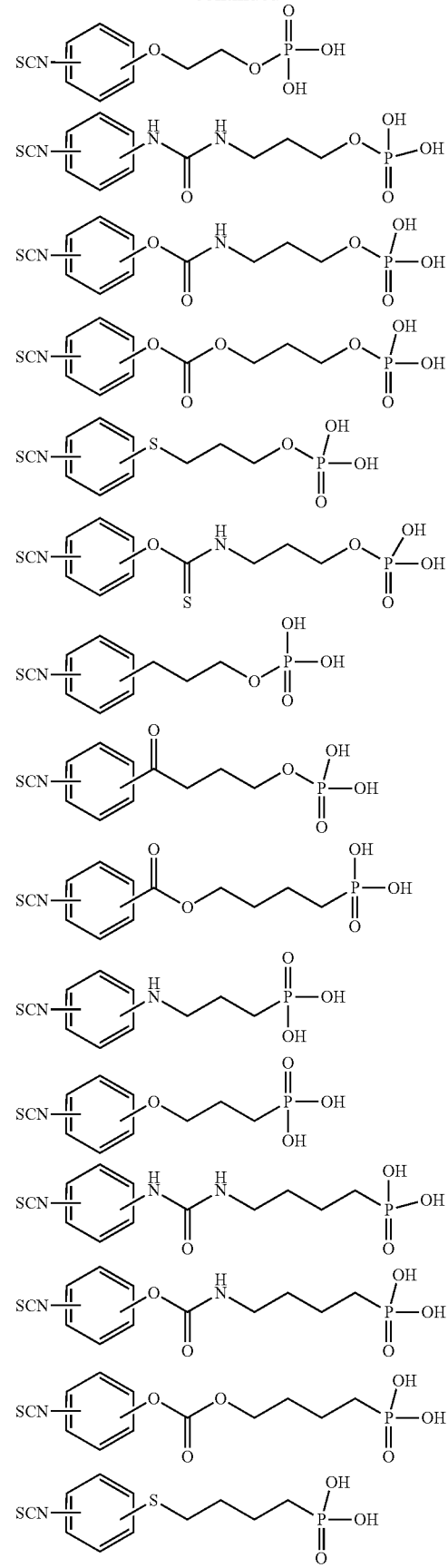

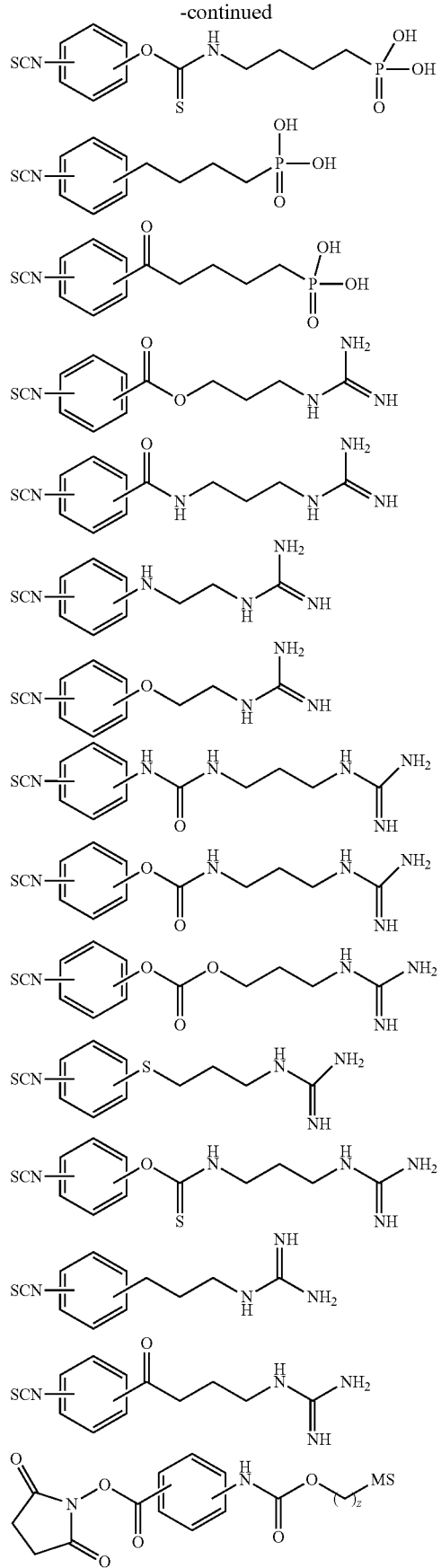
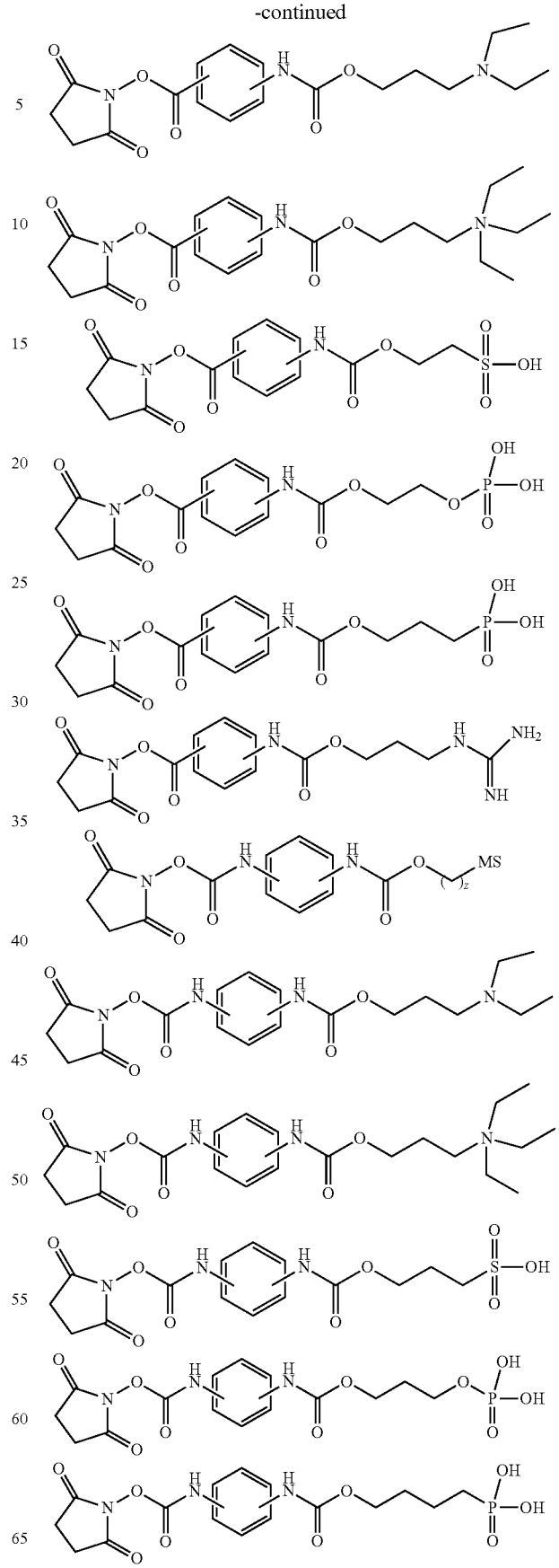

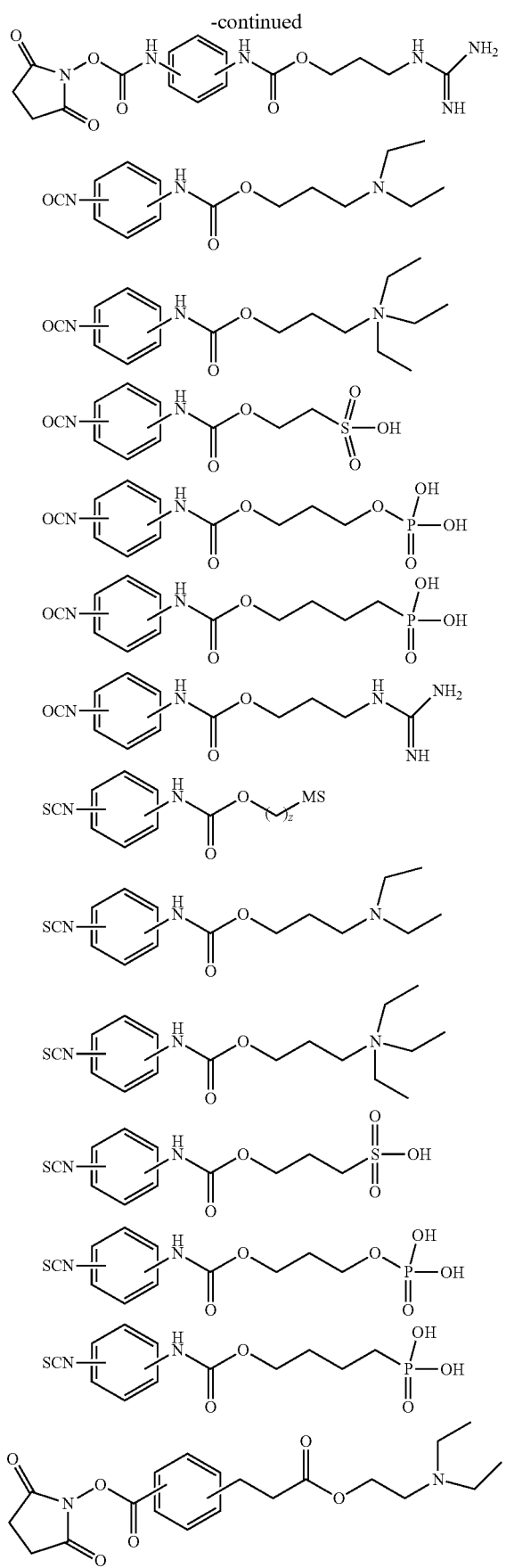

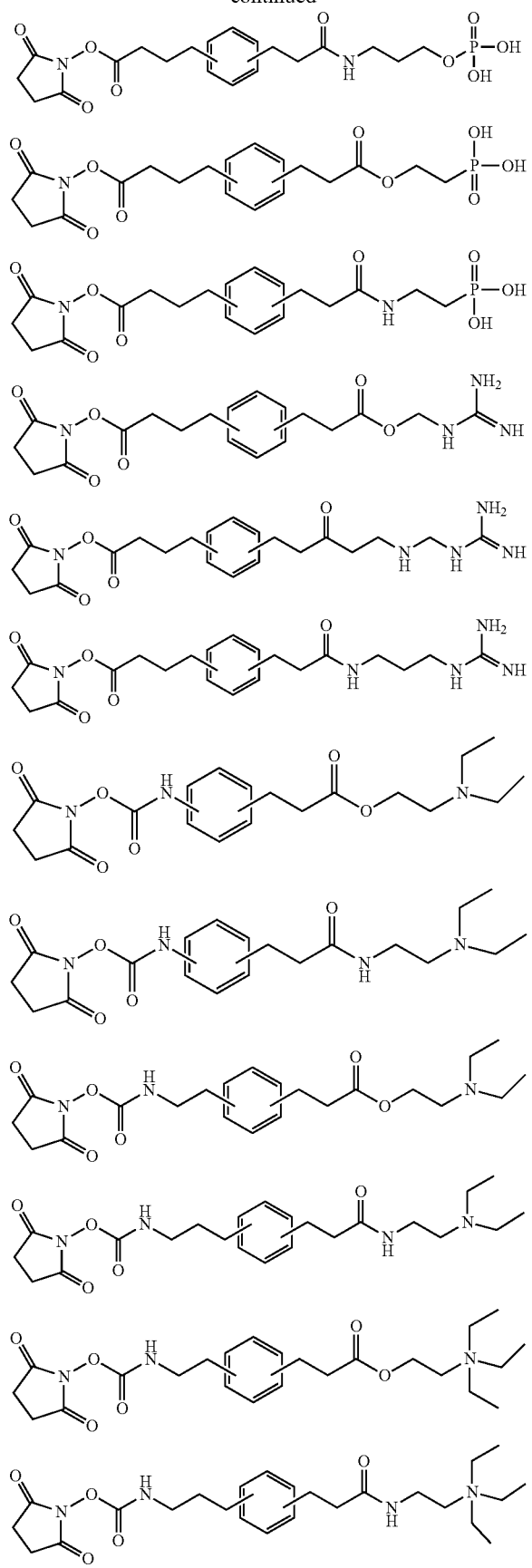
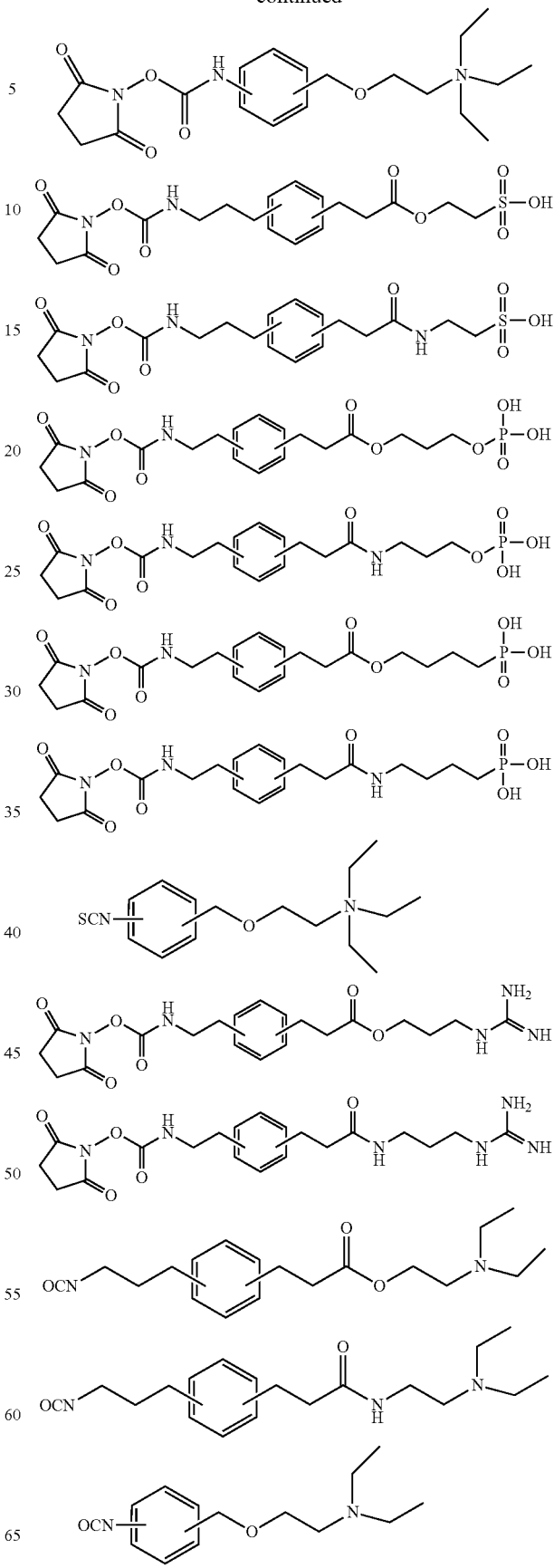

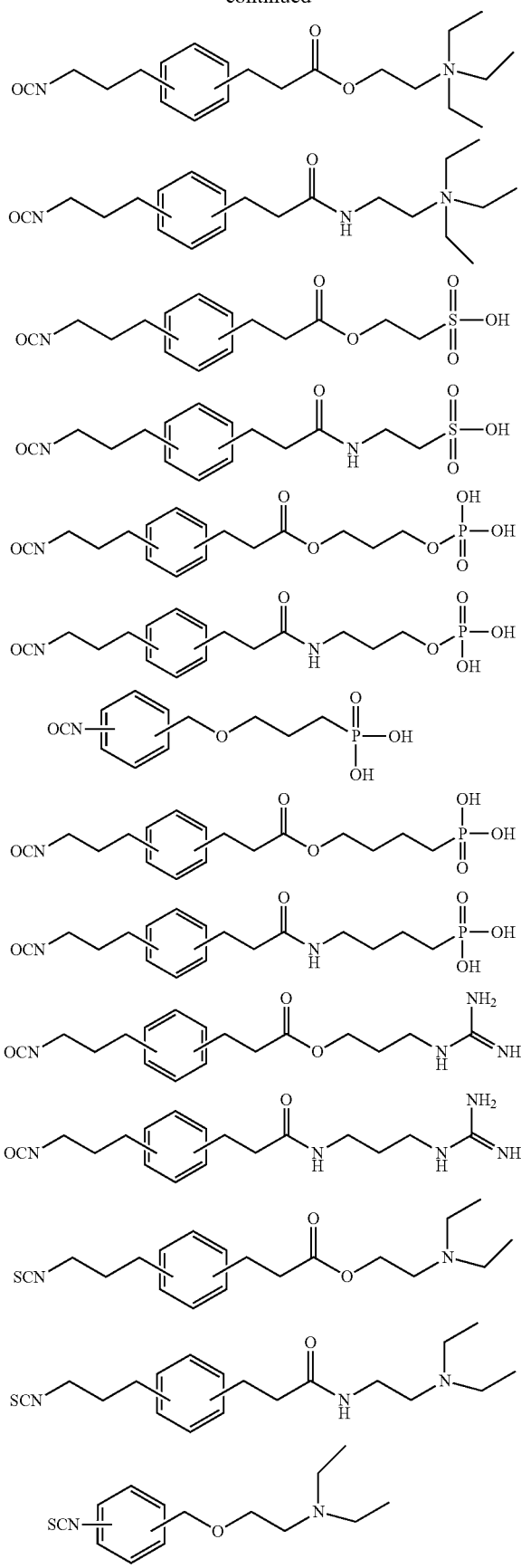
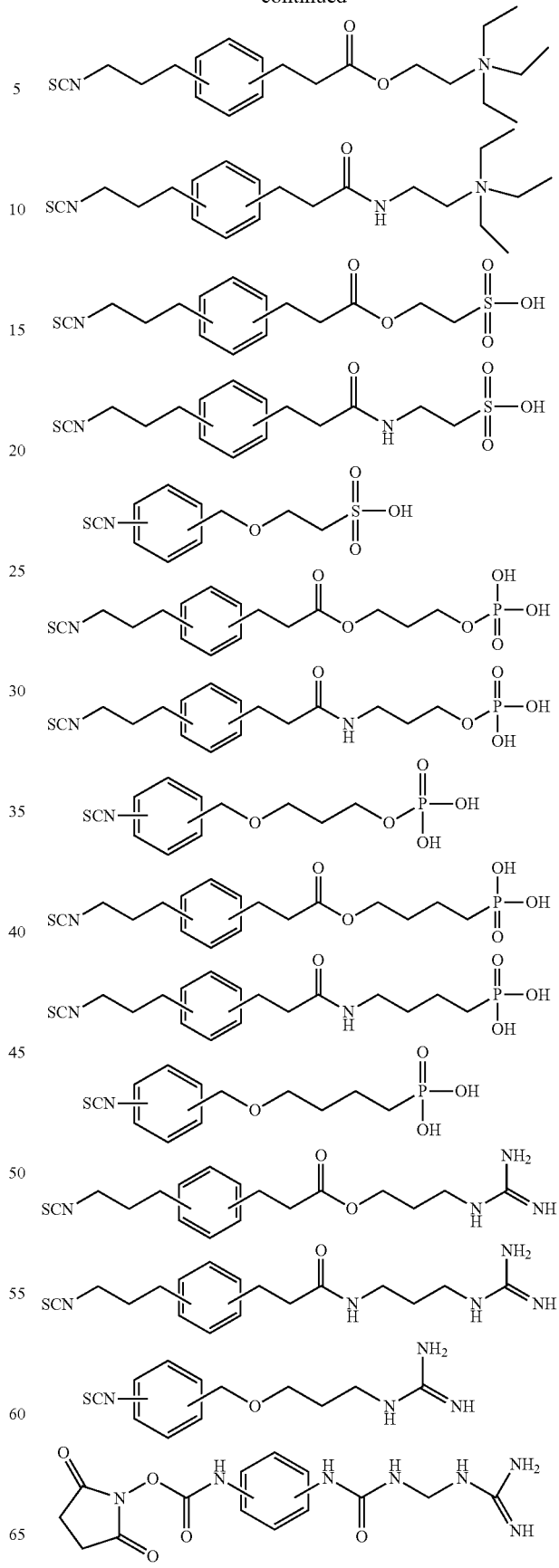

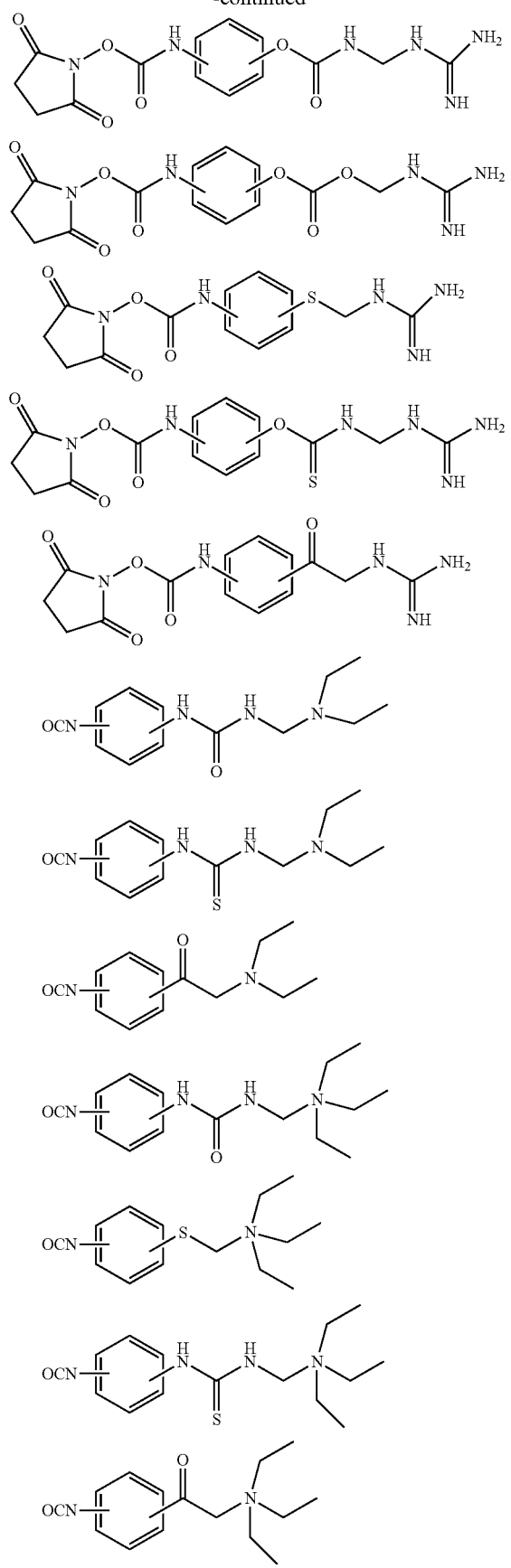
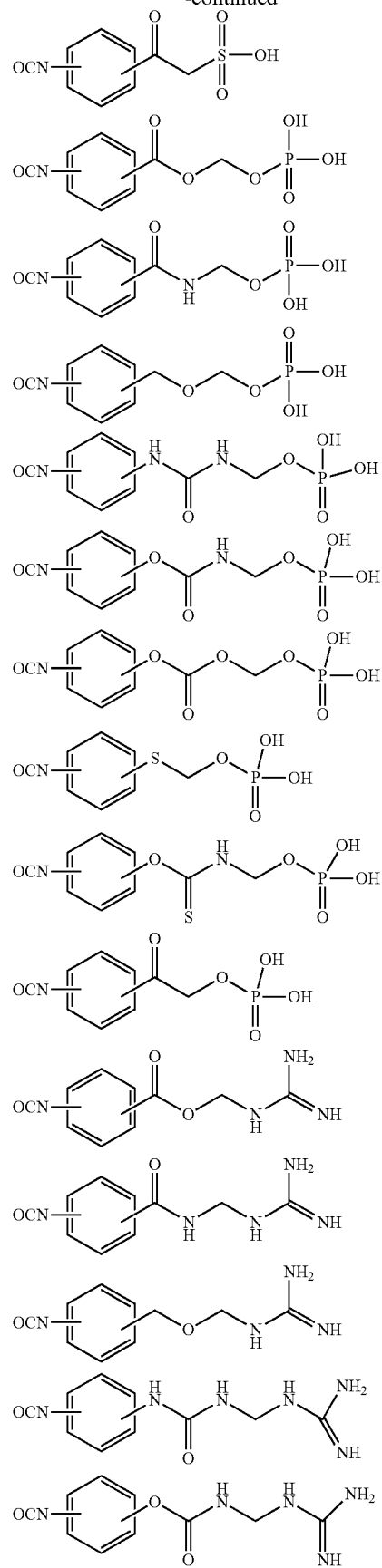

51
-continued

52
-continued

53
-continued
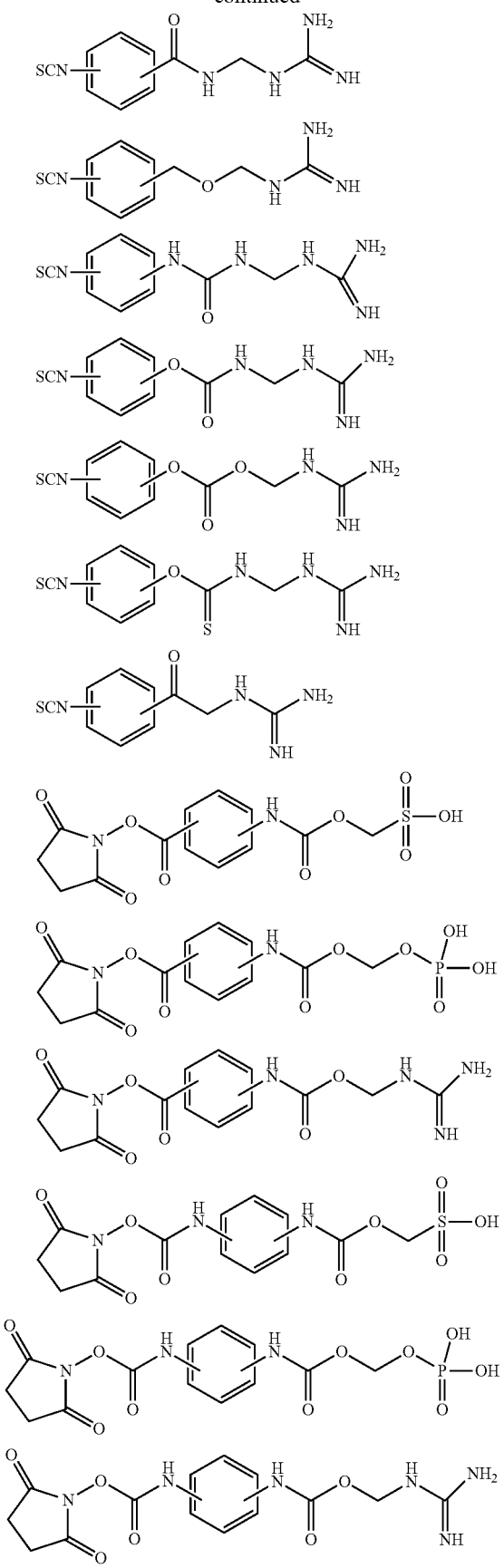
54
-continued
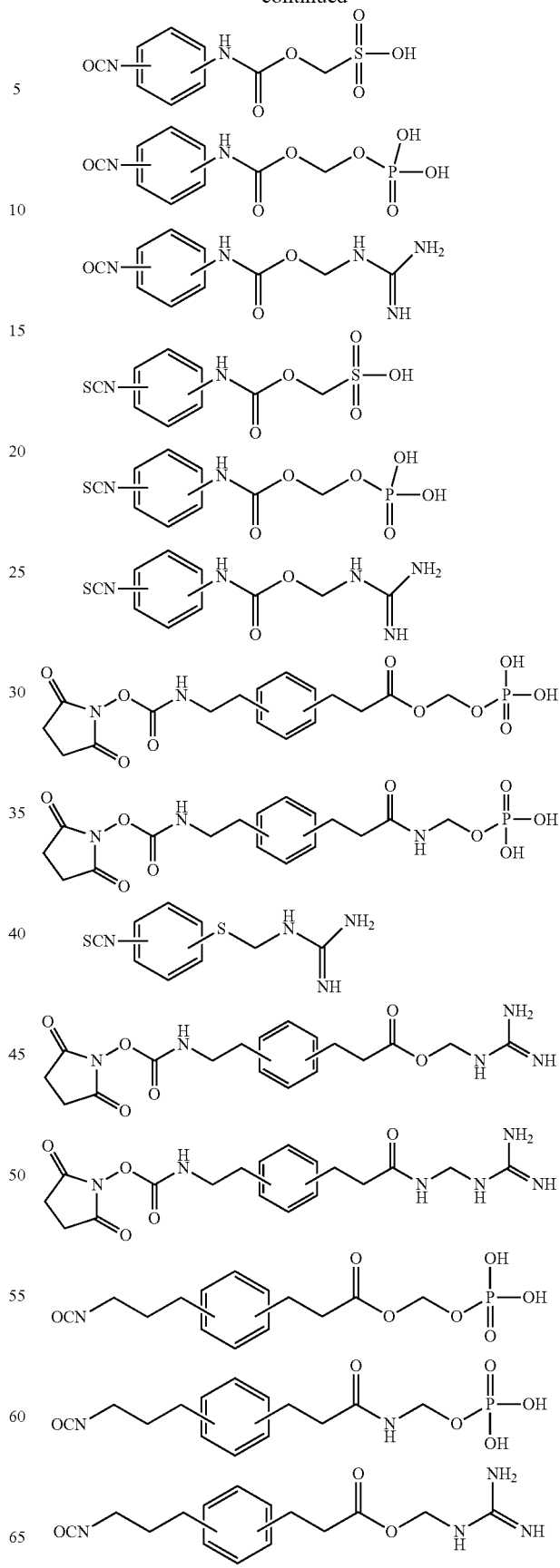

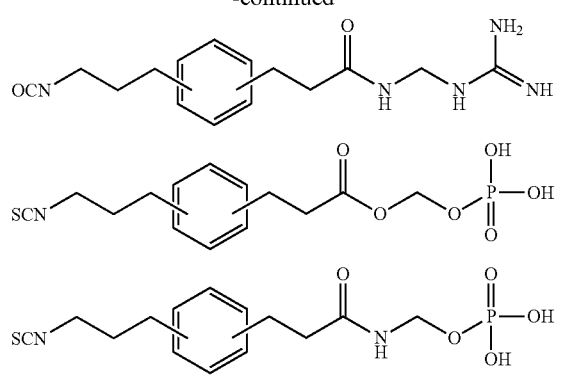
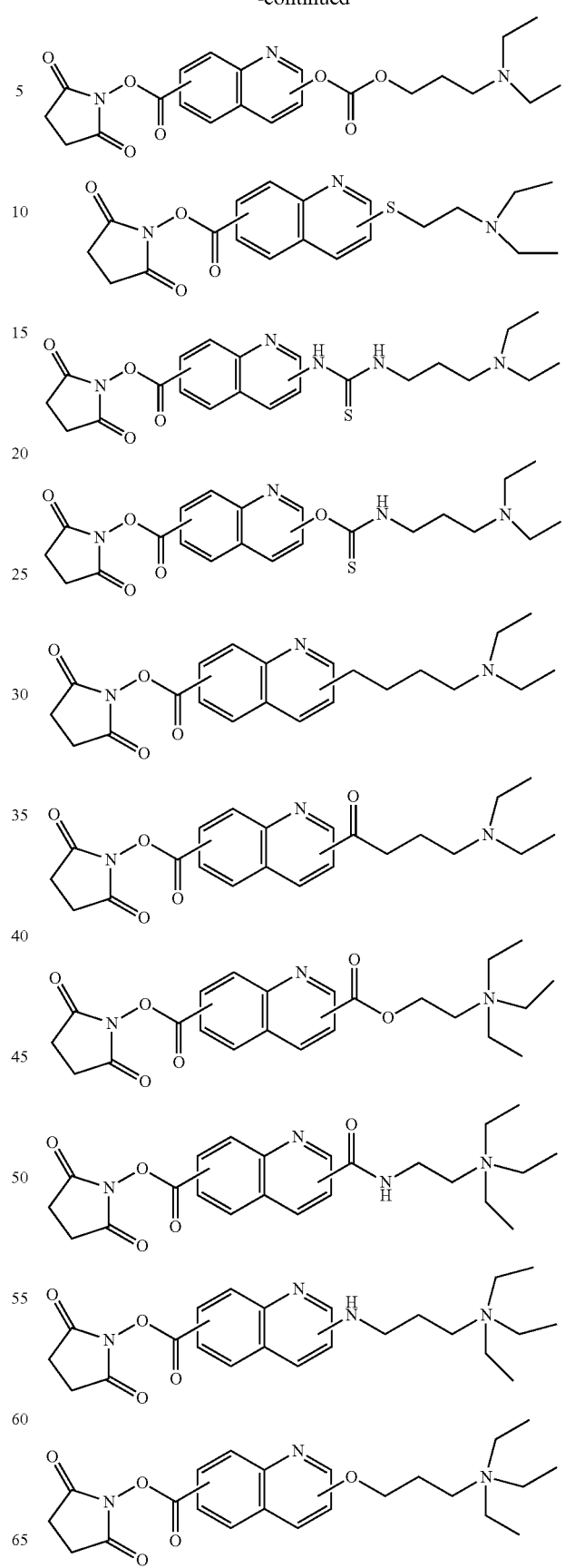

57
-continued
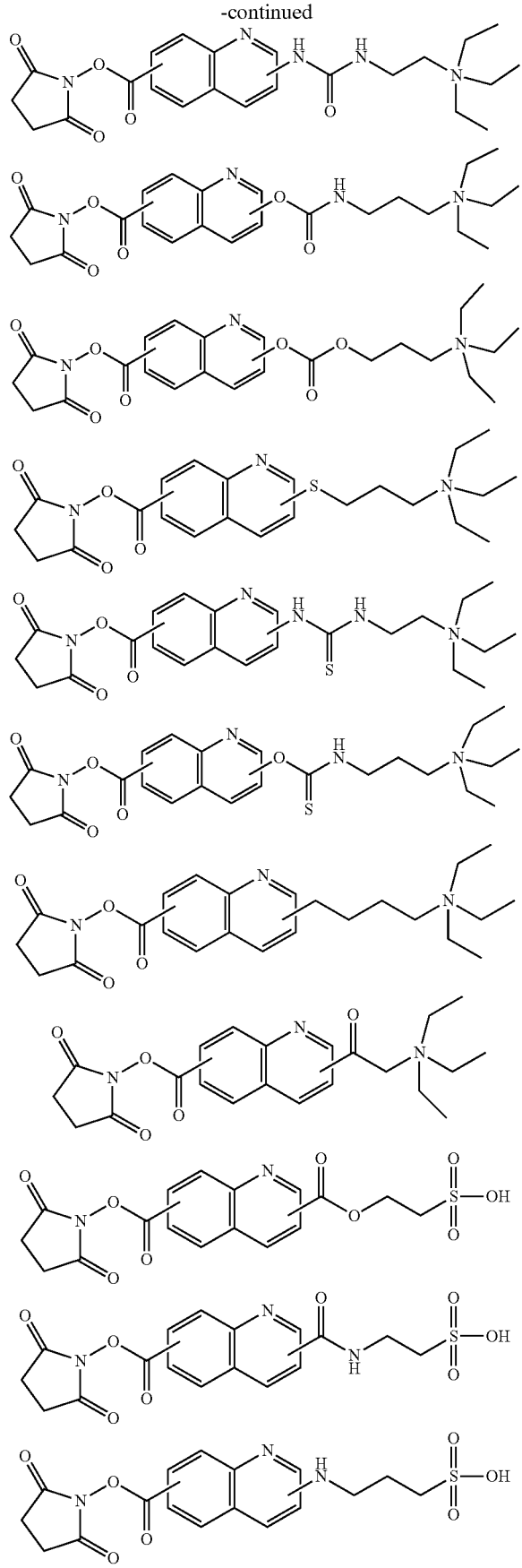
58
-continued
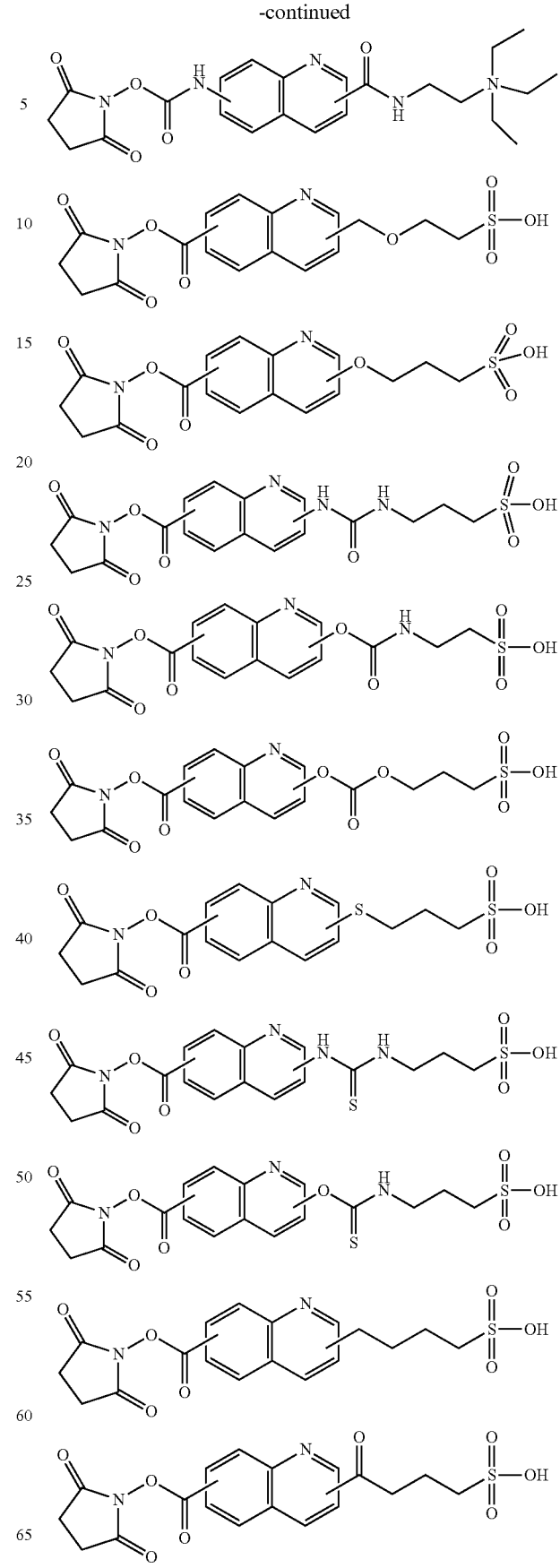

59
-continued
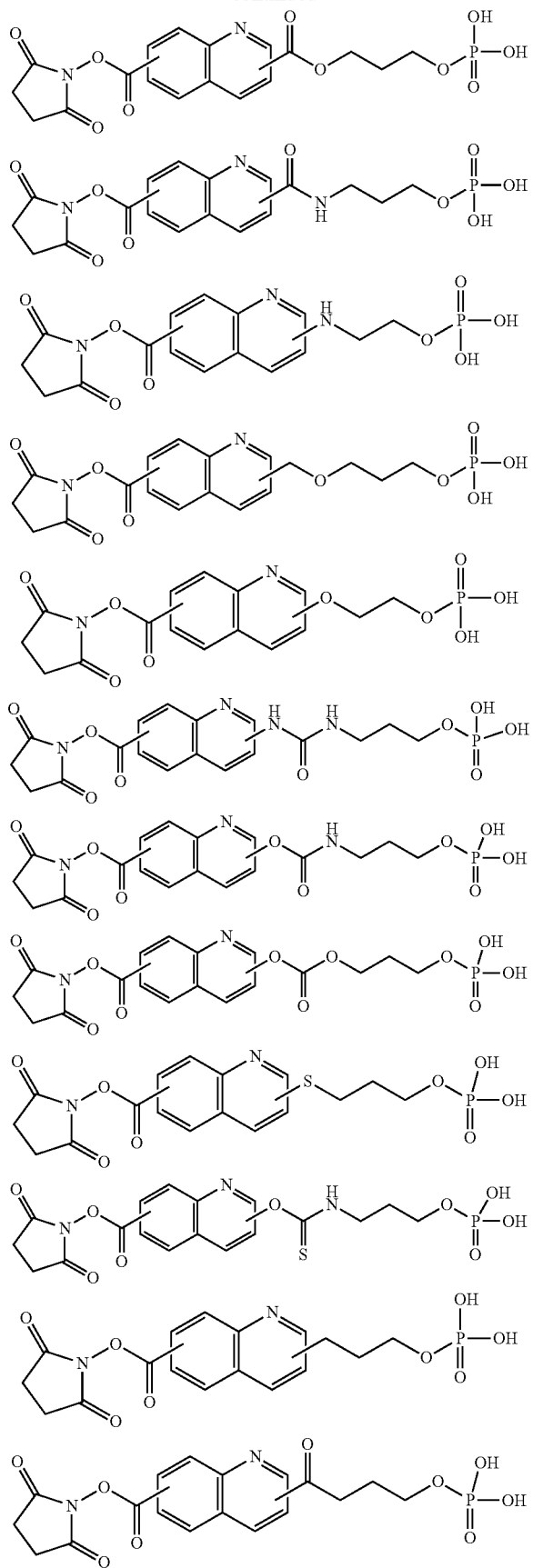
60
-continued
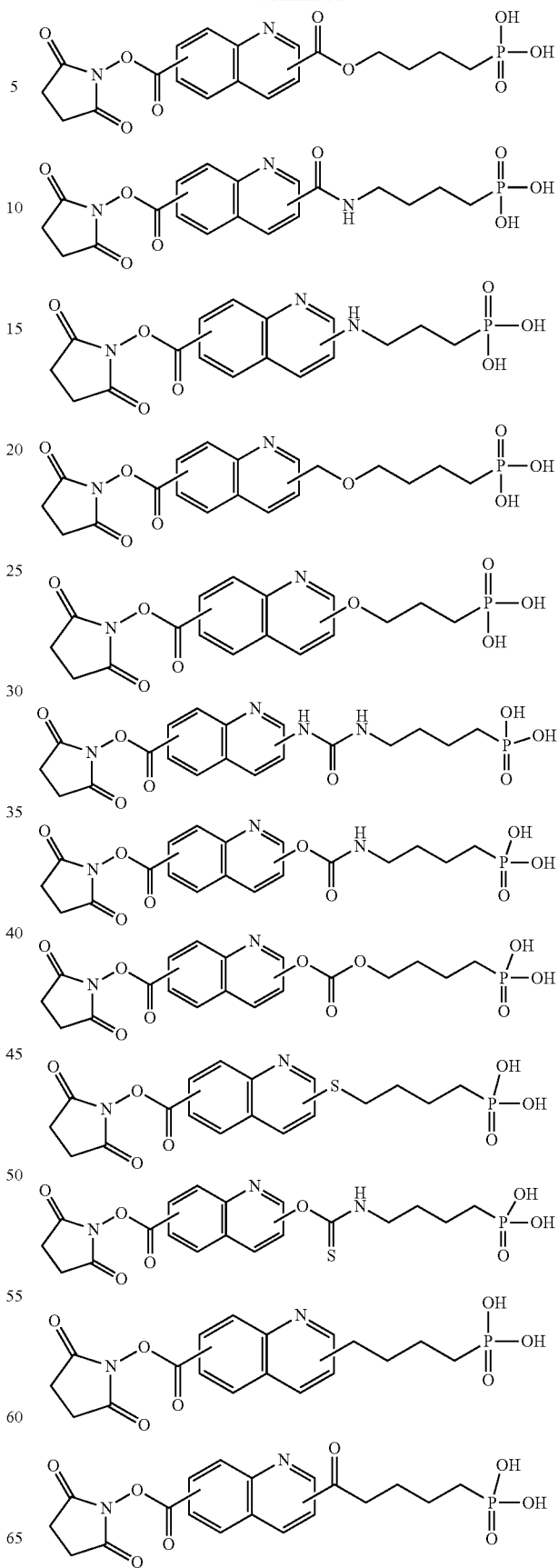

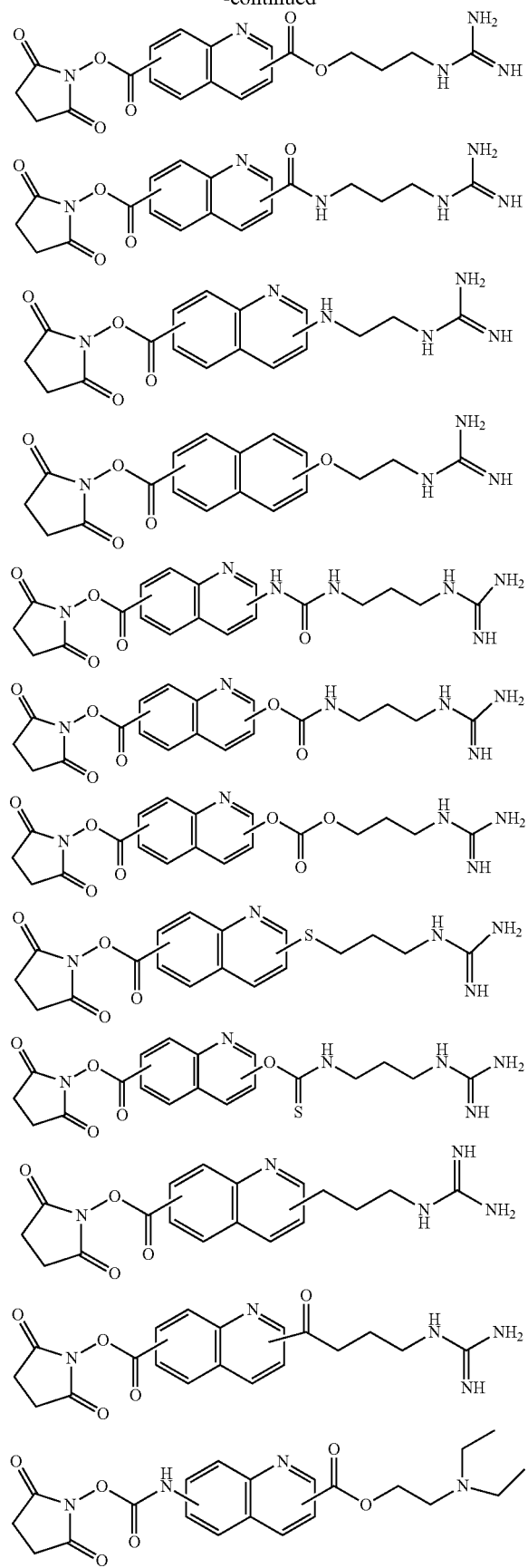
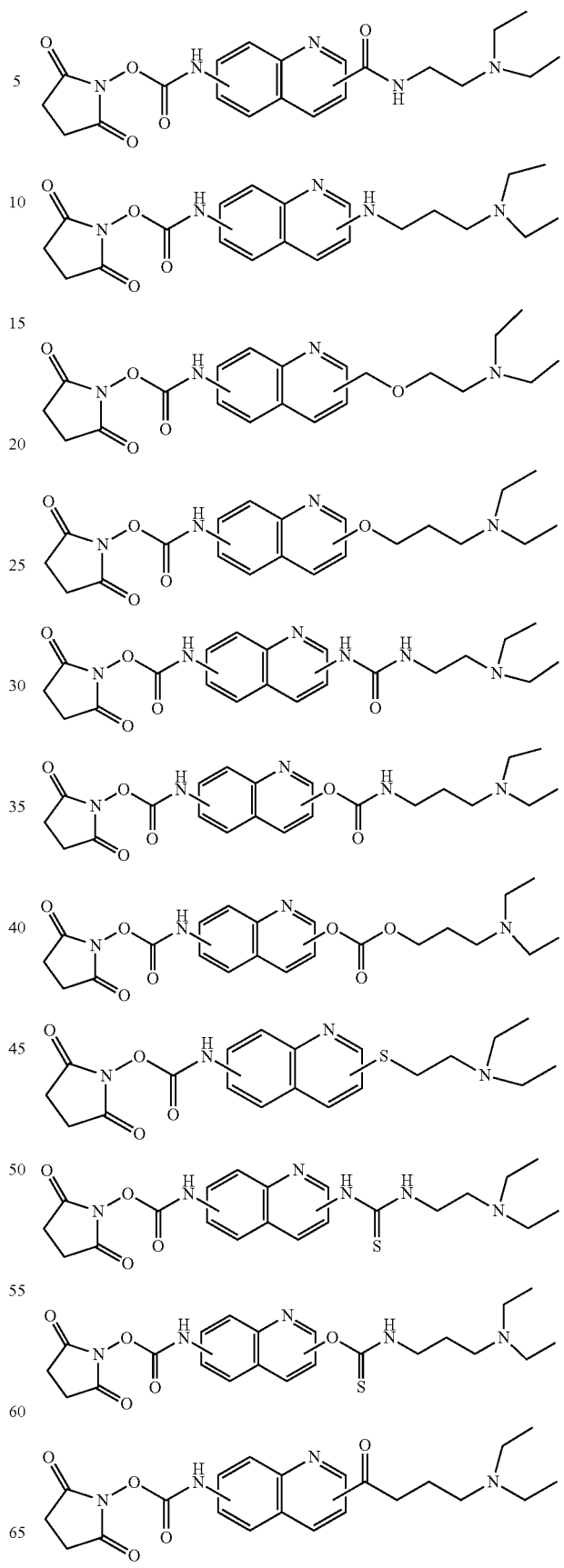

63
-continued
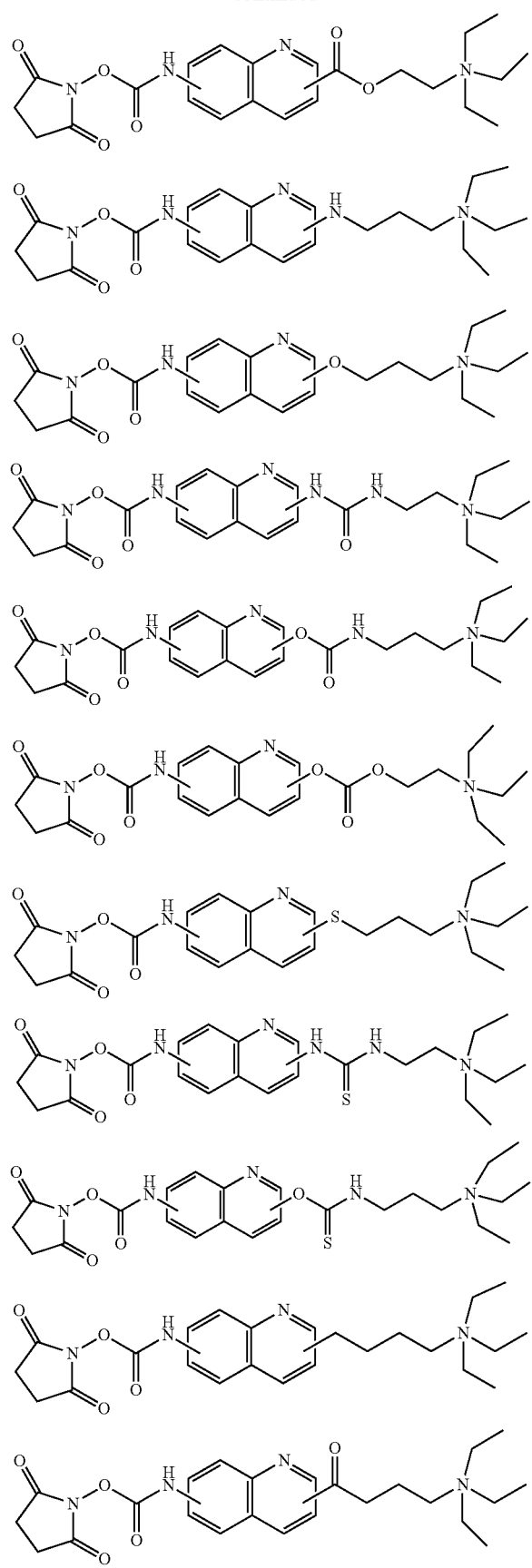
64
-continued
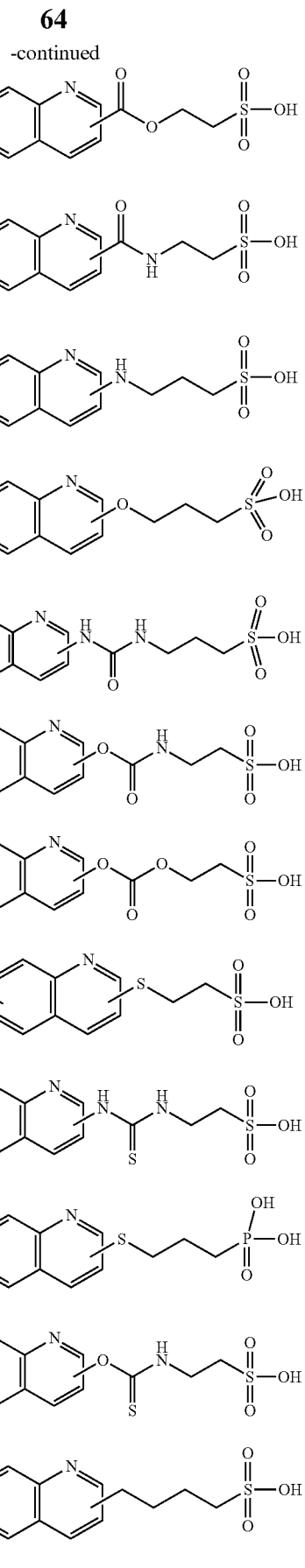

65
-continued
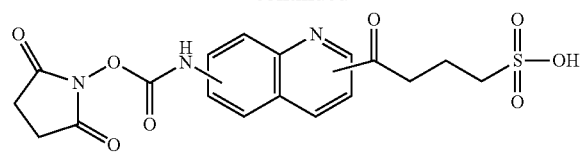
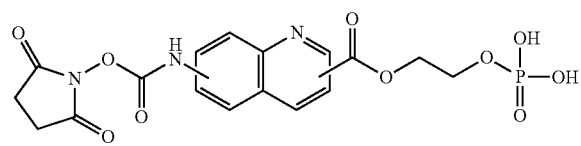
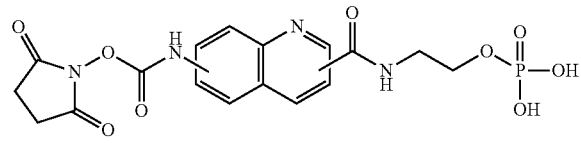
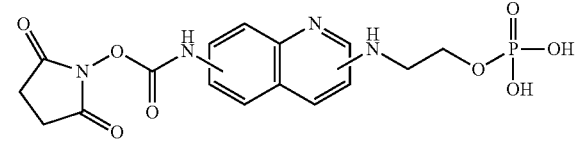
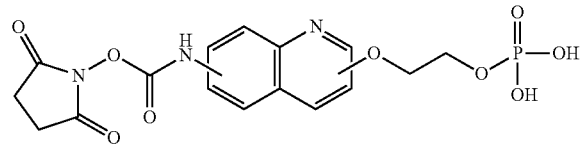
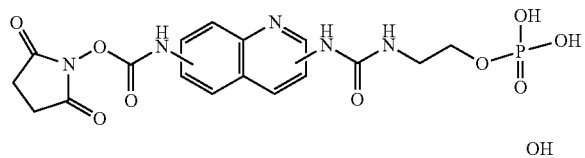
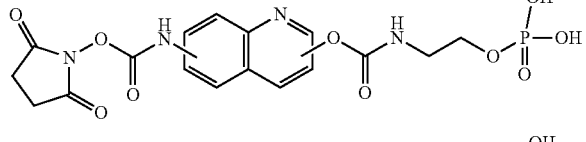
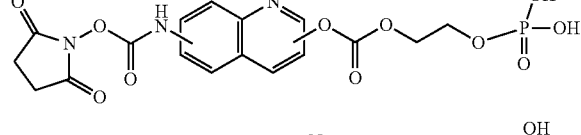
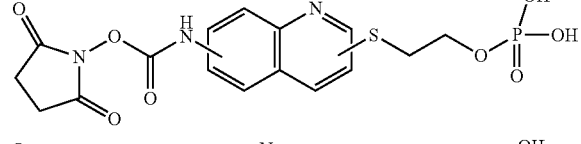
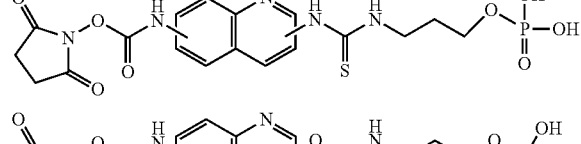
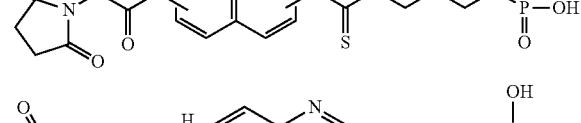
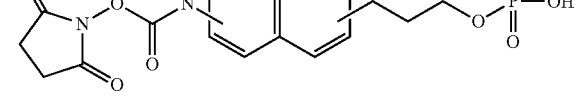
66
-continued
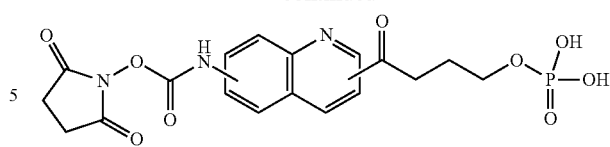
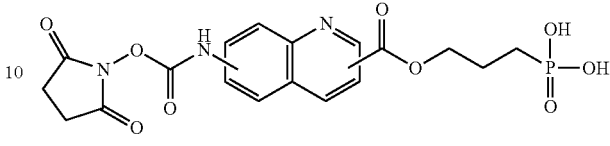
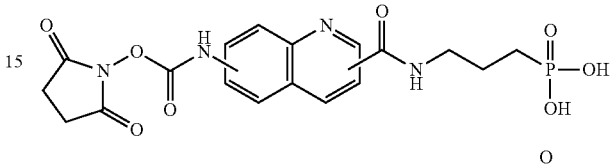
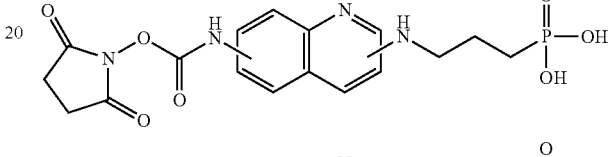
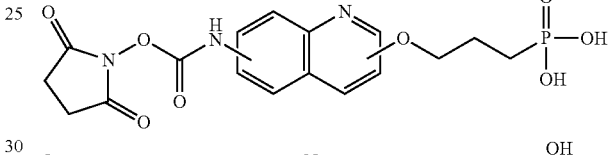
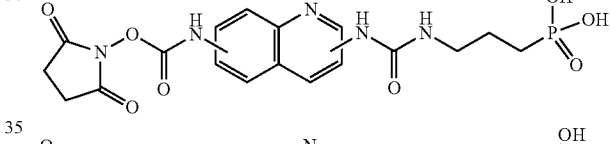
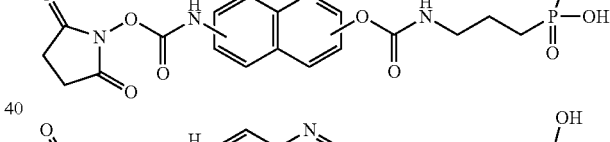
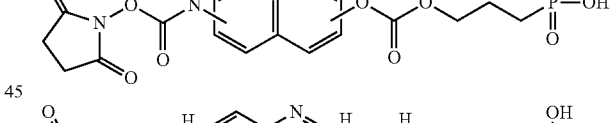
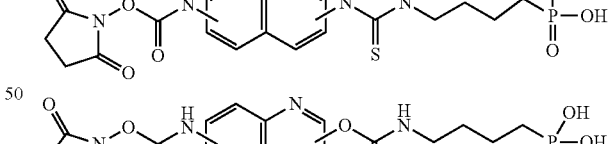
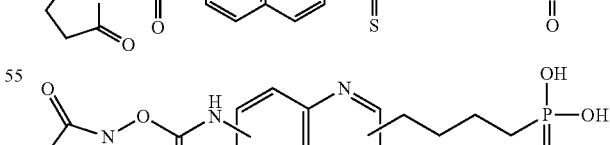
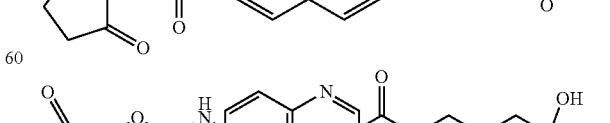
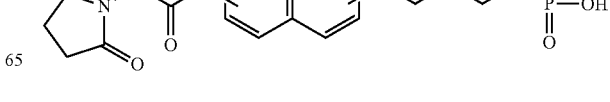

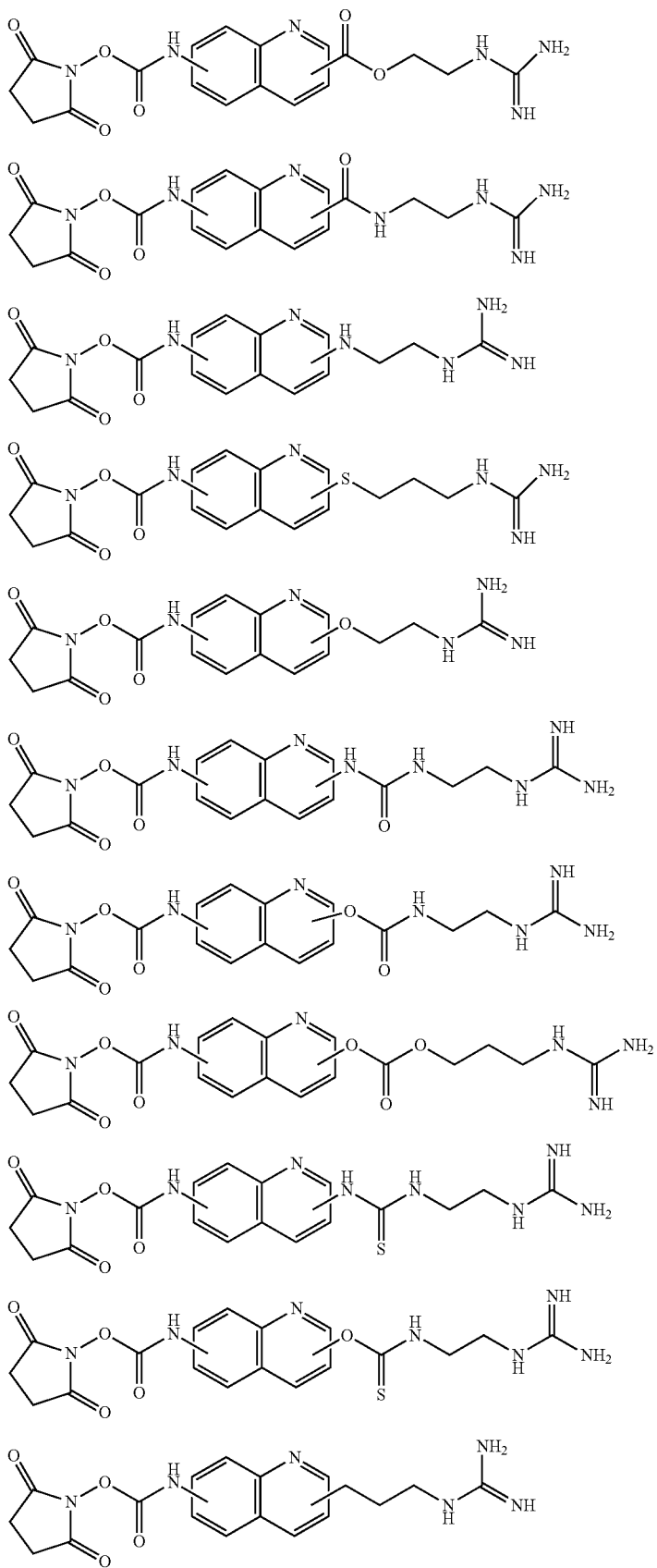

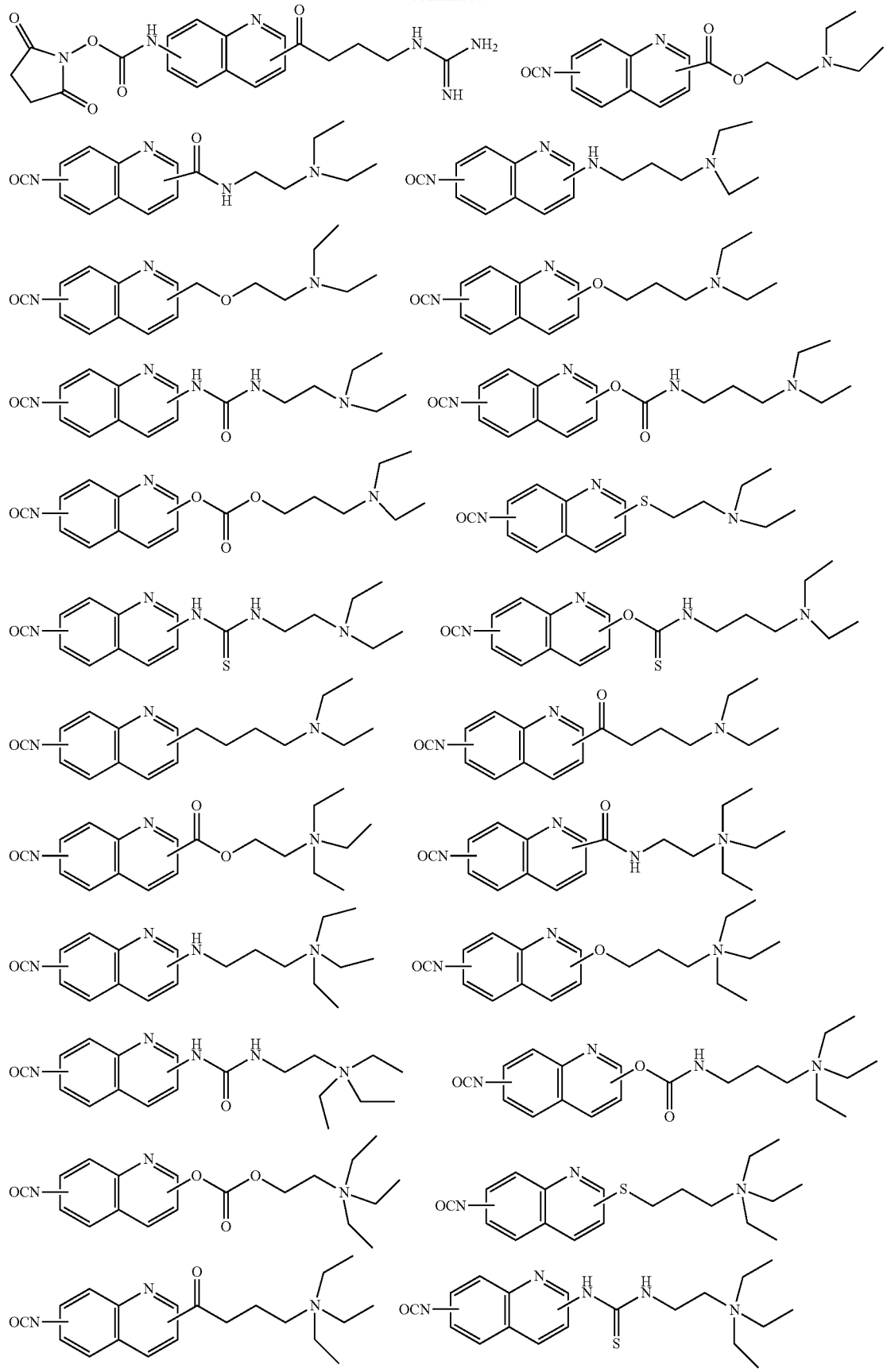

-continued
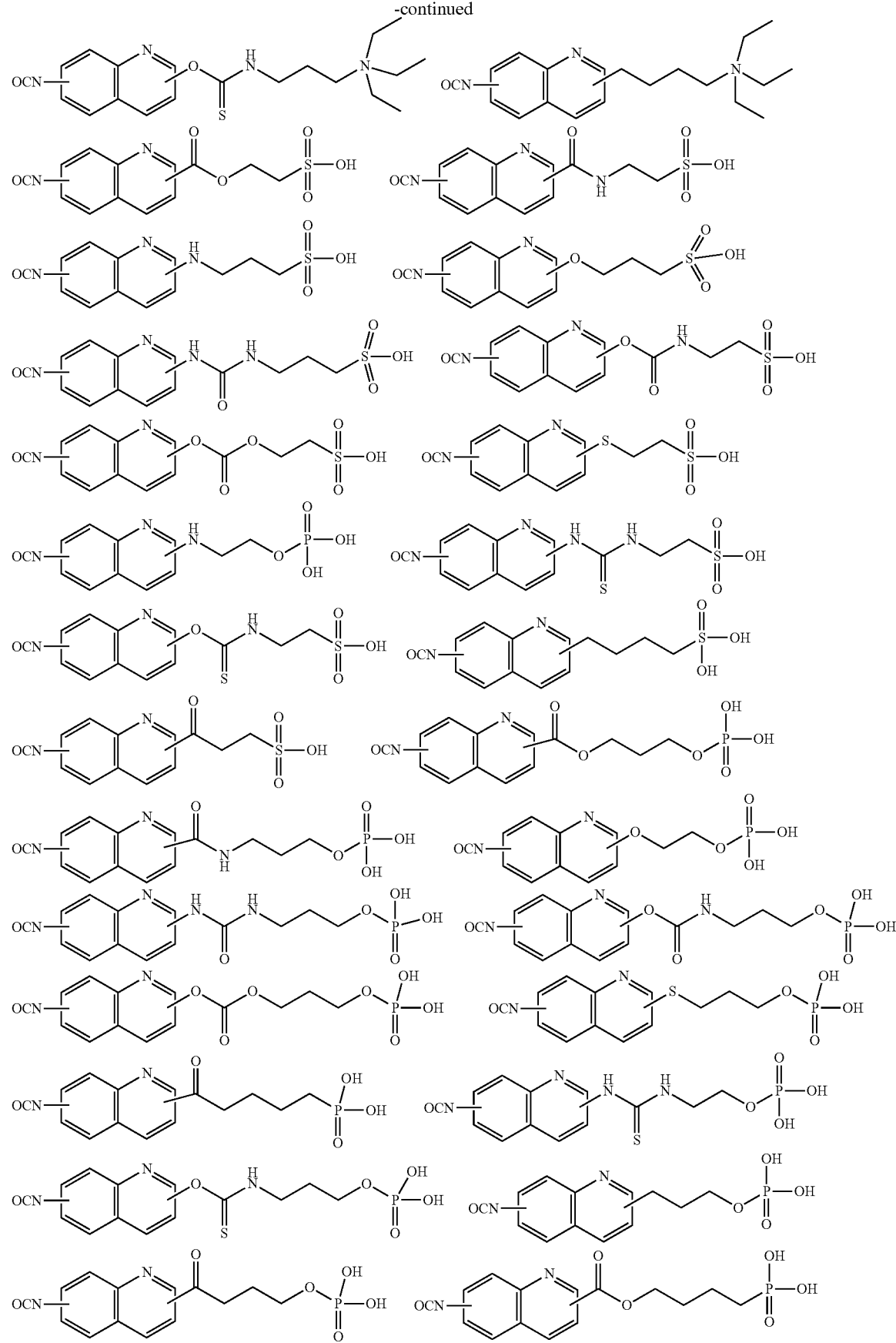

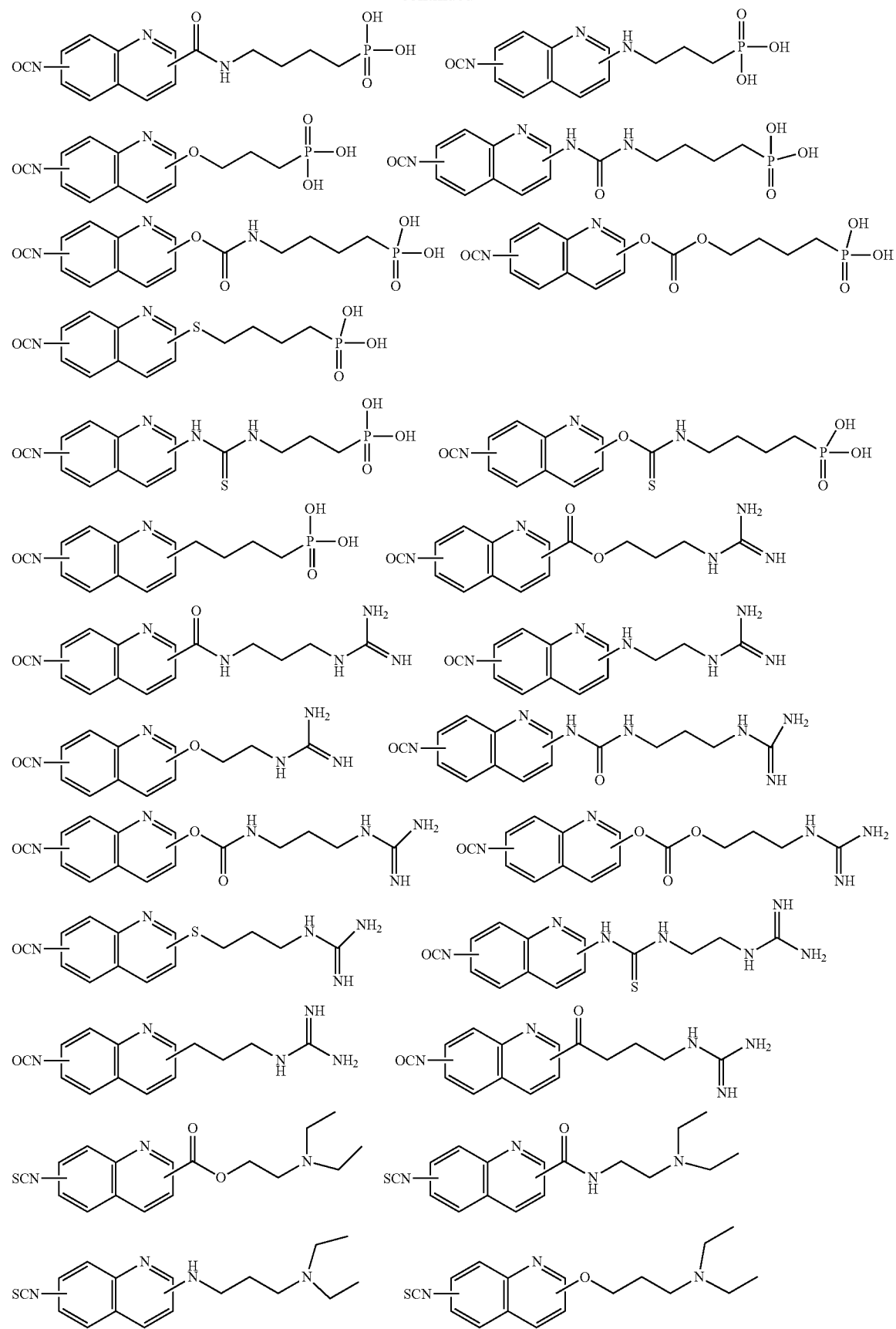

75 76
-continued
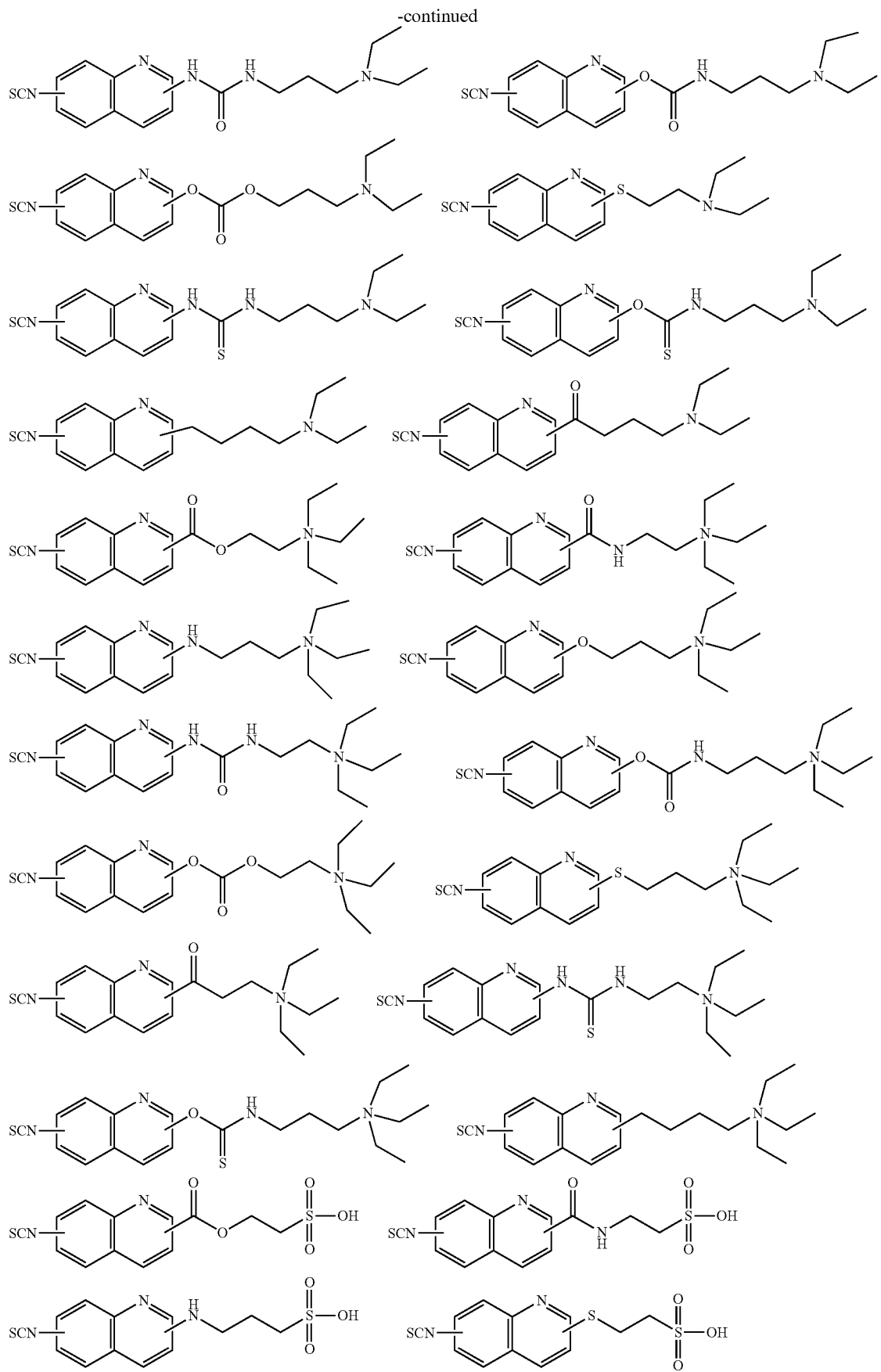

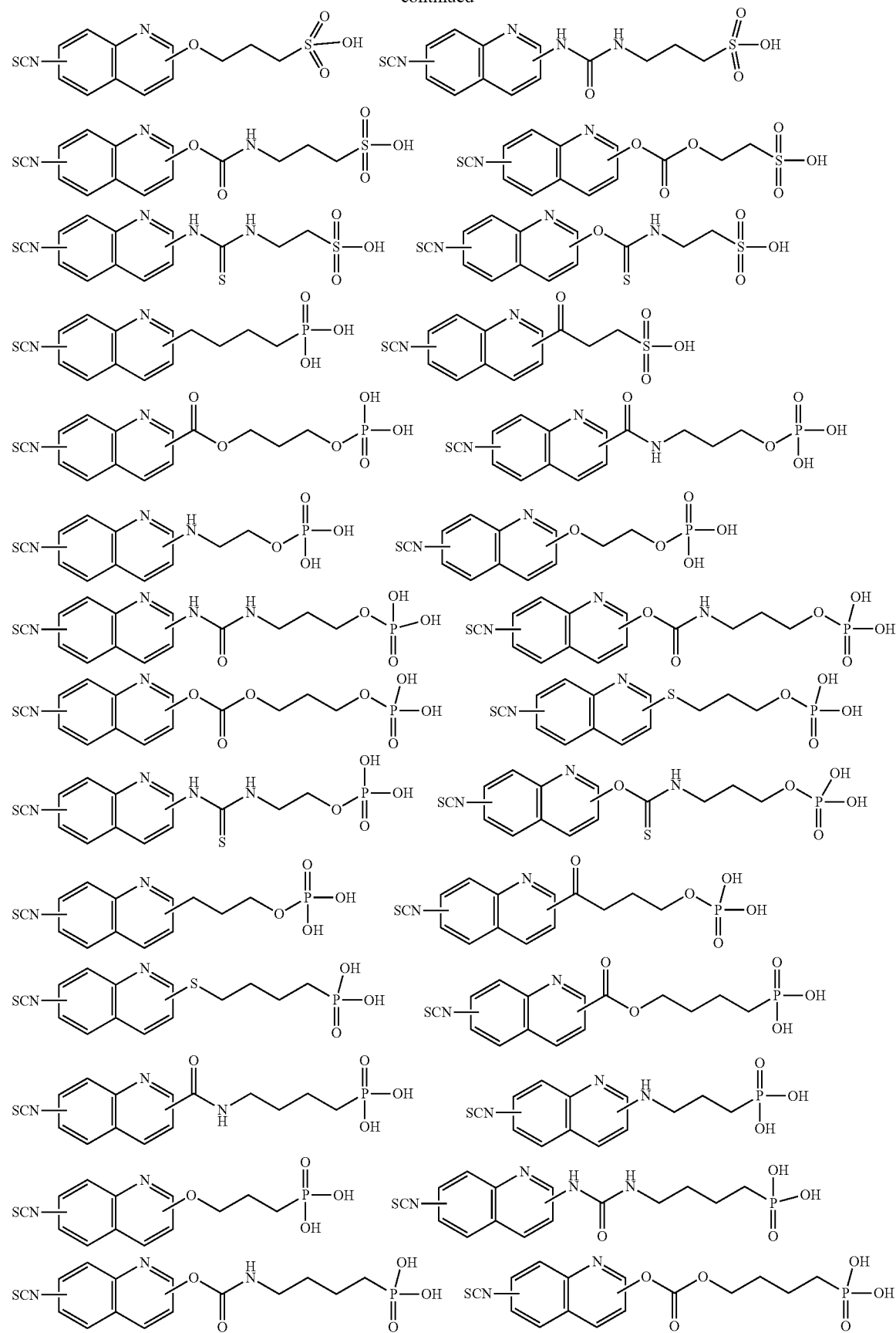

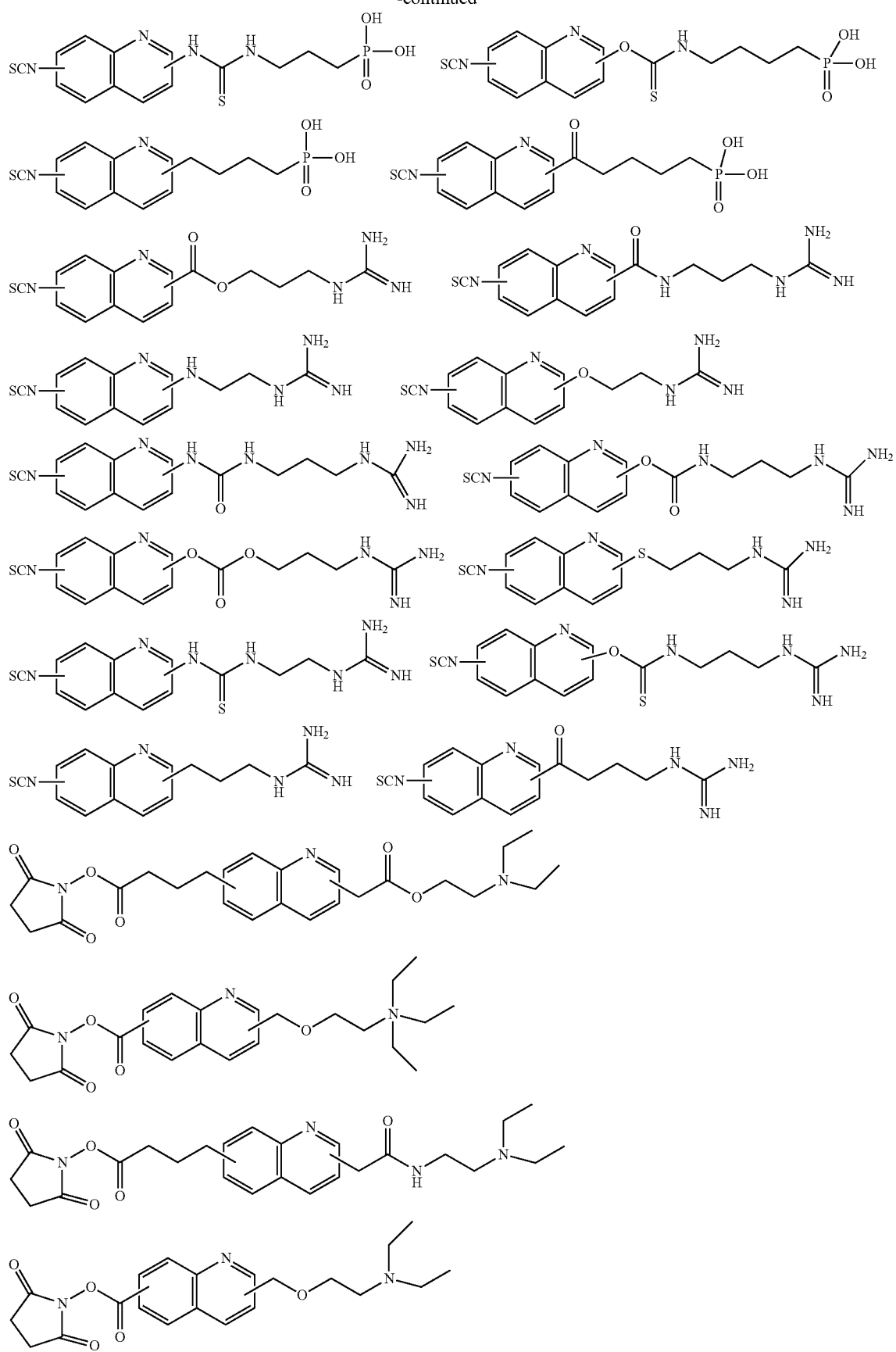

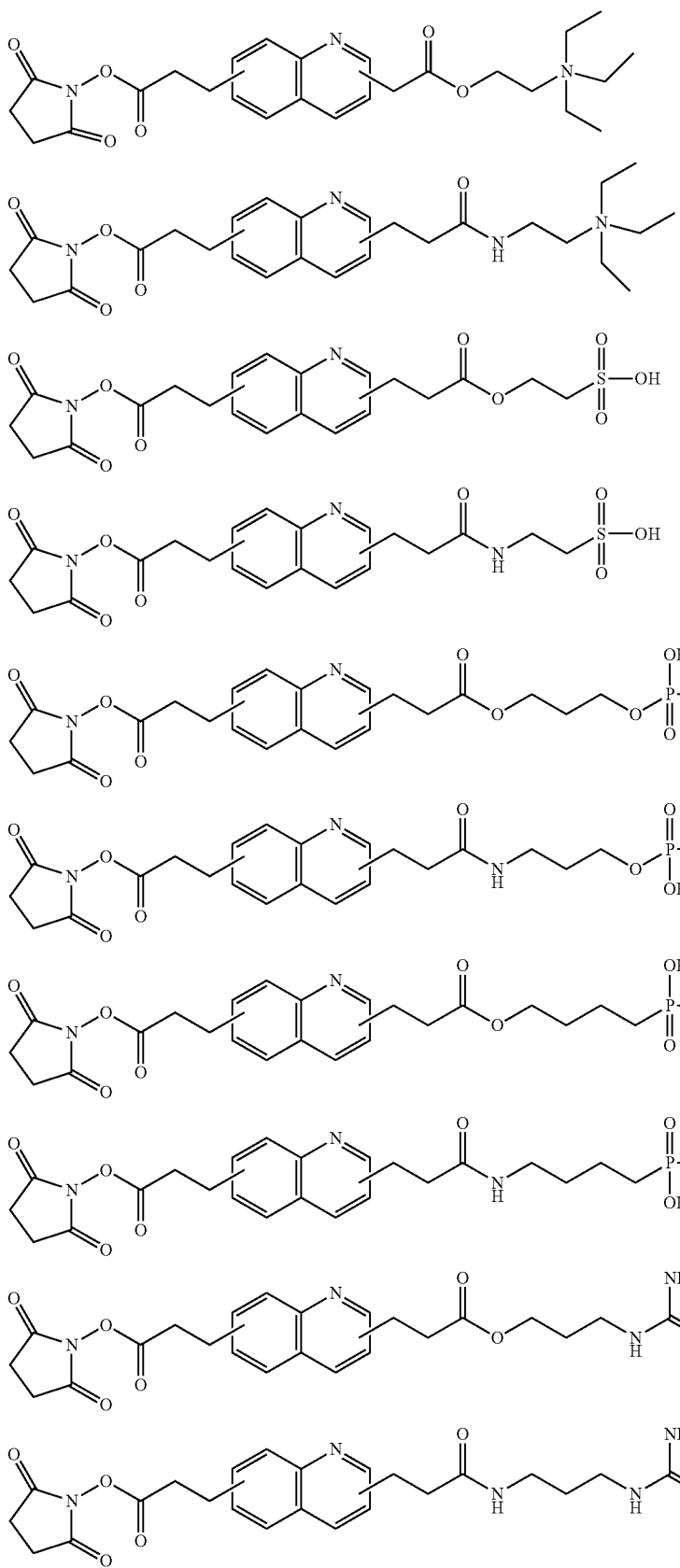

-continued
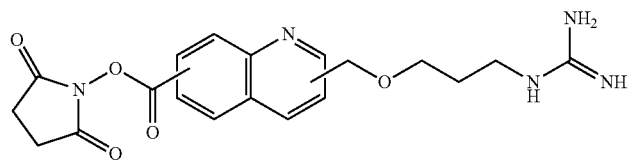
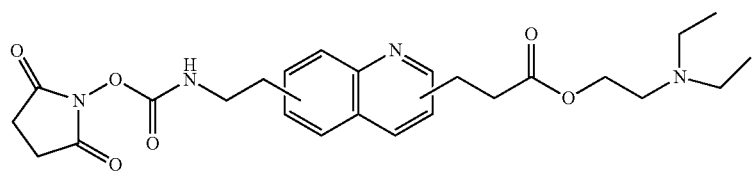
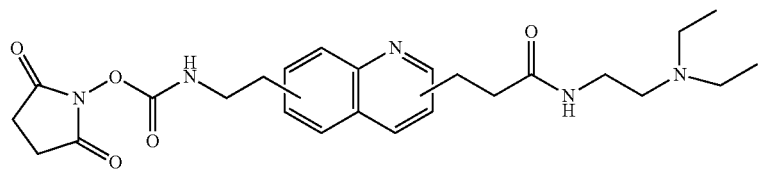
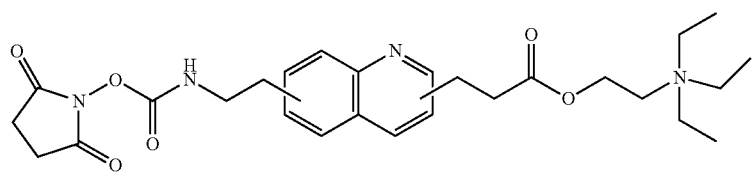
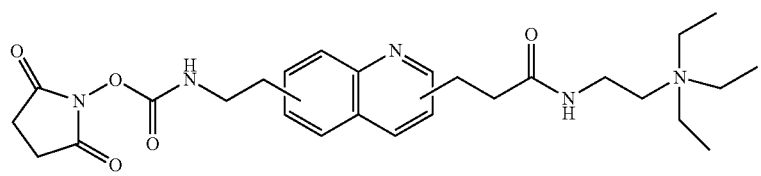
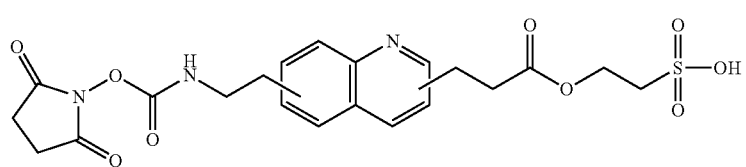
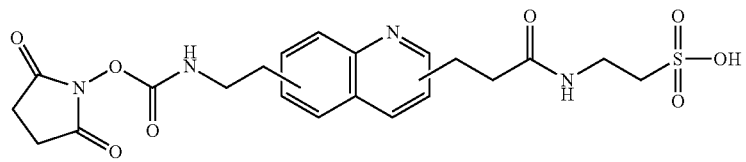
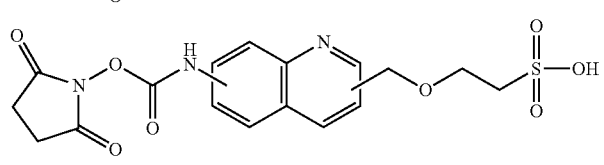
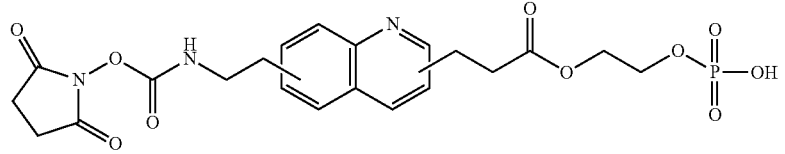
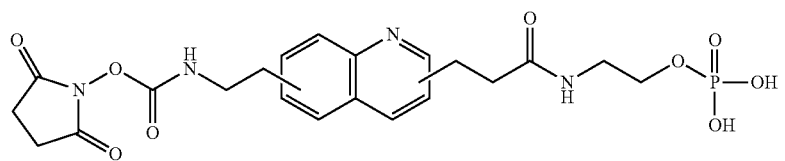

-continued
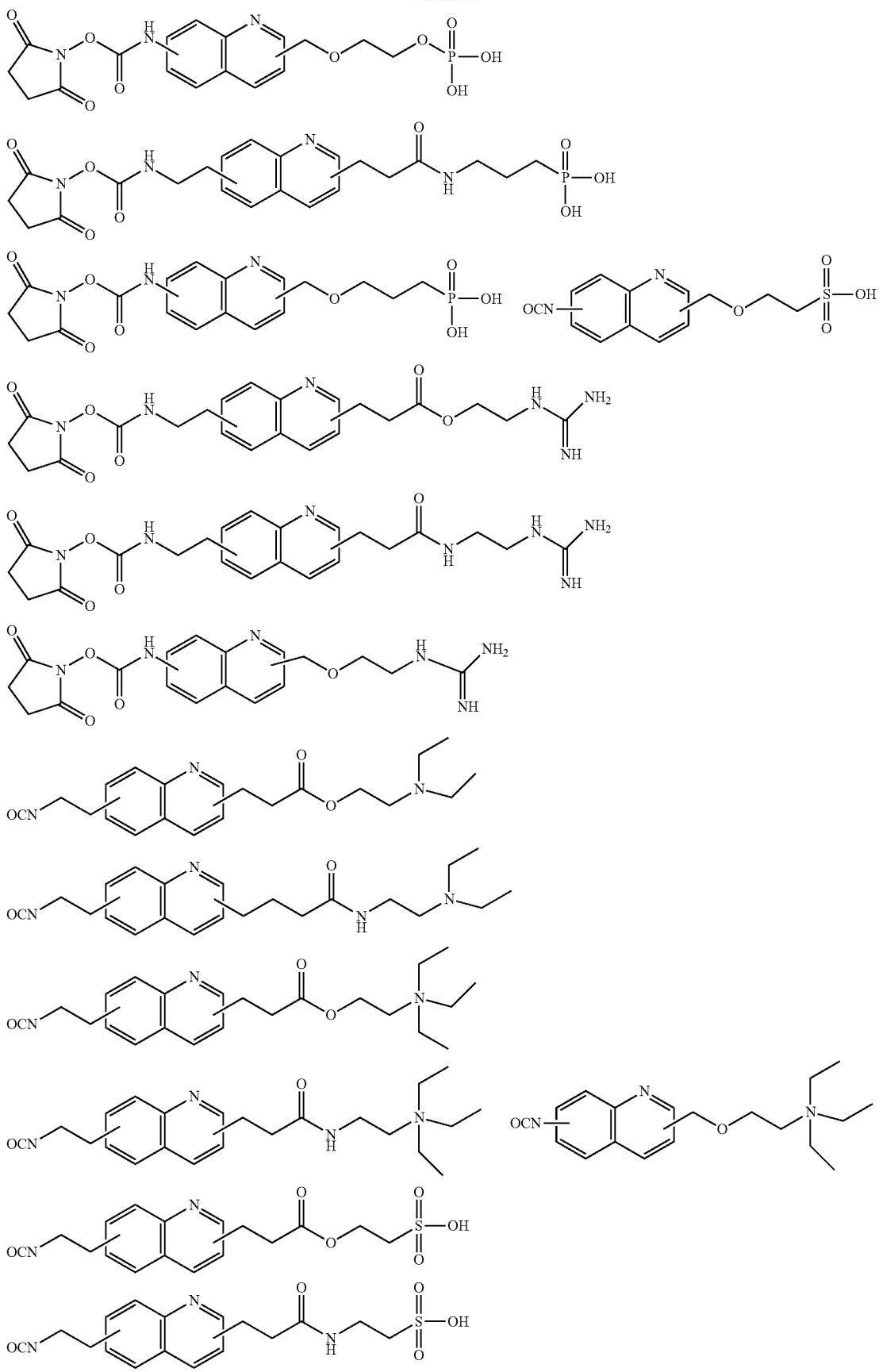

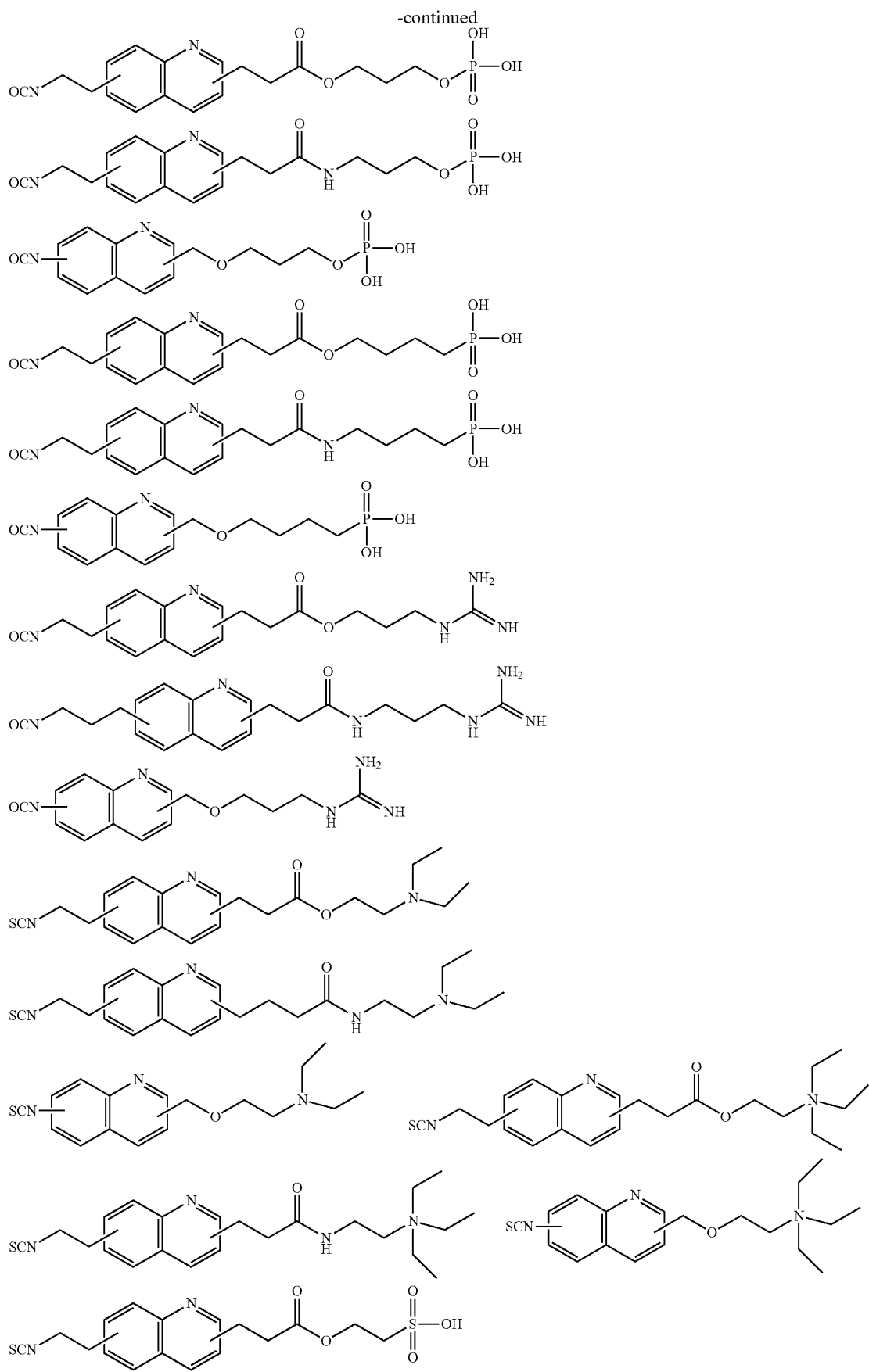

89 90
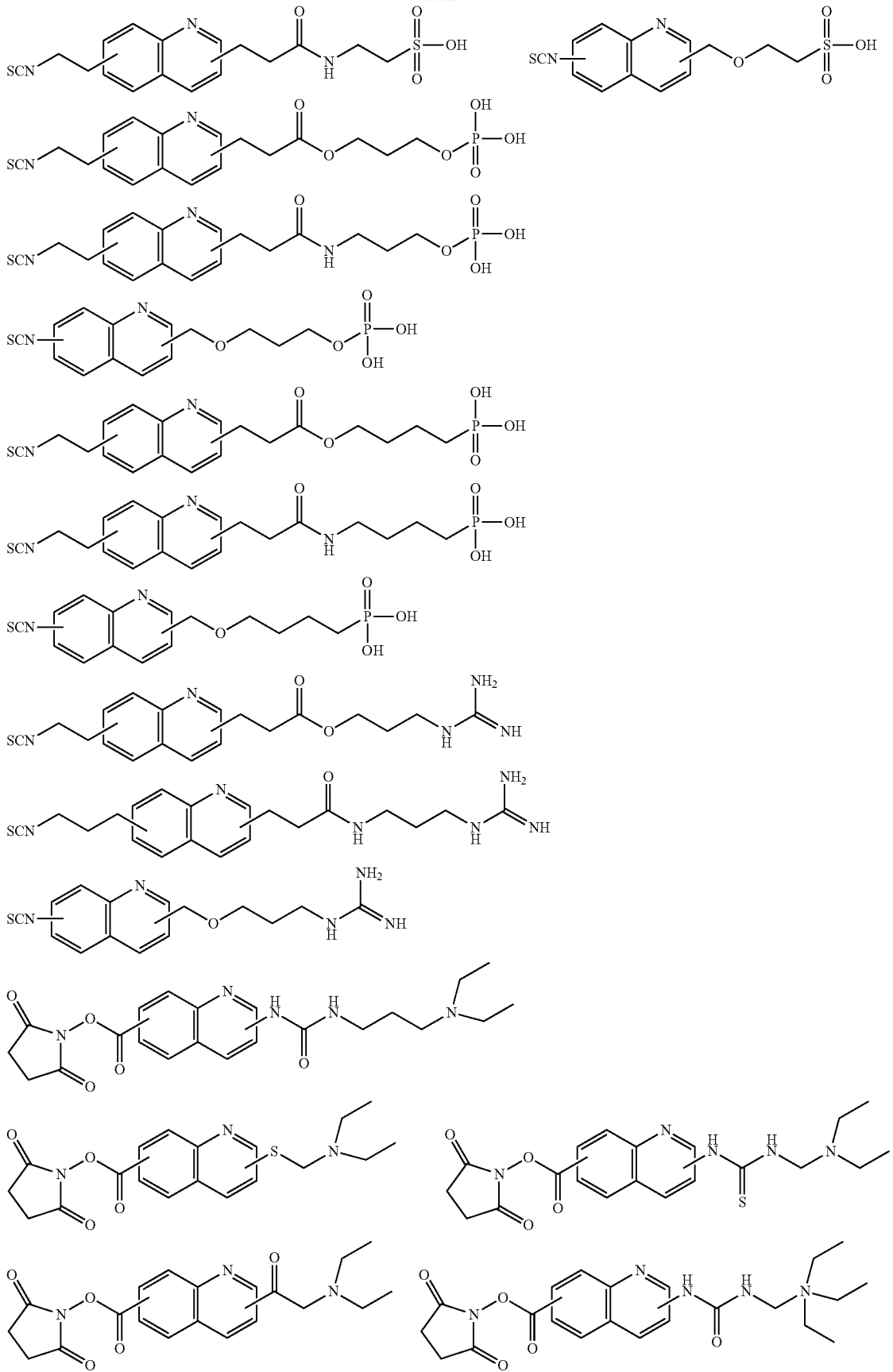
-continued

-continued
91 92
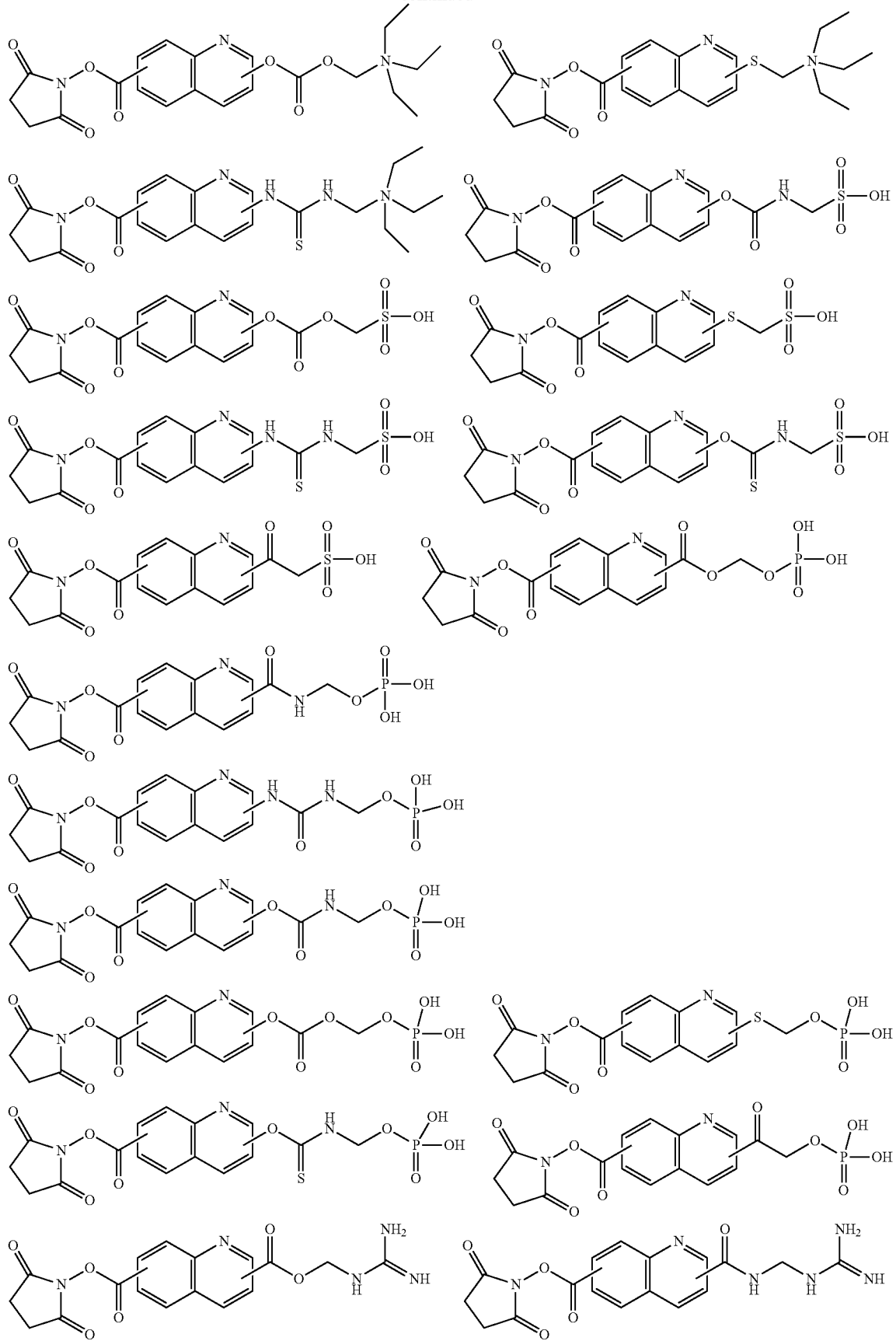

-continued
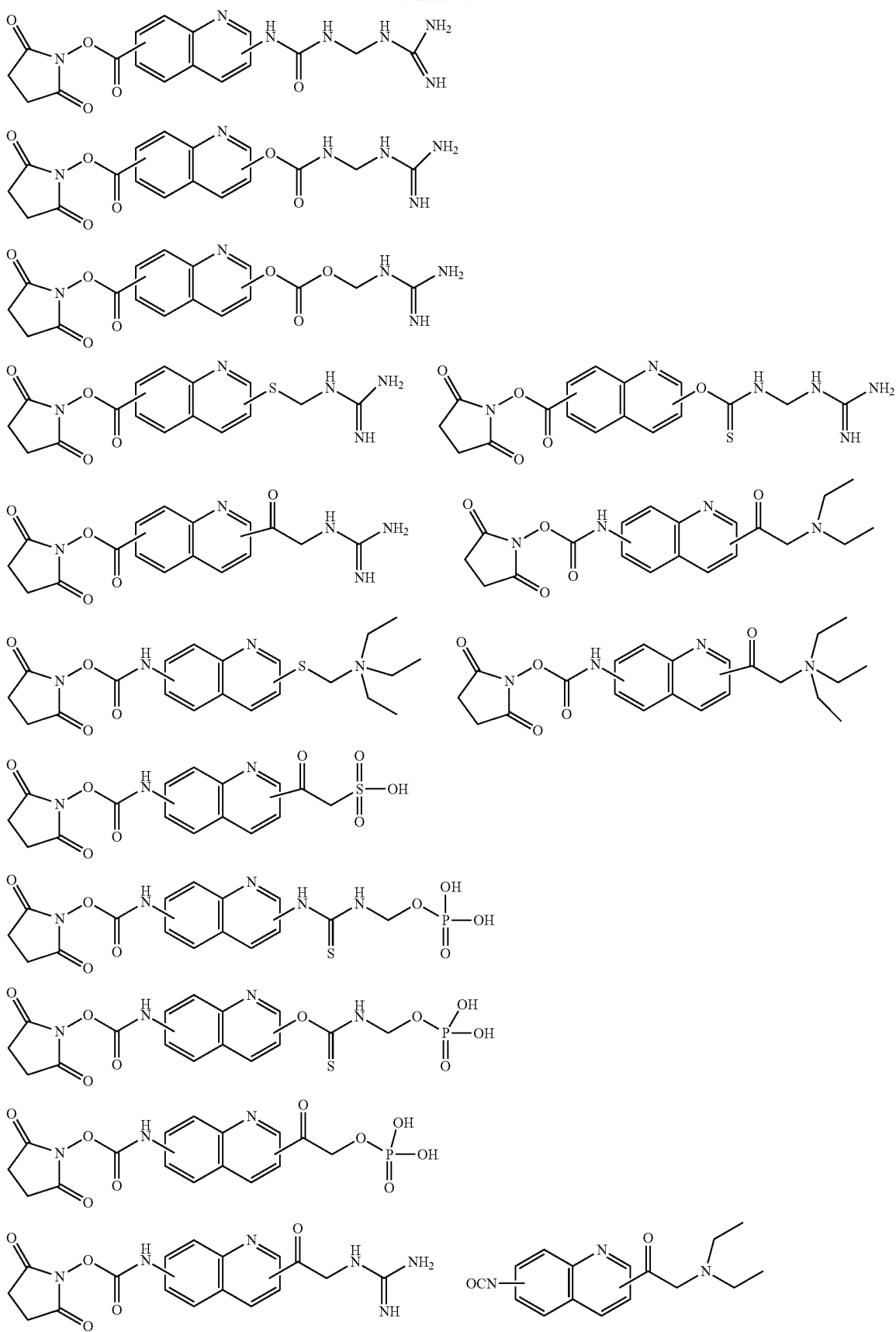

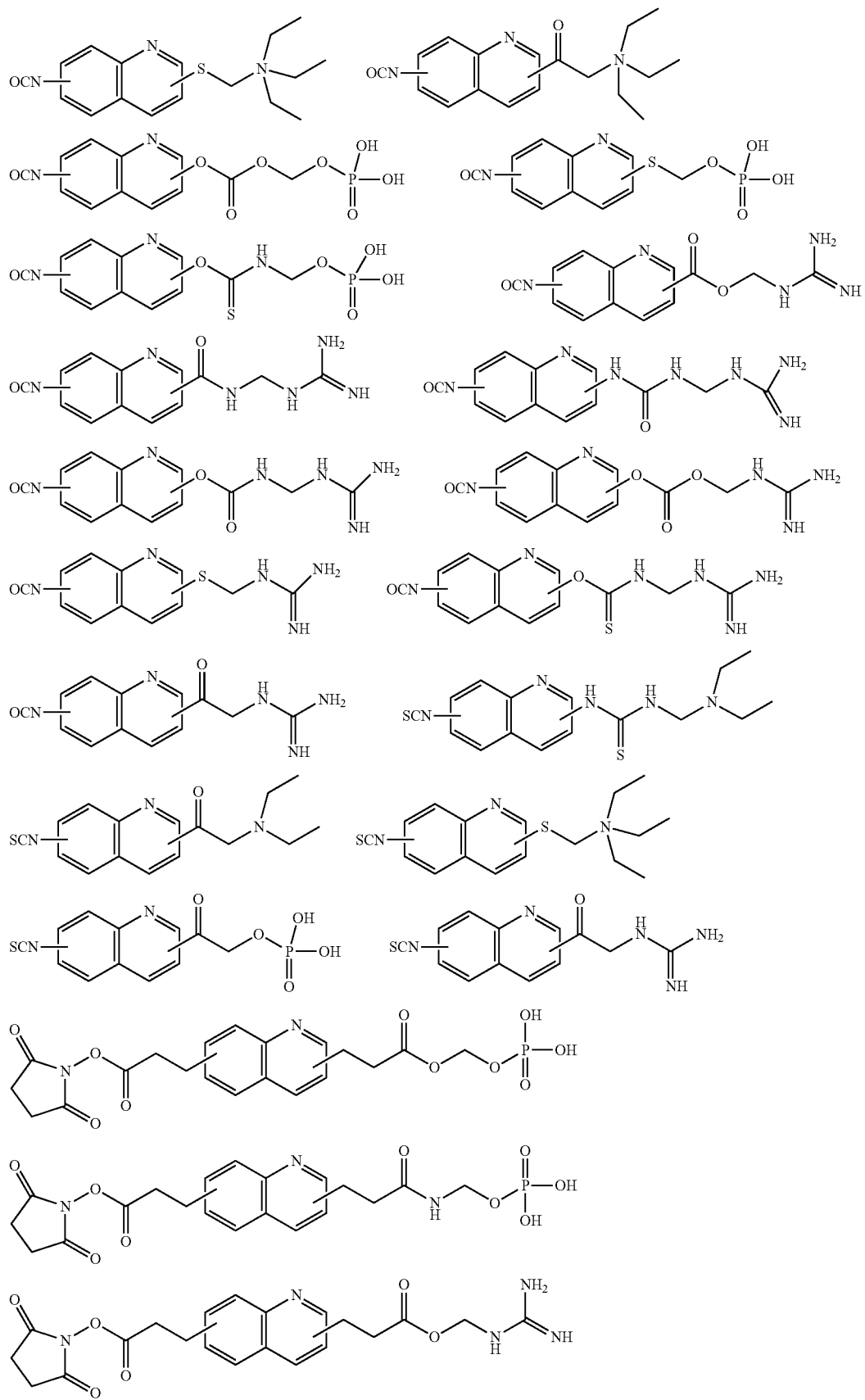

-continued
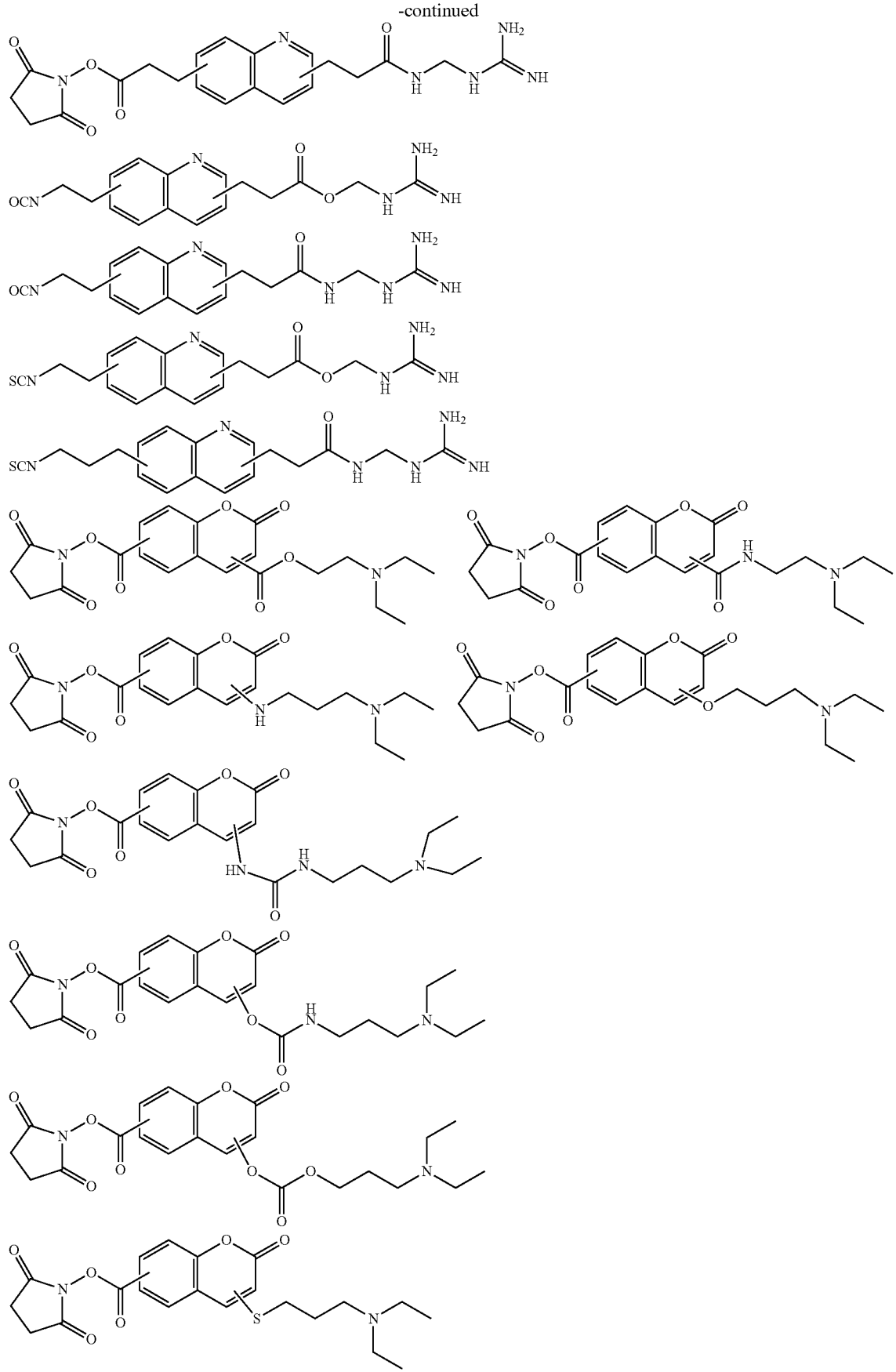

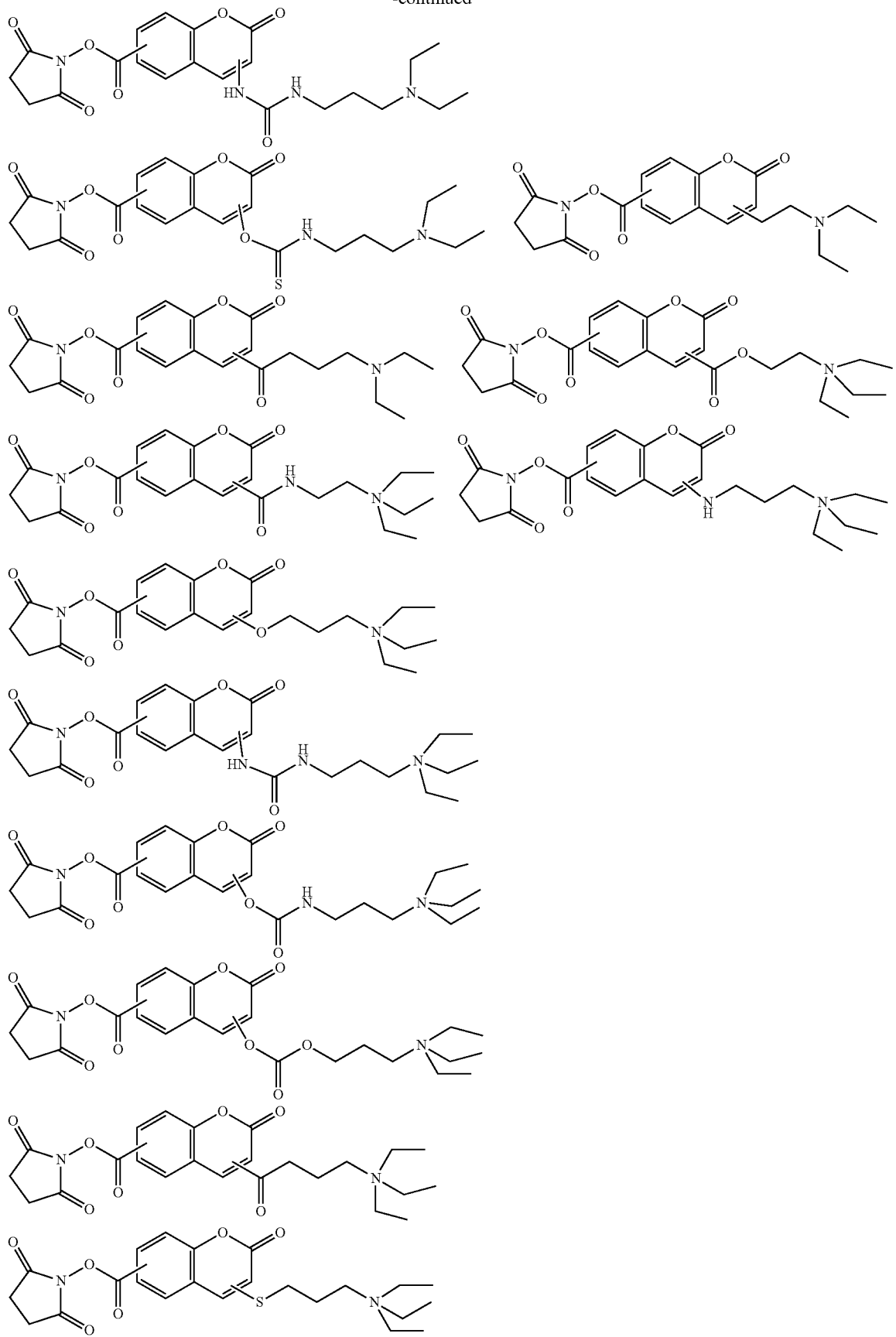

-continued
| 101 | 102 |
|---|---|
| 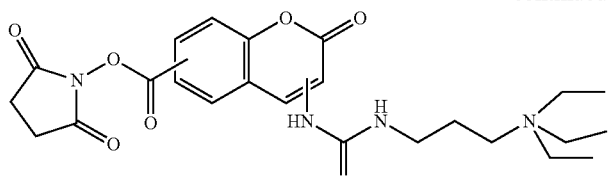 | |
| 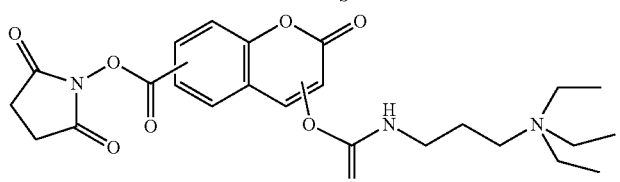 | 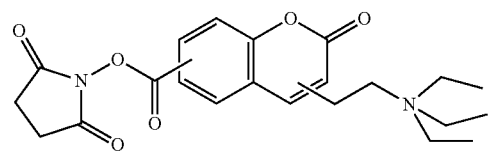 |
| 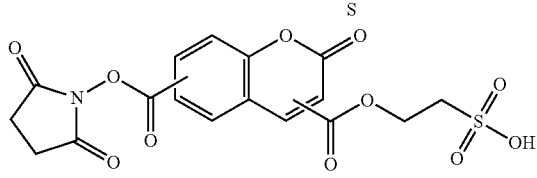 | 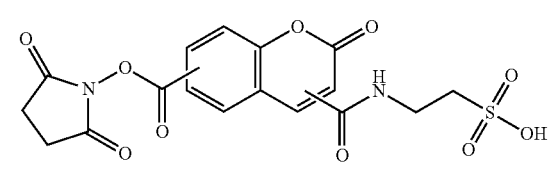 |
| 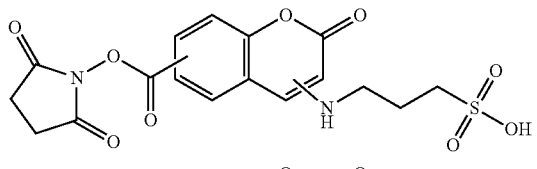 | 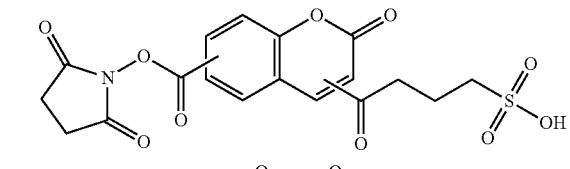 |
| 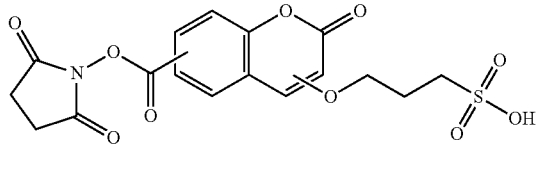 | 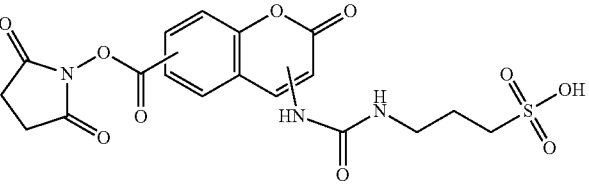 |
| 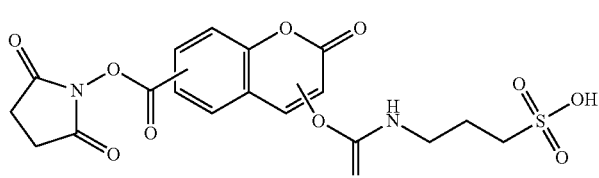 |  |
| 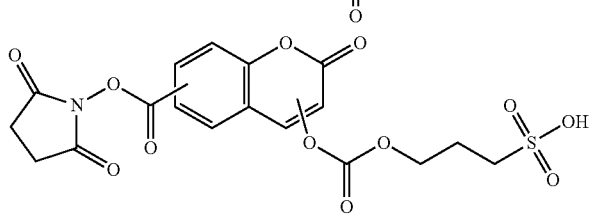 |  |
| 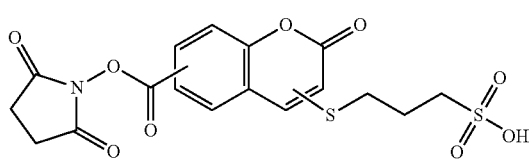 |  |
| 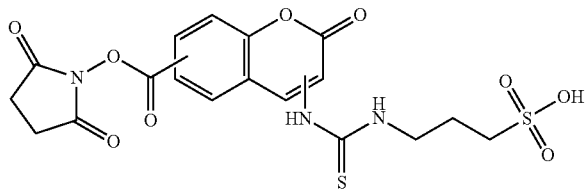 |  |

103 104
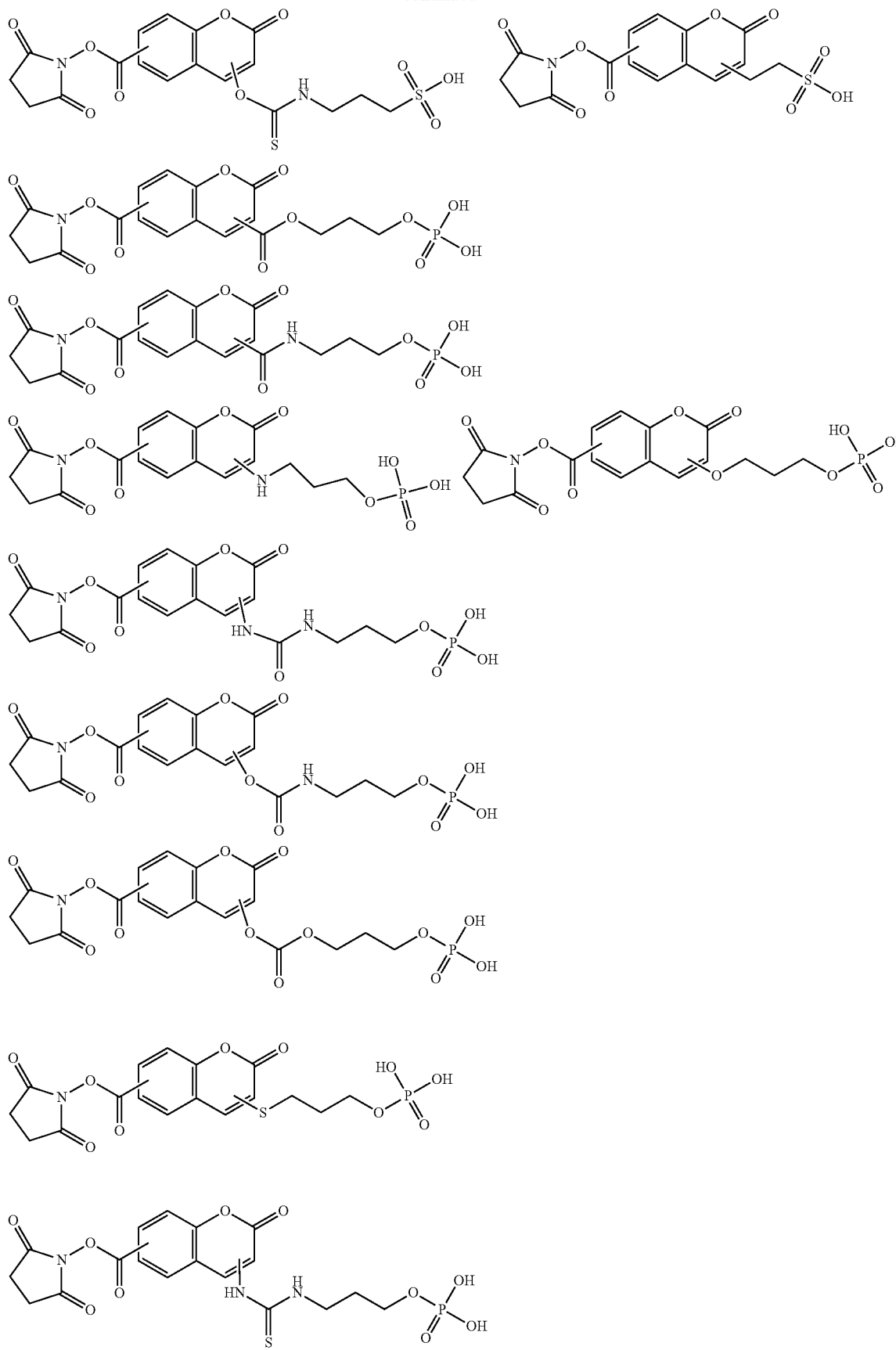

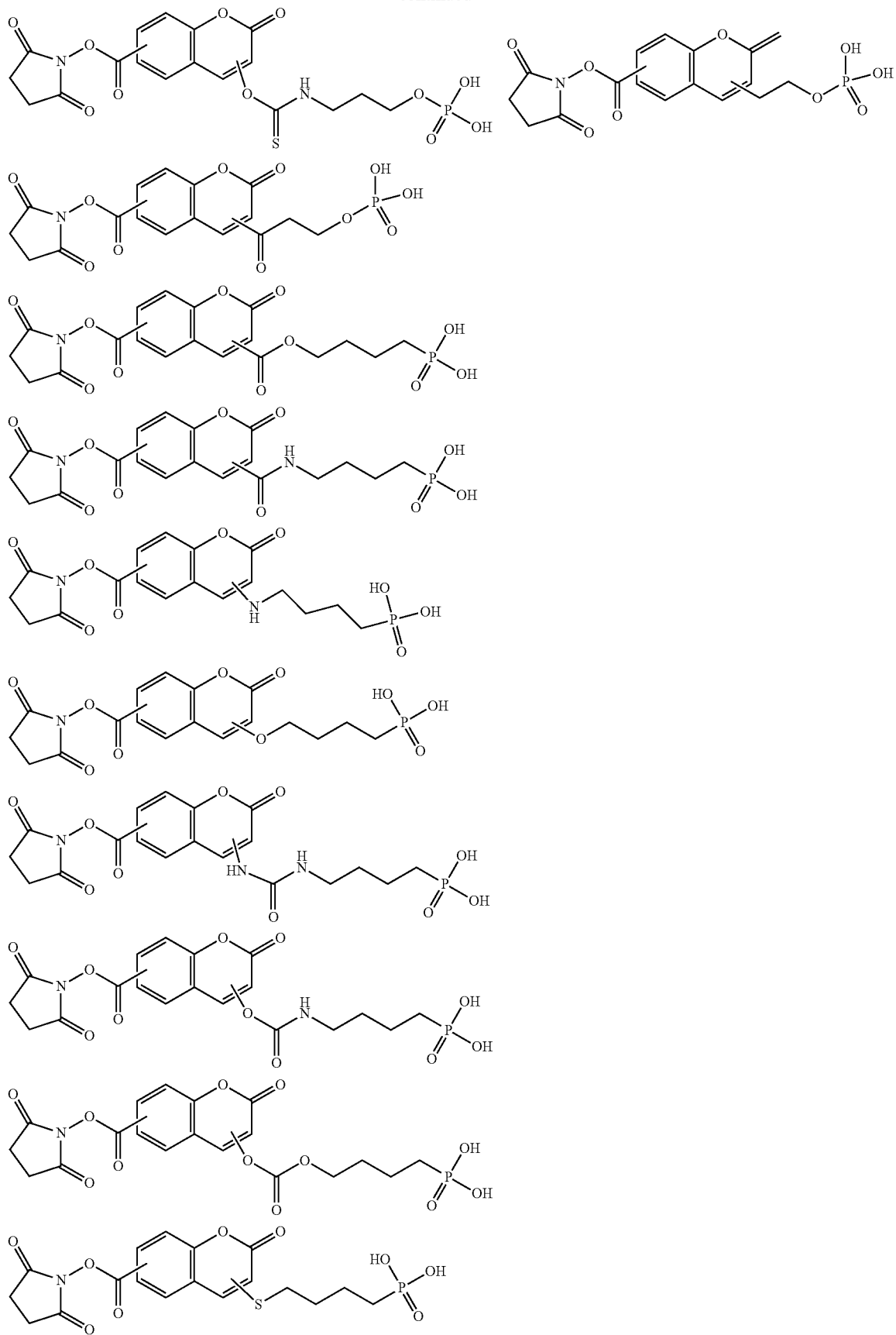

107
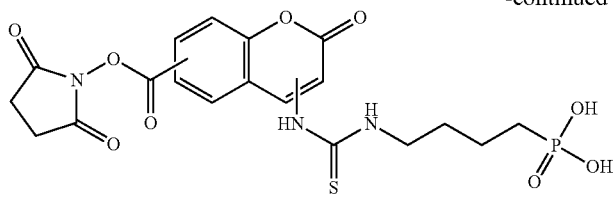
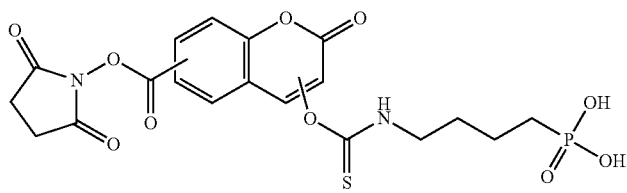
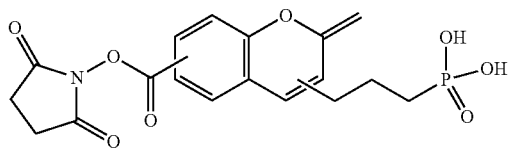 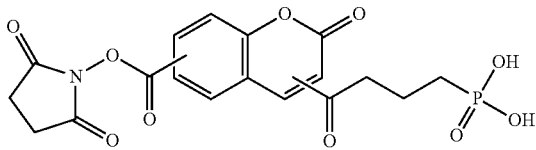
108
-continued
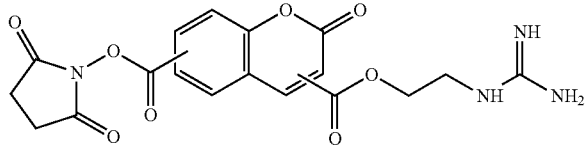
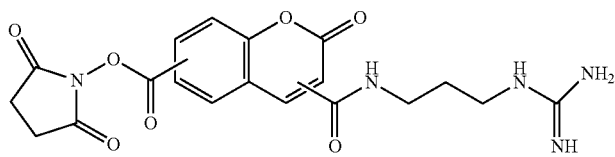
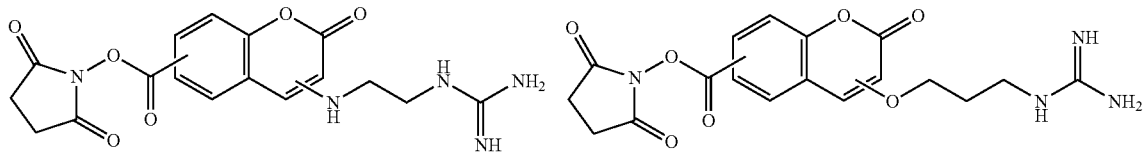
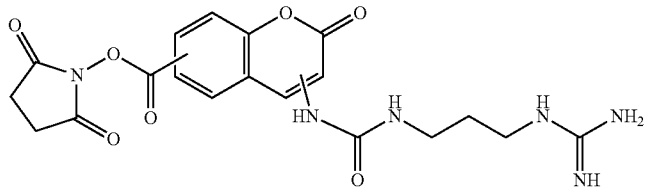
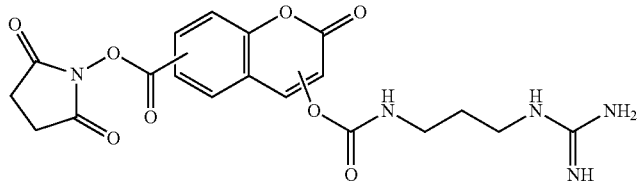
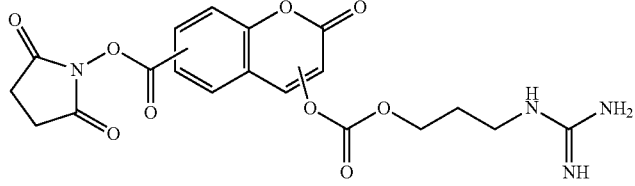
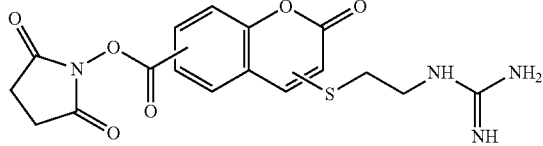

-continued
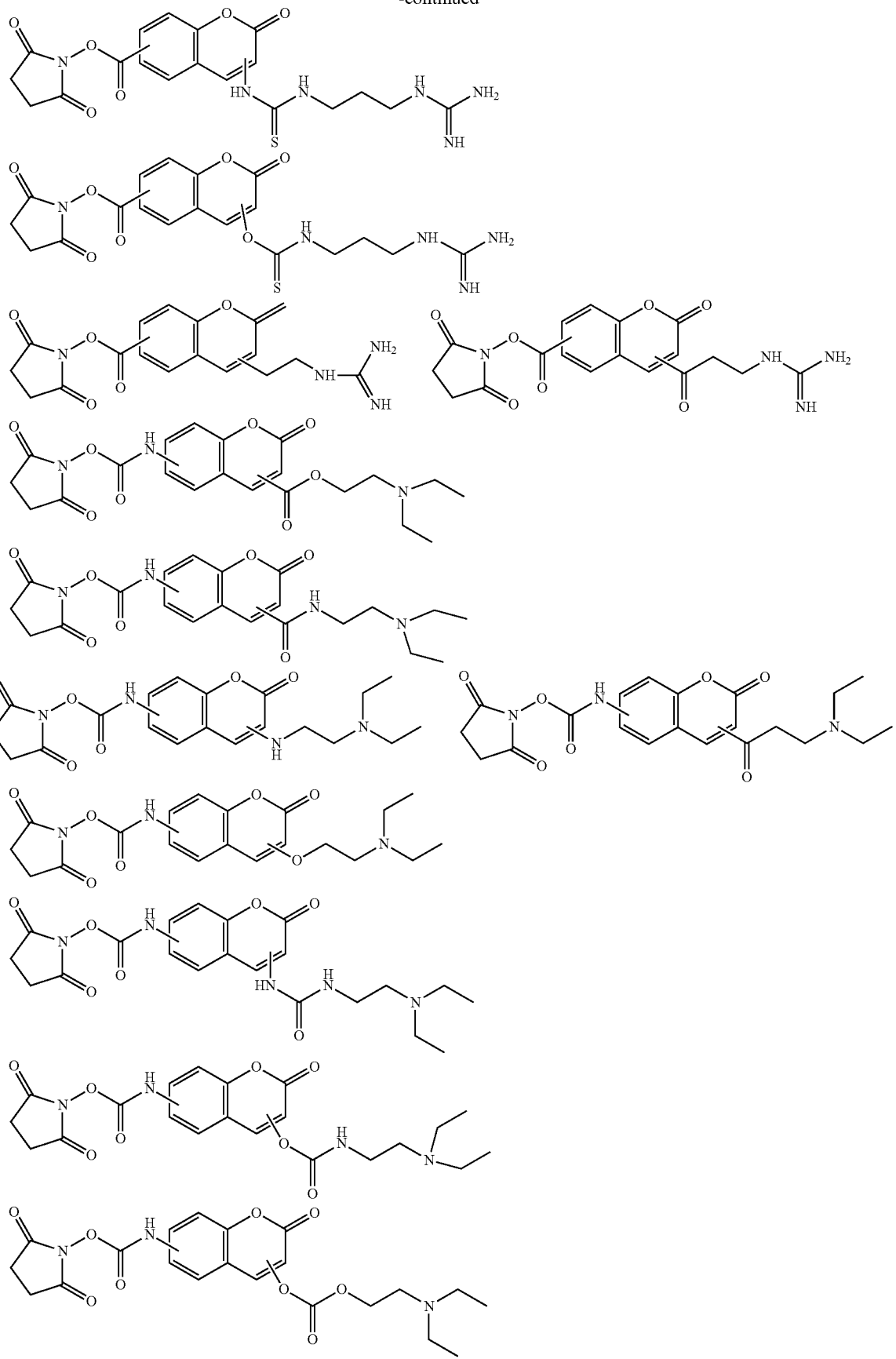

-continued
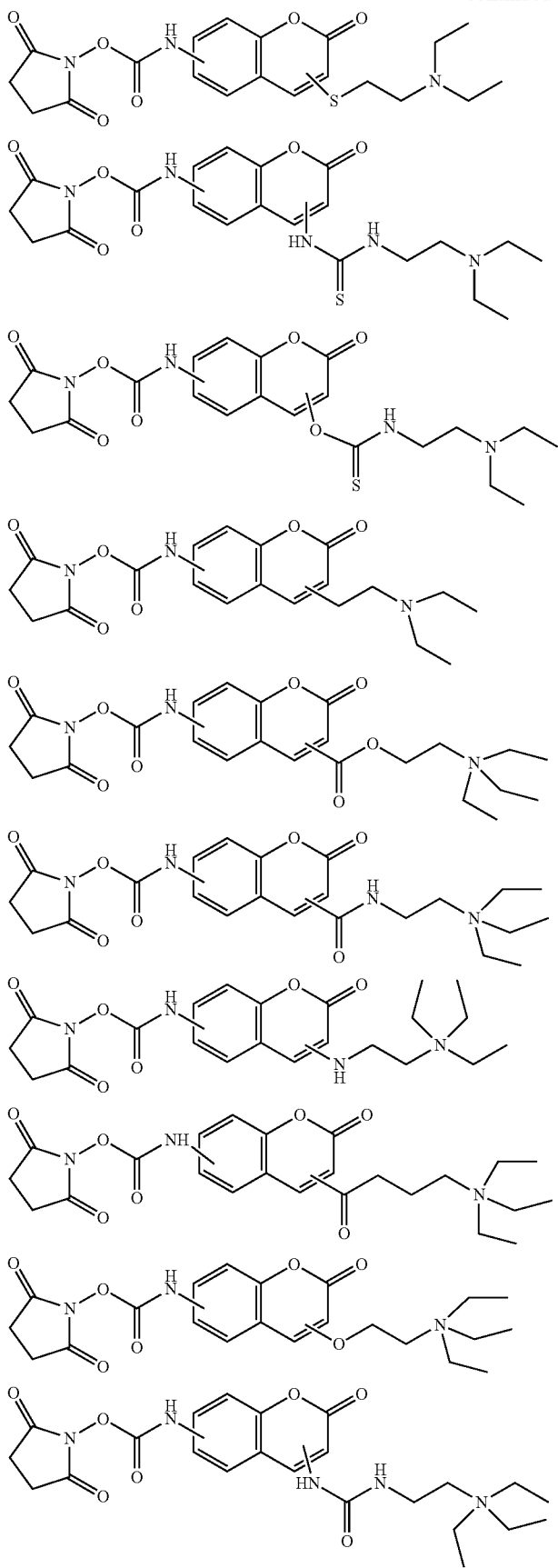

113
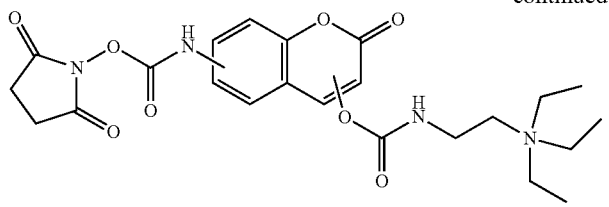
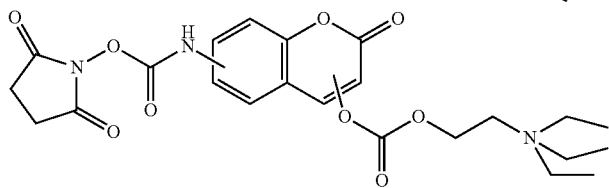
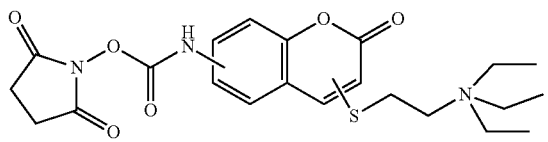
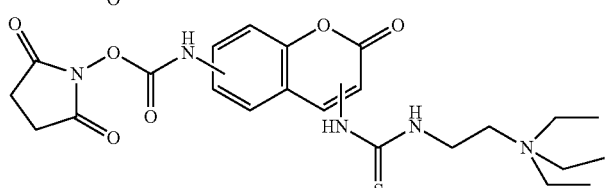
-continued
114
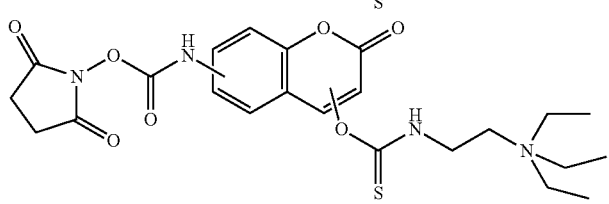
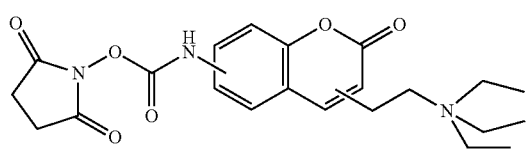
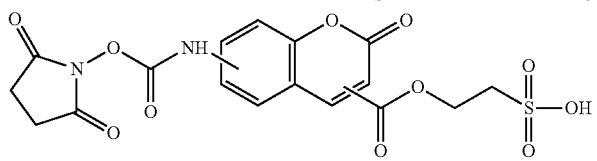
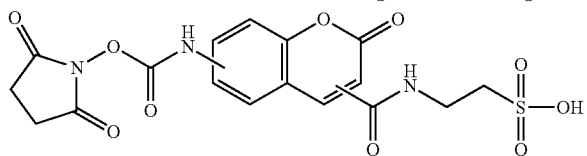
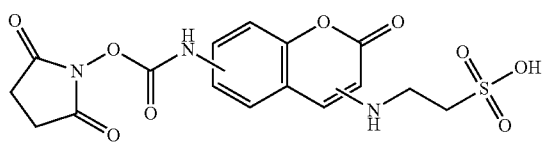
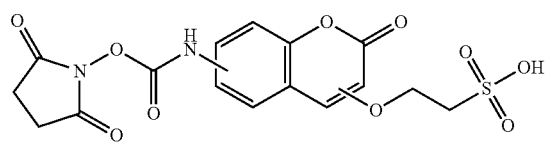
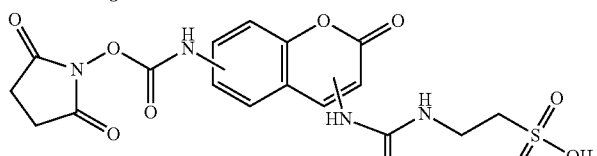
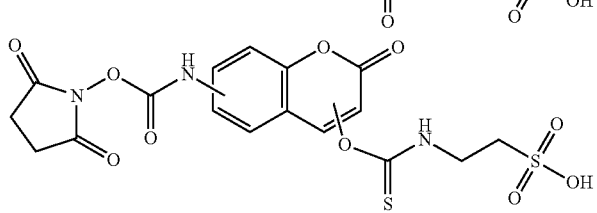

115 116
-continued
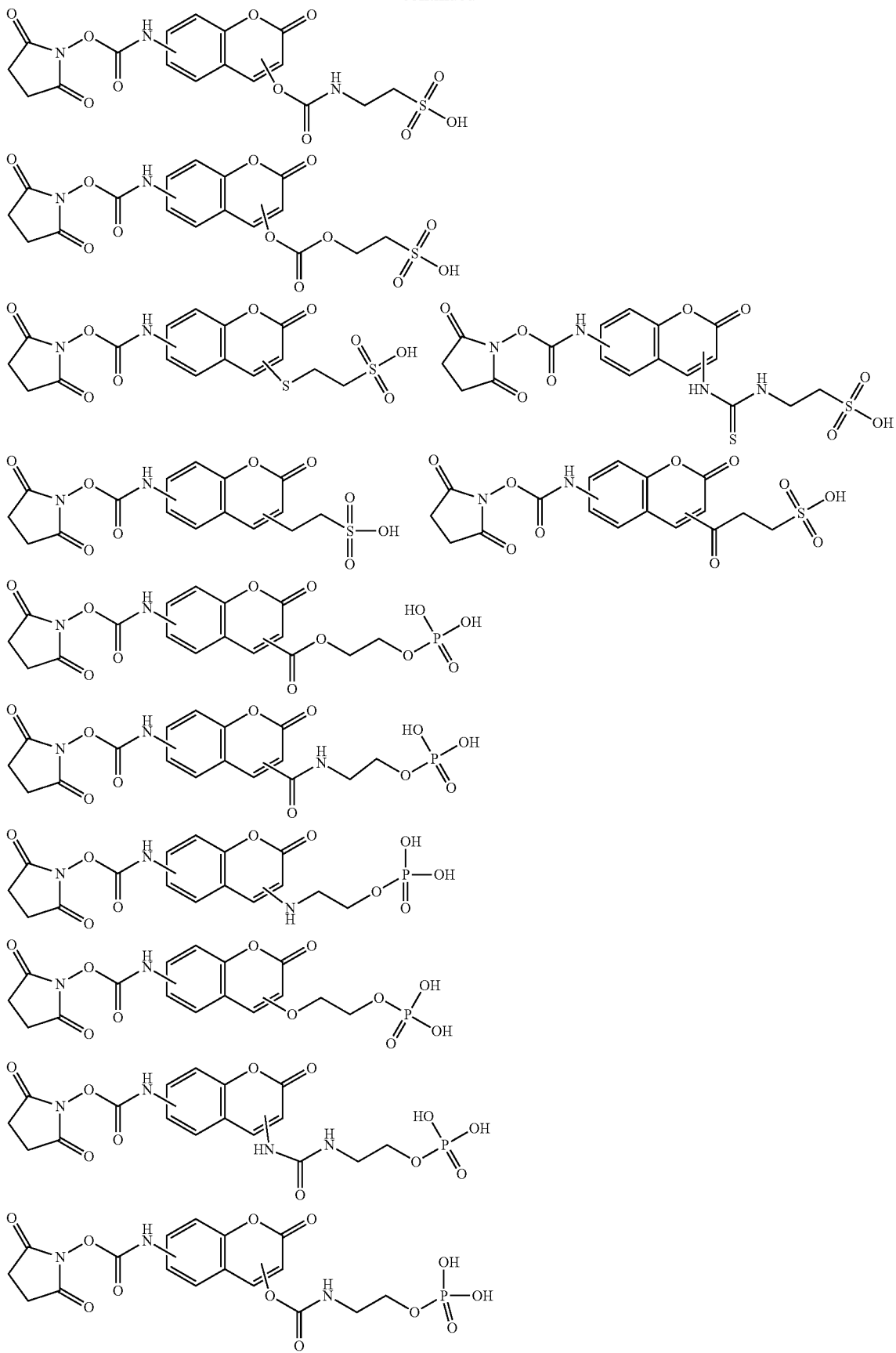

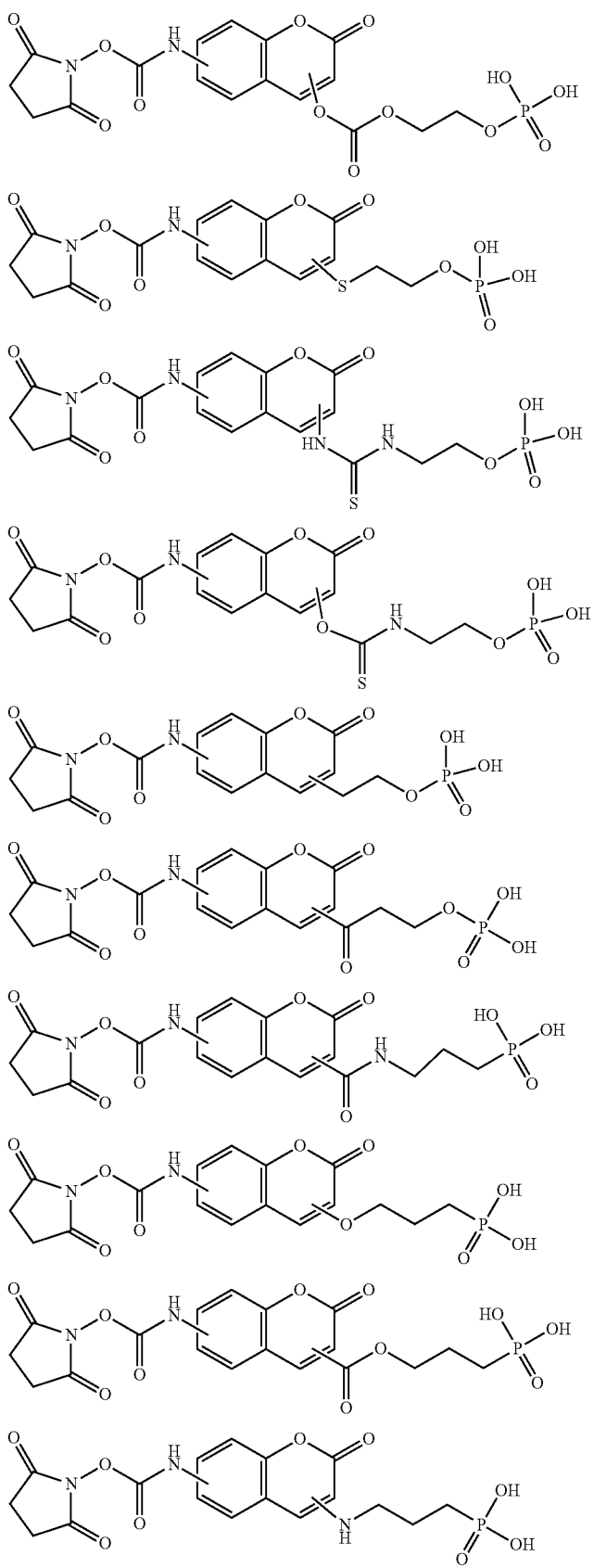

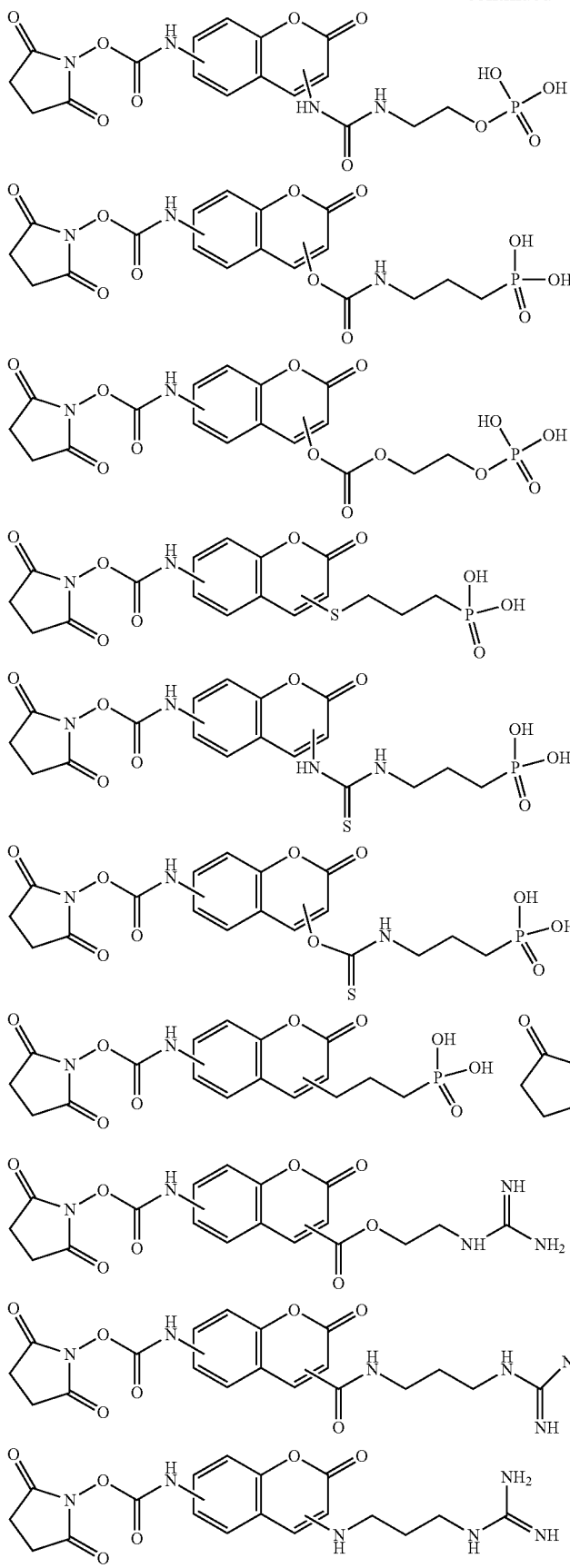

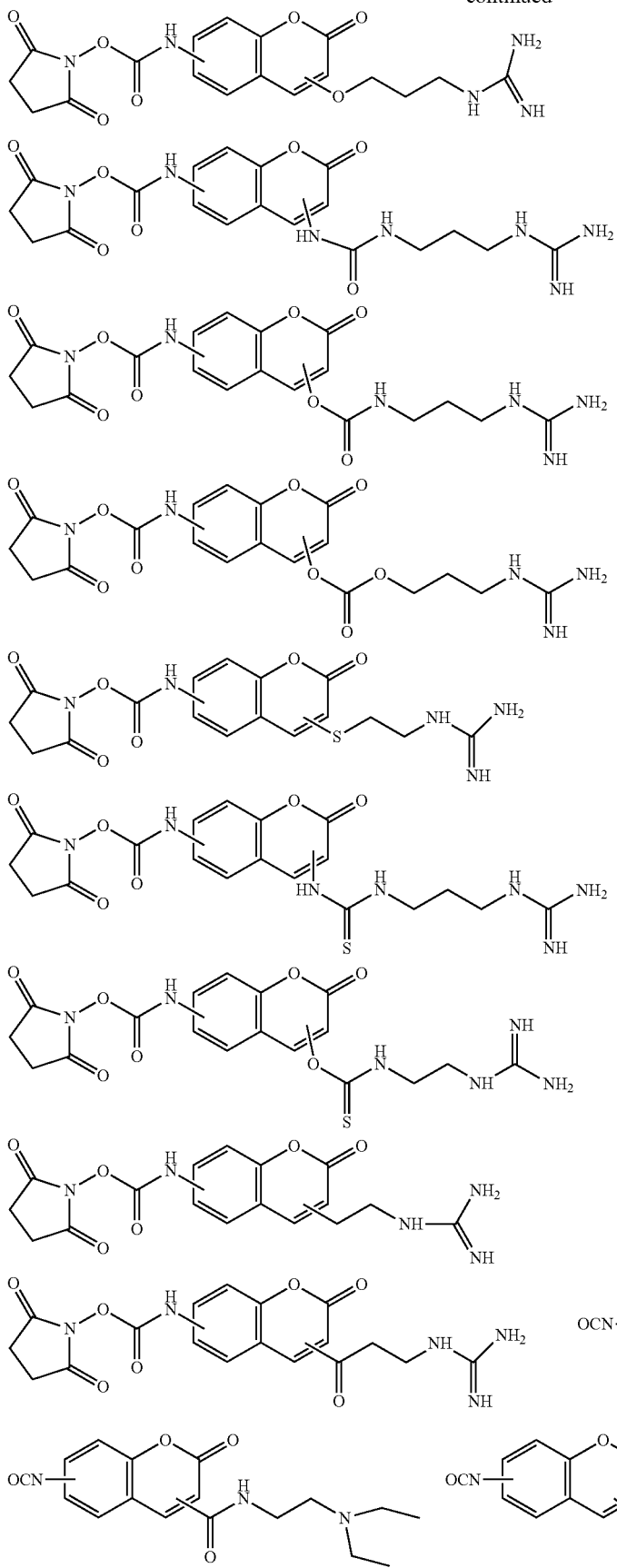

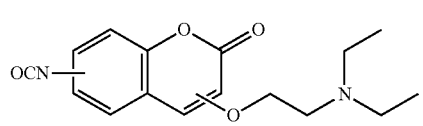
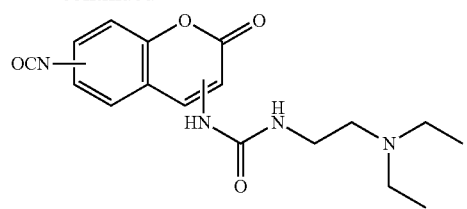
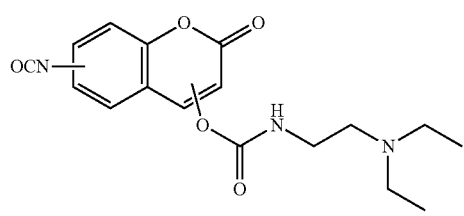
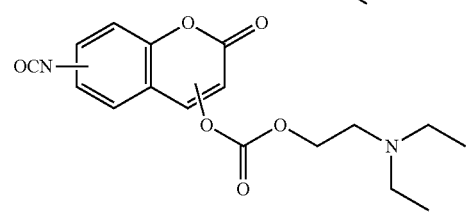
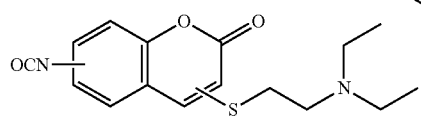
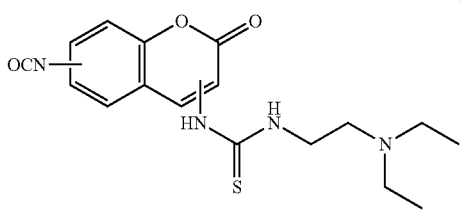
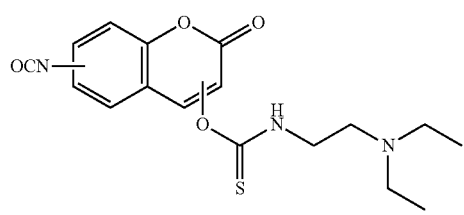
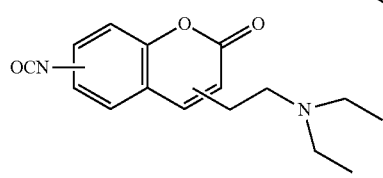
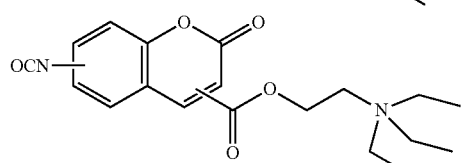
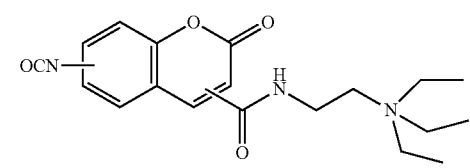
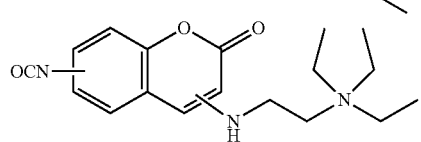
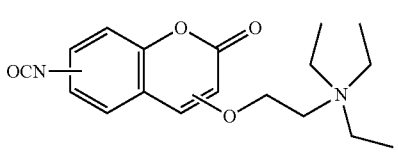
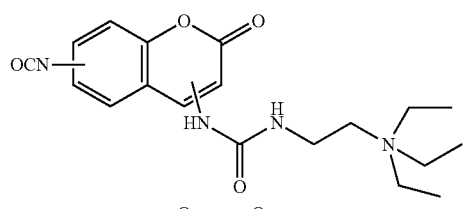
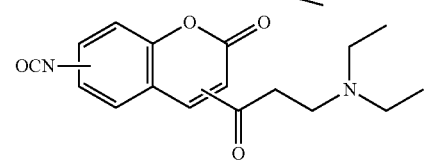
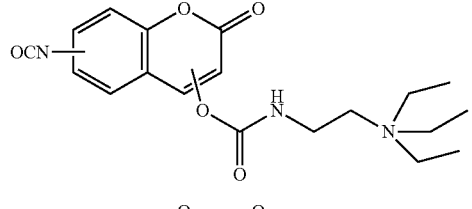
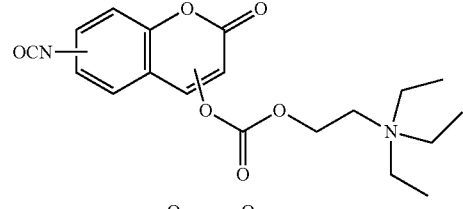
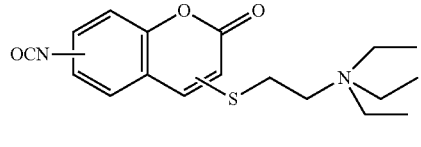
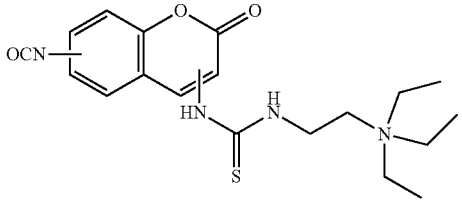

125
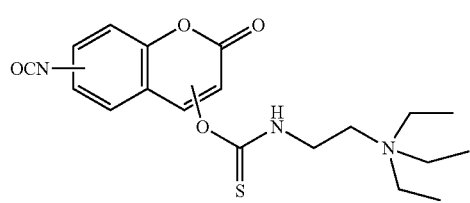
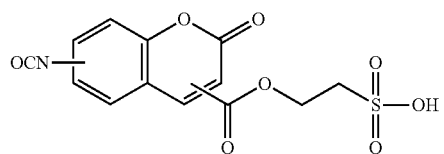
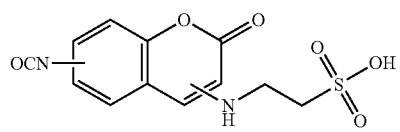
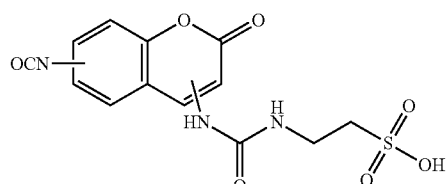
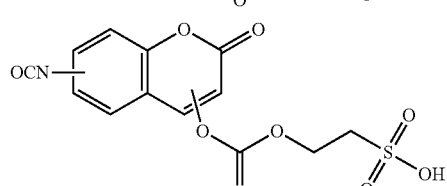
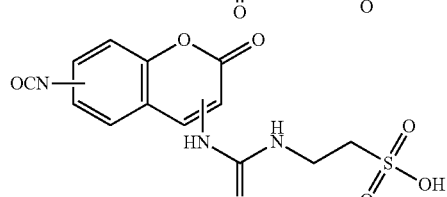
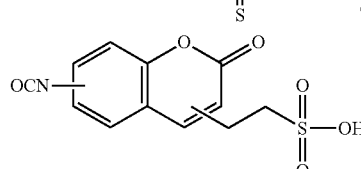
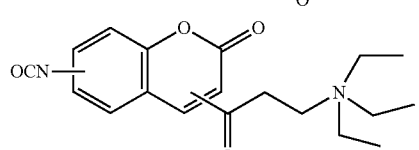
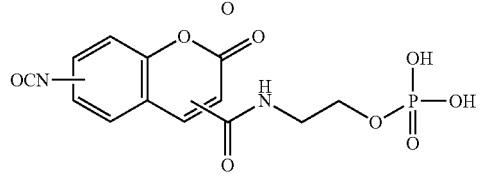
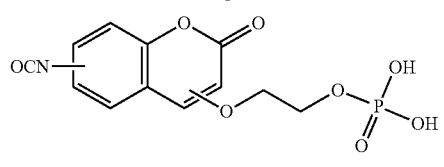
126
-continued
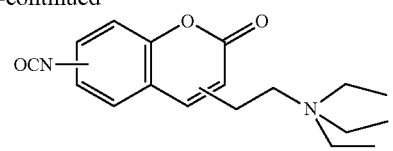
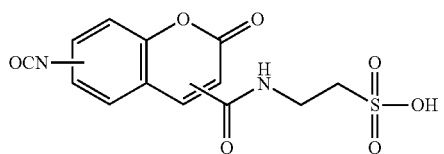
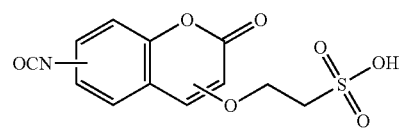
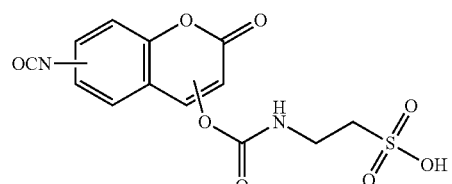
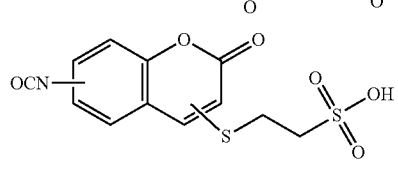
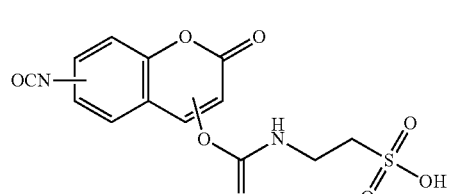
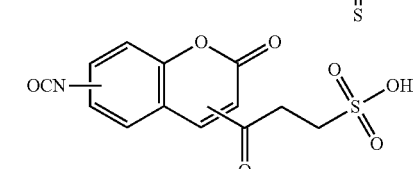
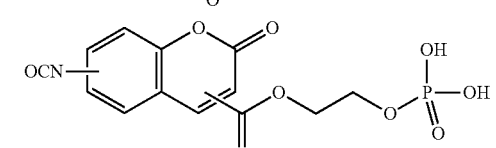
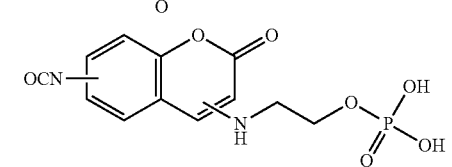
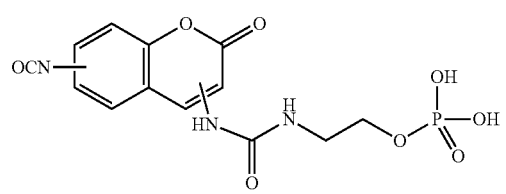

127
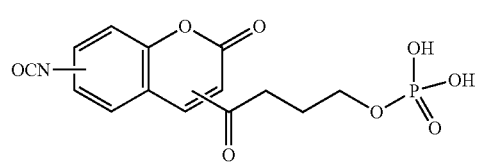
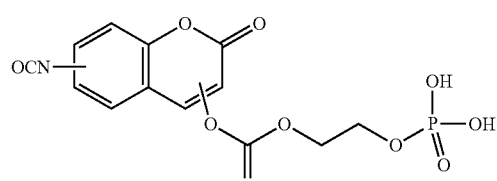
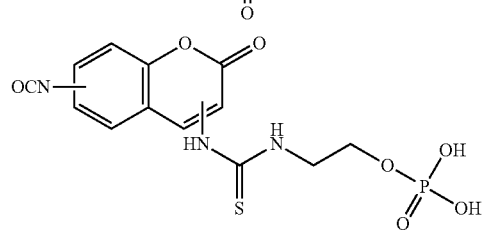
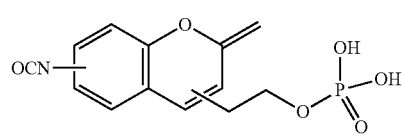
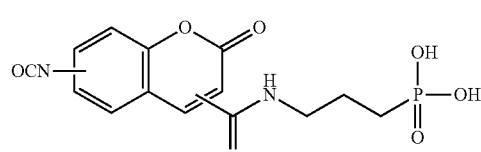
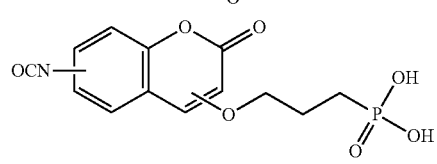
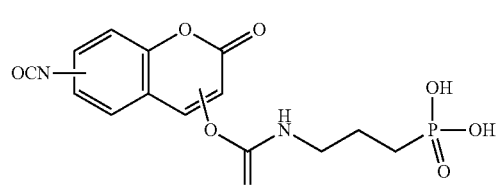
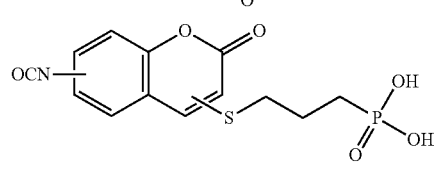
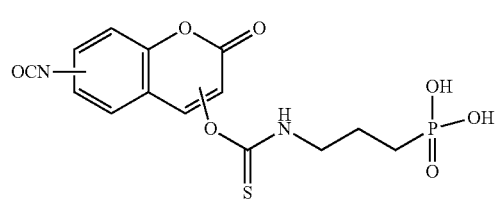
128
-continued
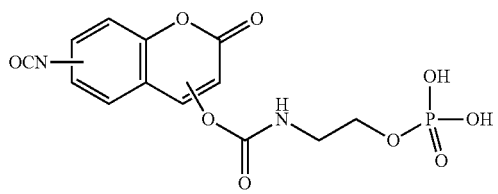
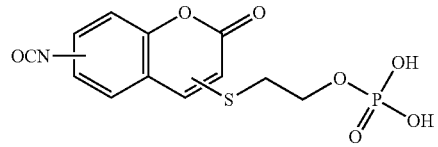
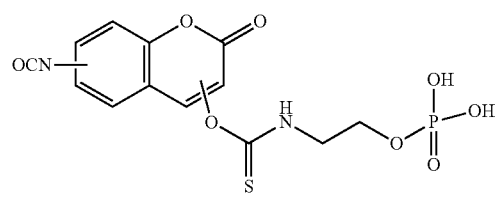
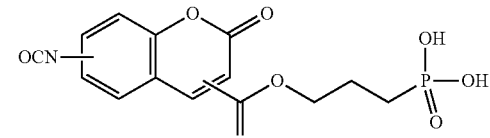
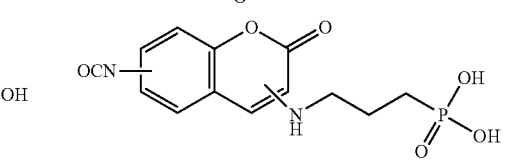
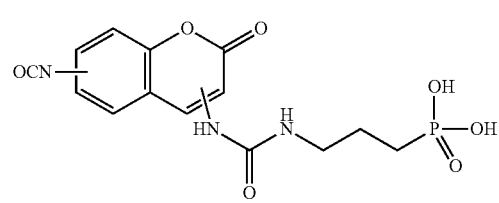
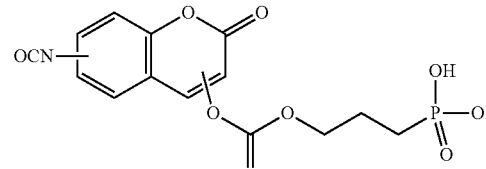
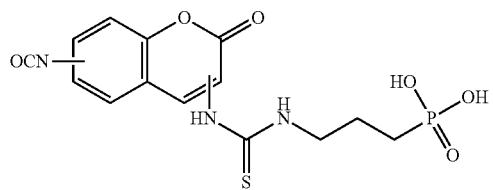
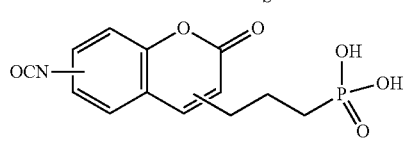

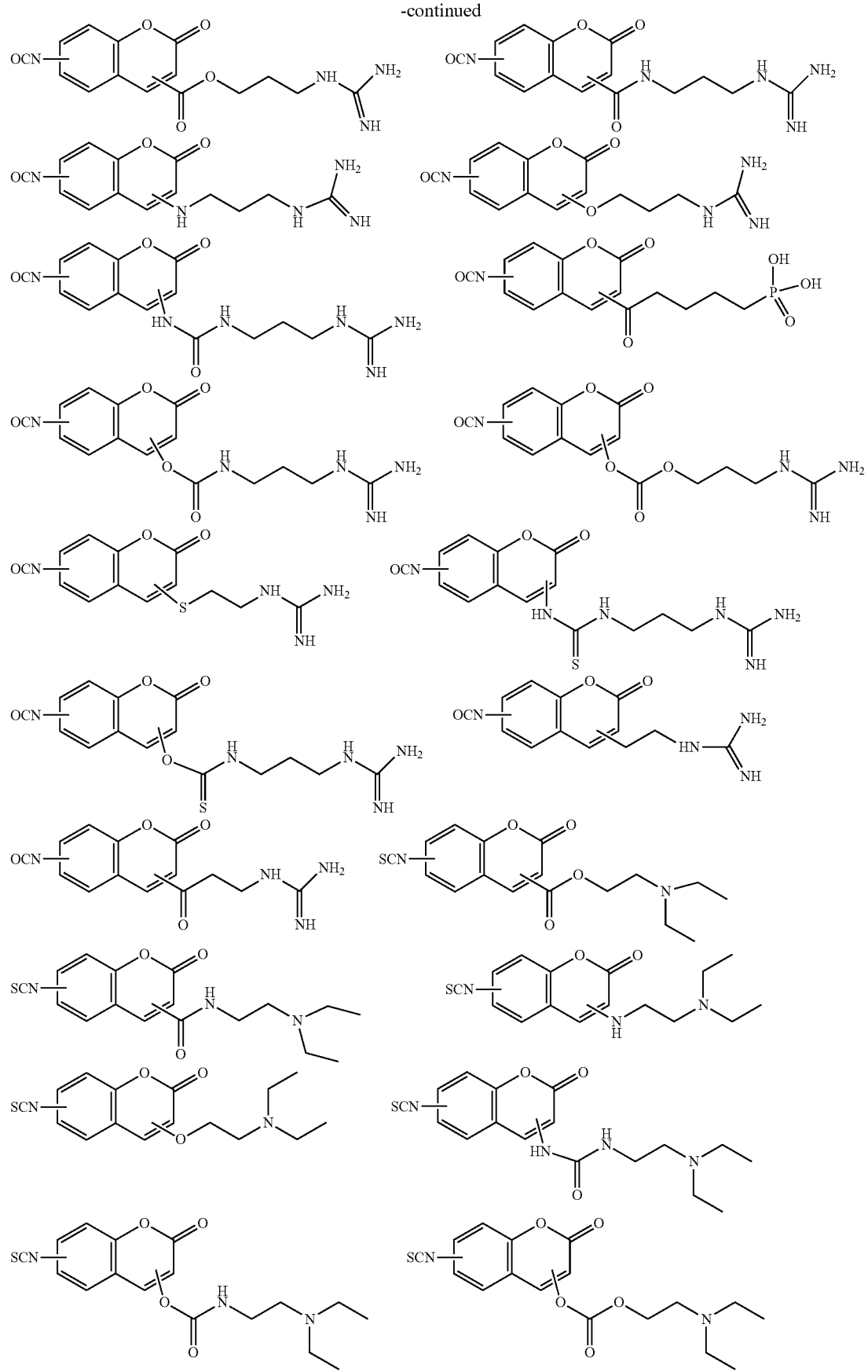

131
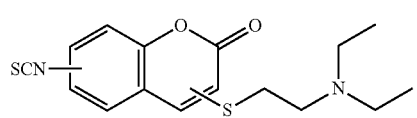
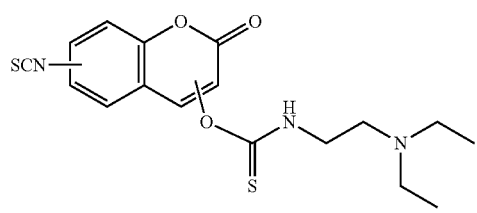
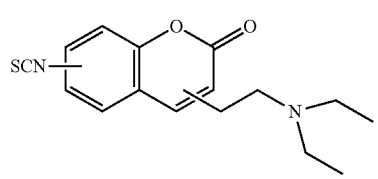
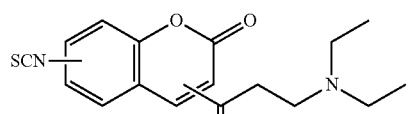
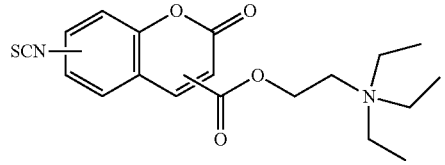
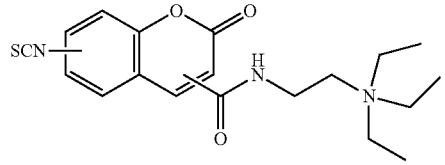
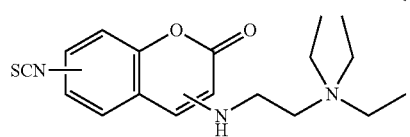
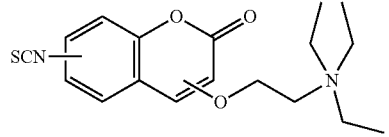
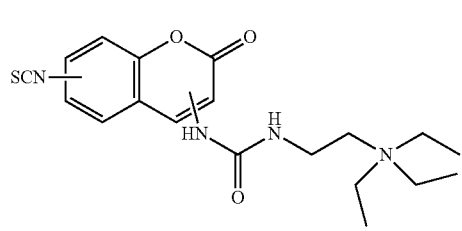
132
-continued
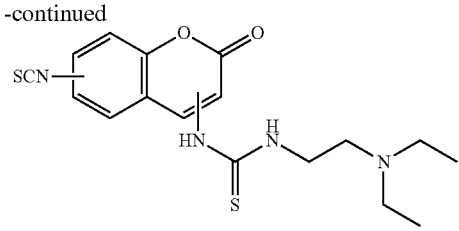
-continued
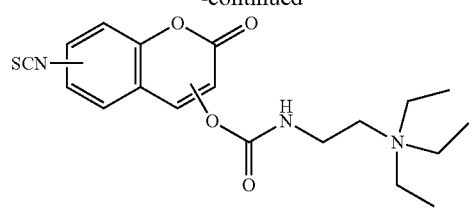
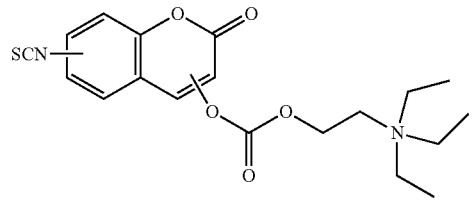
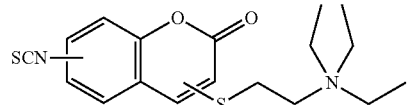
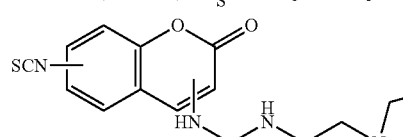
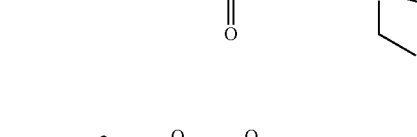
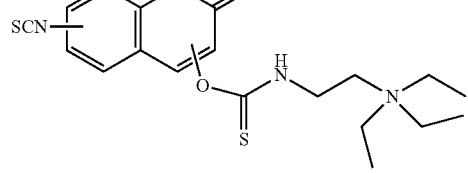
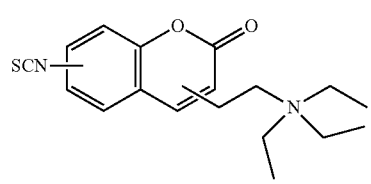

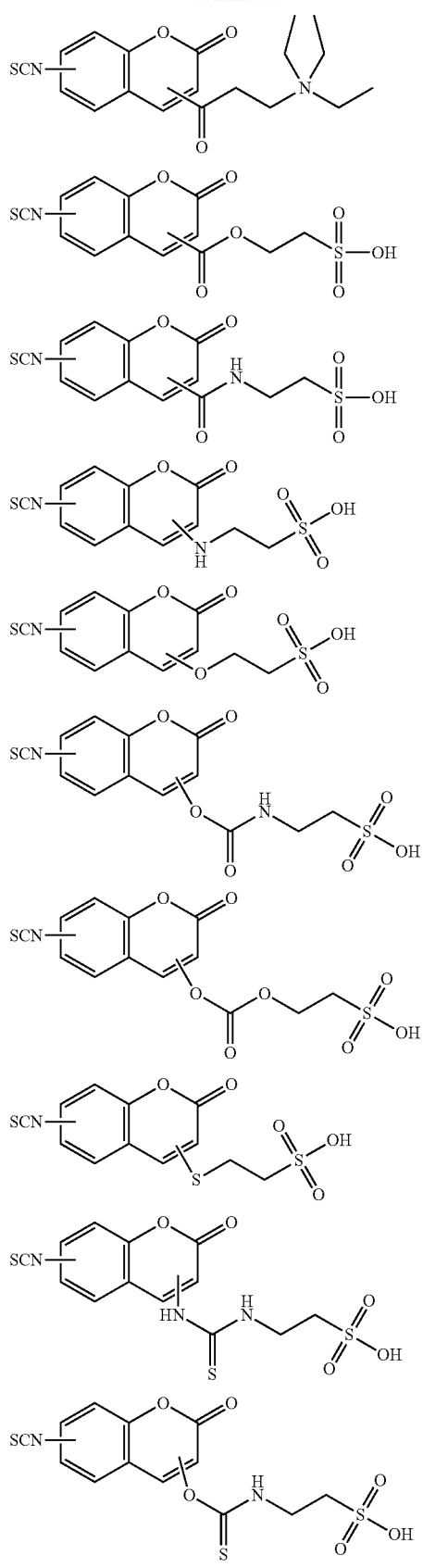
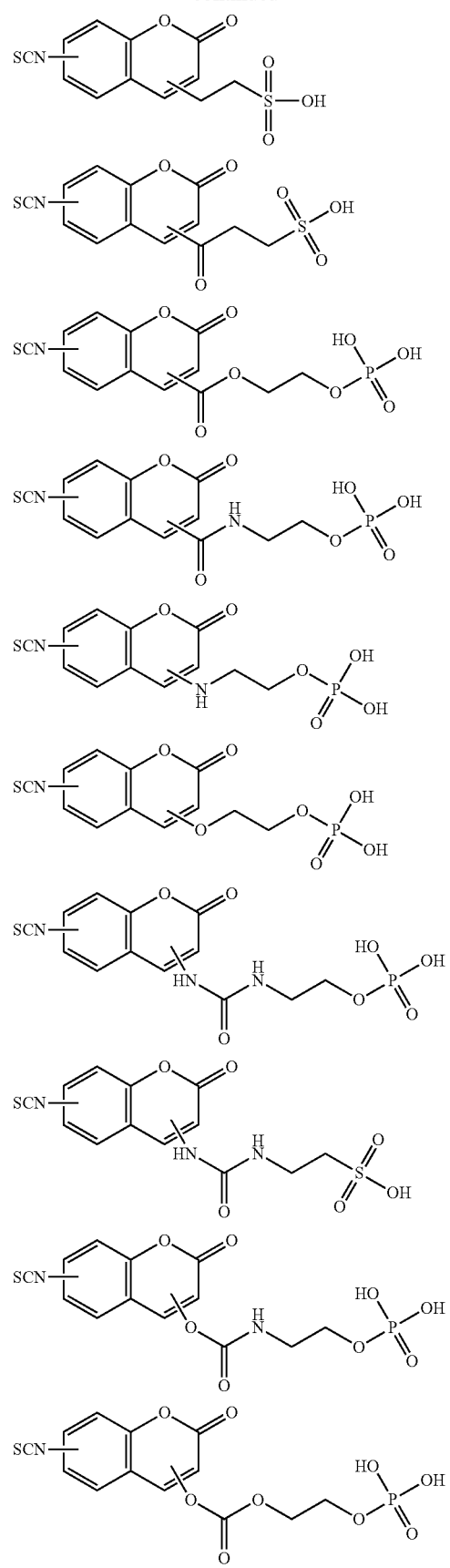

135
-continued
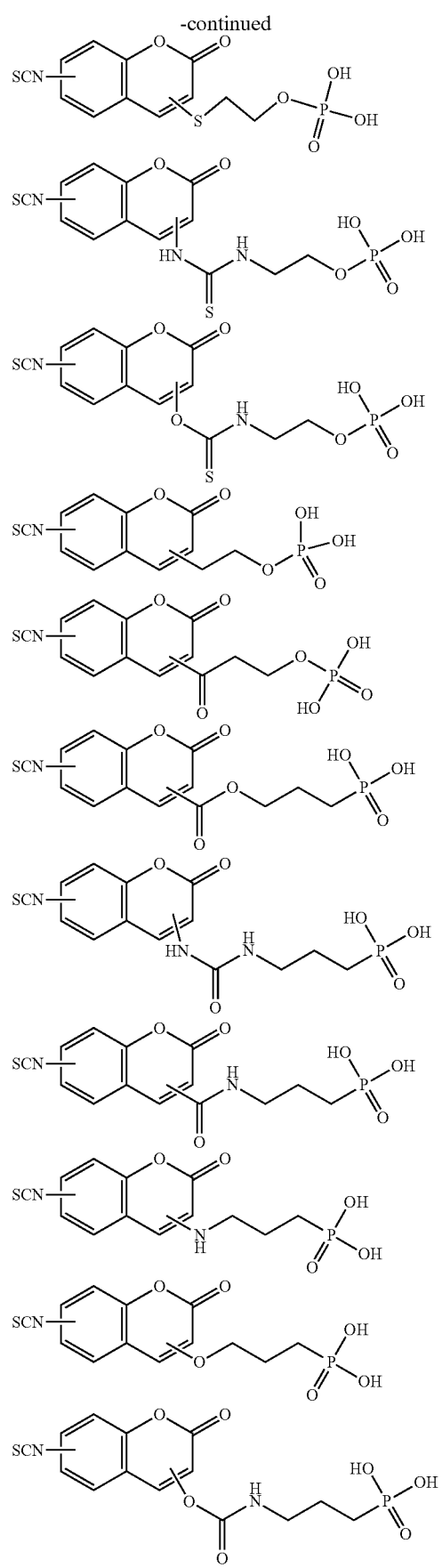
136
-continued
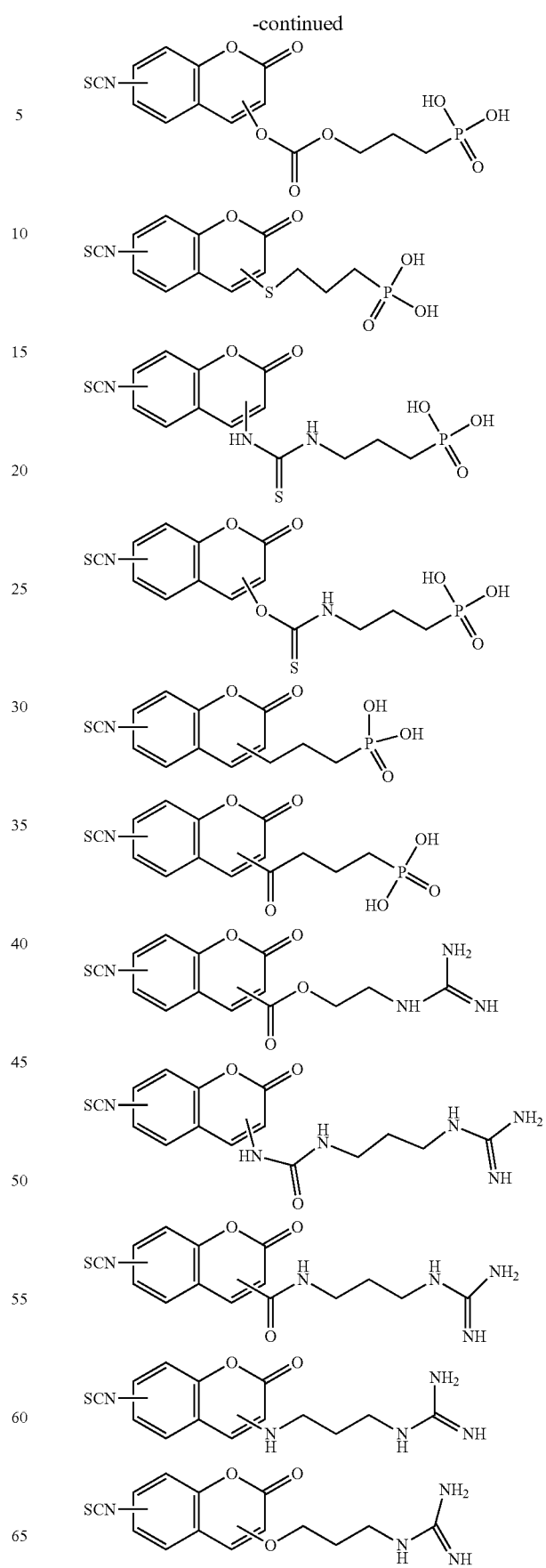

137
-continued
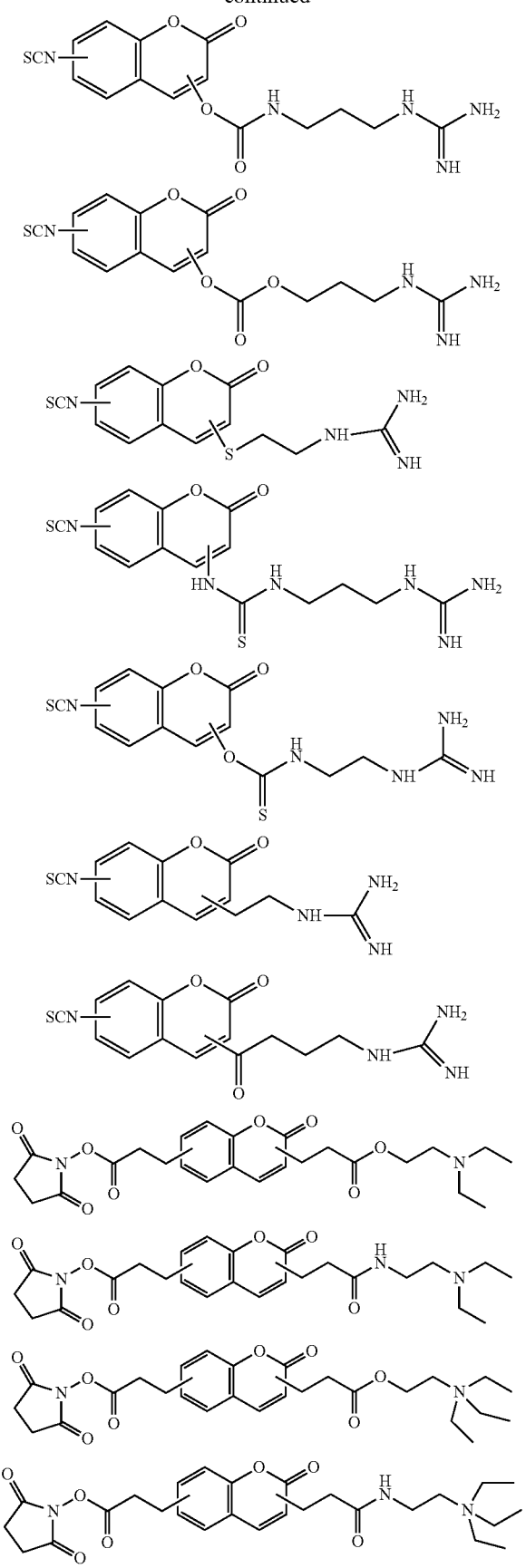
138
-continued
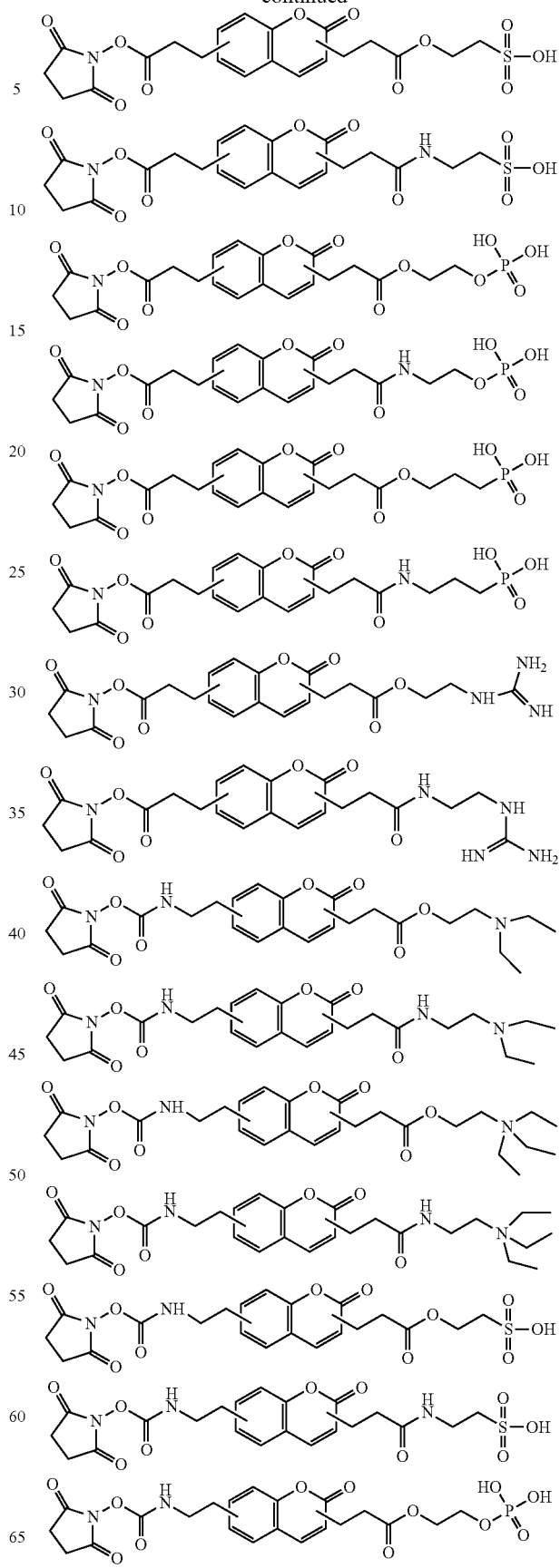

-continued
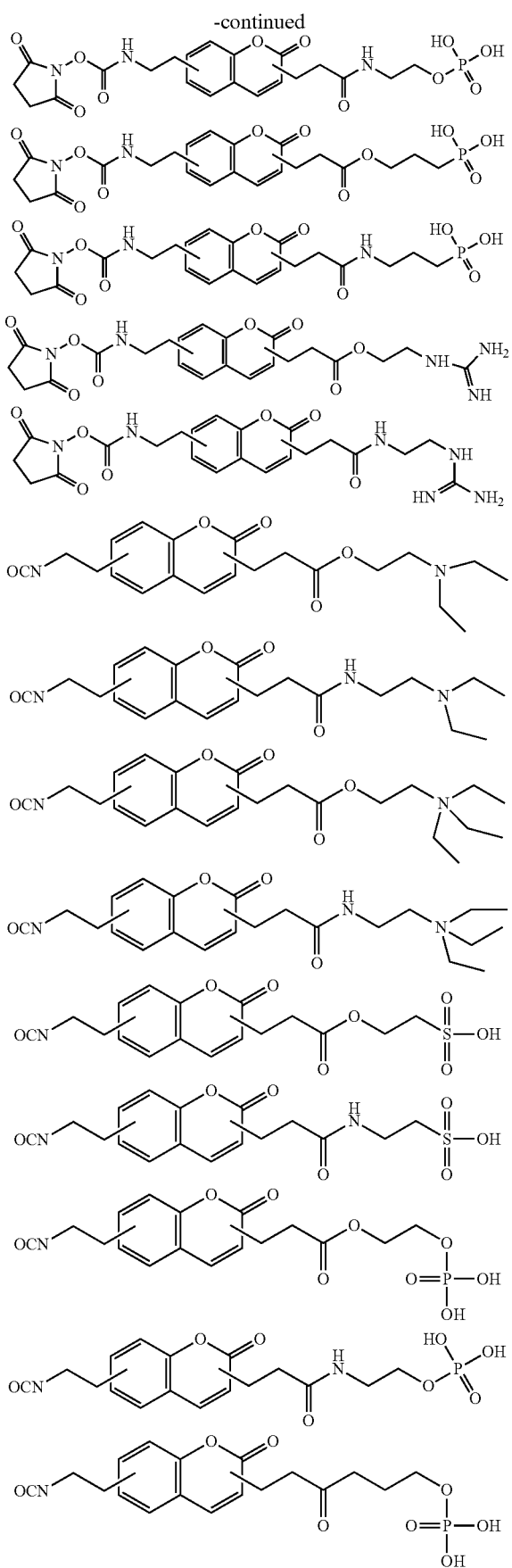
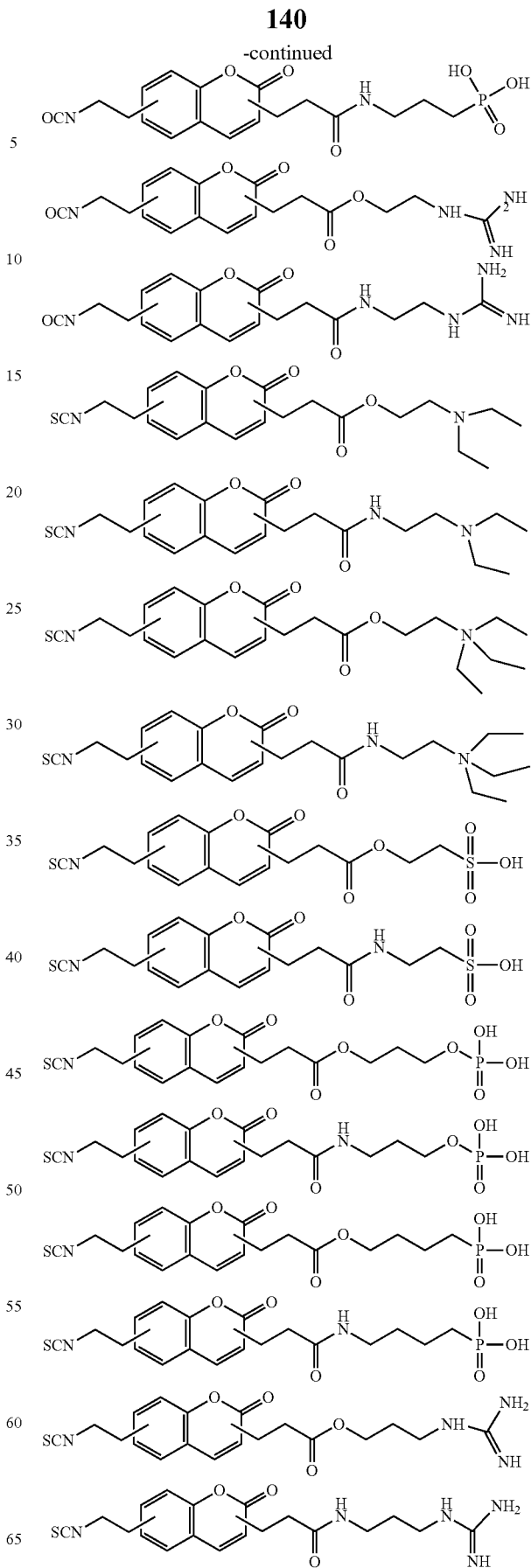

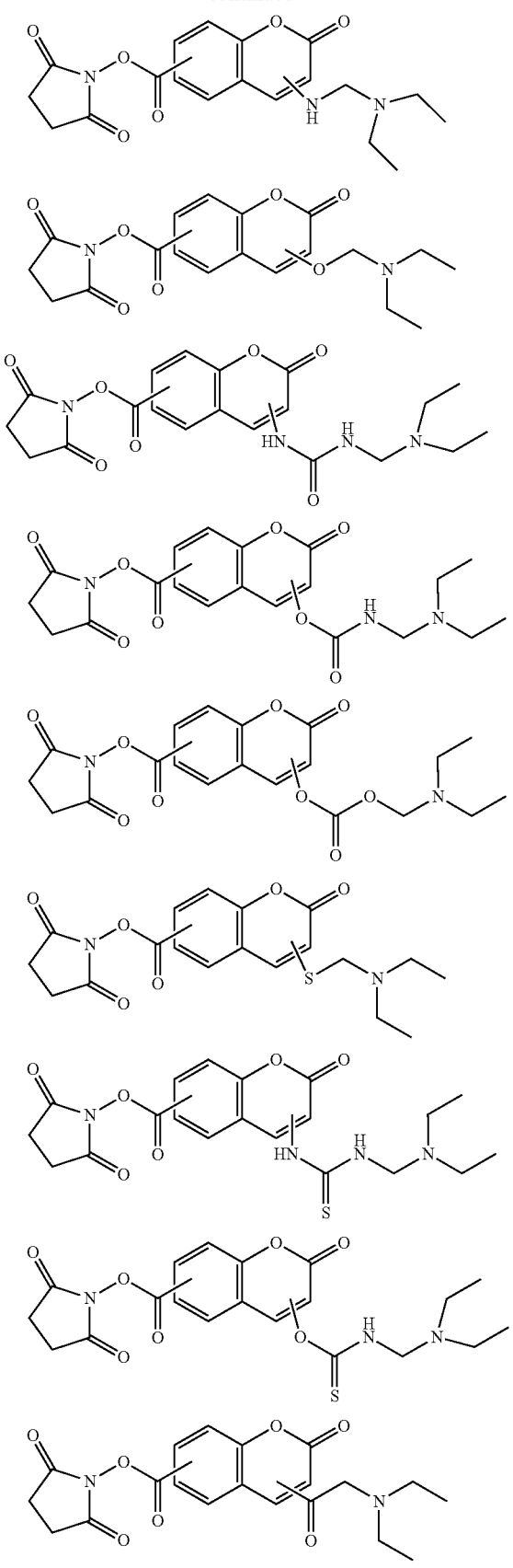
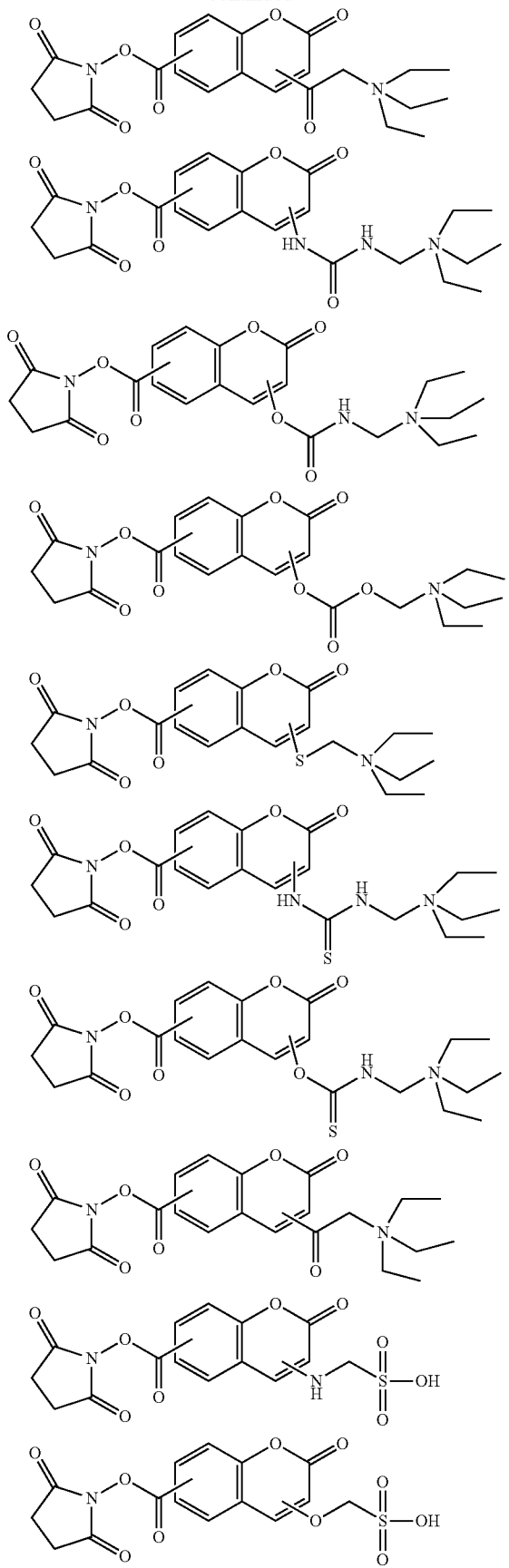

143
-continued
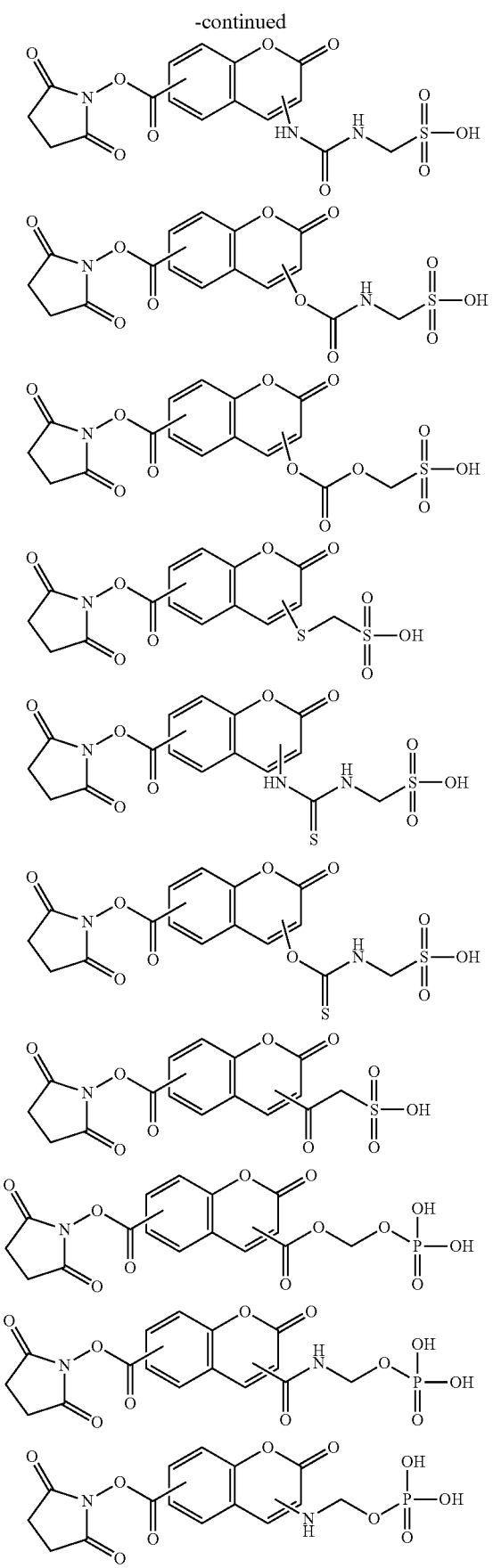
144
-continued
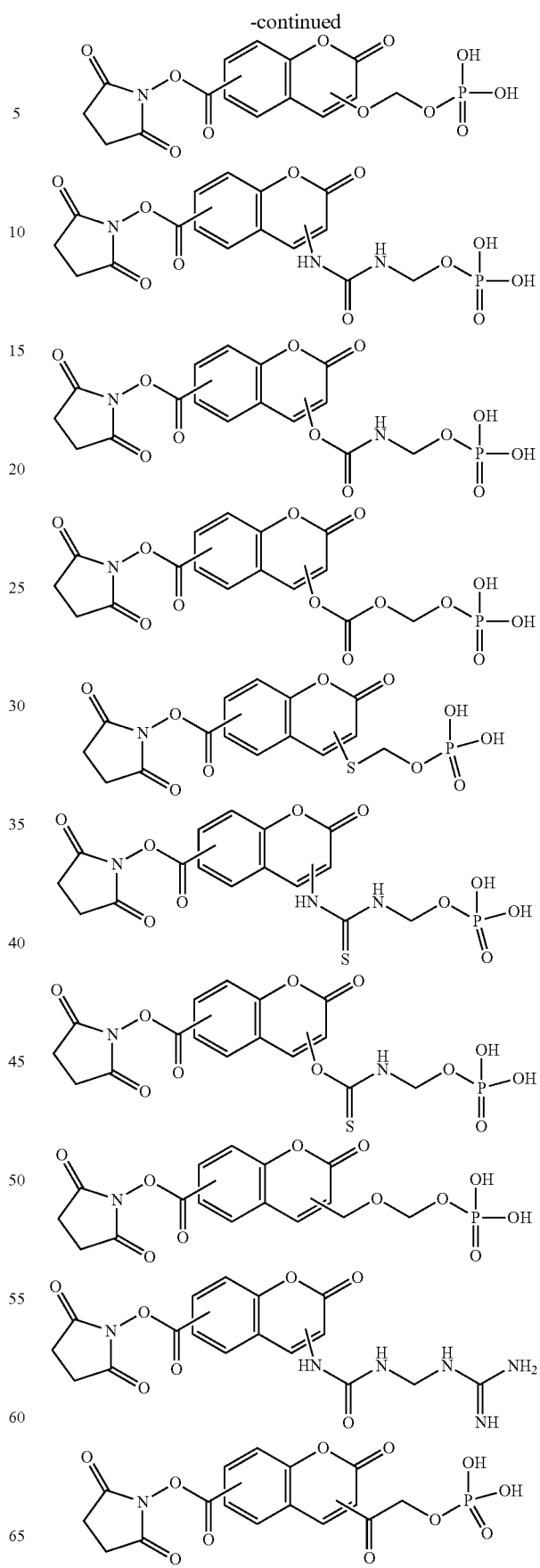

145
-continued
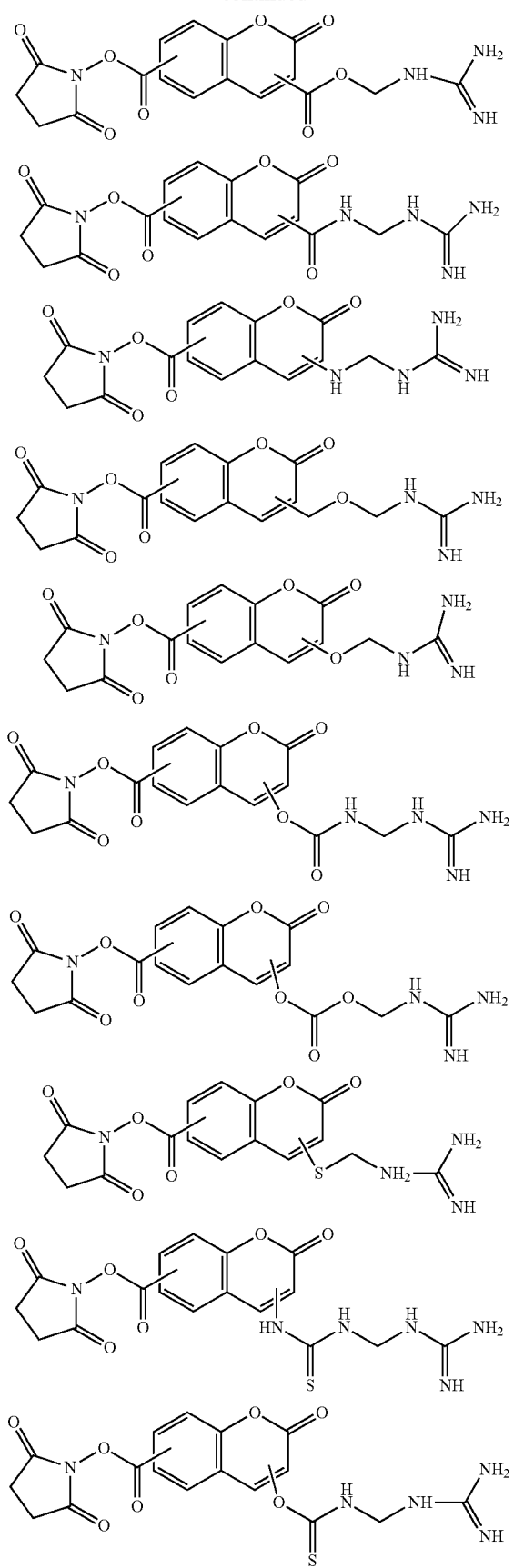
146
-continued
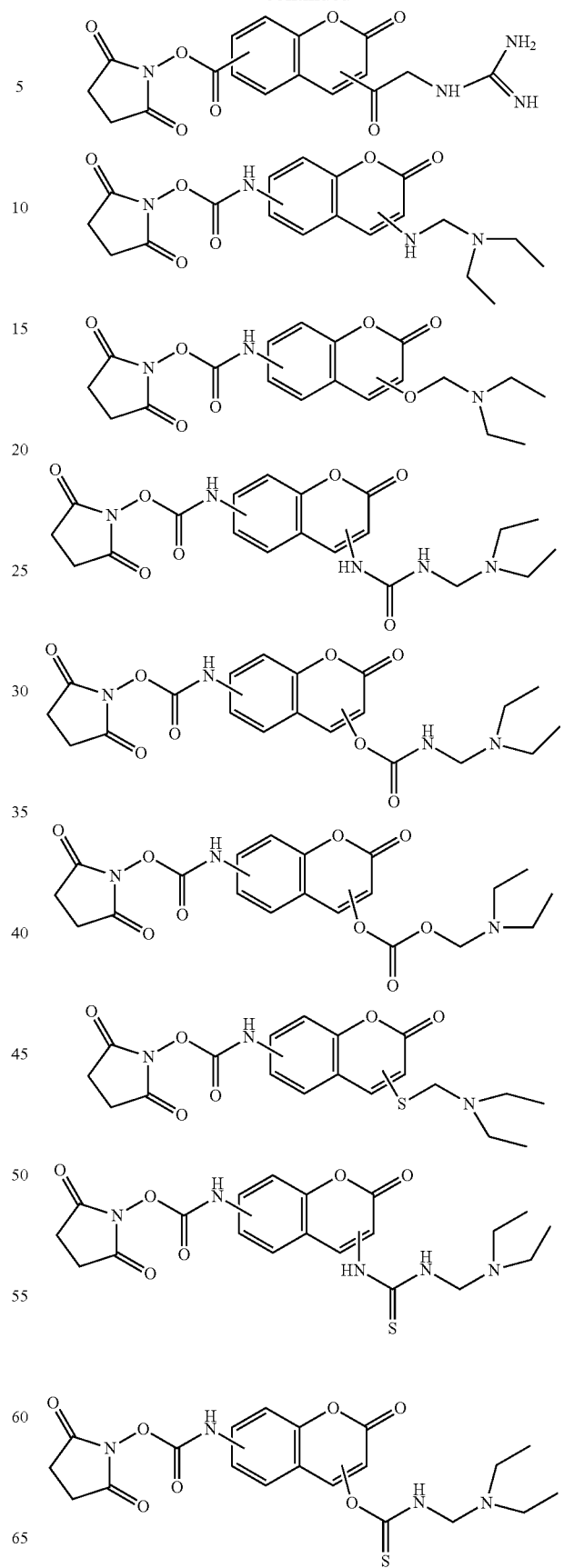

147
-continued
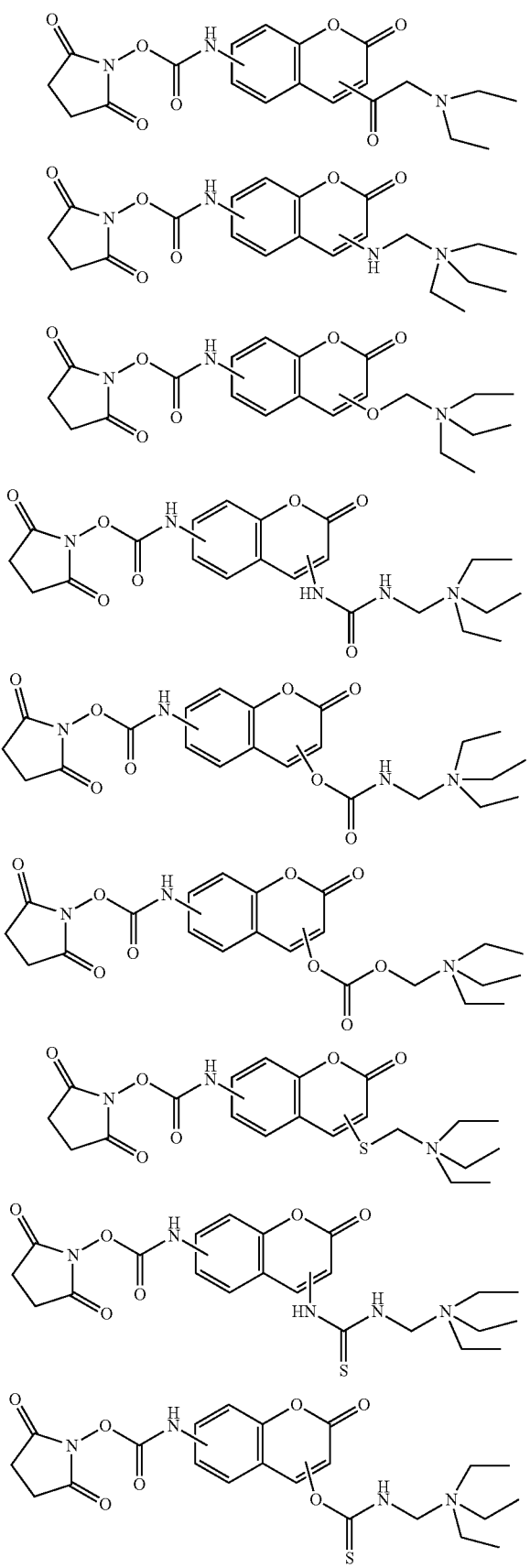
148
-continued
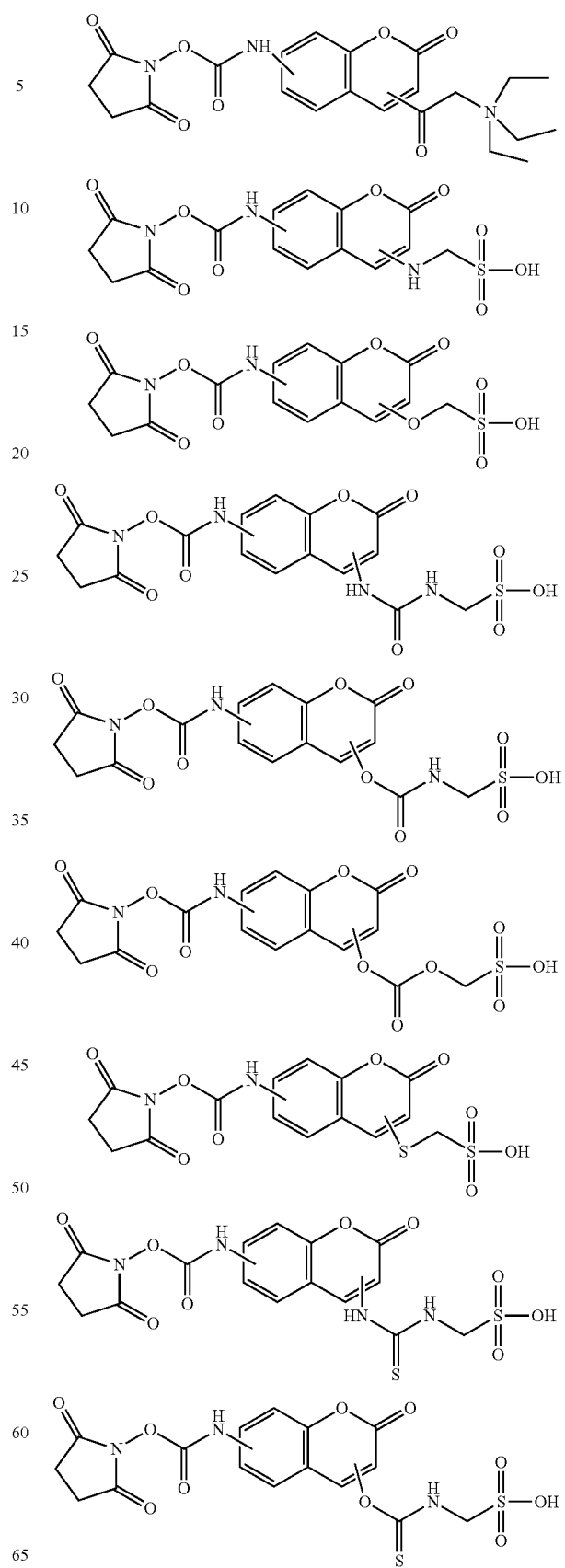

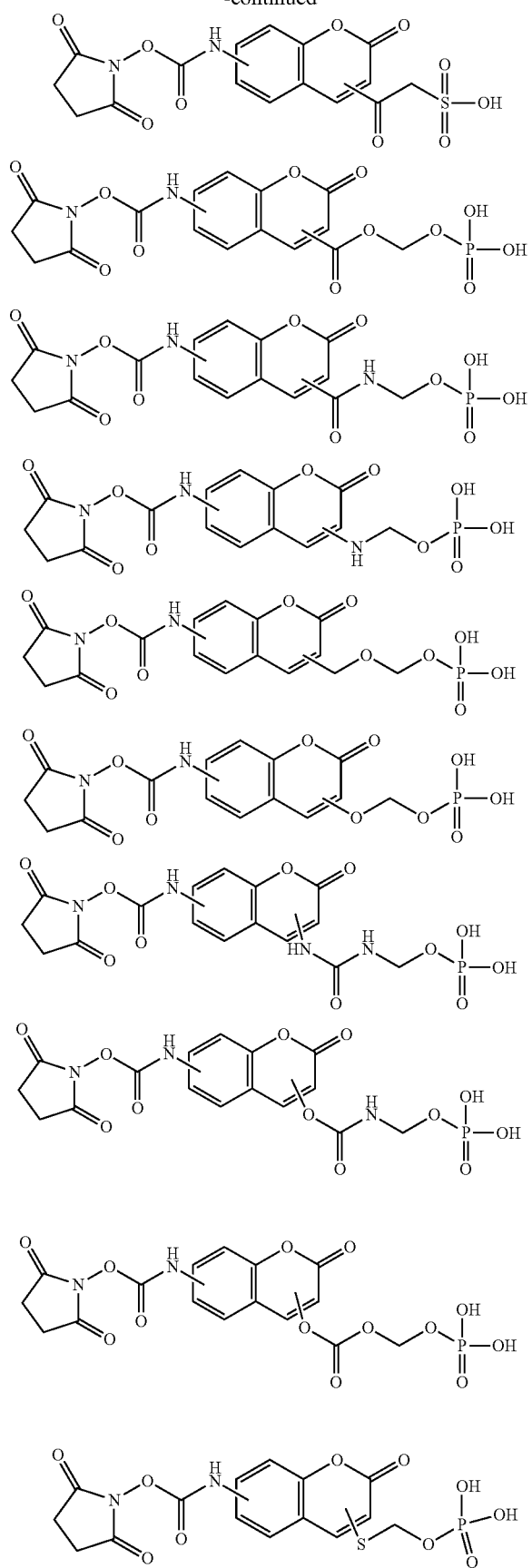

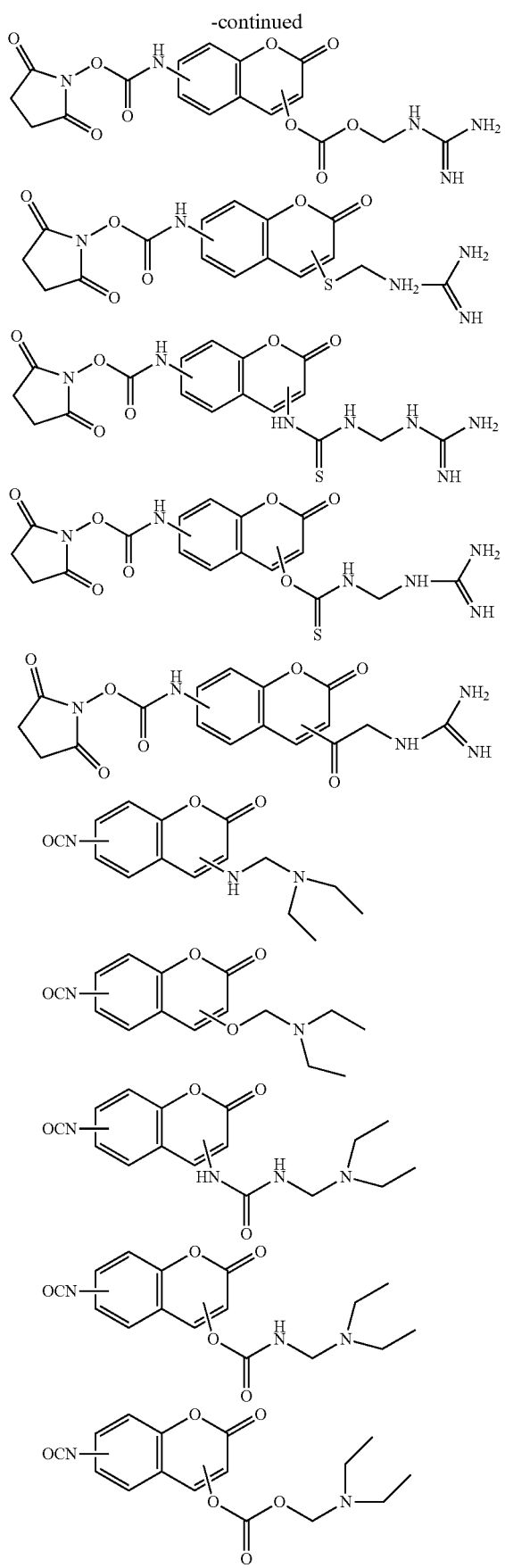
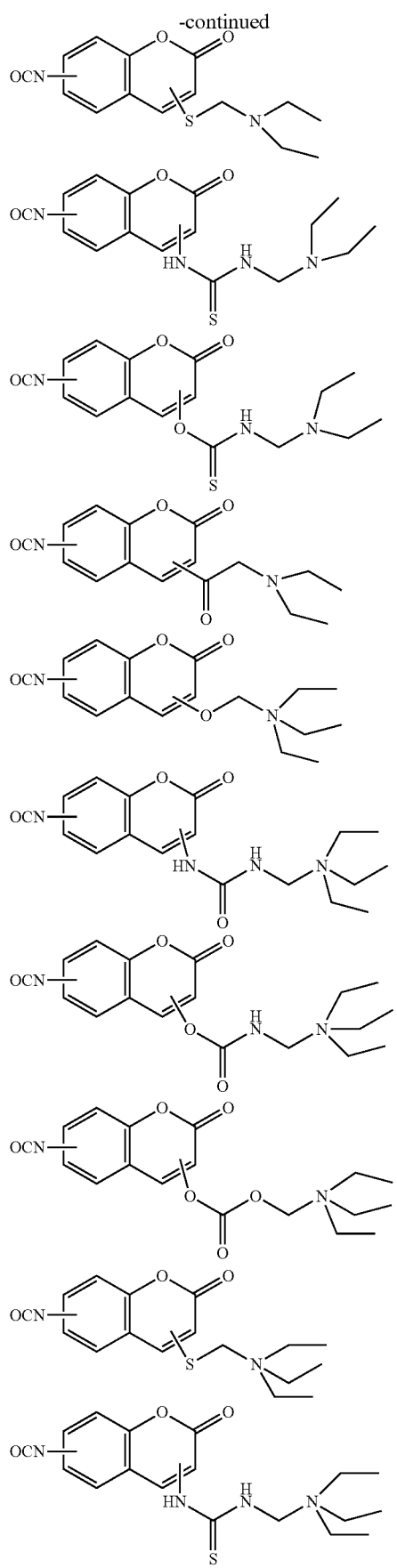

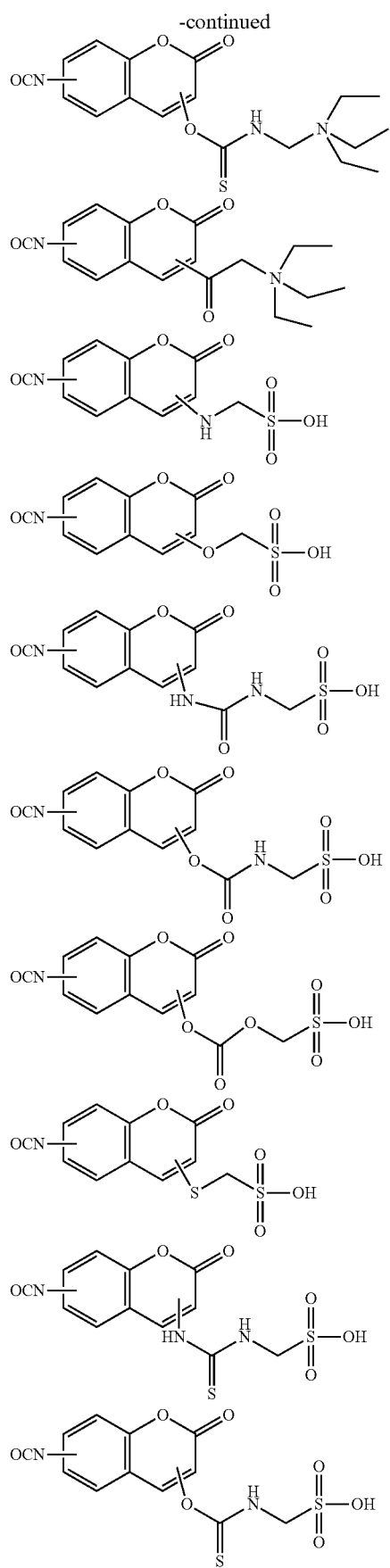
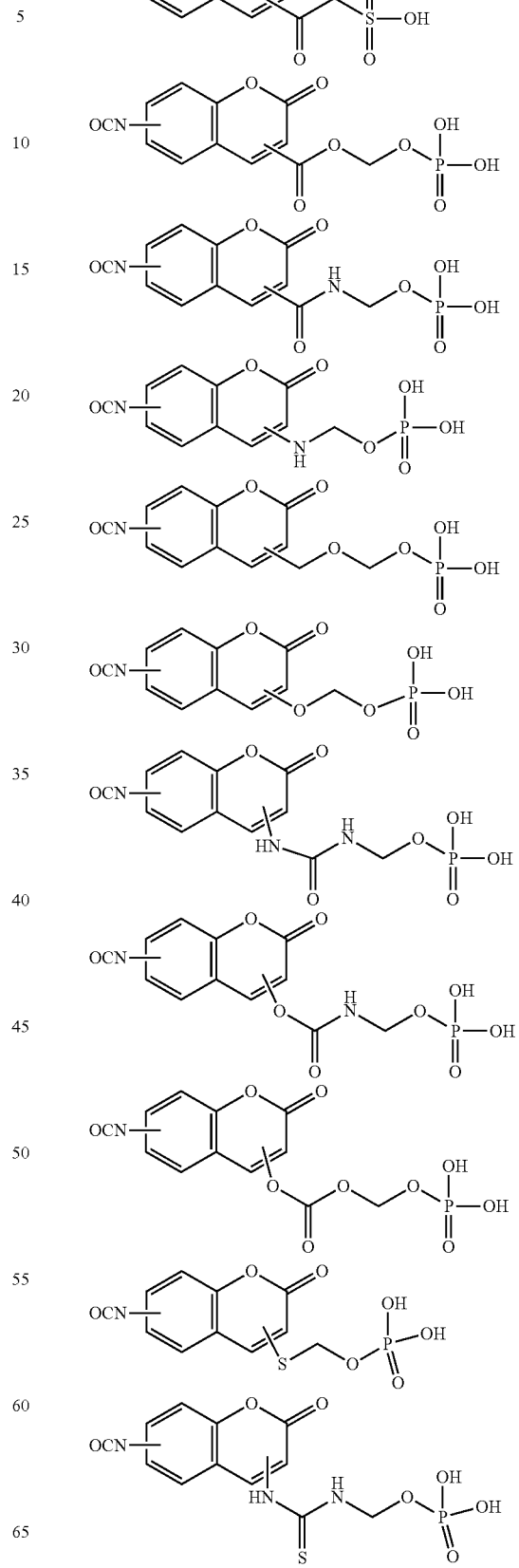

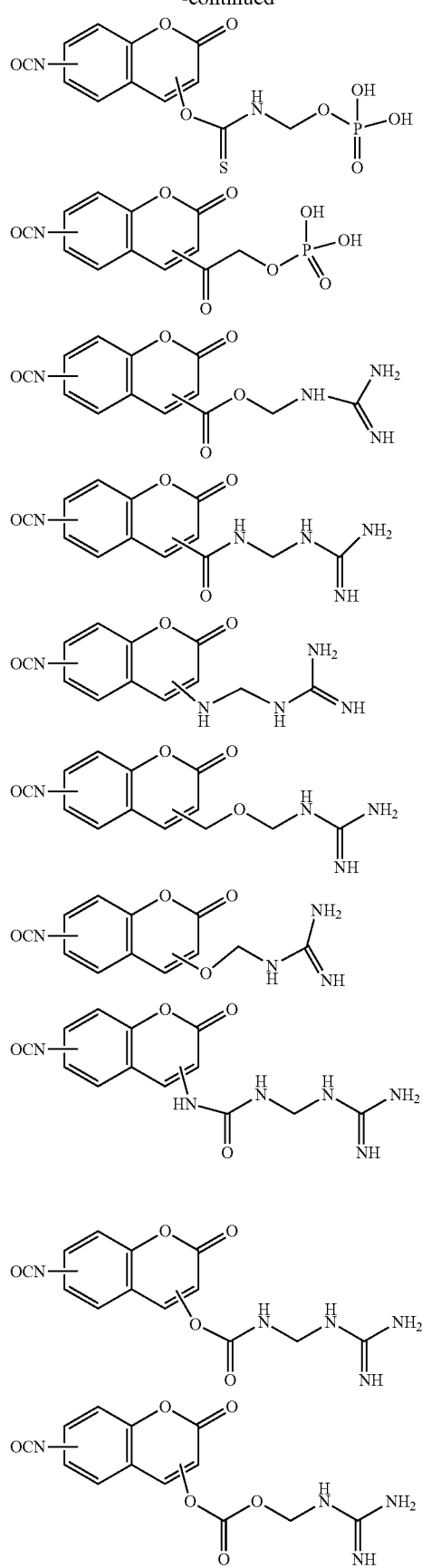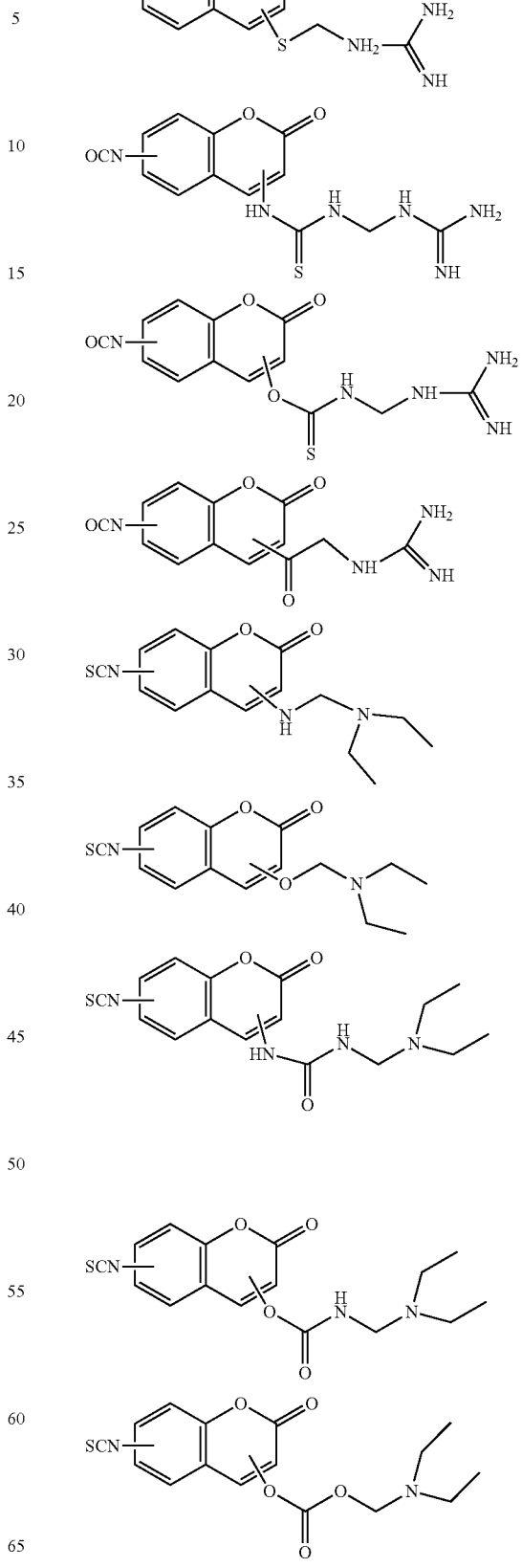

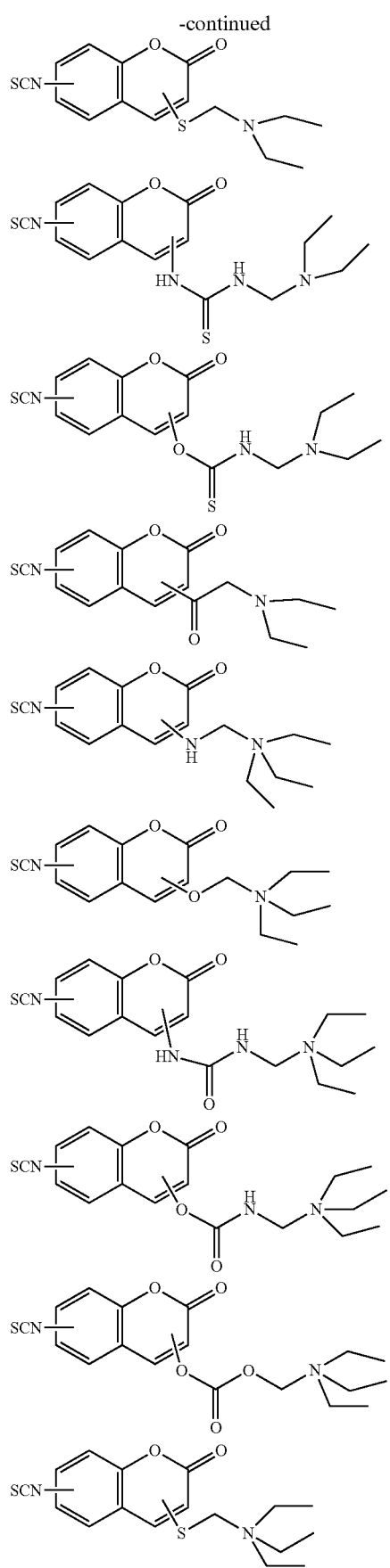
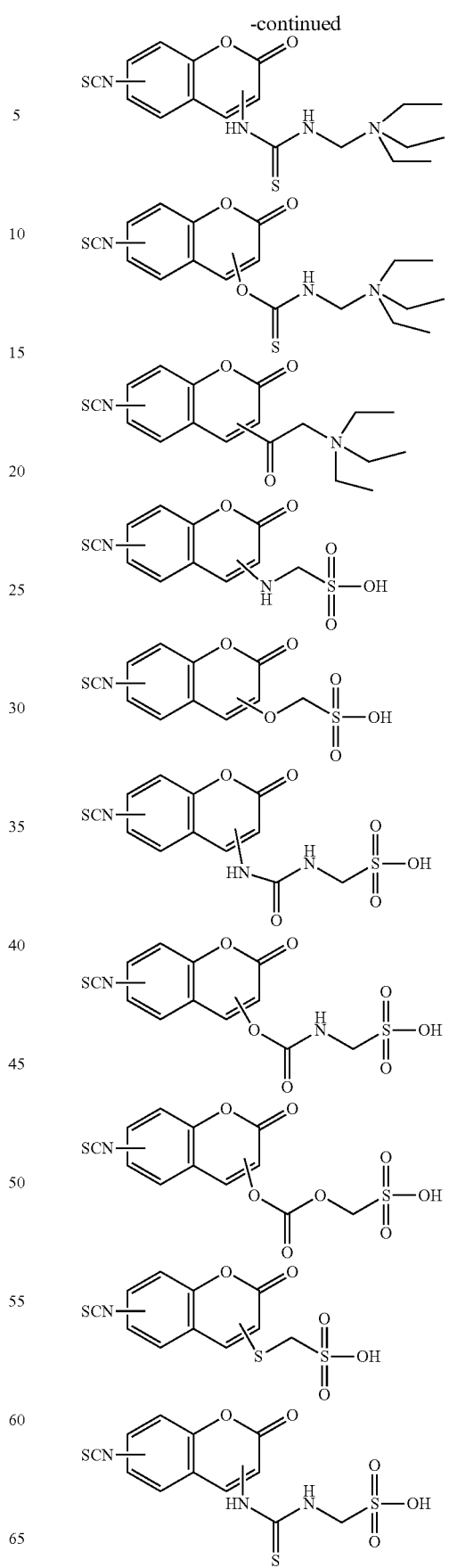

-continued
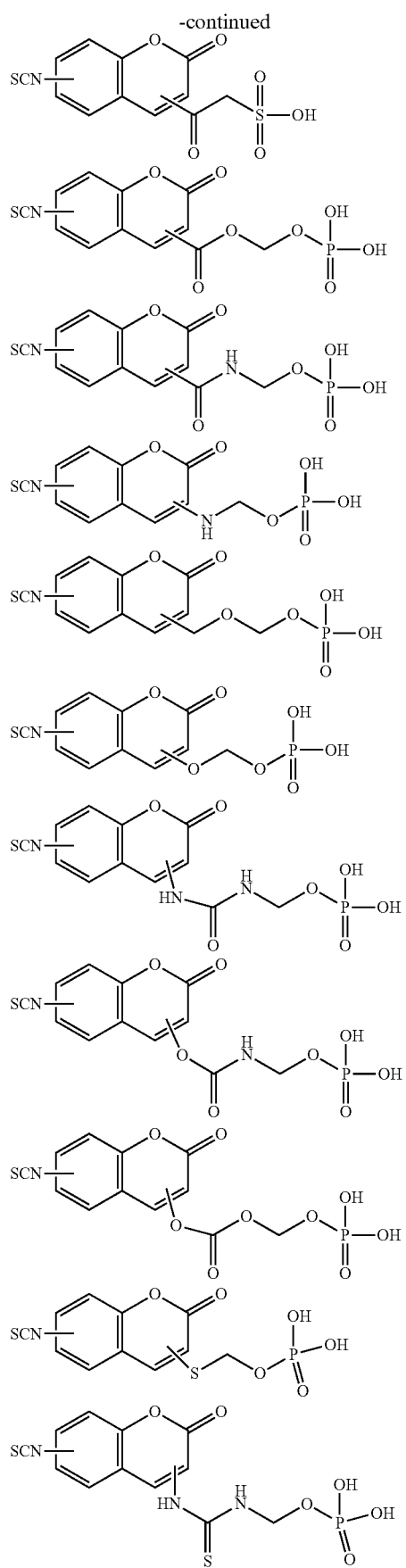
-continued
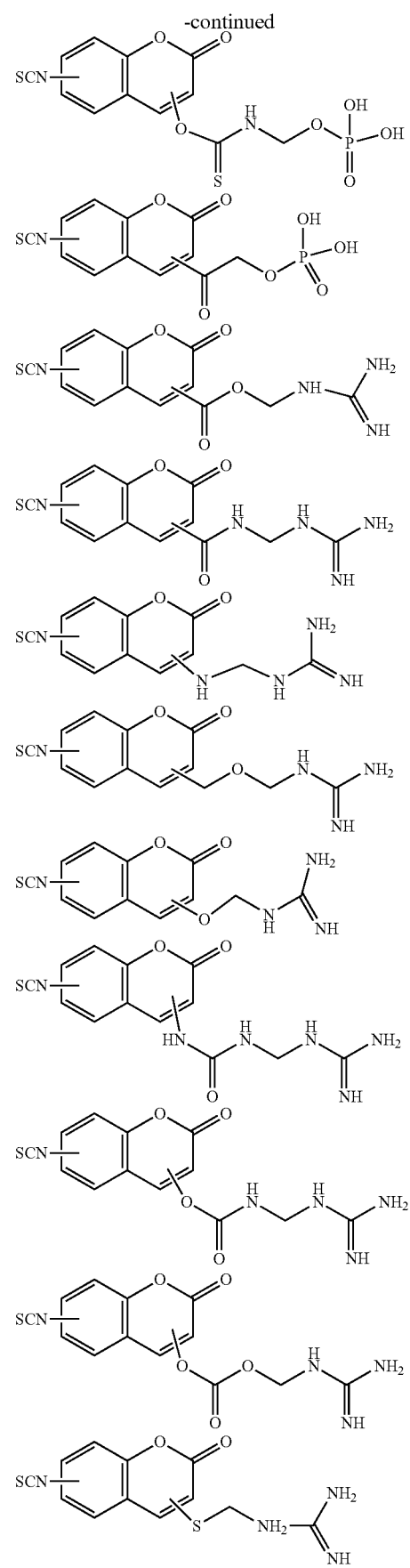

161
-continued
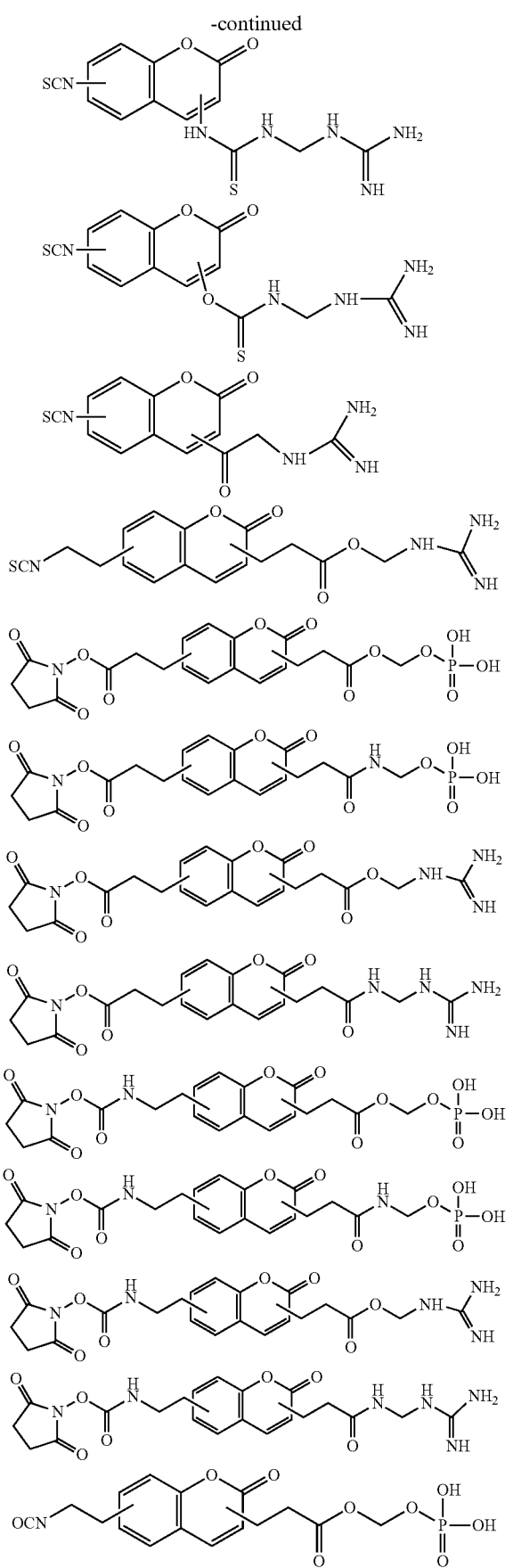
162
-continued
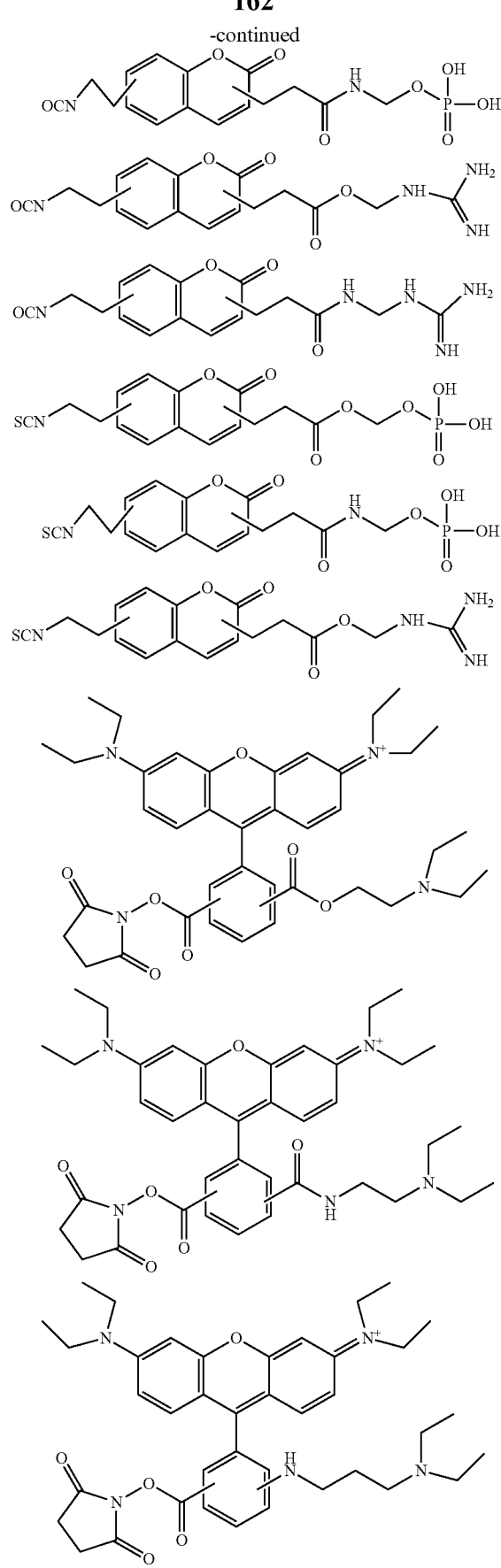

163
-continued
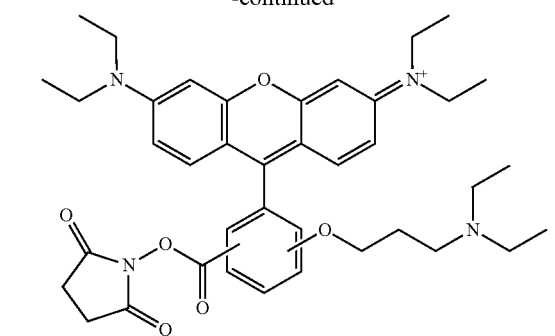
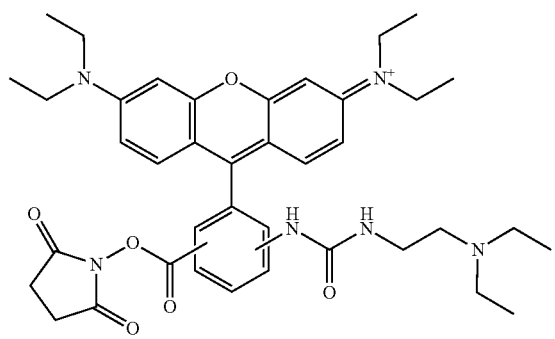
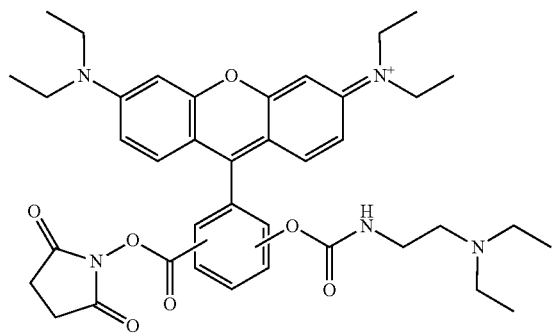
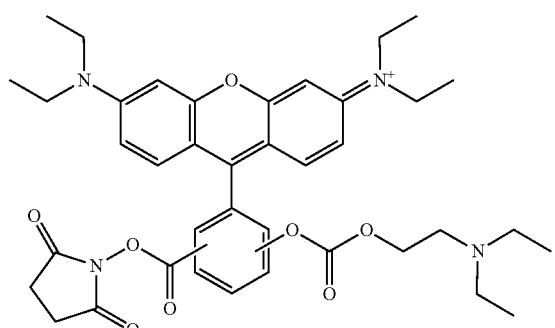
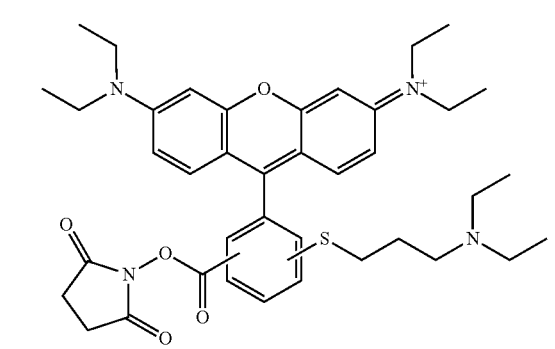
164
-continued
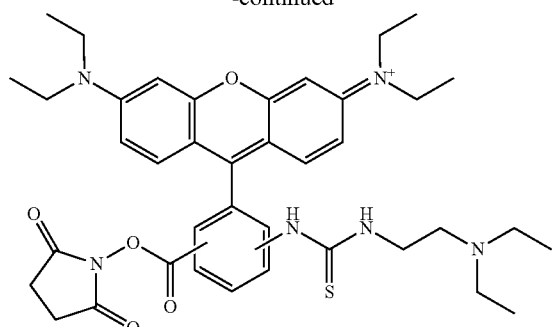
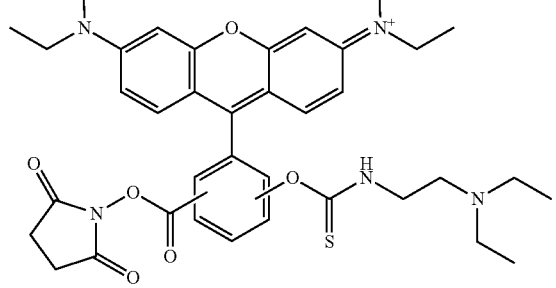
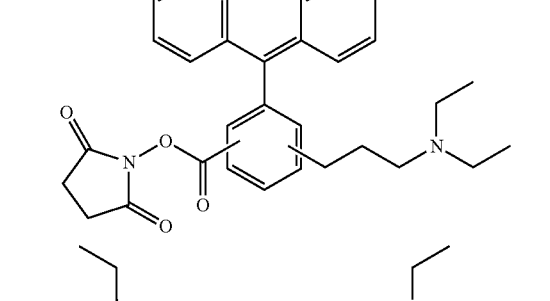
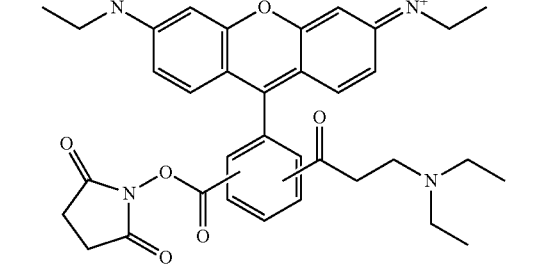
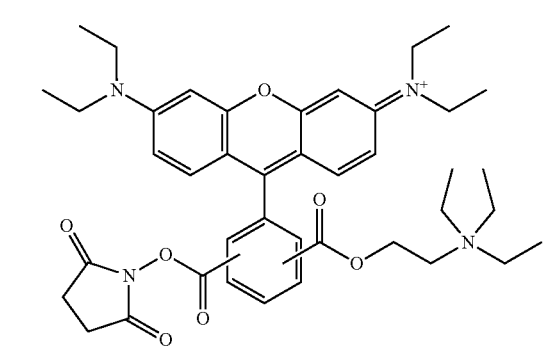

165
-continued
166
-continued
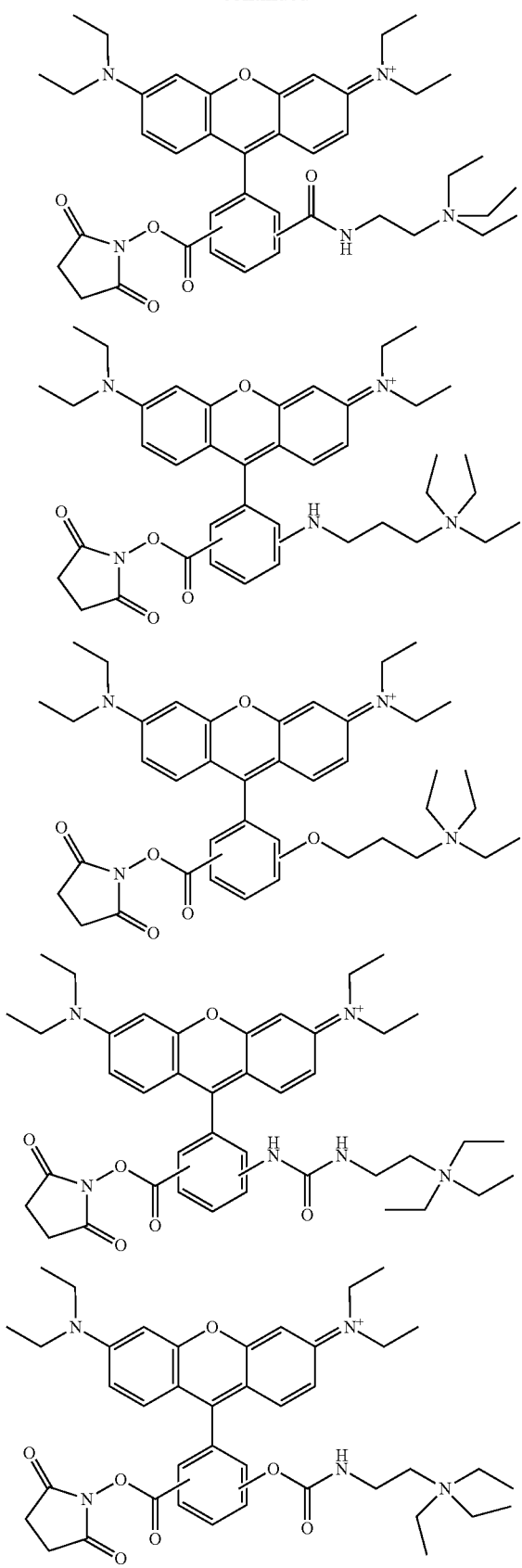
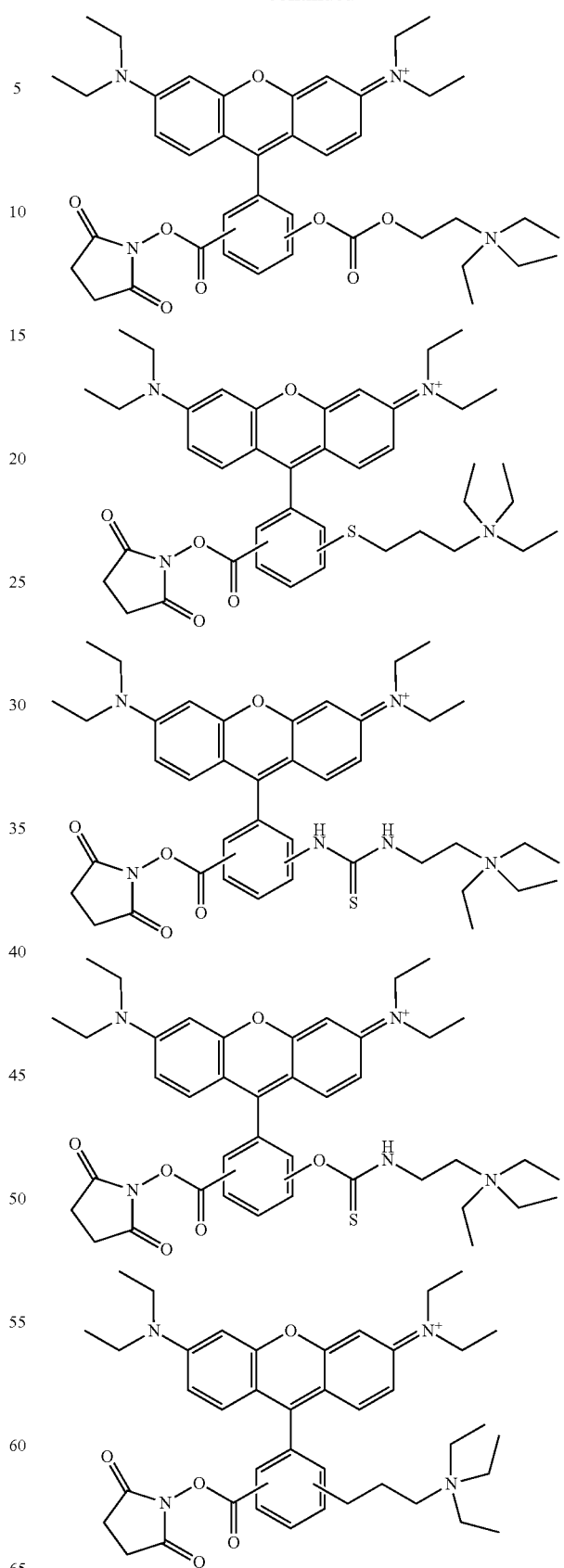

167
-continued
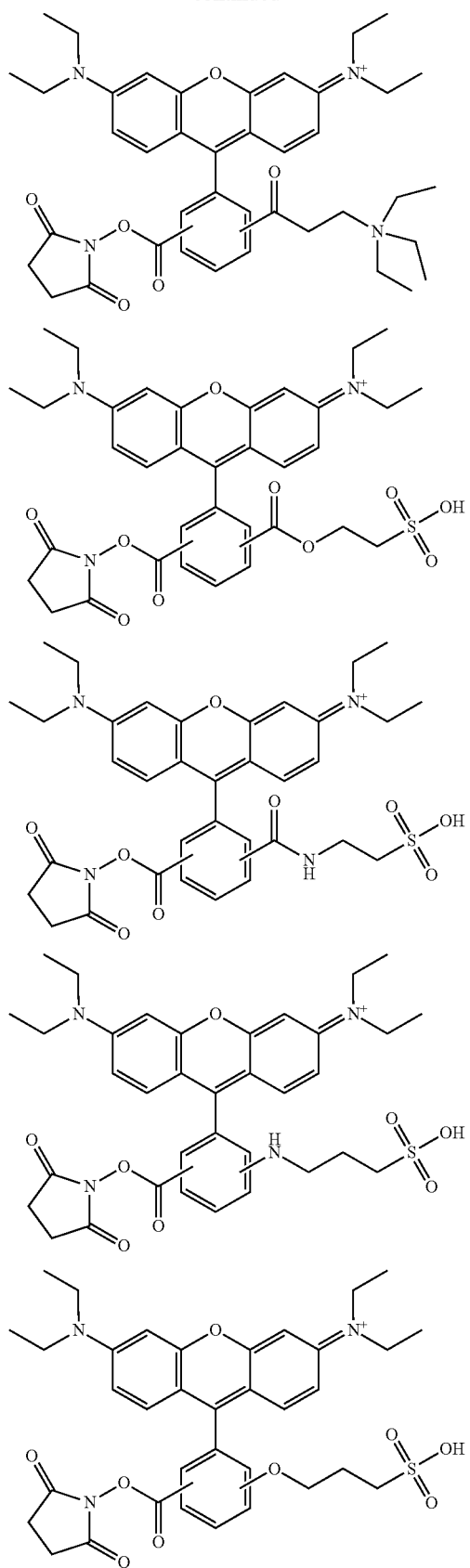
168
-continued
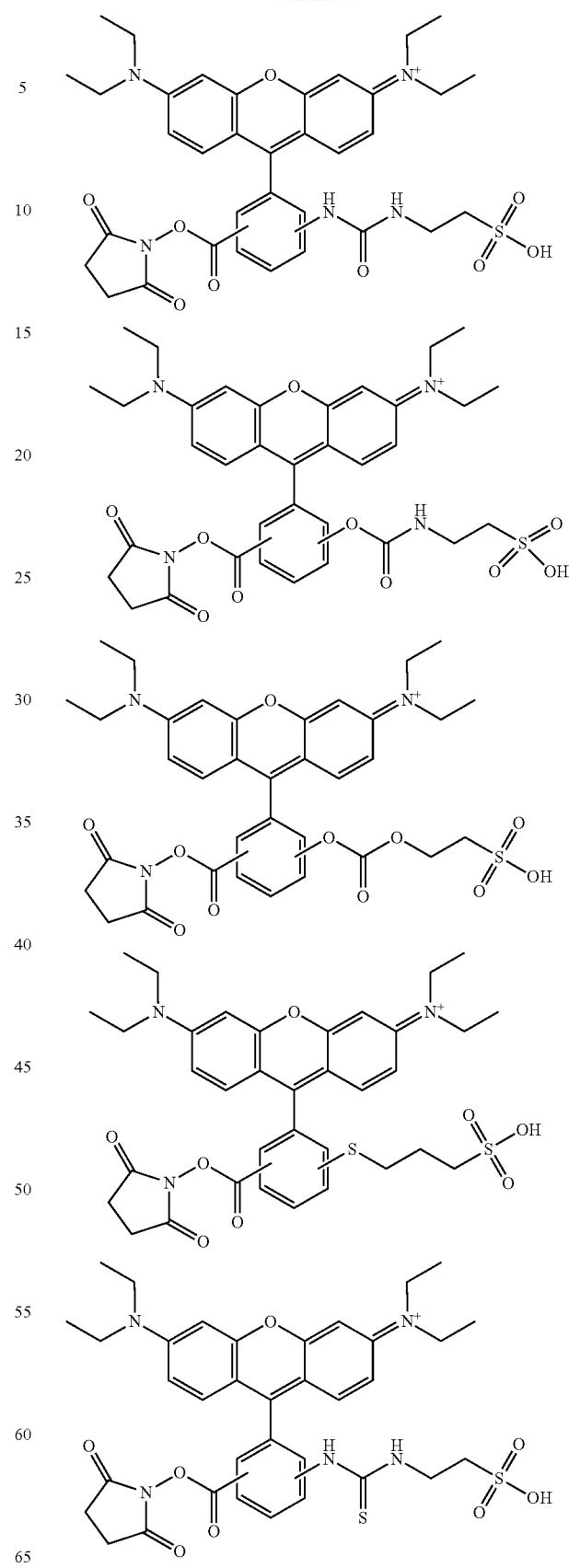

169
-continued
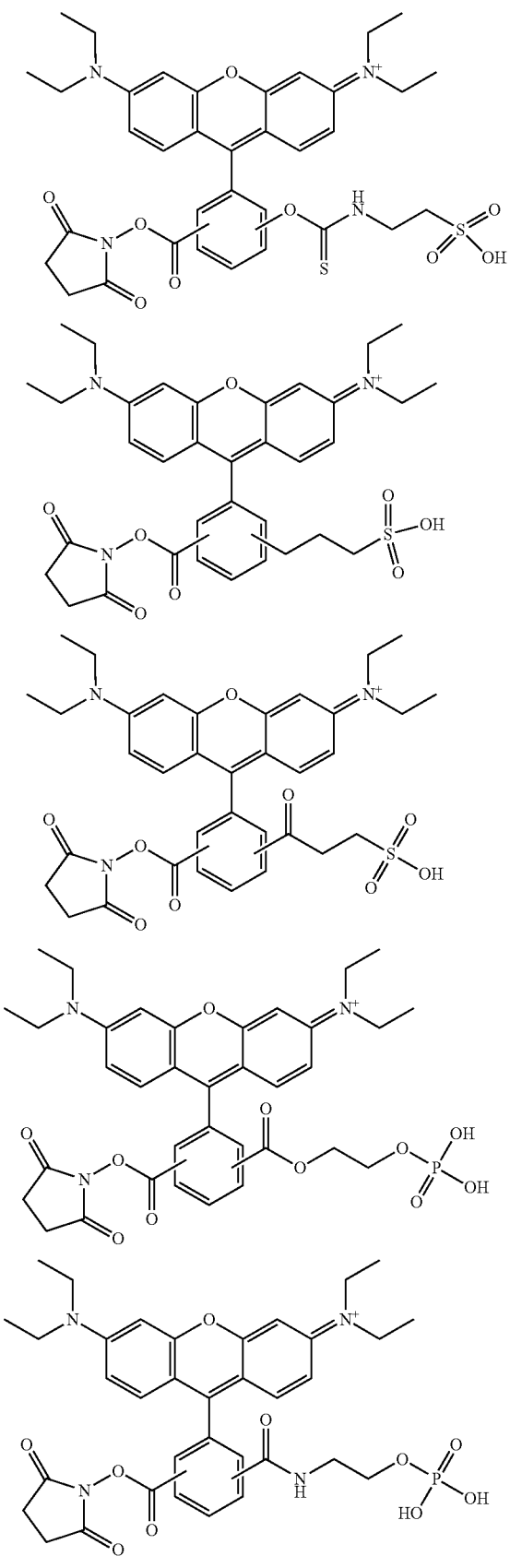
170
-continued
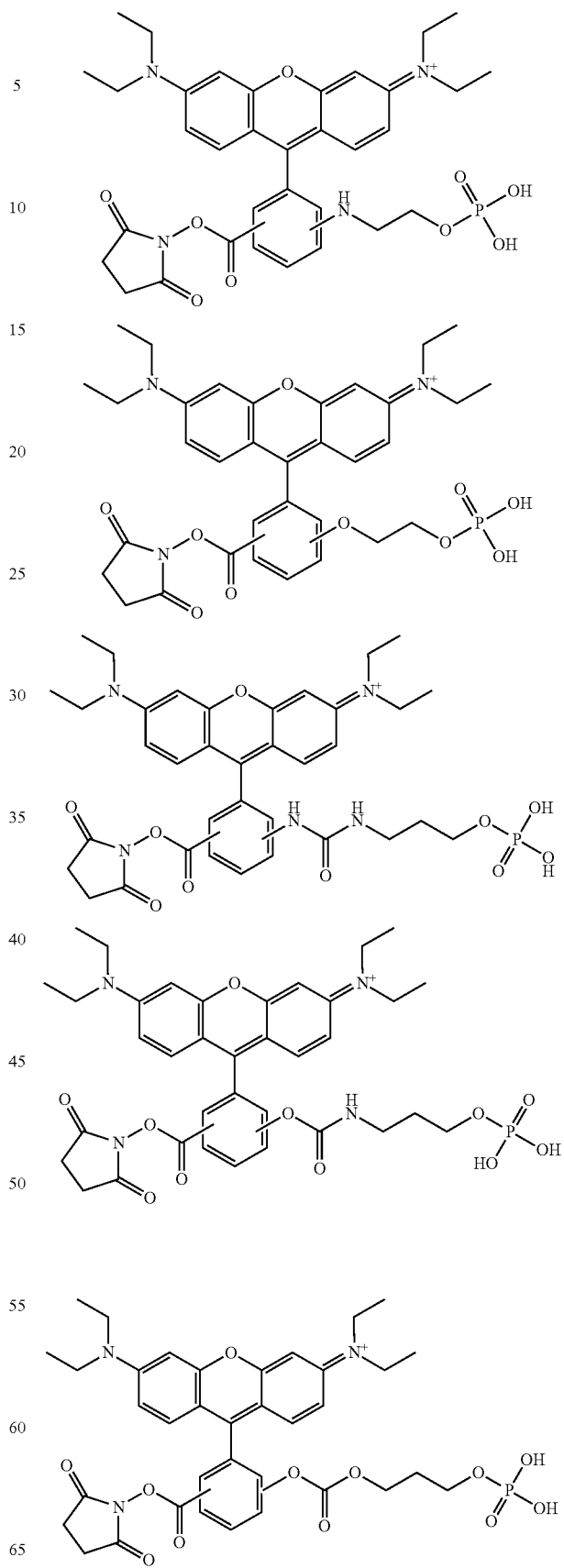

171
-continued
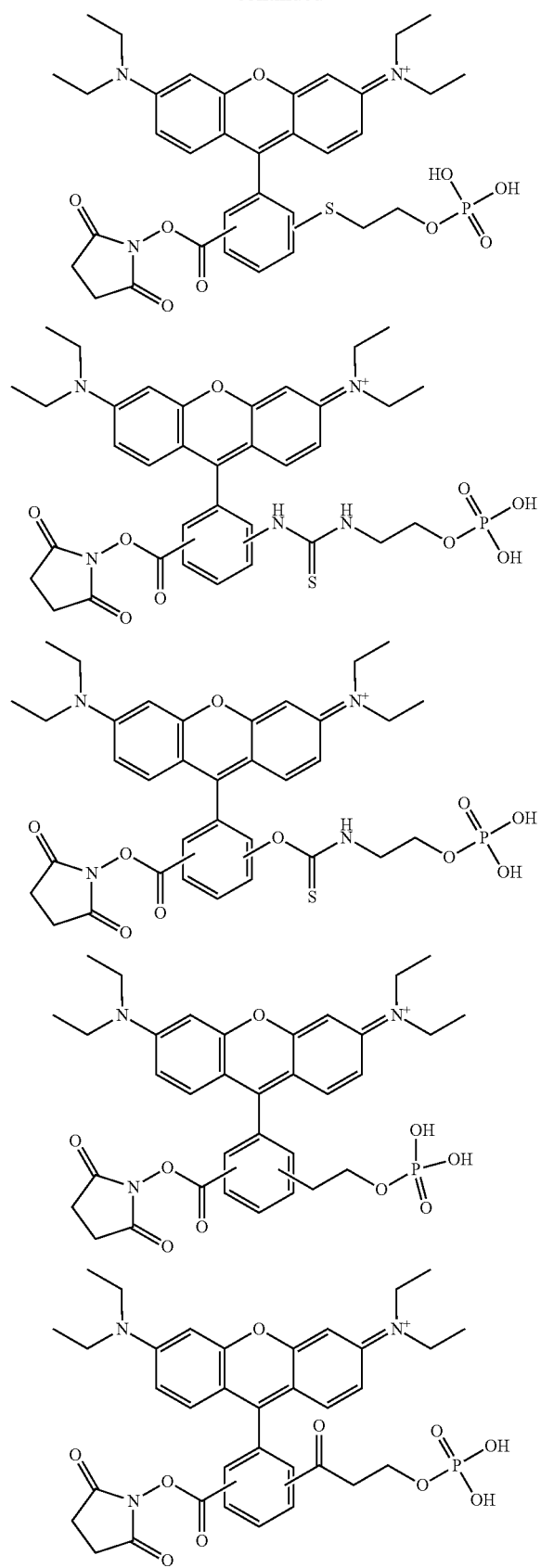
172
-continued
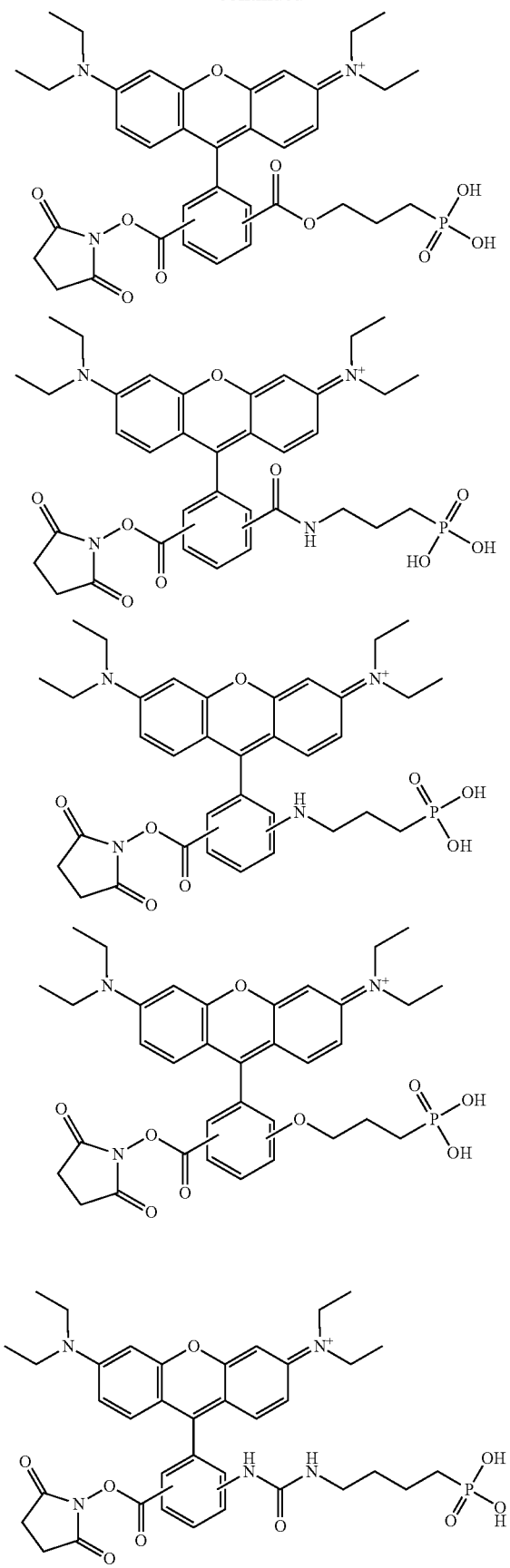

173
-continued
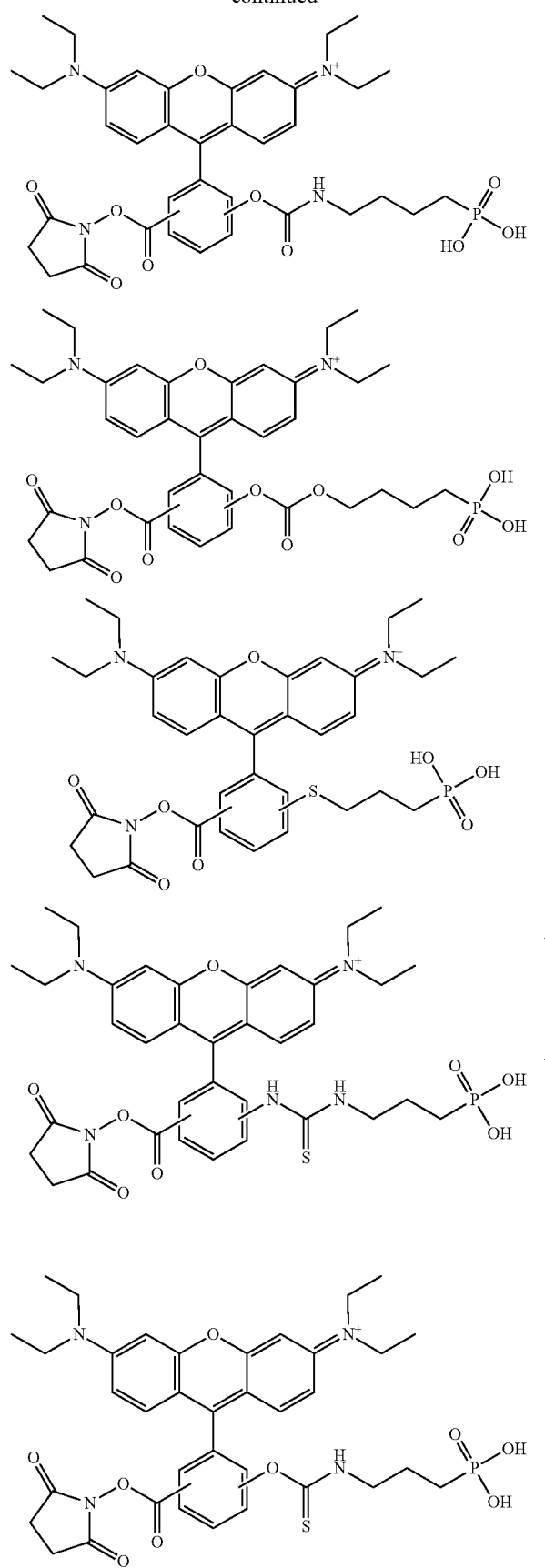
174
-continued
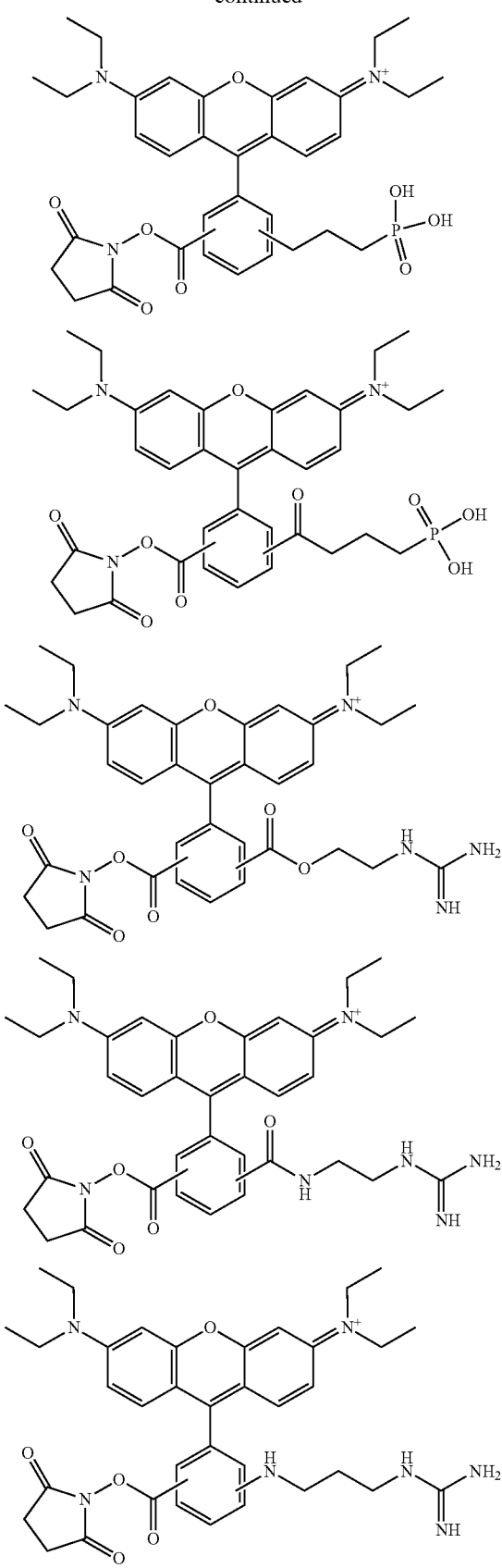

175
-continued
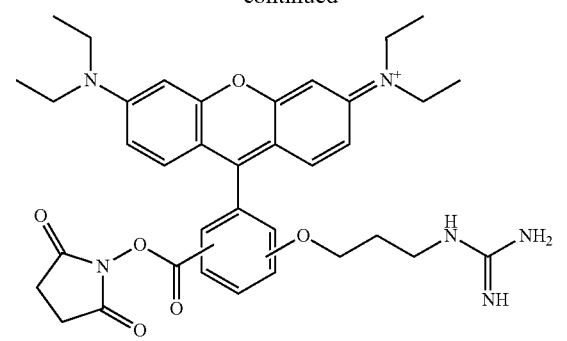
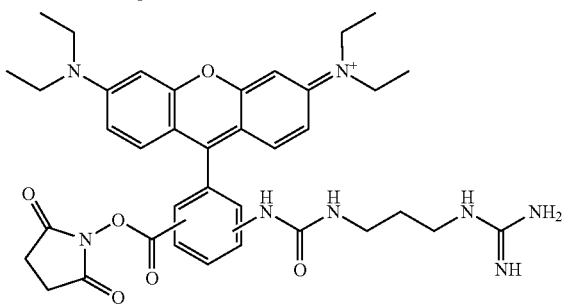
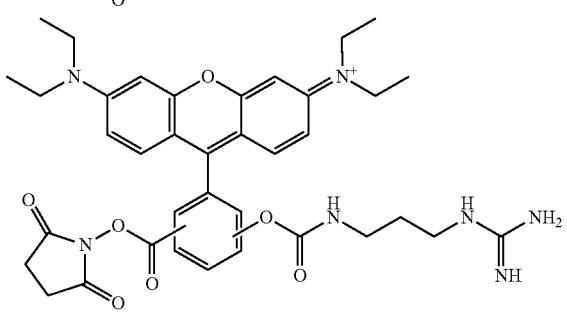
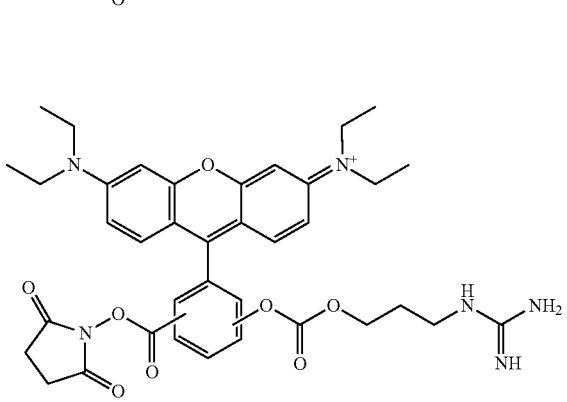
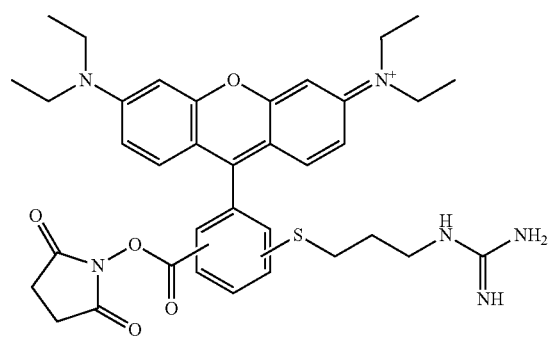
176
-continued
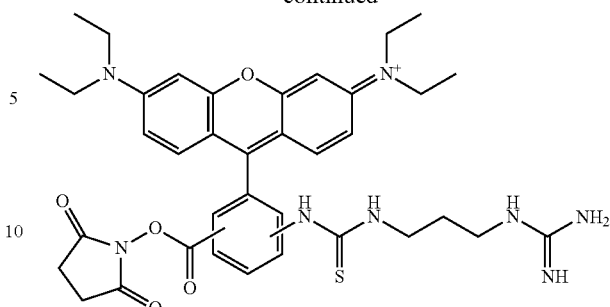
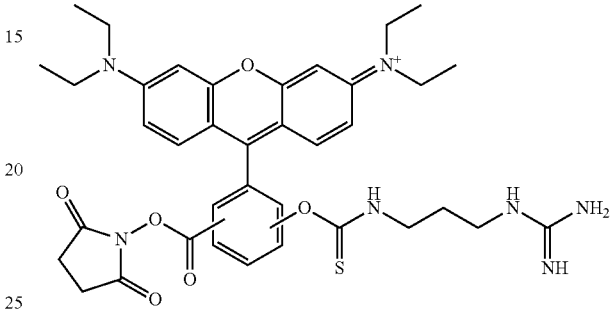
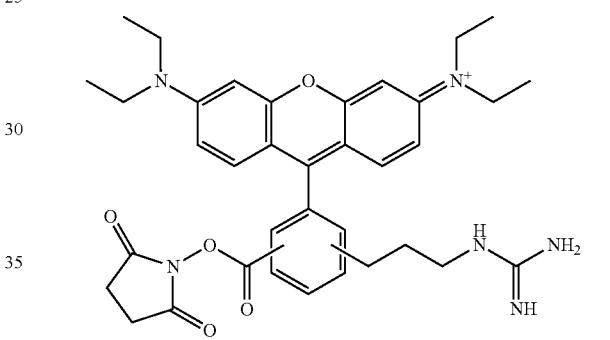
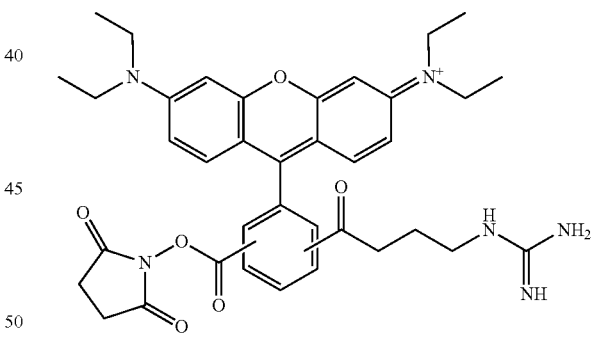
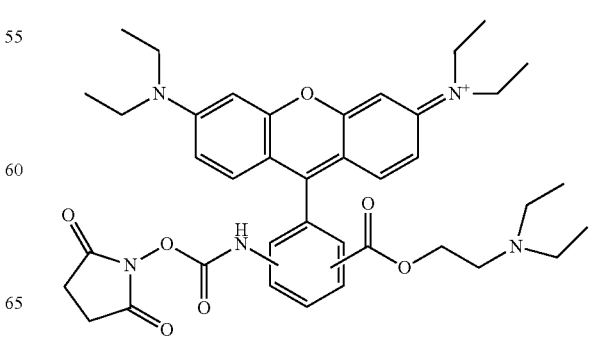

177
-continued
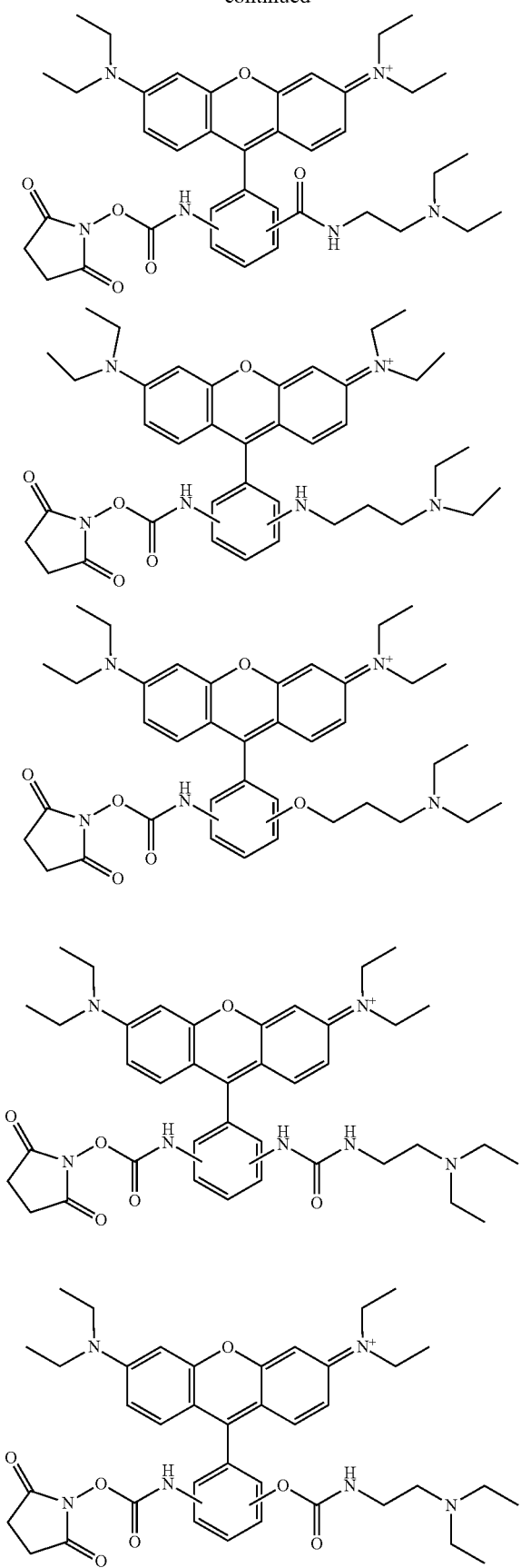
178
-continued
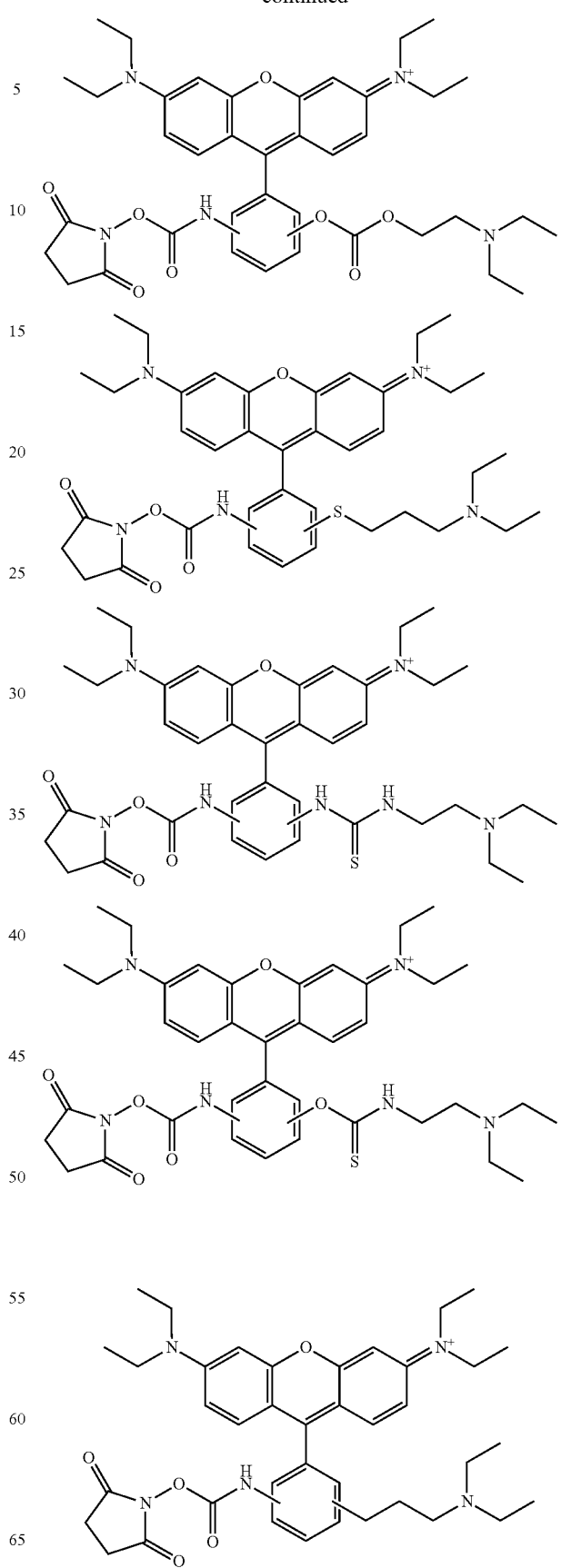

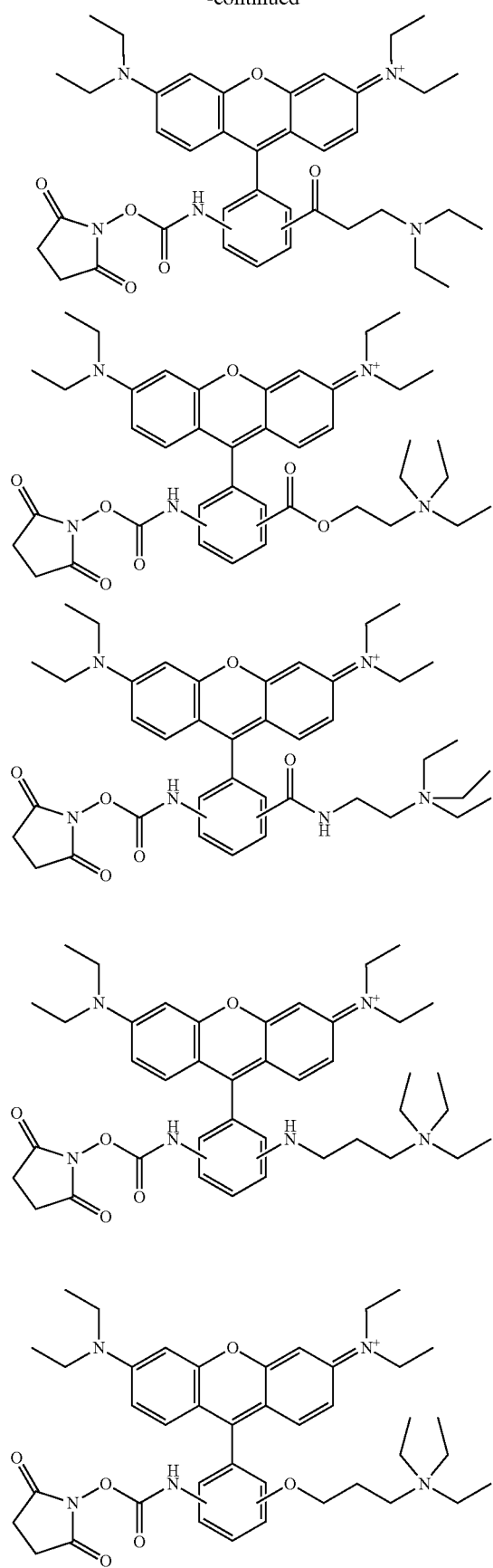

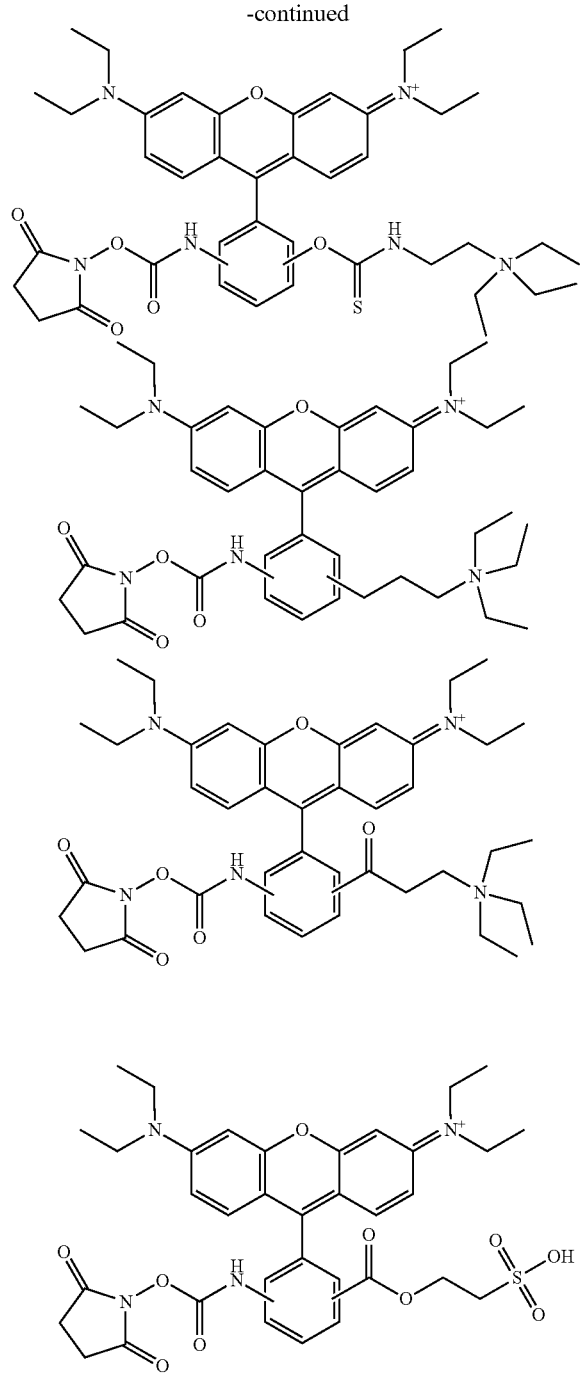
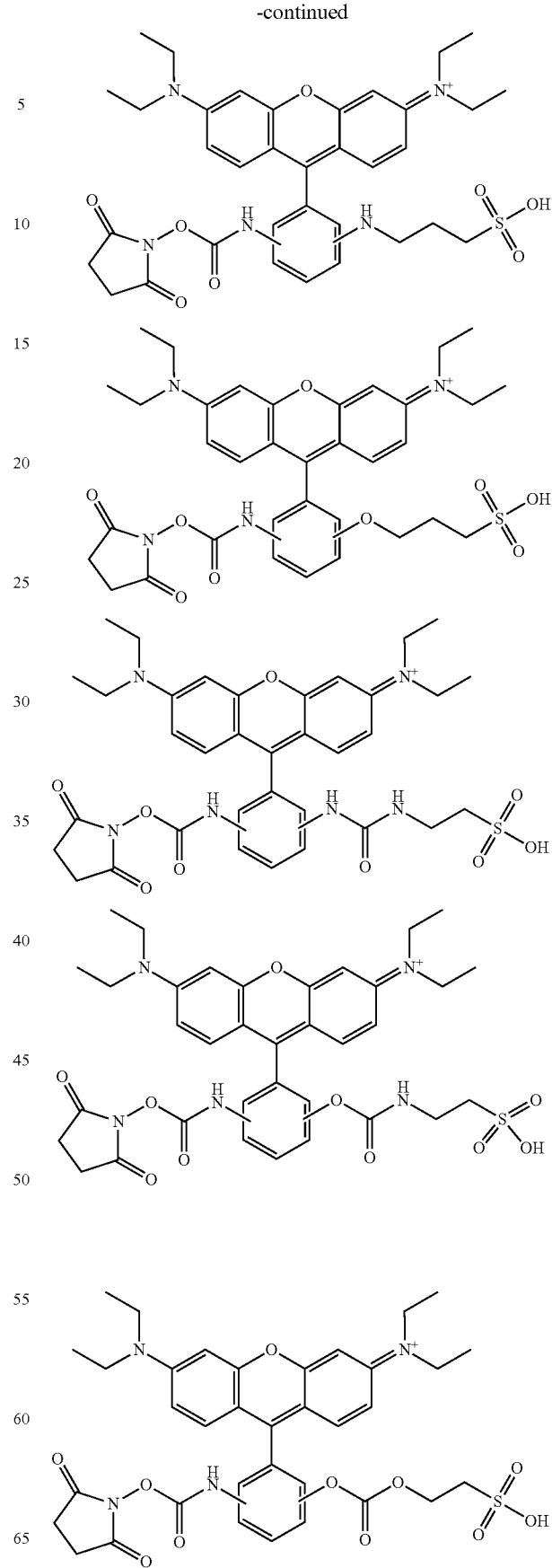

183
-continued
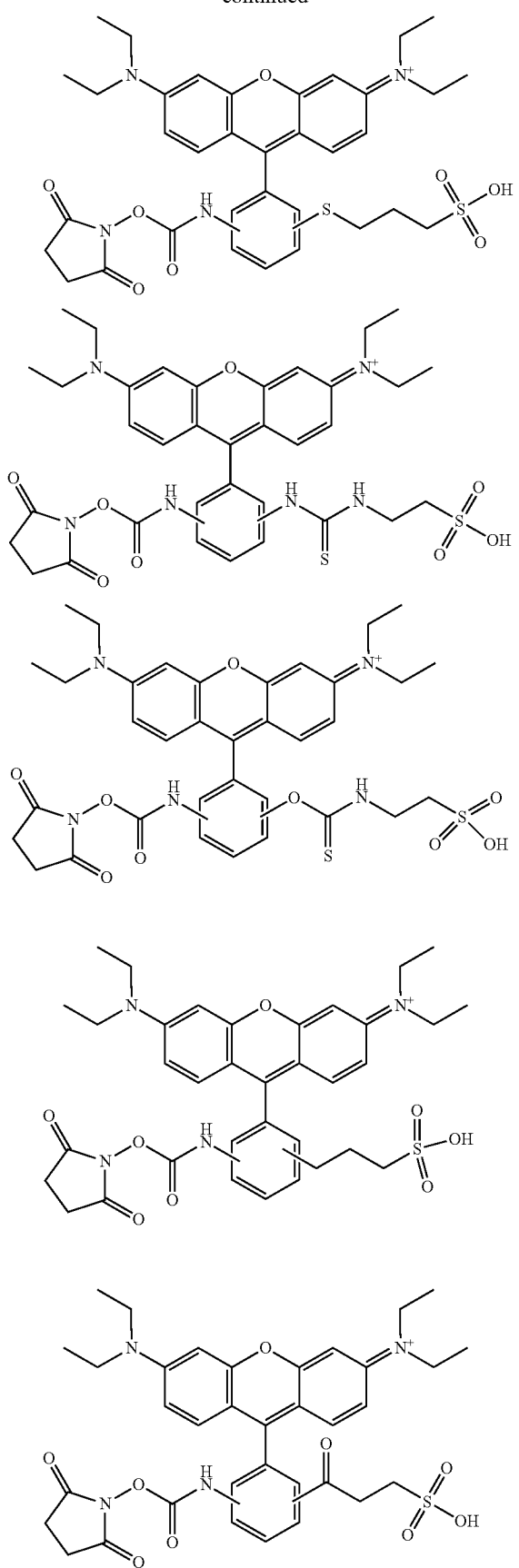
184
-continued
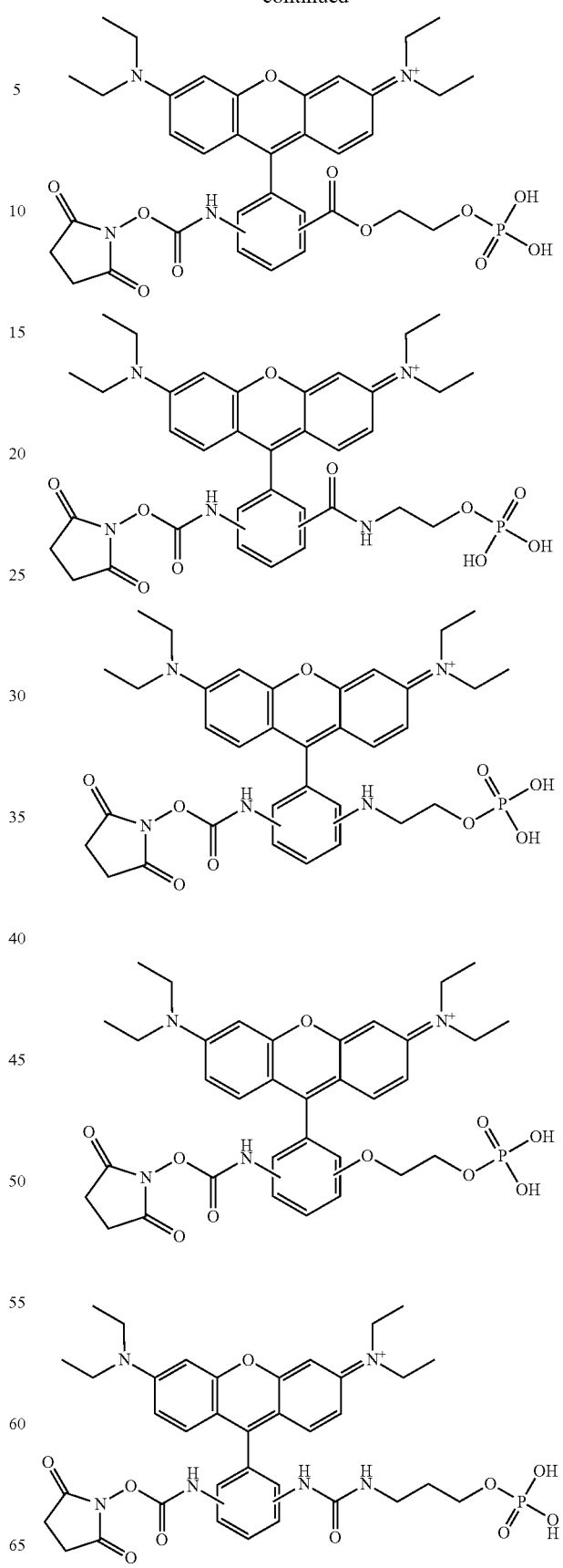

185
-continued
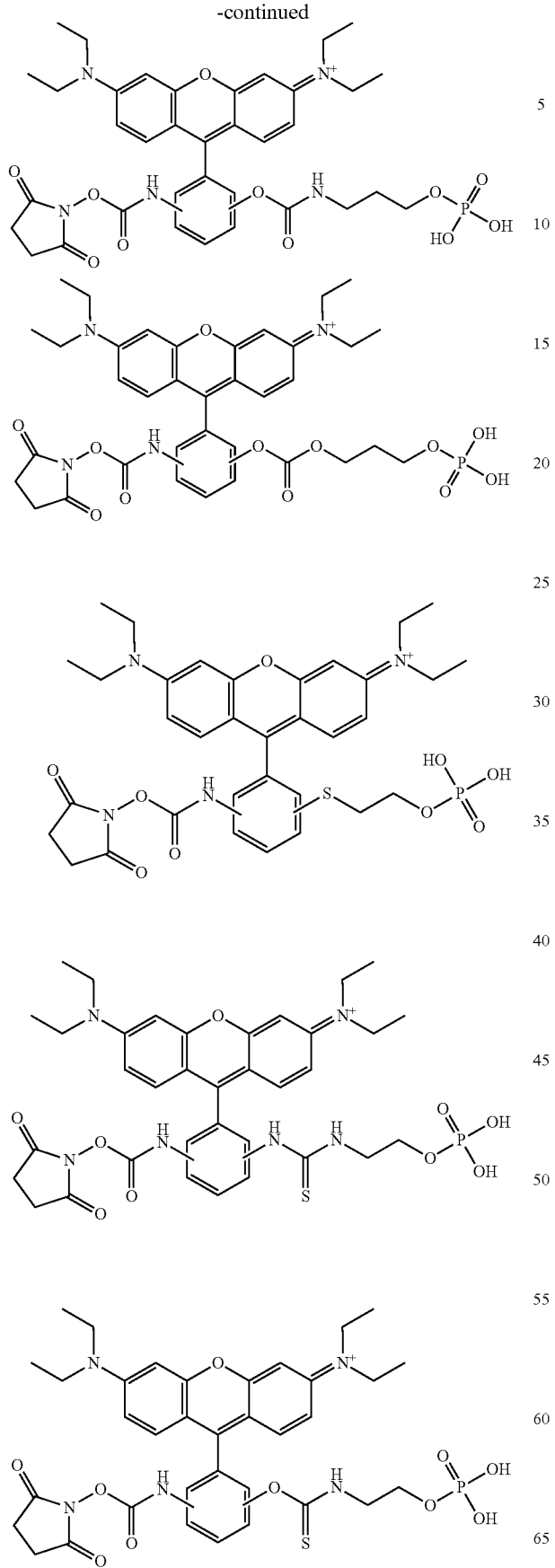
186
-continued
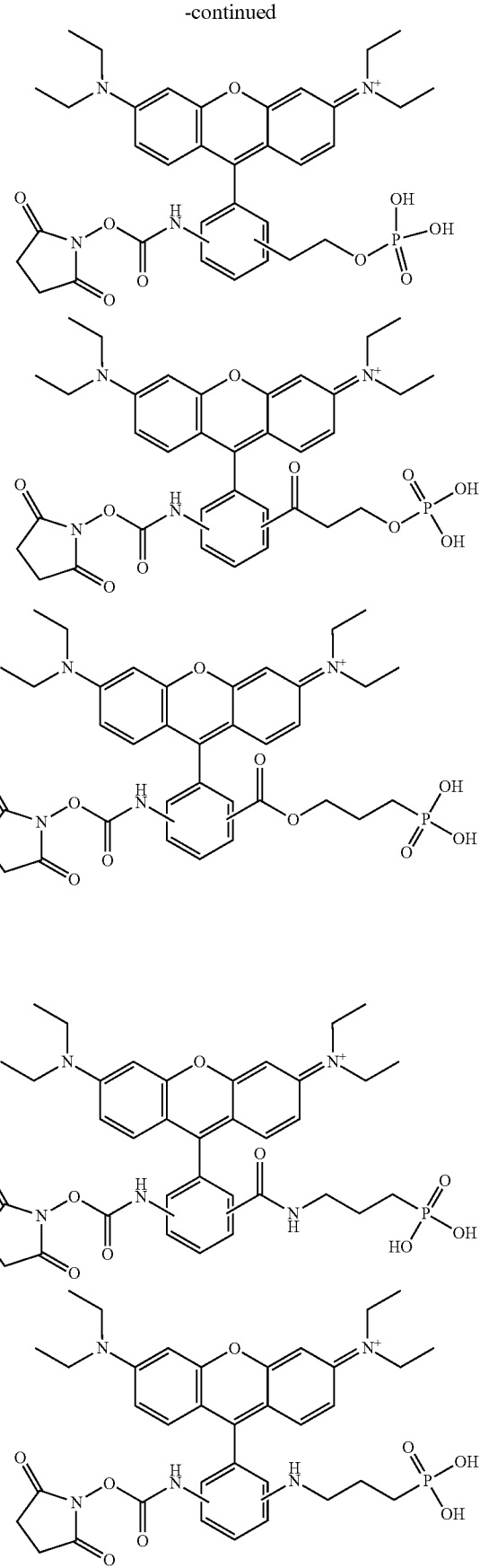

187
-continued
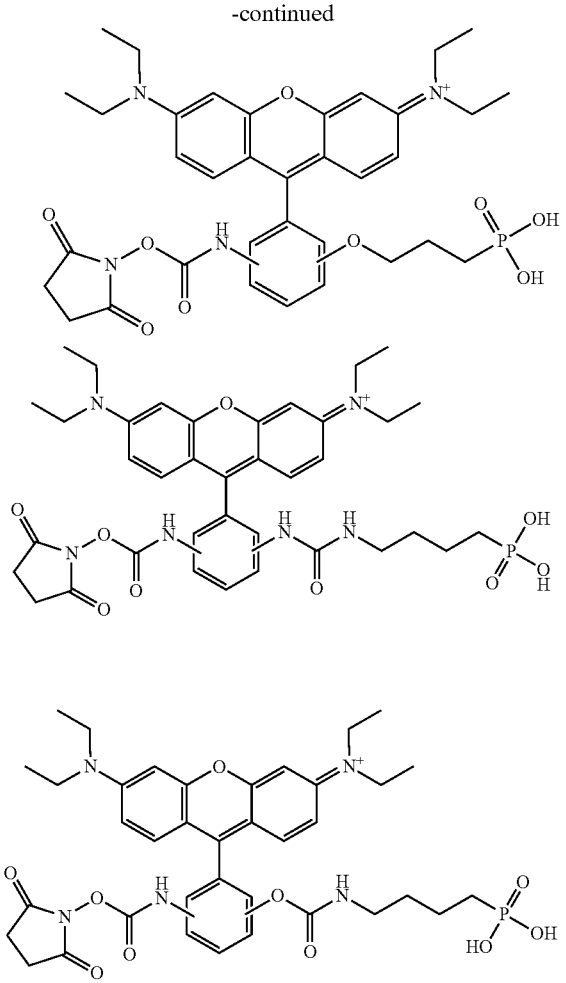
188
-continued
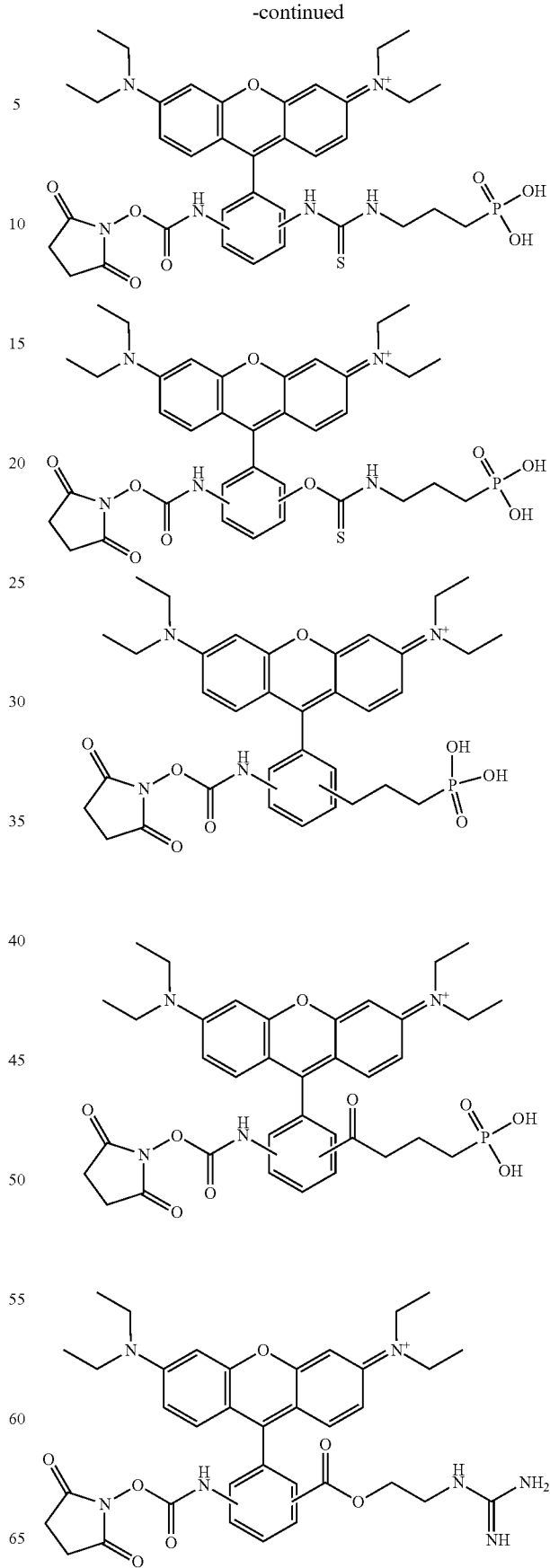

189
-continued
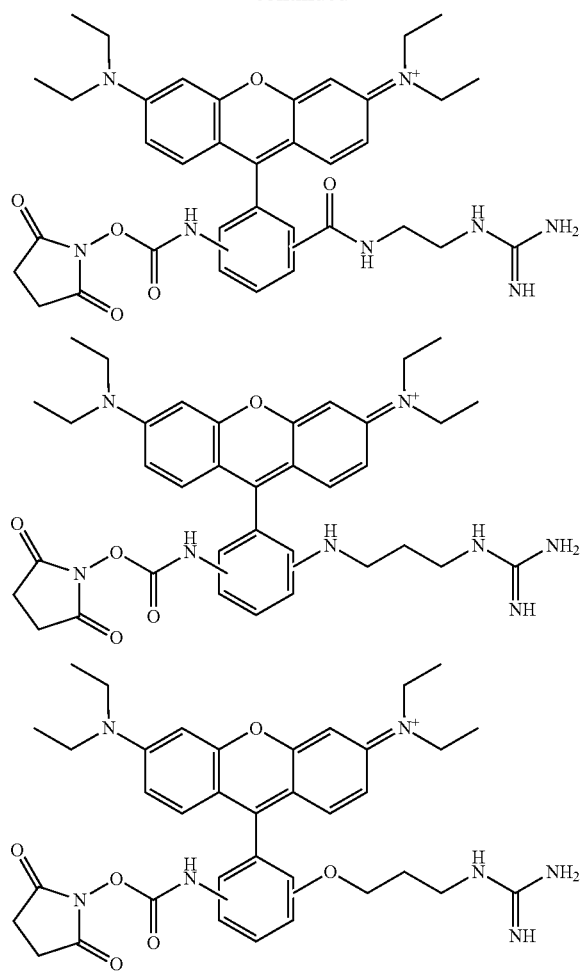
190
-continued
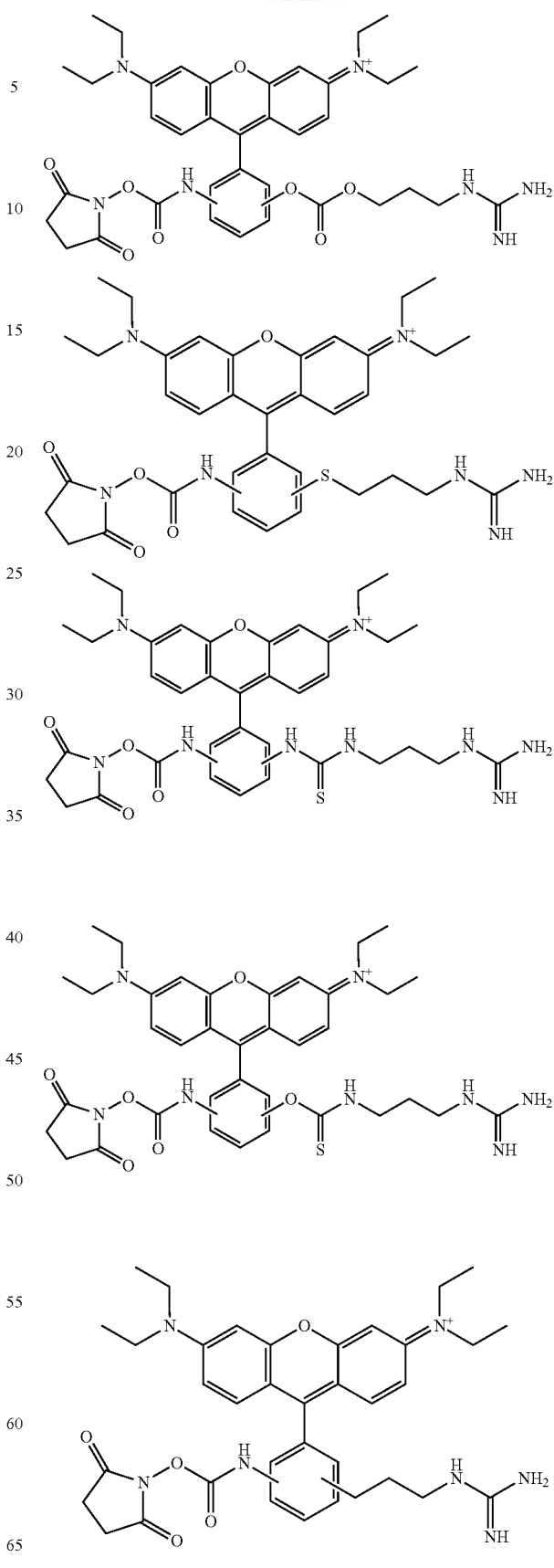

191
-continued
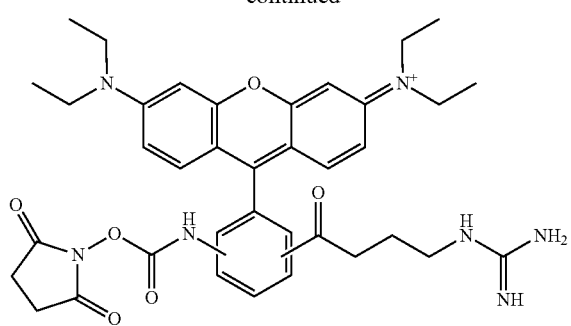
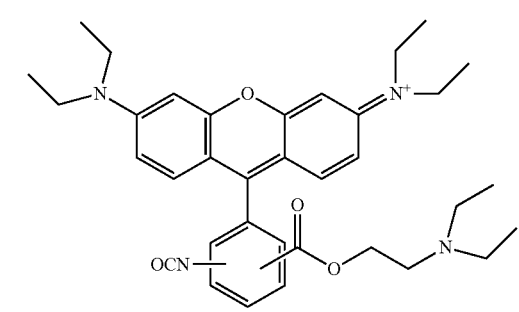
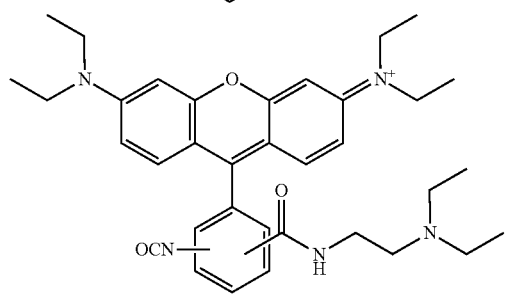
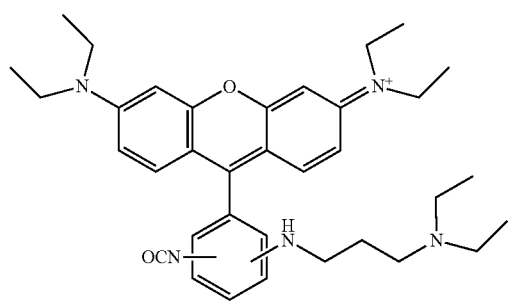
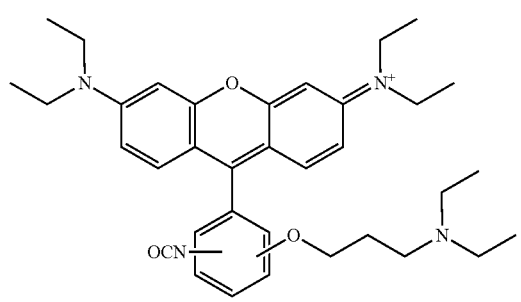
192
-continued
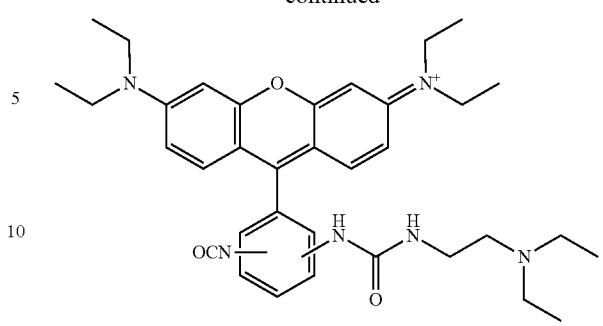
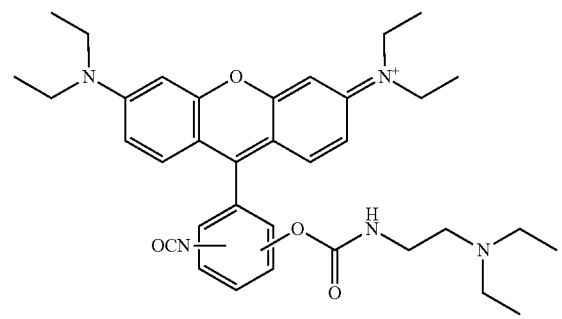
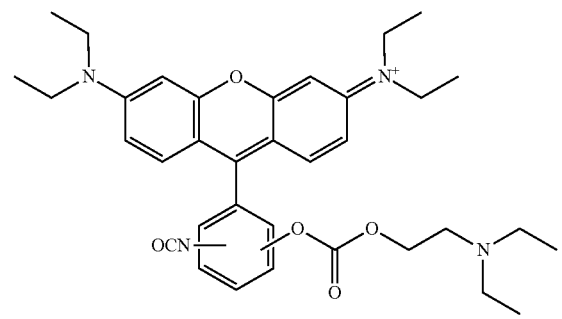
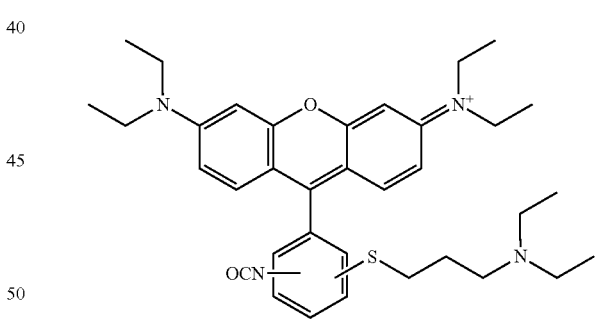
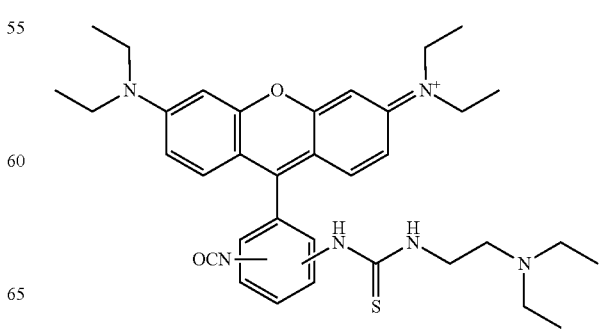

193
-continued
194
-continued
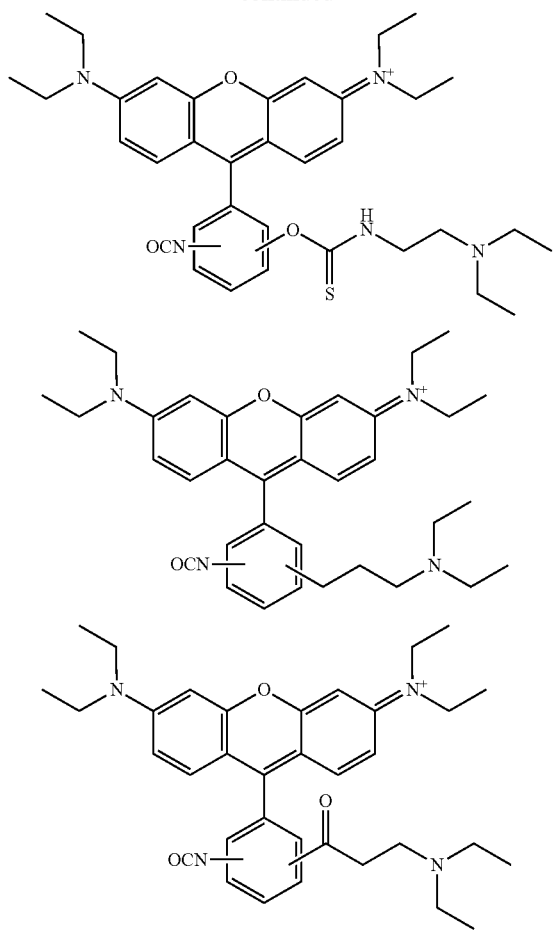
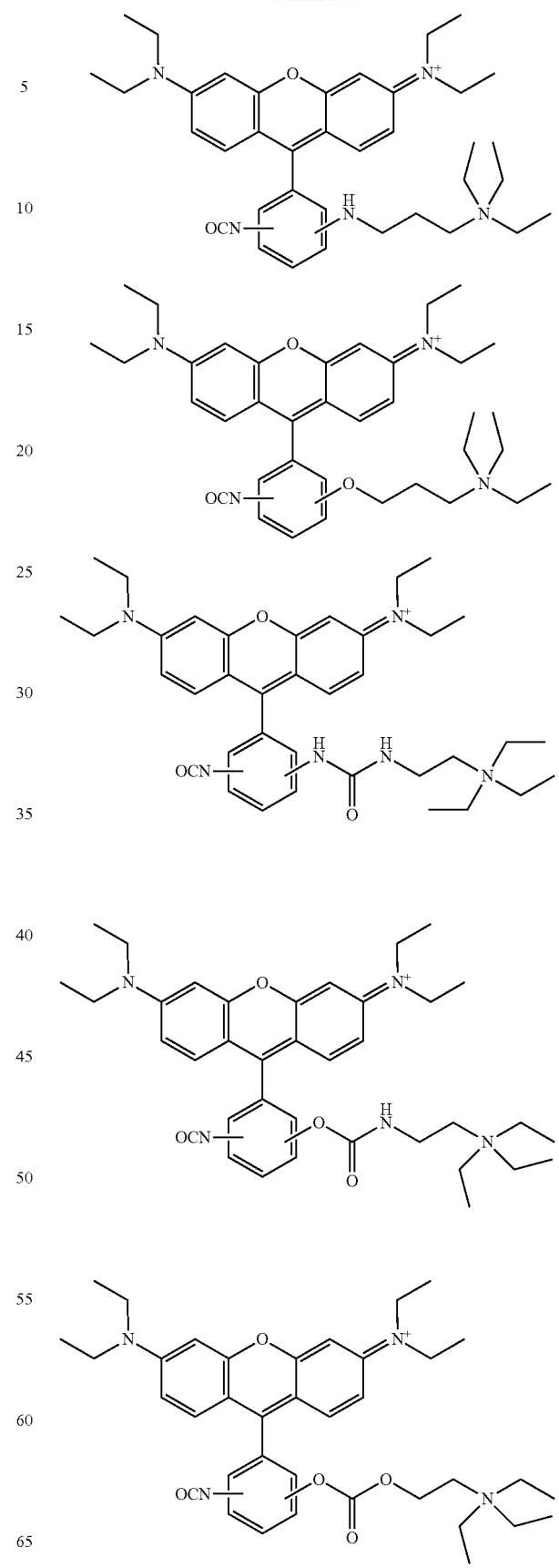

195
-continued
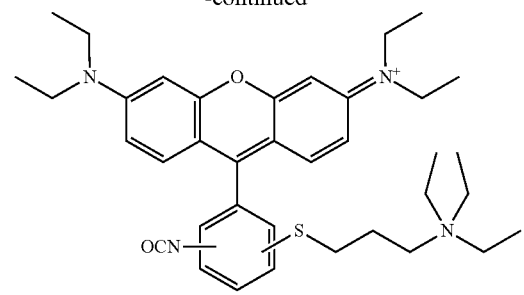
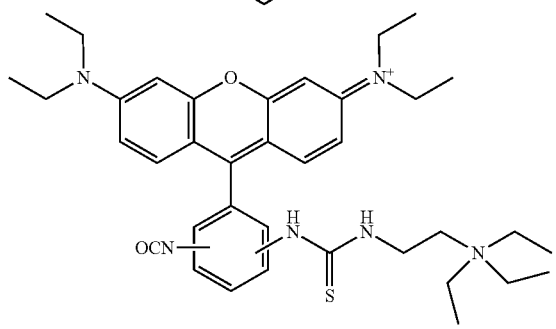
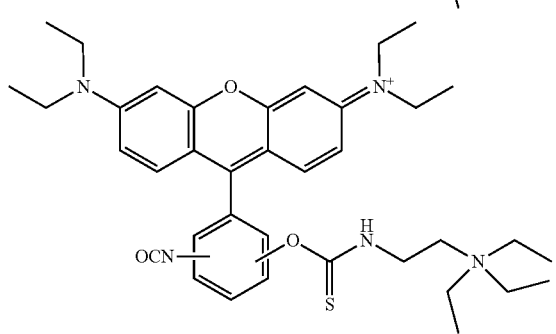
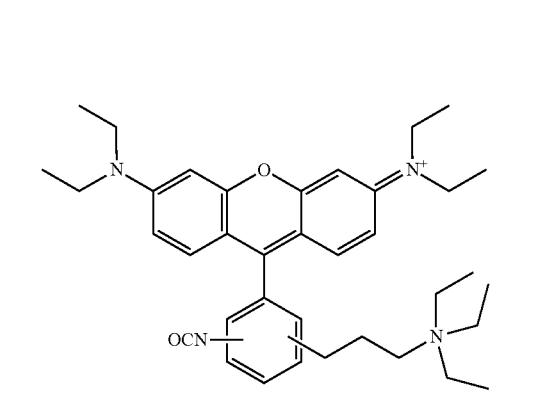
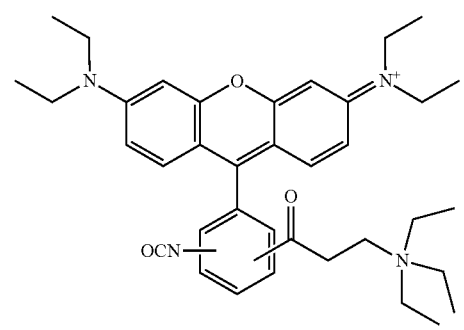
196
-continued
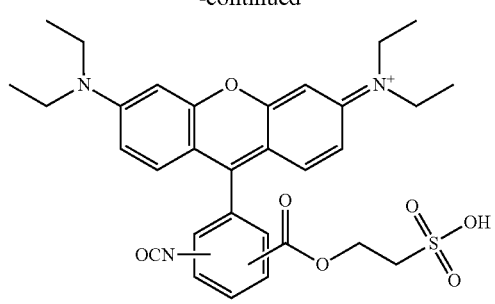
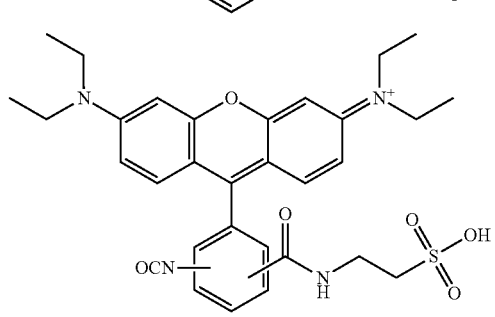
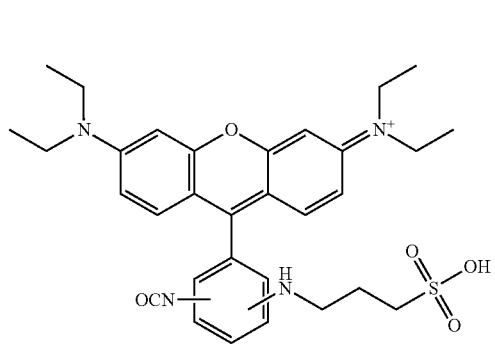
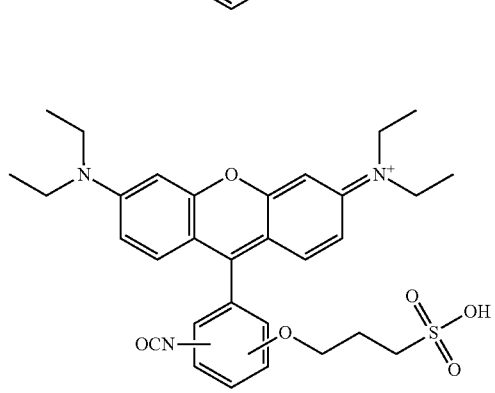
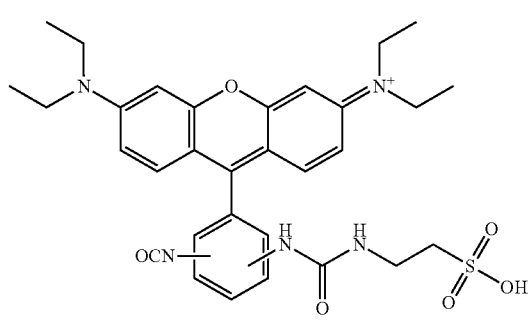

197
-continued
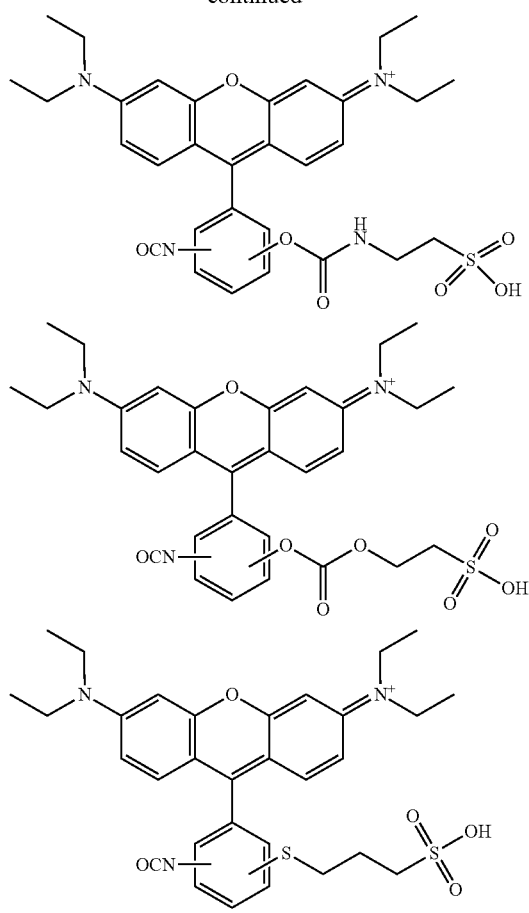
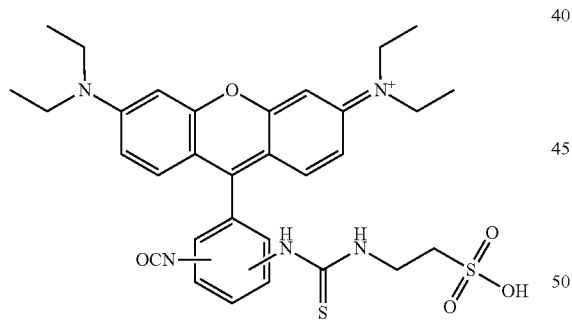
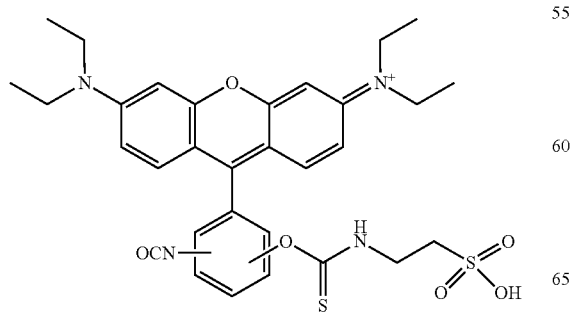
198
-continued
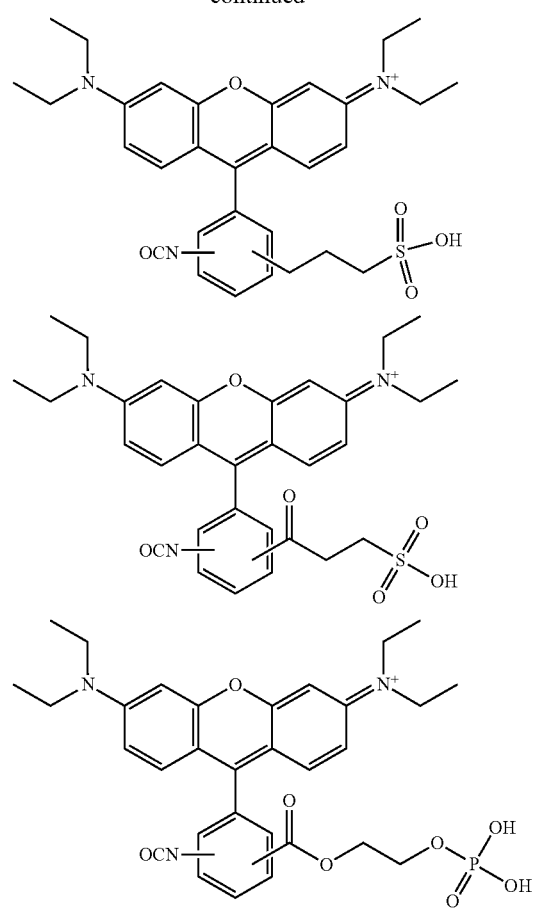
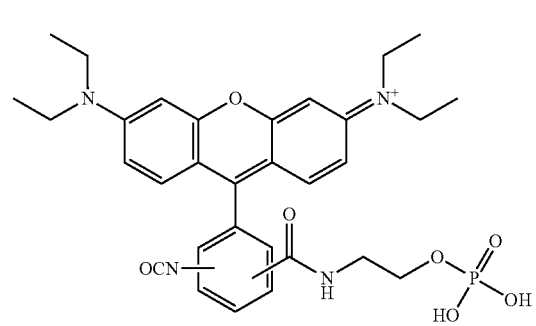
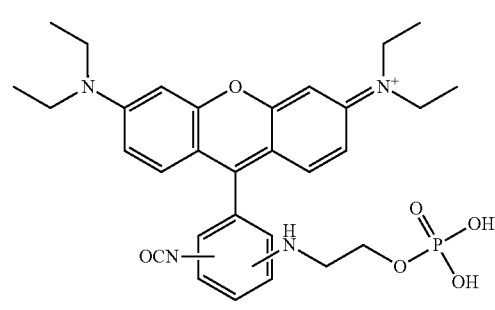

199
-continued
200
-continued
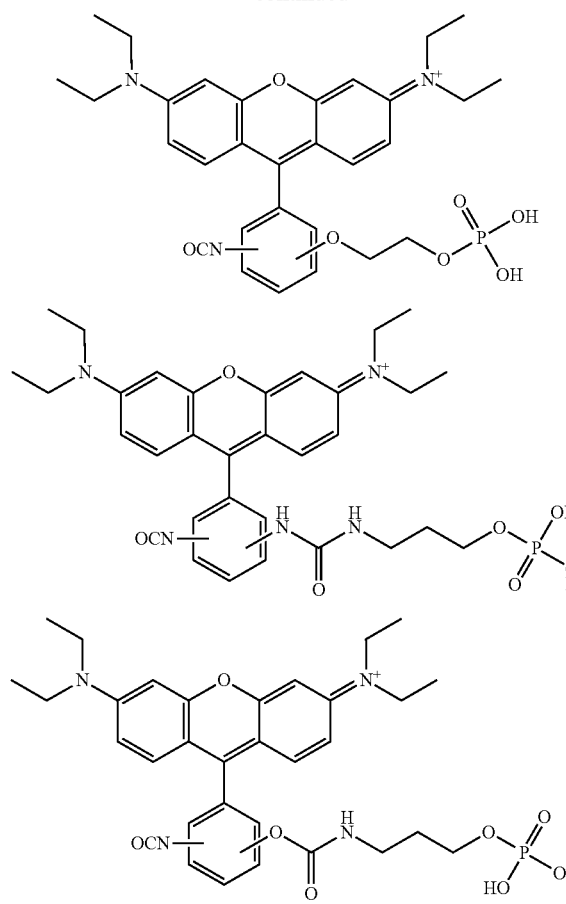
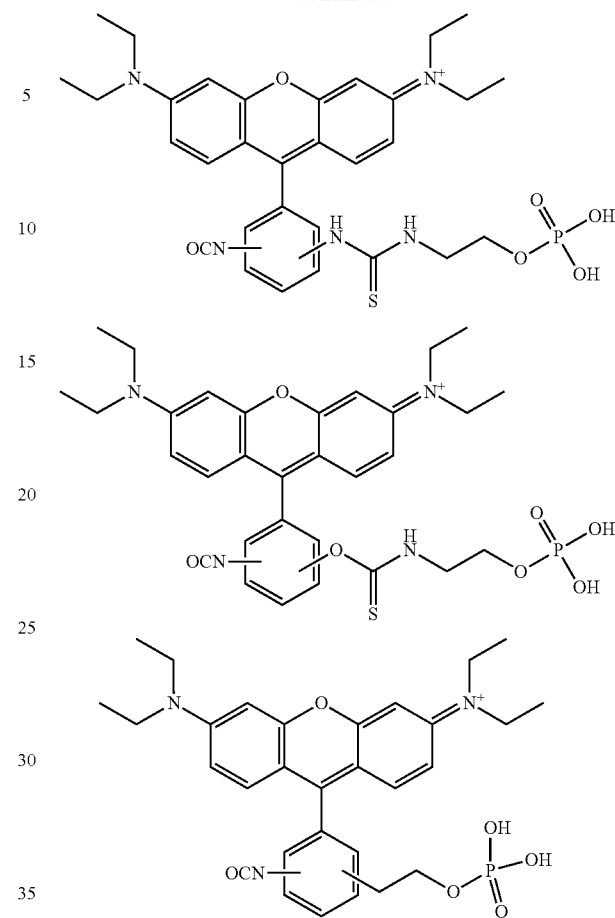
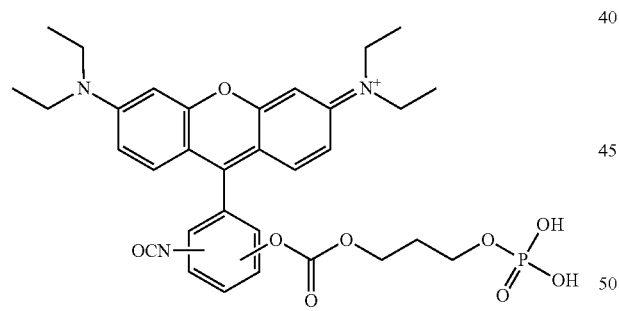
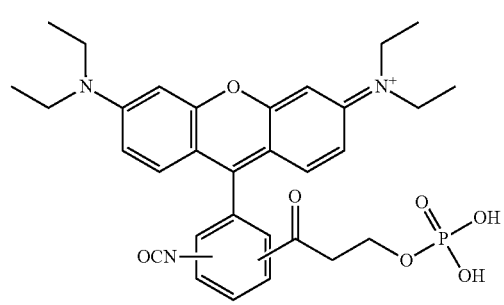
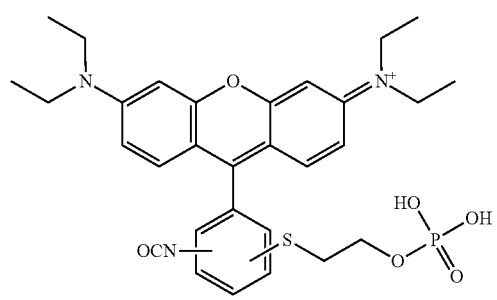
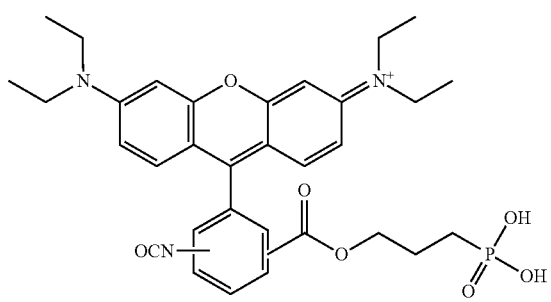

201
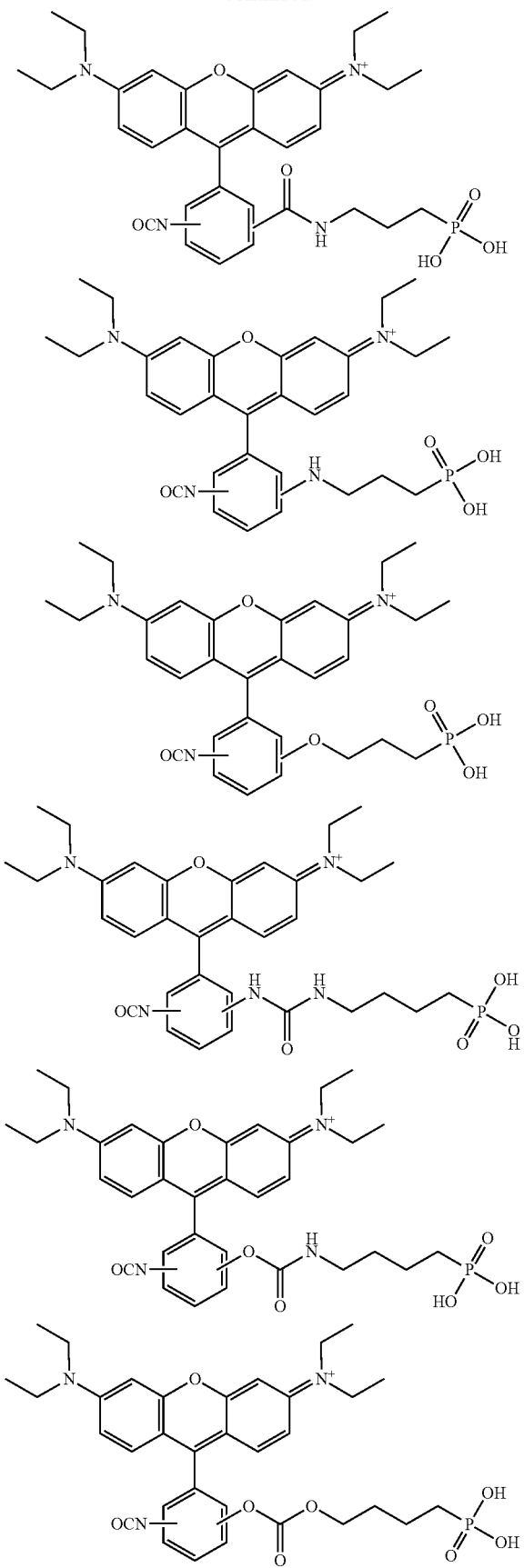
202
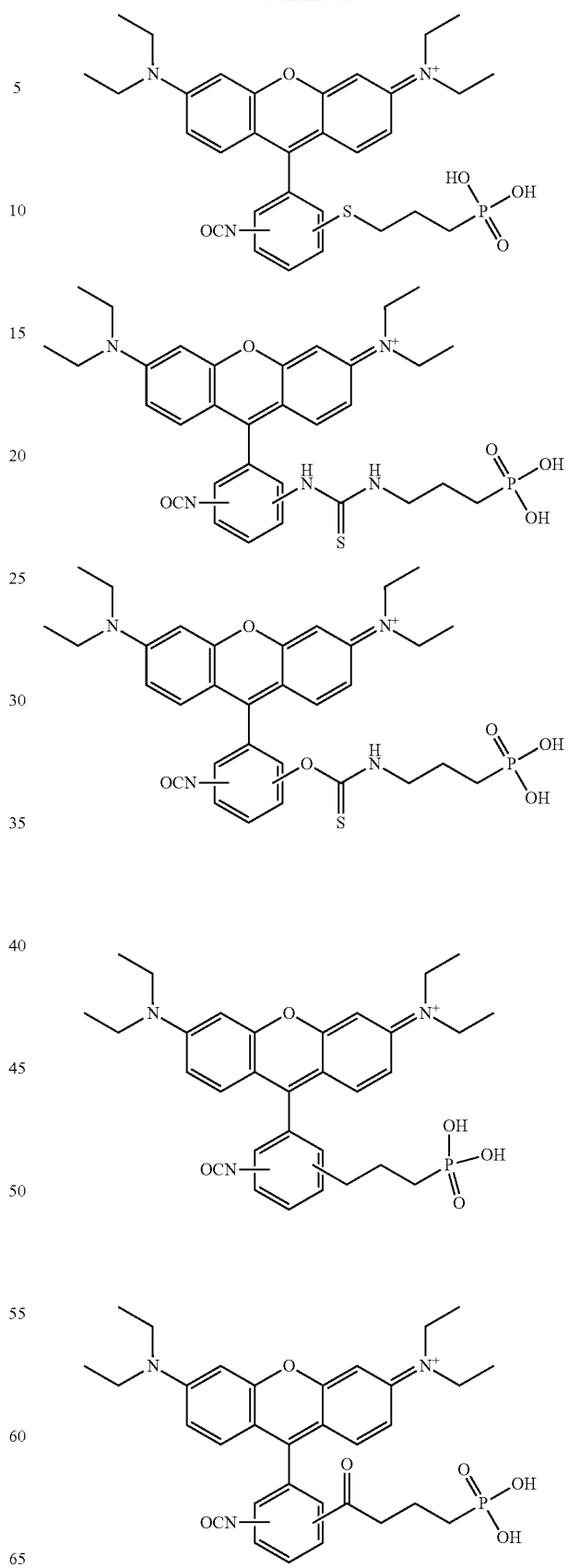

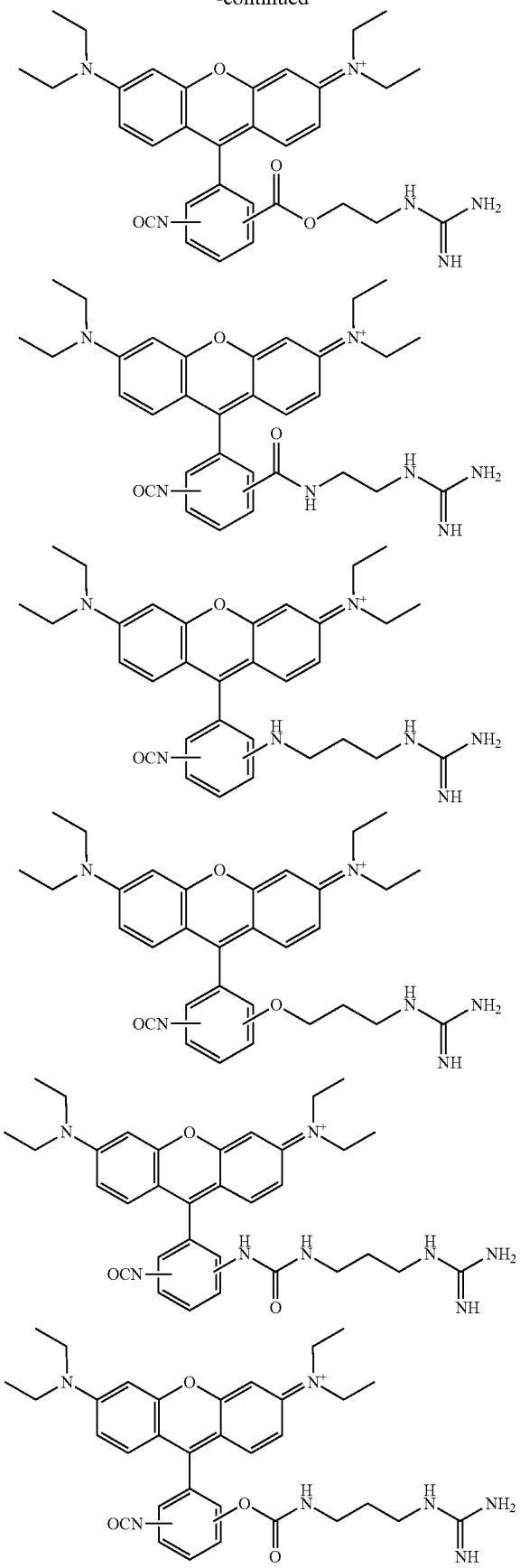
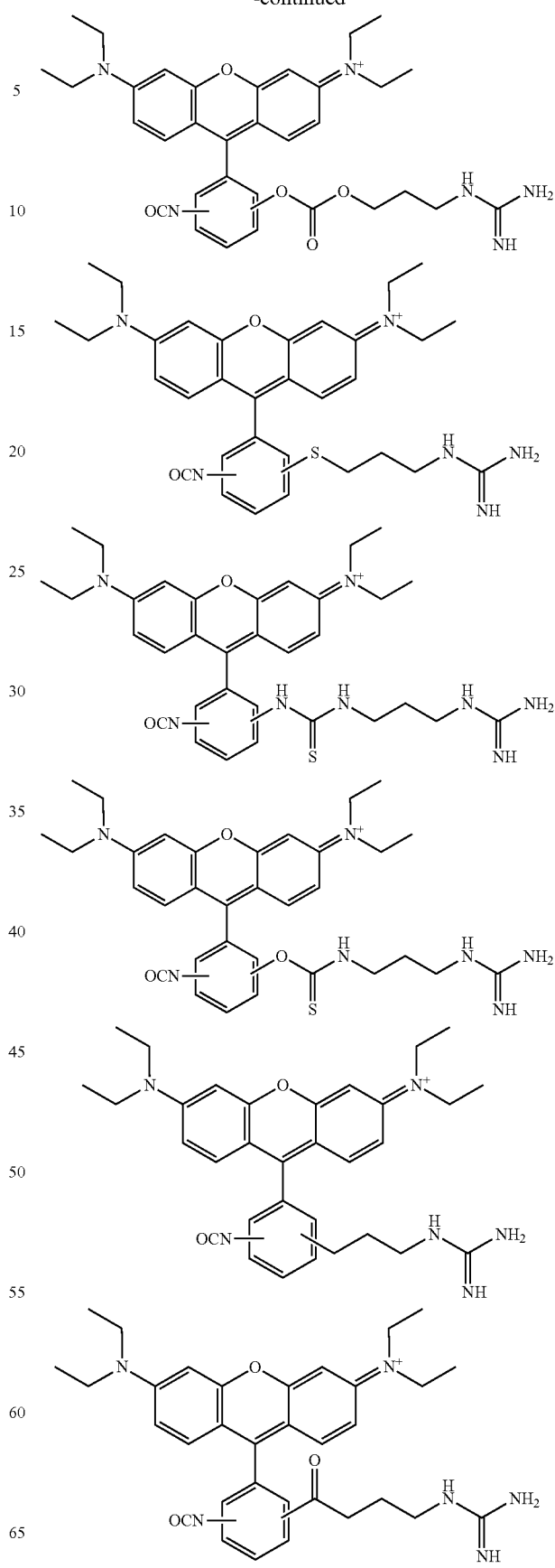

| 205 -continued | 206 -continued |
|---|---|
| 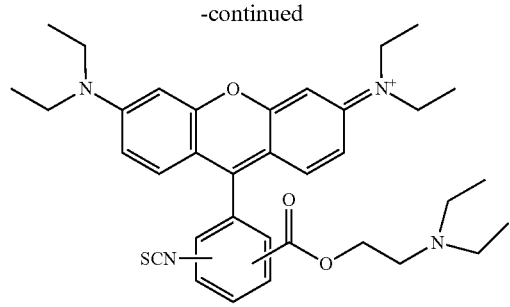 | 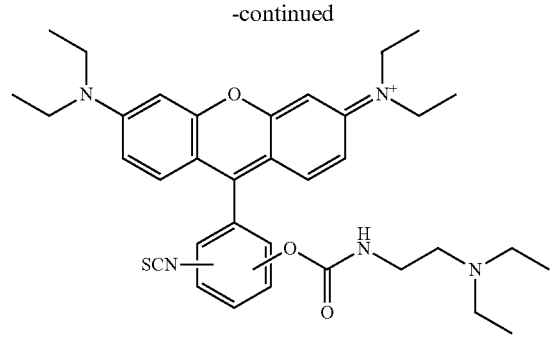 |
| 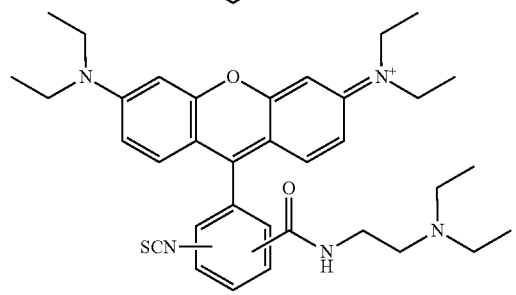 | 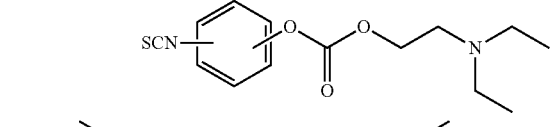 |
| 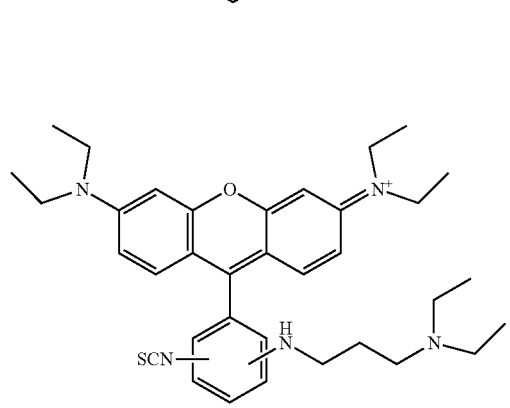 | 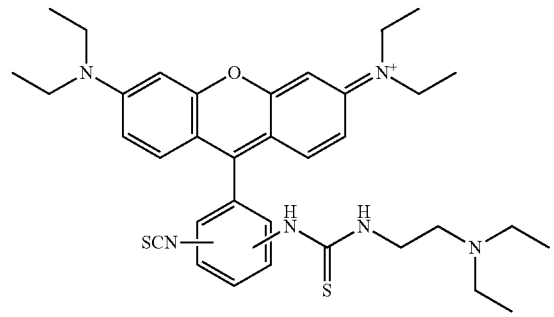 |
| 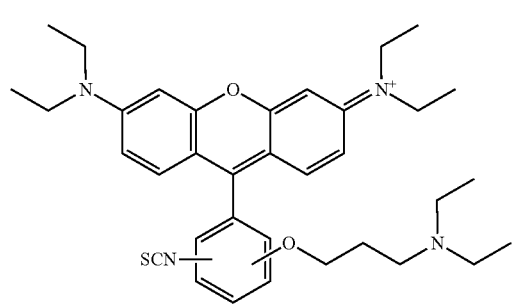 | |
| 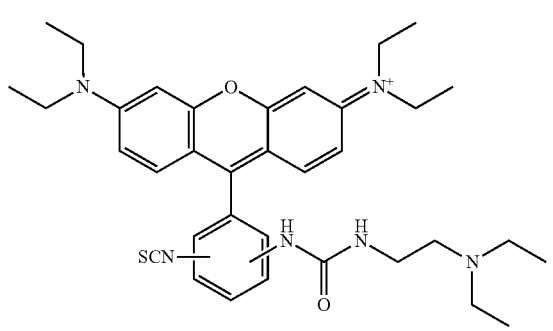 | 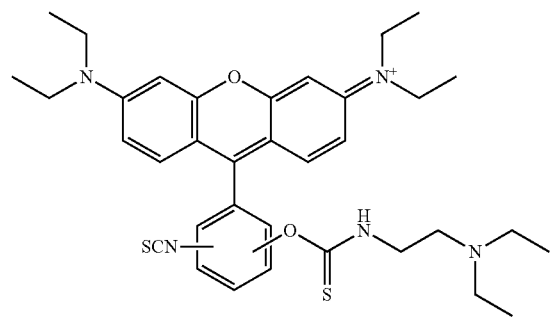 |

207
-continued
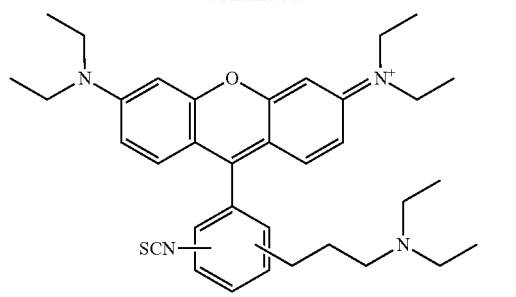
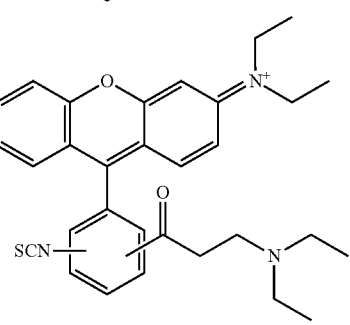
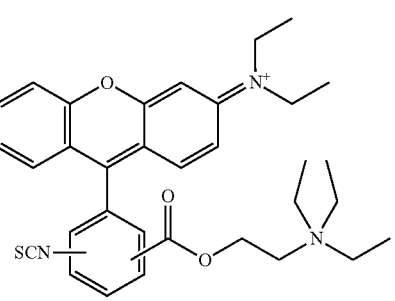
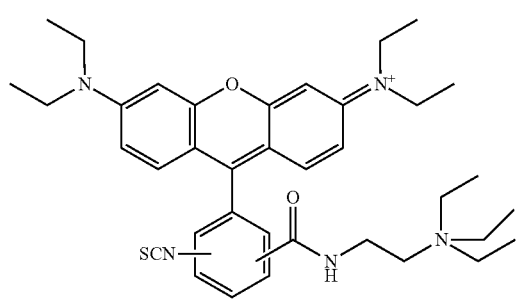
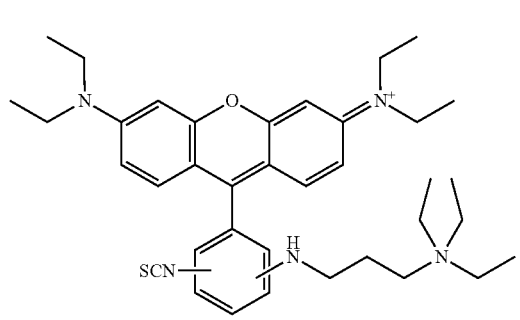
208
-continued
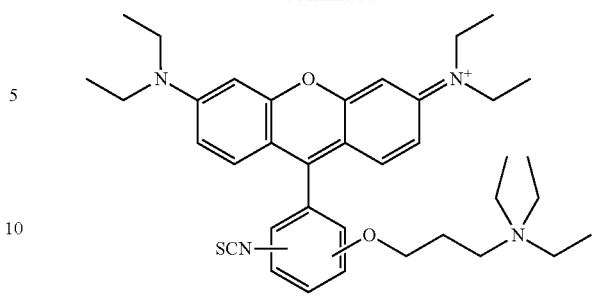
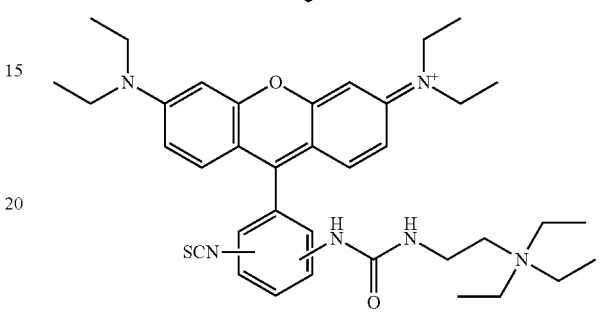
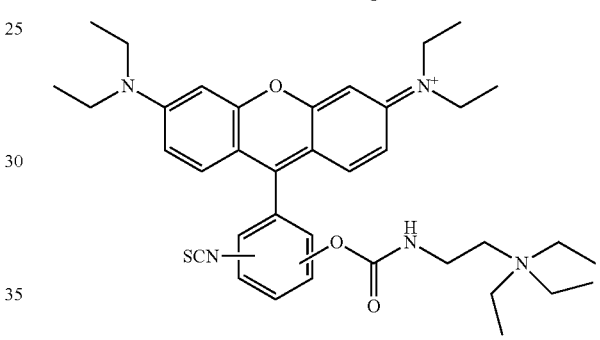
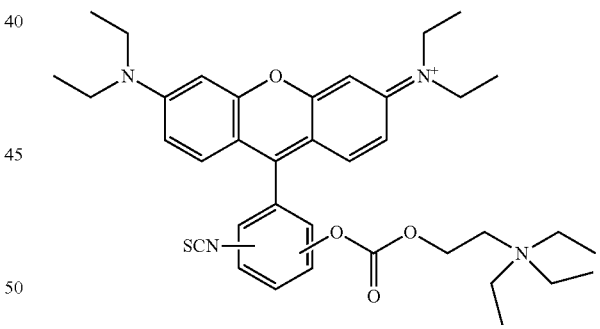
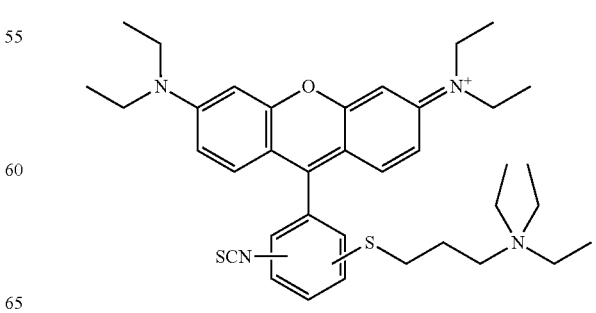

209
-continued
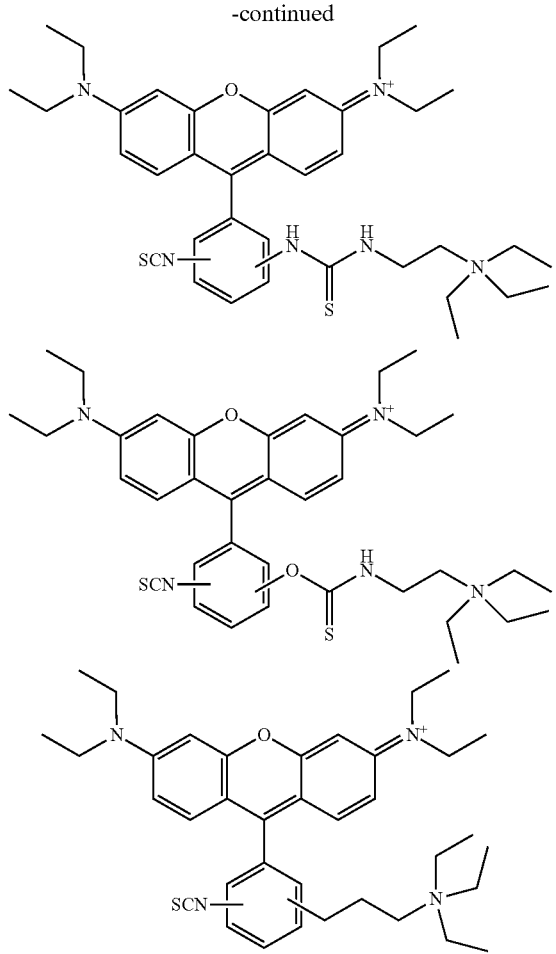
210
-continued
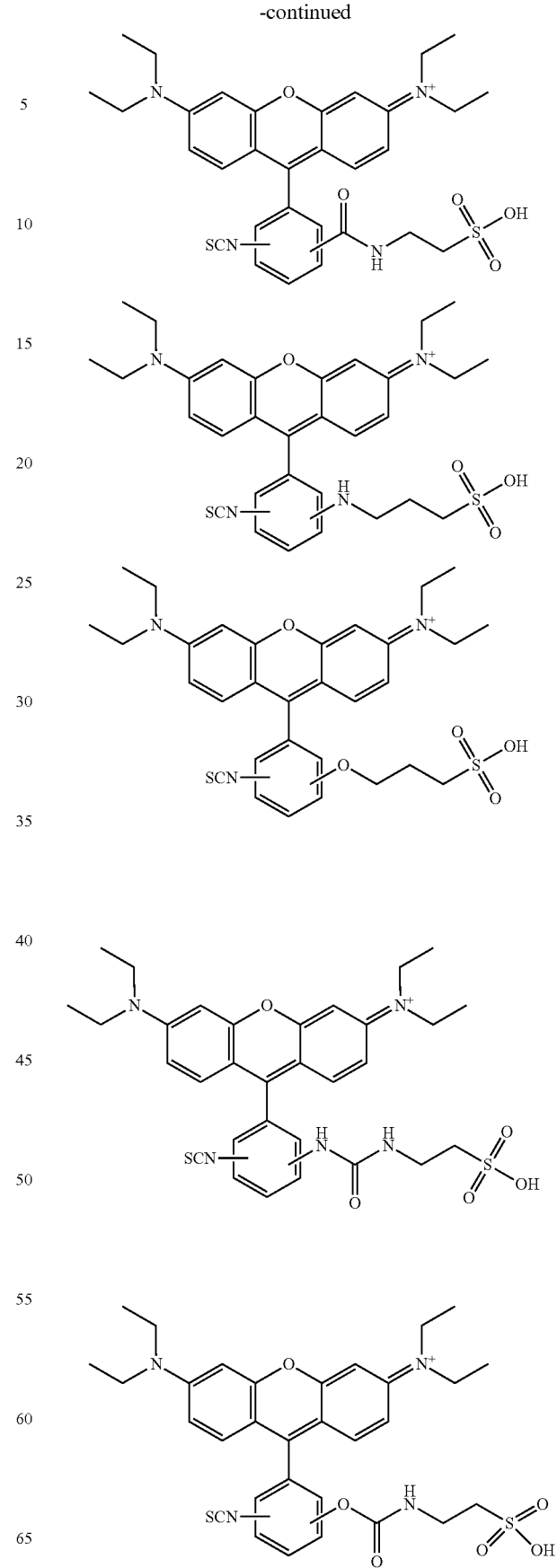

211
-continued
212
-continued
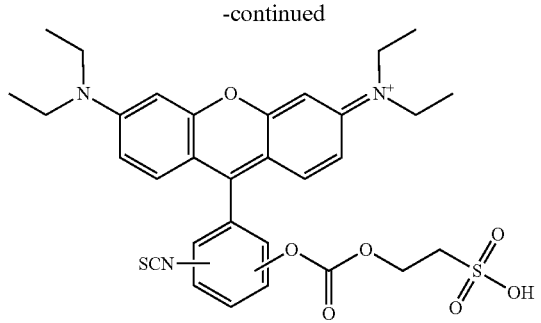
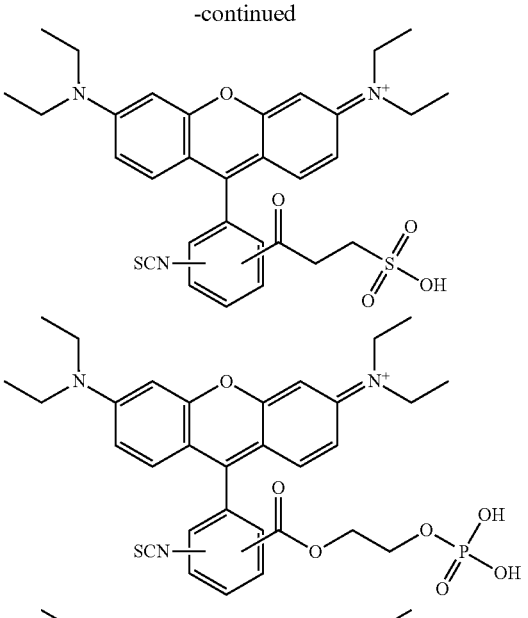
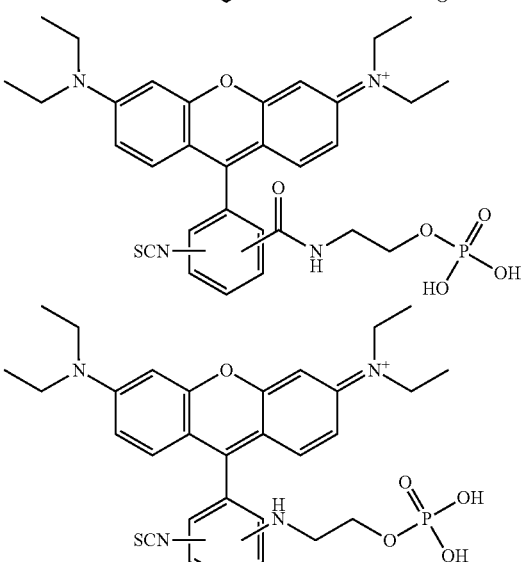
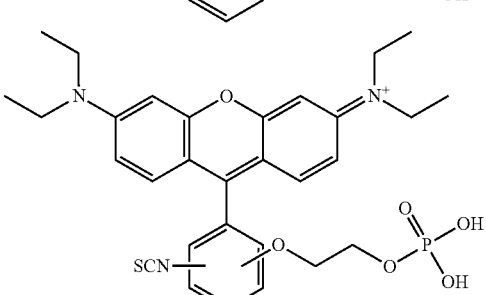
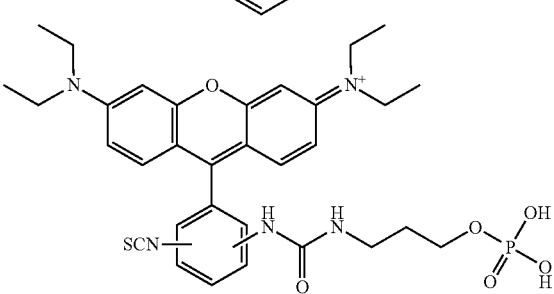

213
-continued
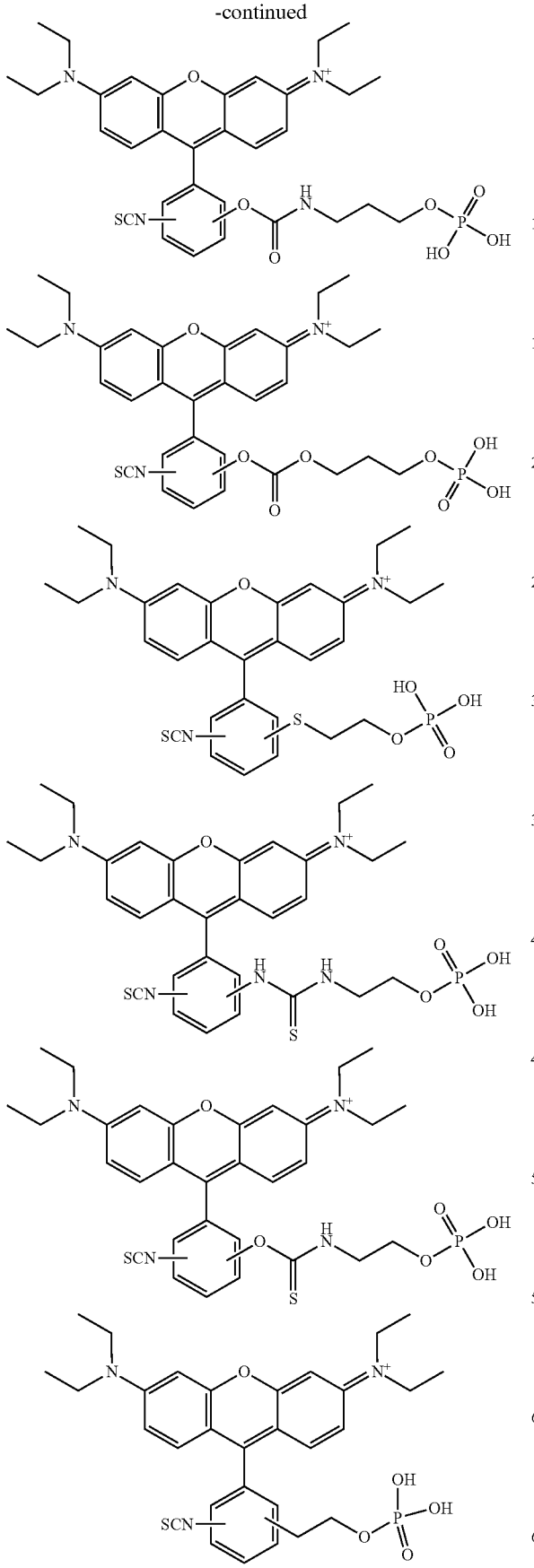
214
-continued
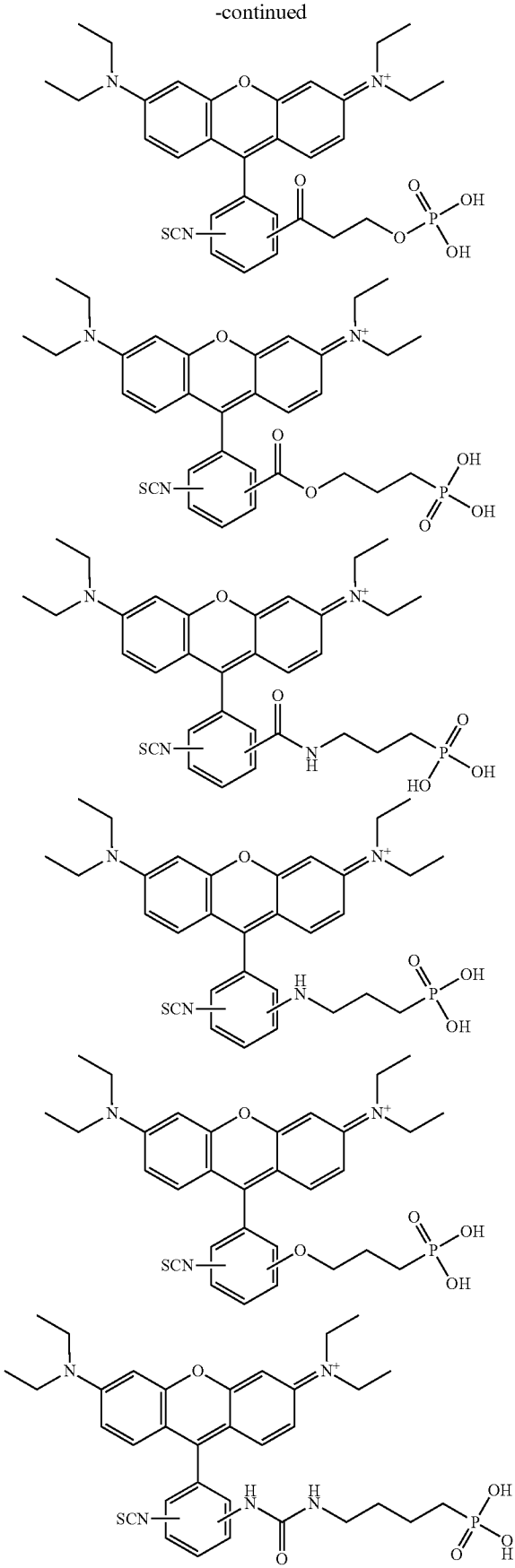

215
-continued
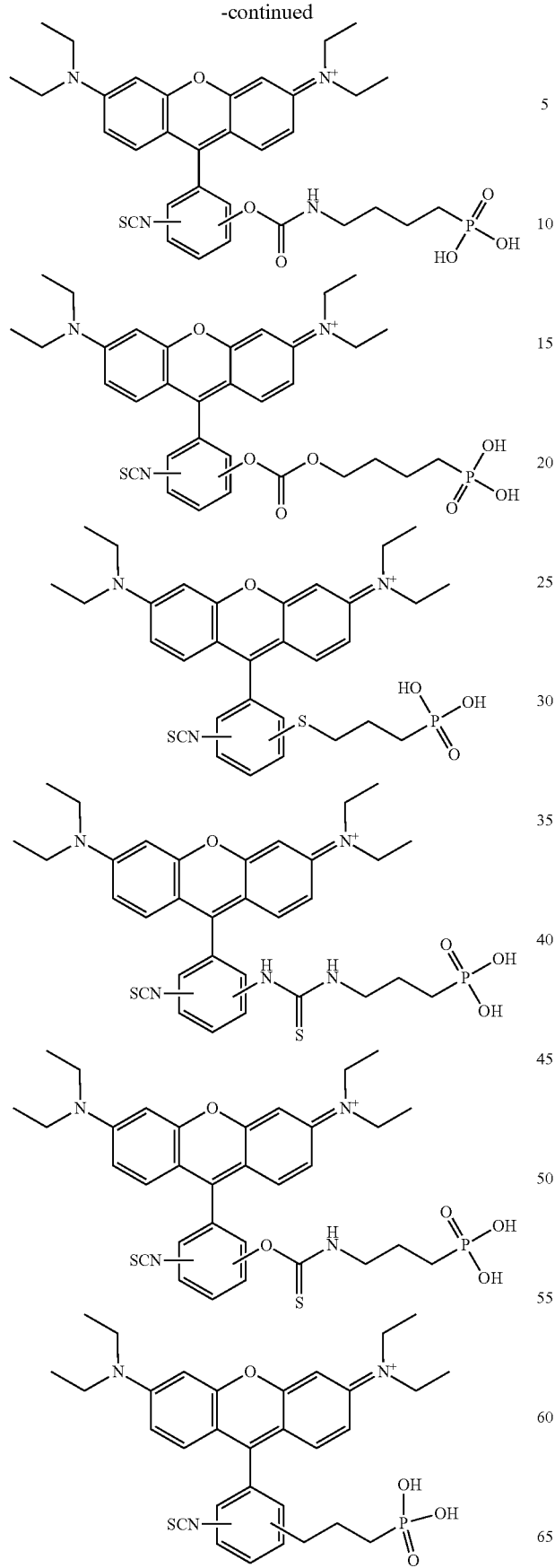
216
-continued
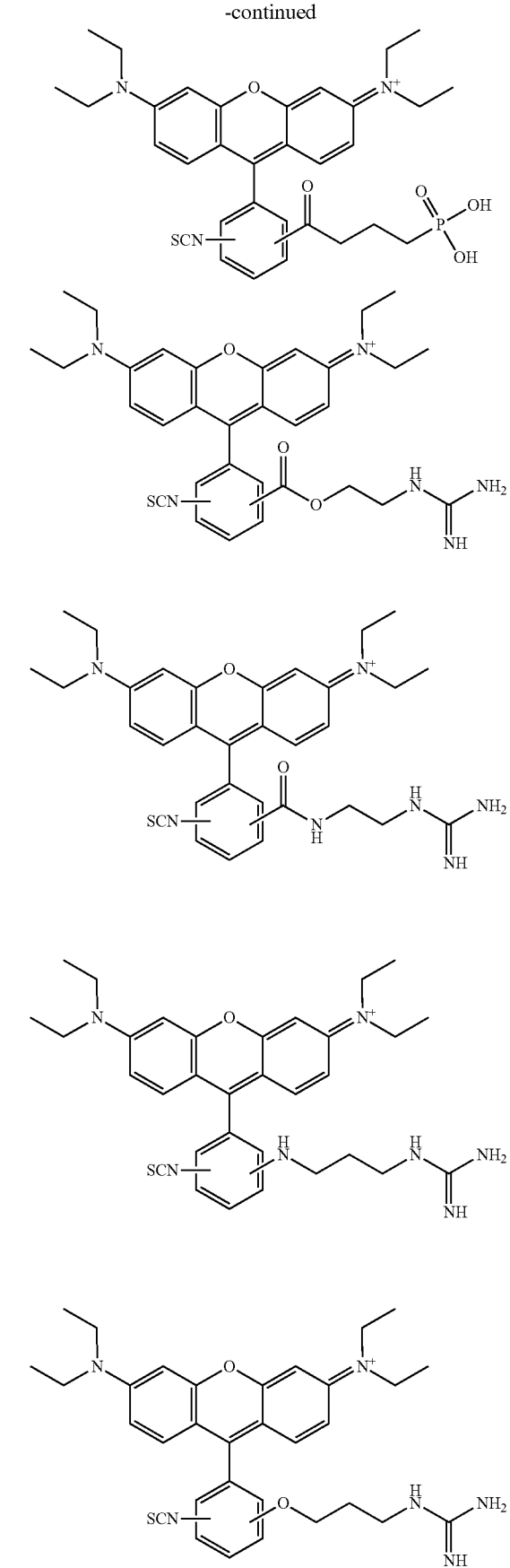

217
-continued
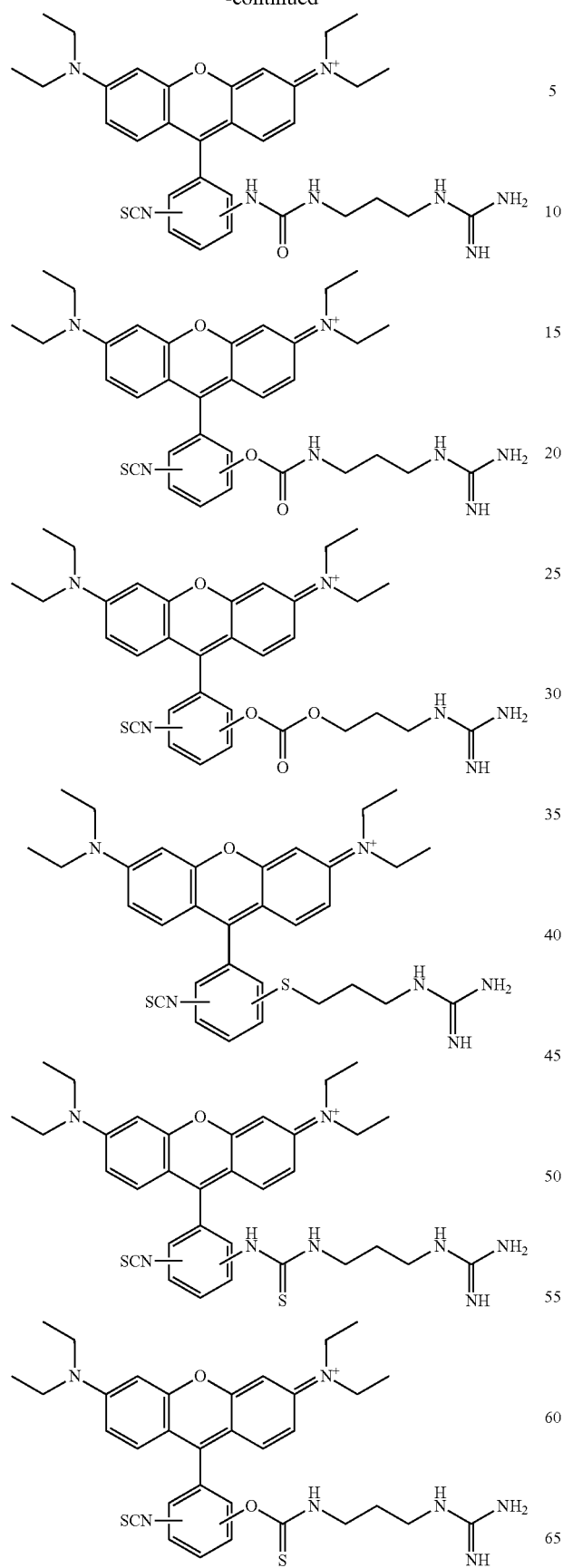
218
-continued
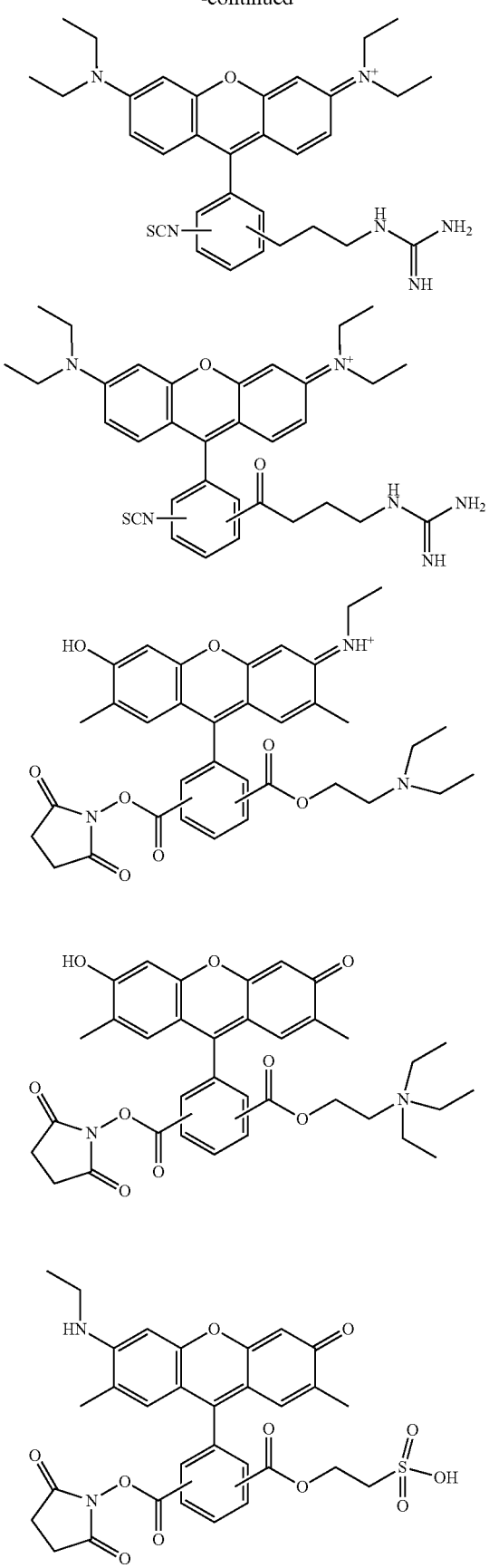

-continued
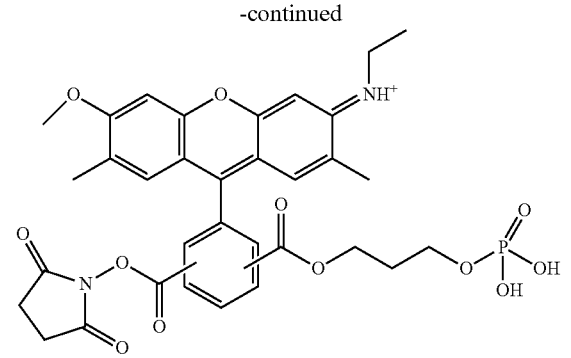
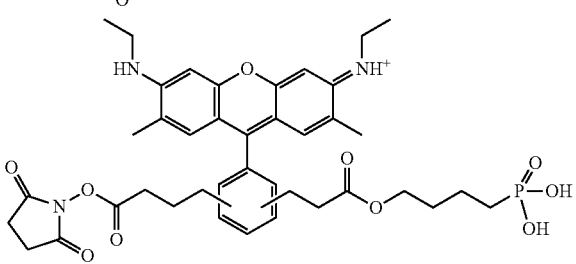
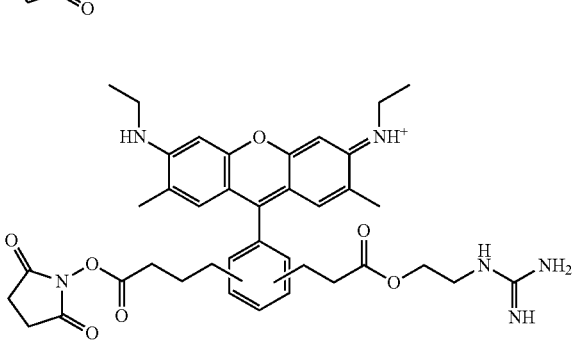
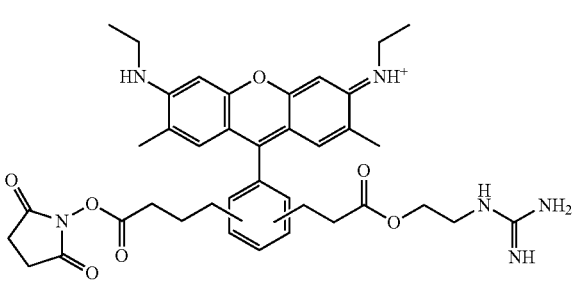
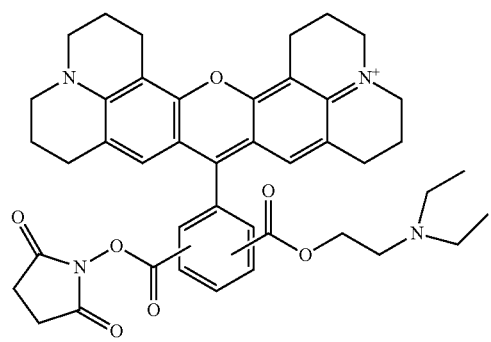
-continued
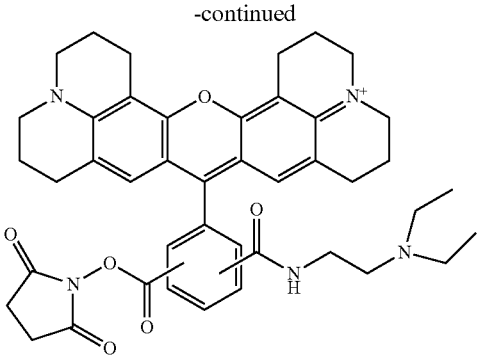
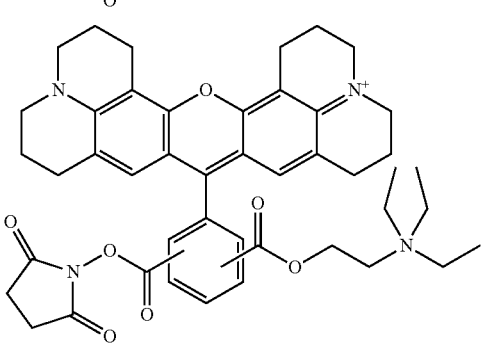
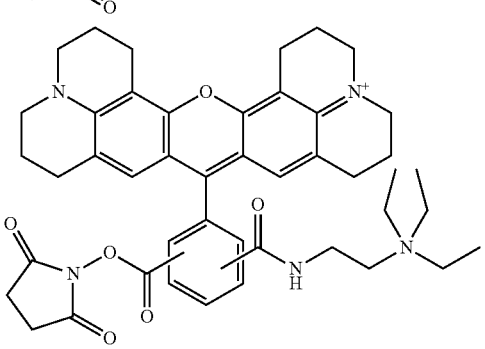
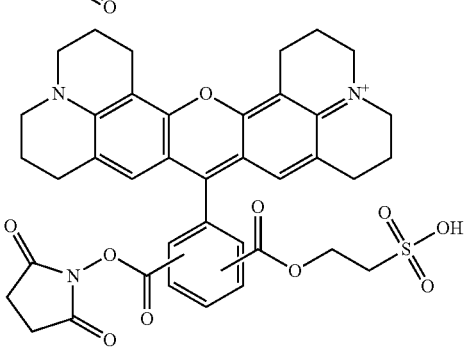
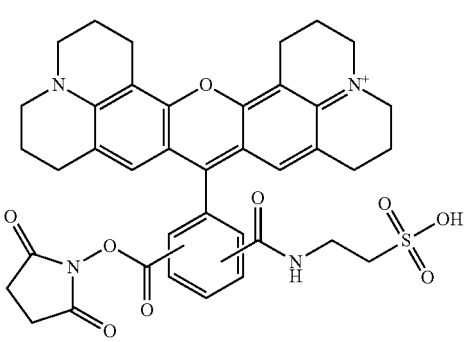

| 221 | 222 |
|---|---|
| -continued | -continued |
| 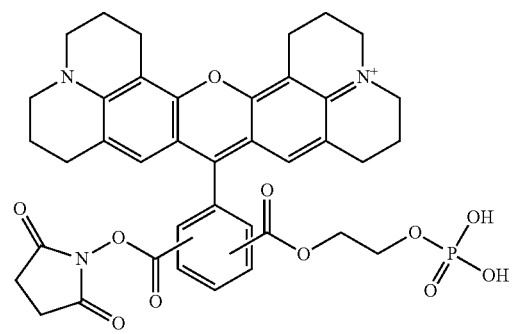 | 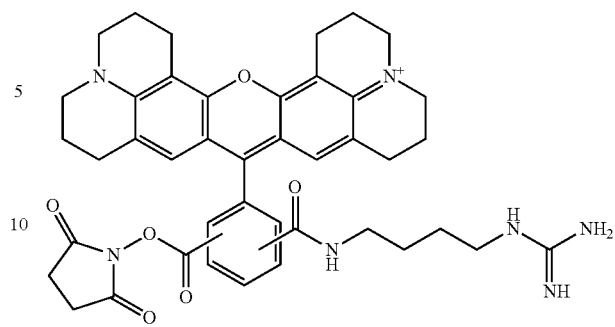 |
| 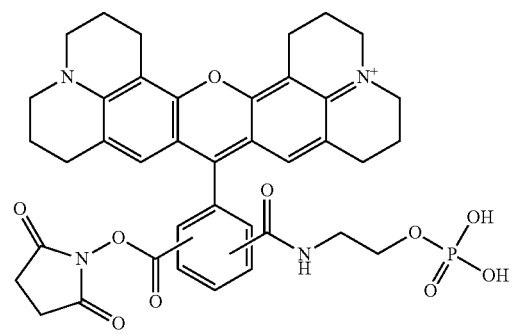 | 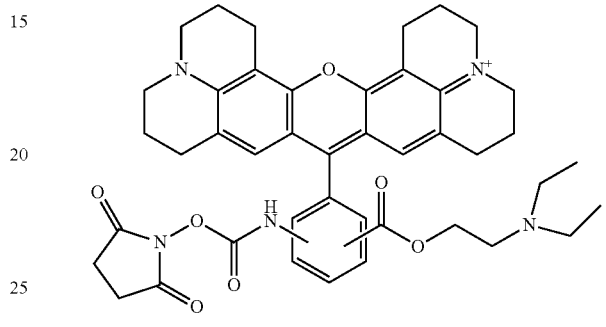 |
| 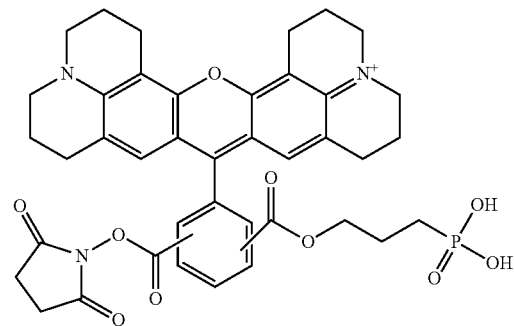 | 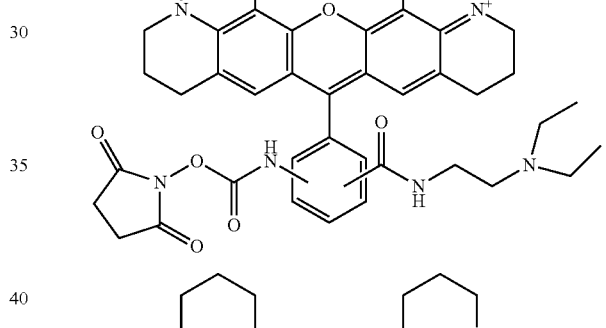 |
| 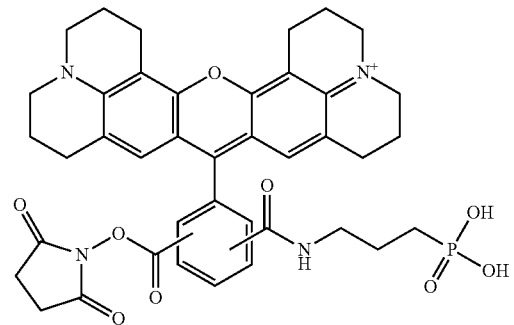 | 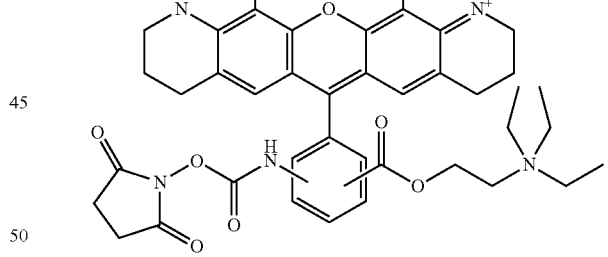 |
| 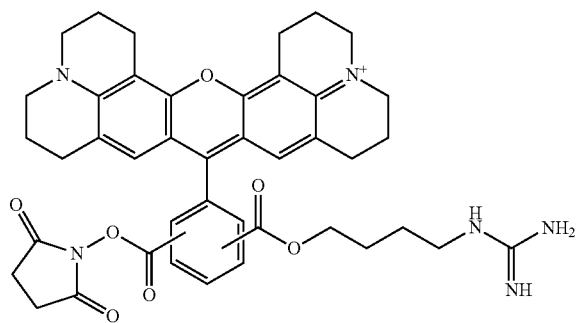 | 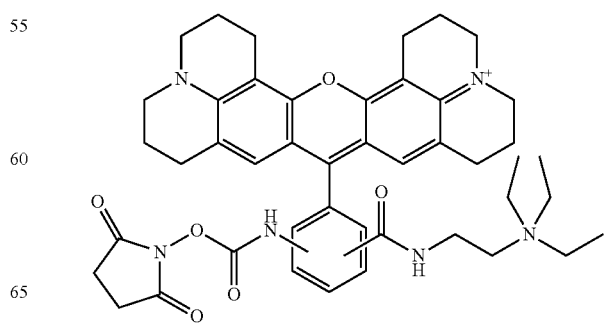 |

223
-continued
224
-continued
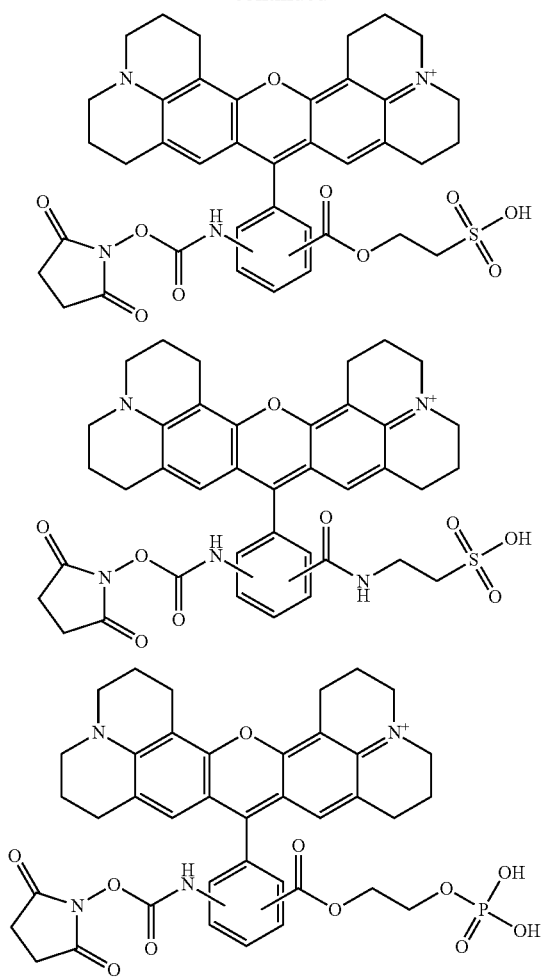
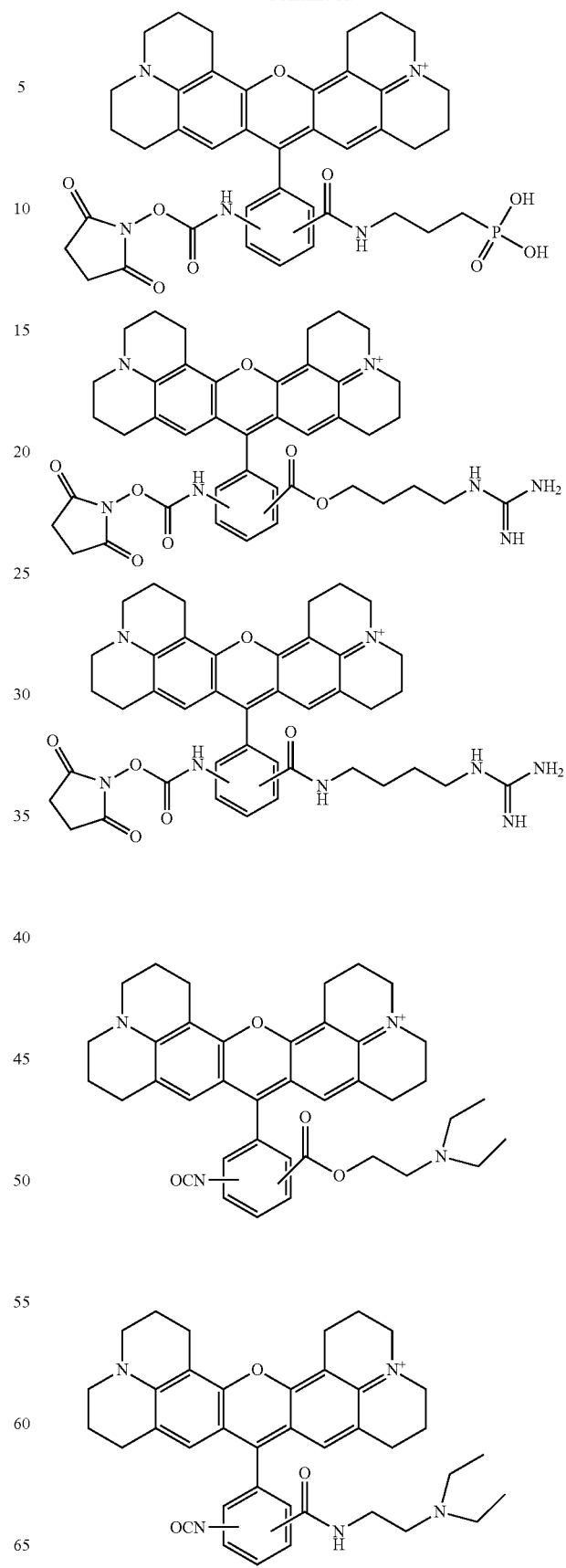

225
-continued
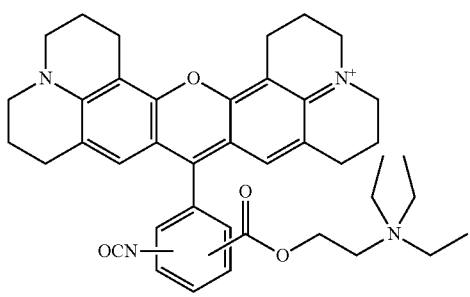
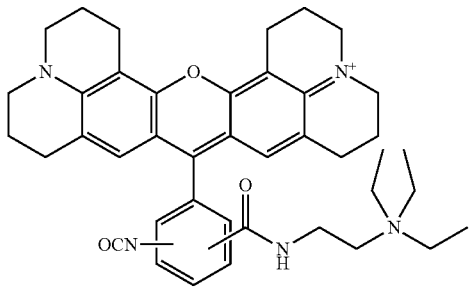
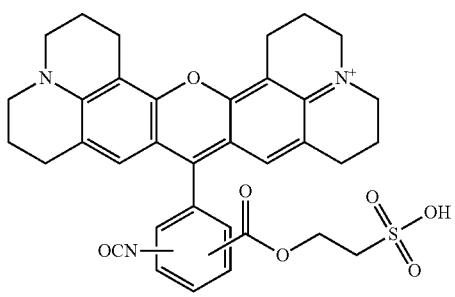
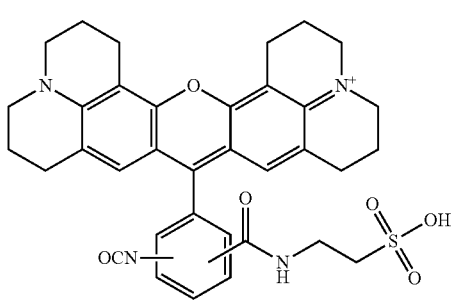
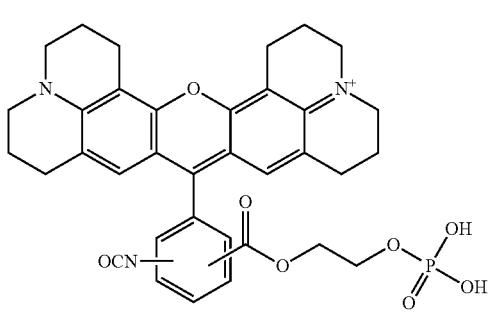
226
-continued
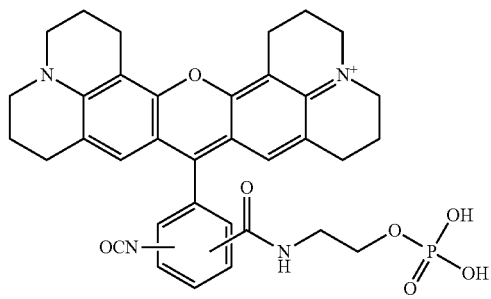
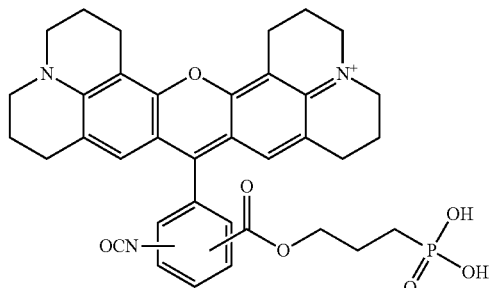
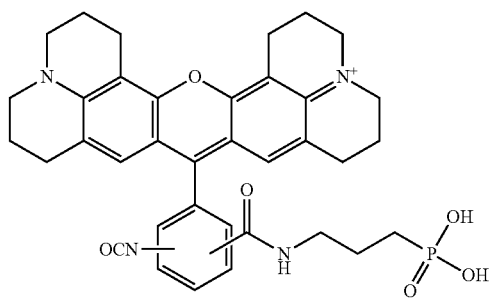
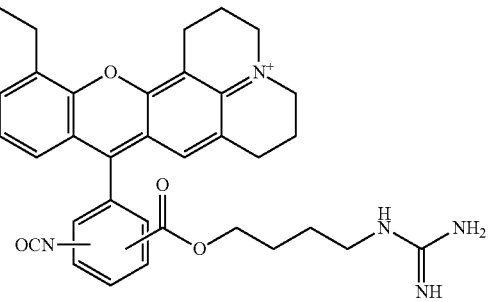
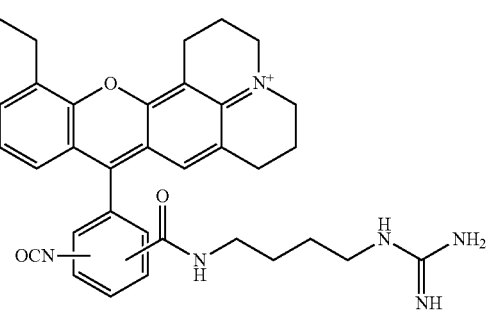

| 227 -continued | 228 -continued |
|---|---|
| 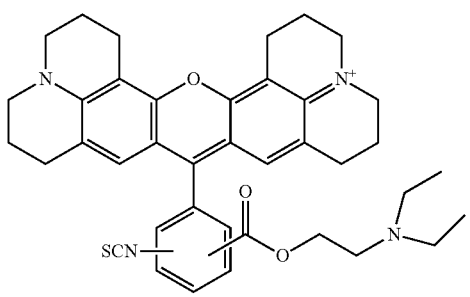 | 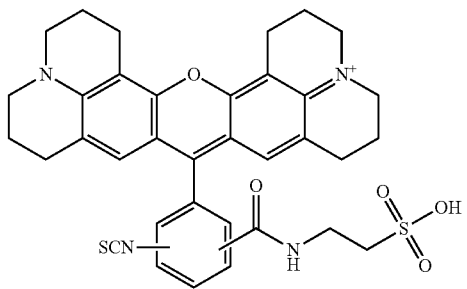 |
| 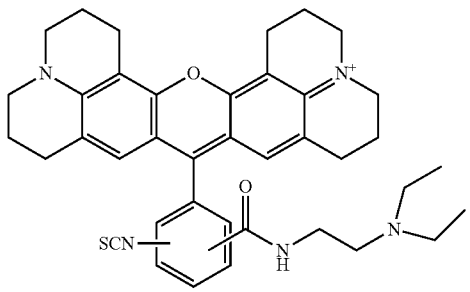 | 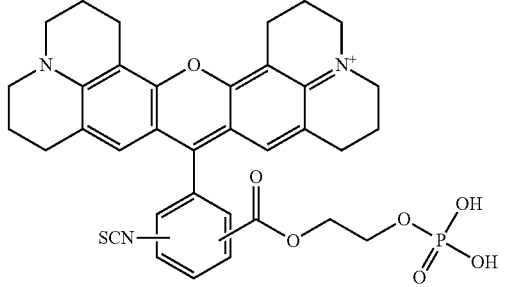 |
| 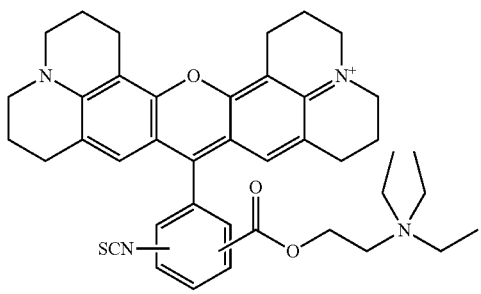 | 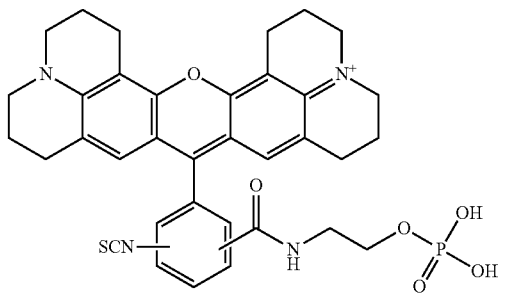 |
| 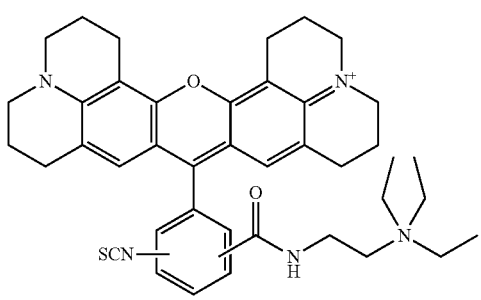 | 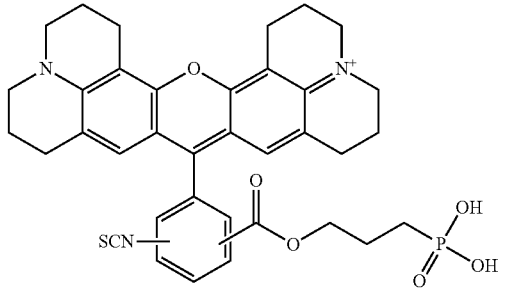 |
| 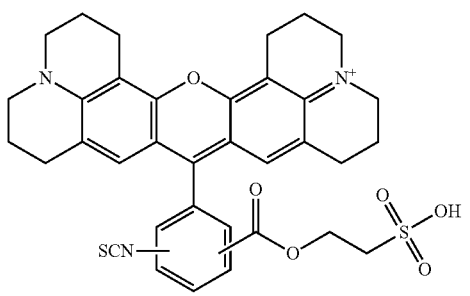 | 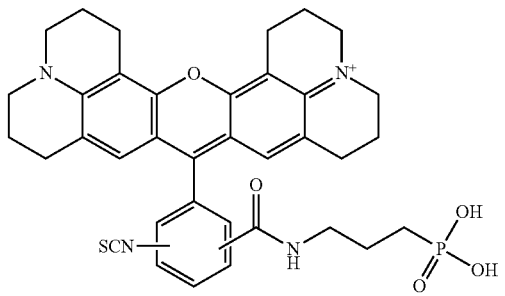 |

229
-continued
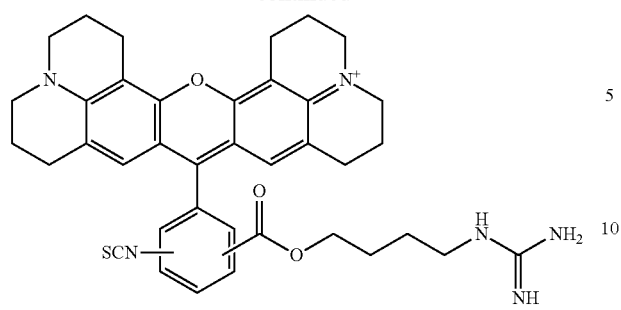
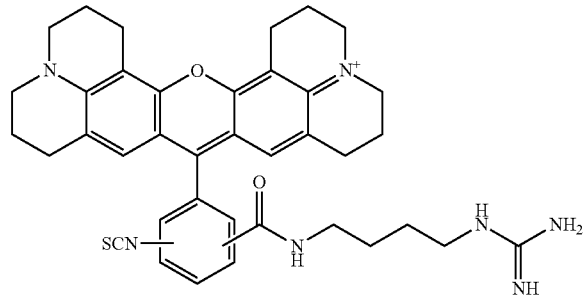
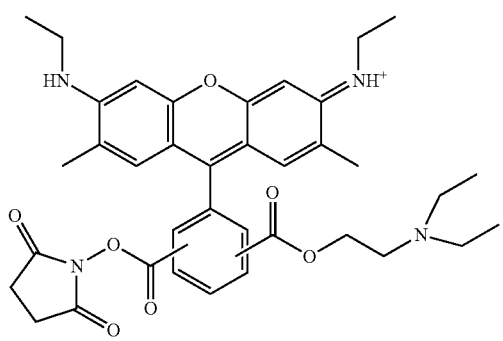
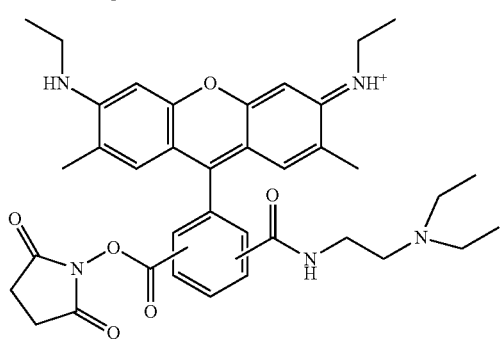
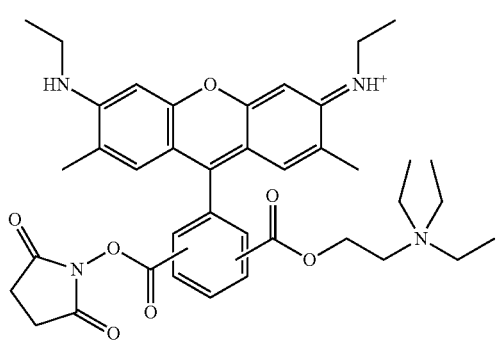
230
-continued
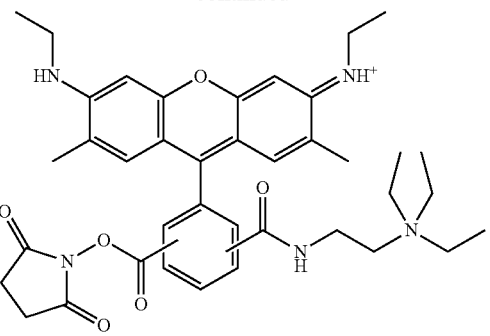
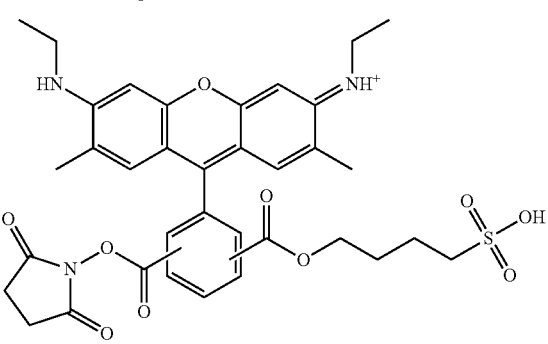
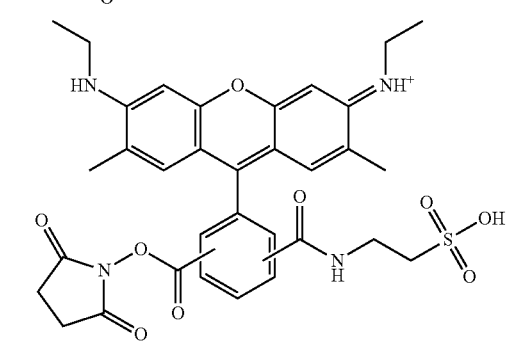
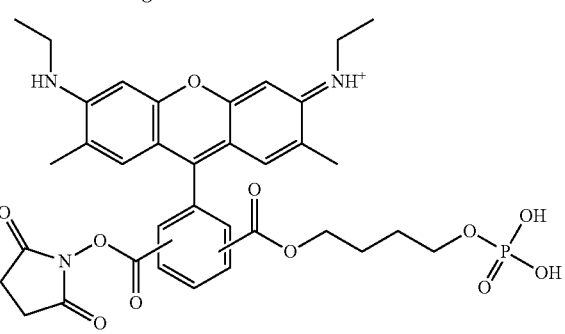
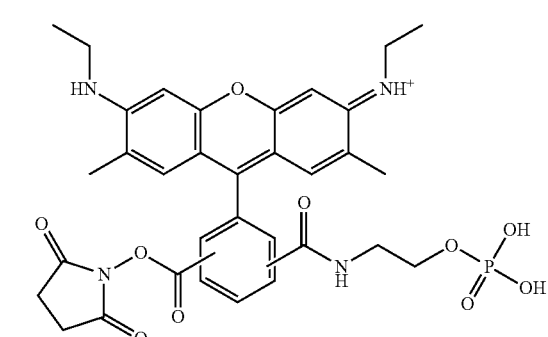

231
-continued
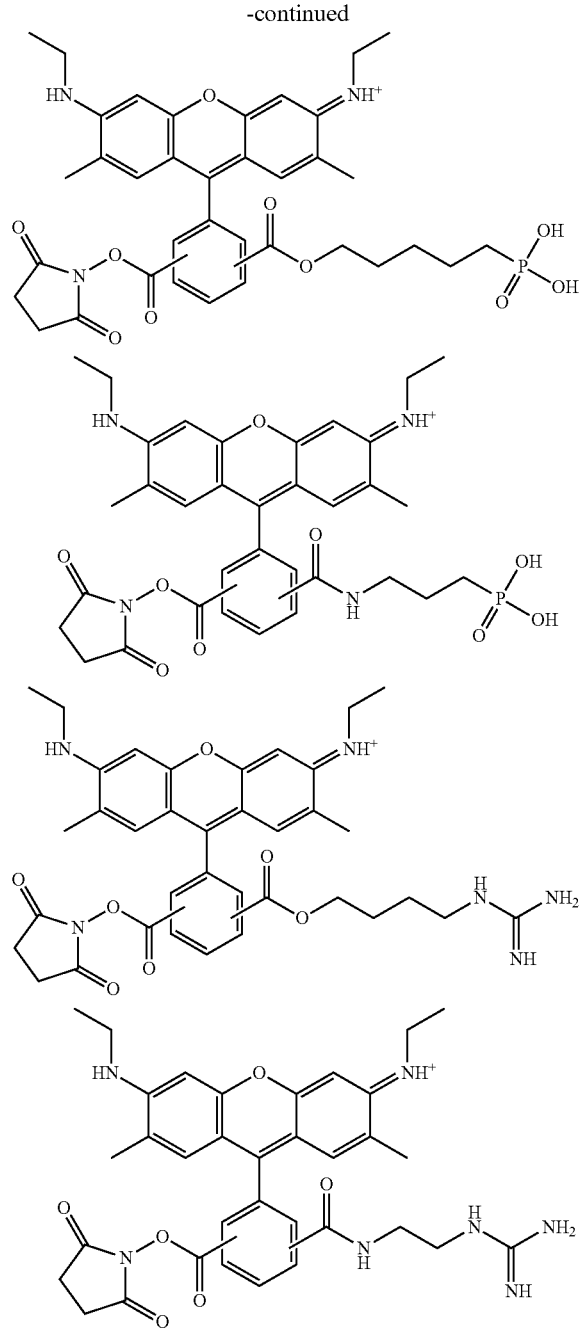
232
-continued
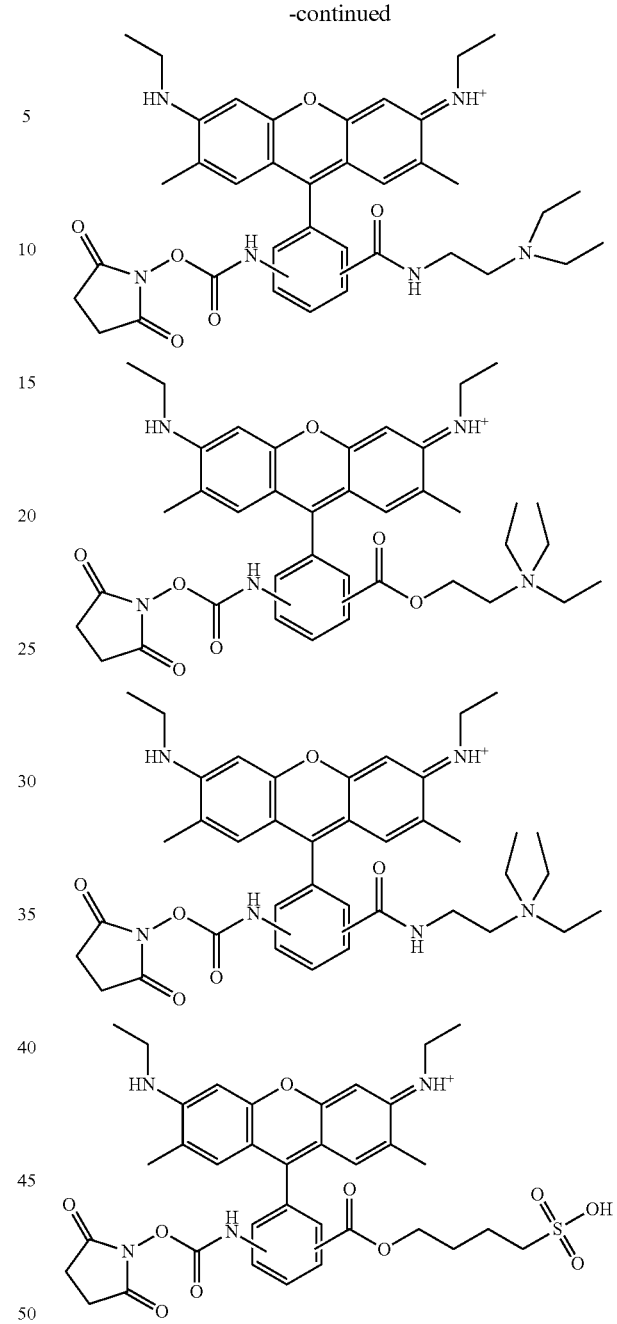
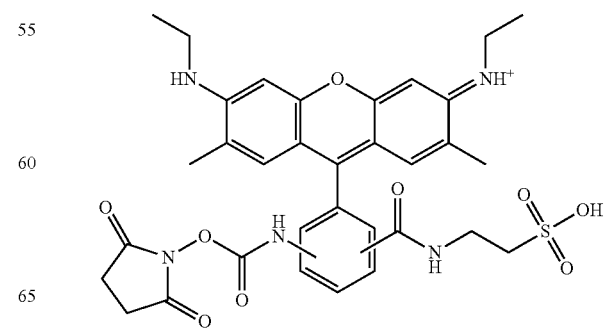

233
-continued
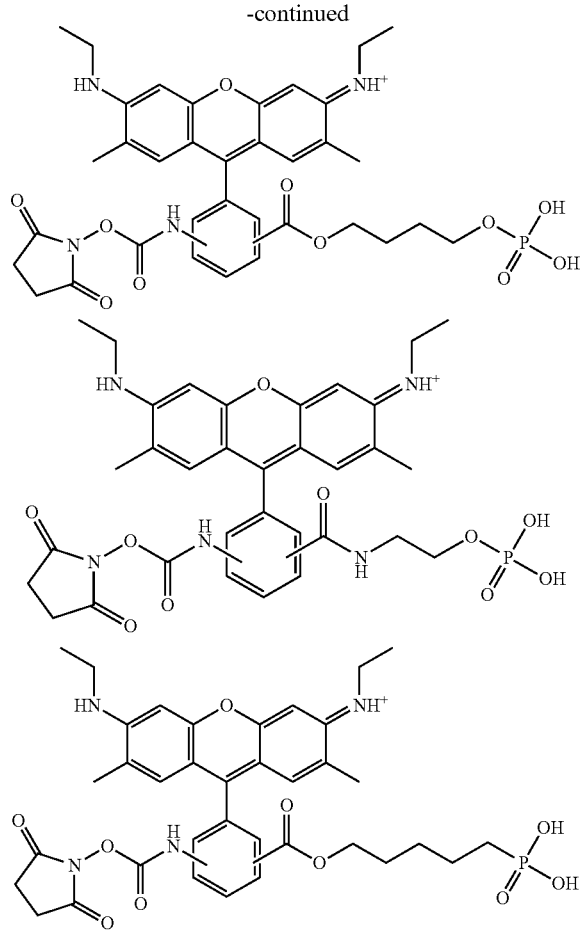
234
-continued
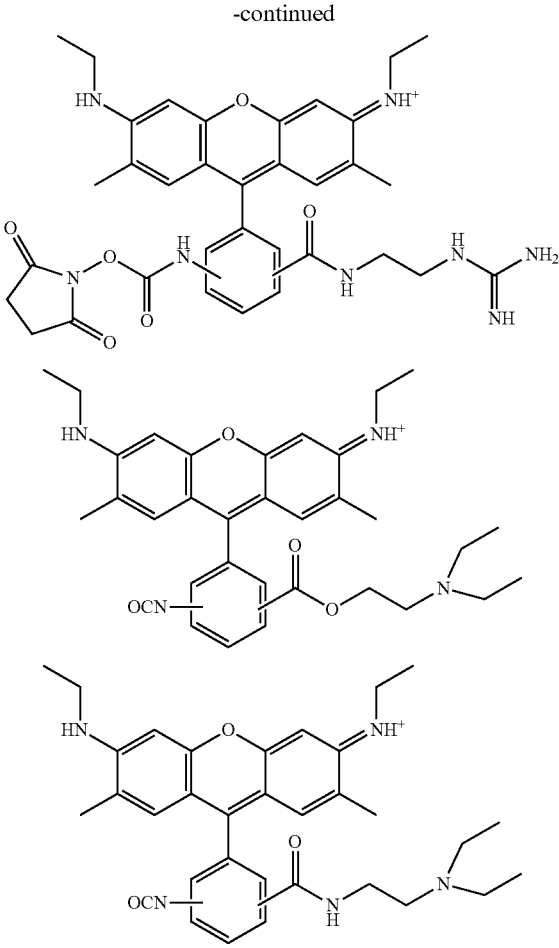
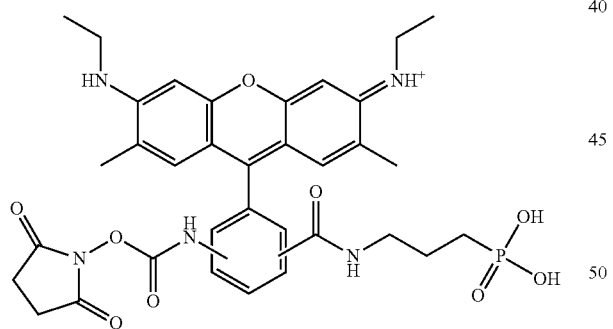
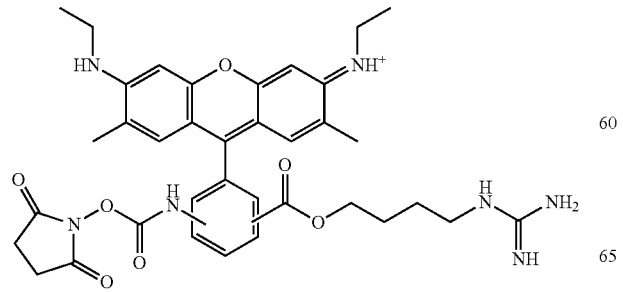
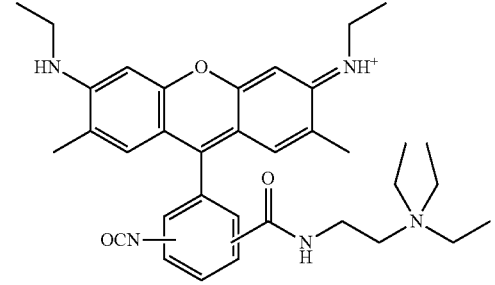

235
-continued
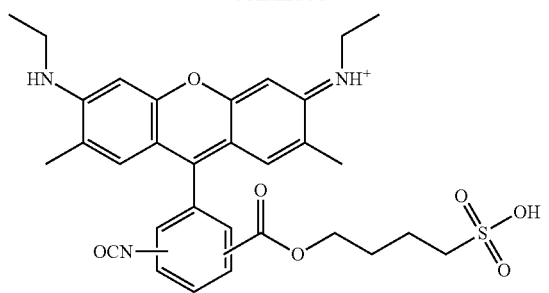
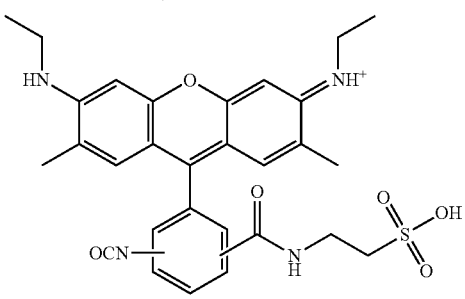
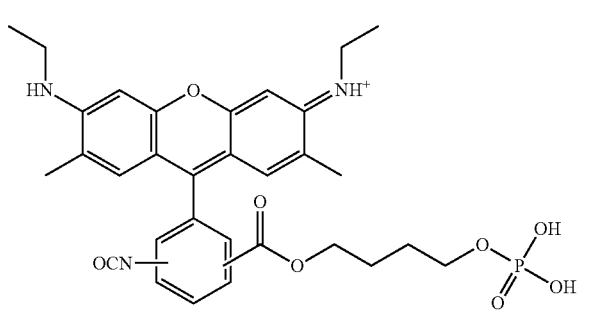
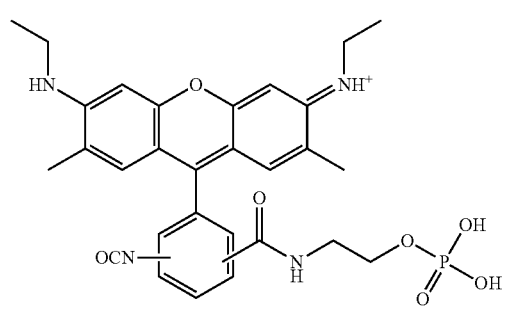
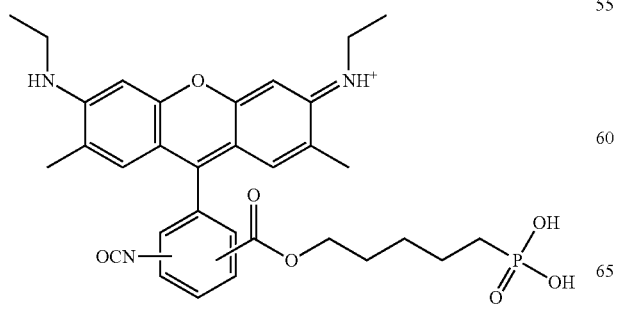
236
-continued
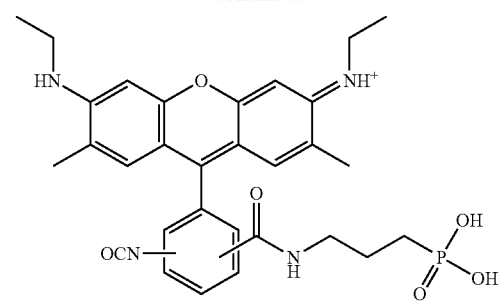
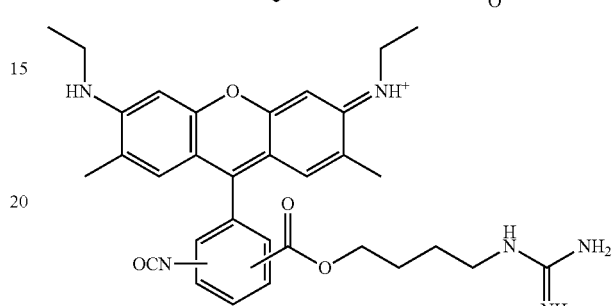
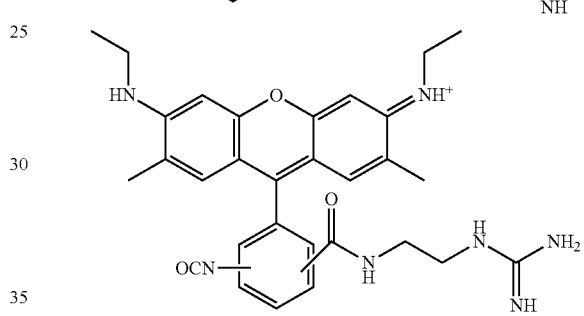
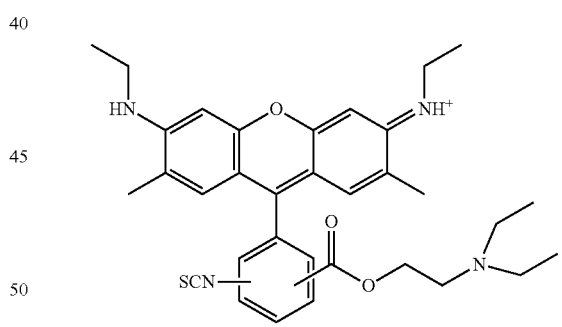
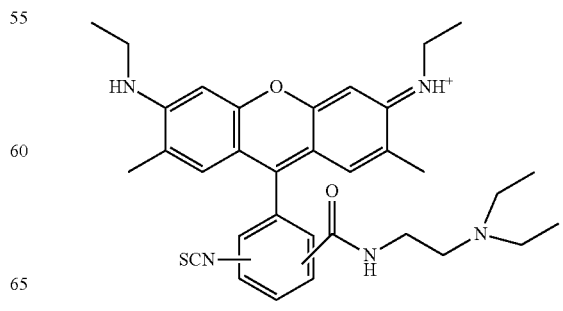

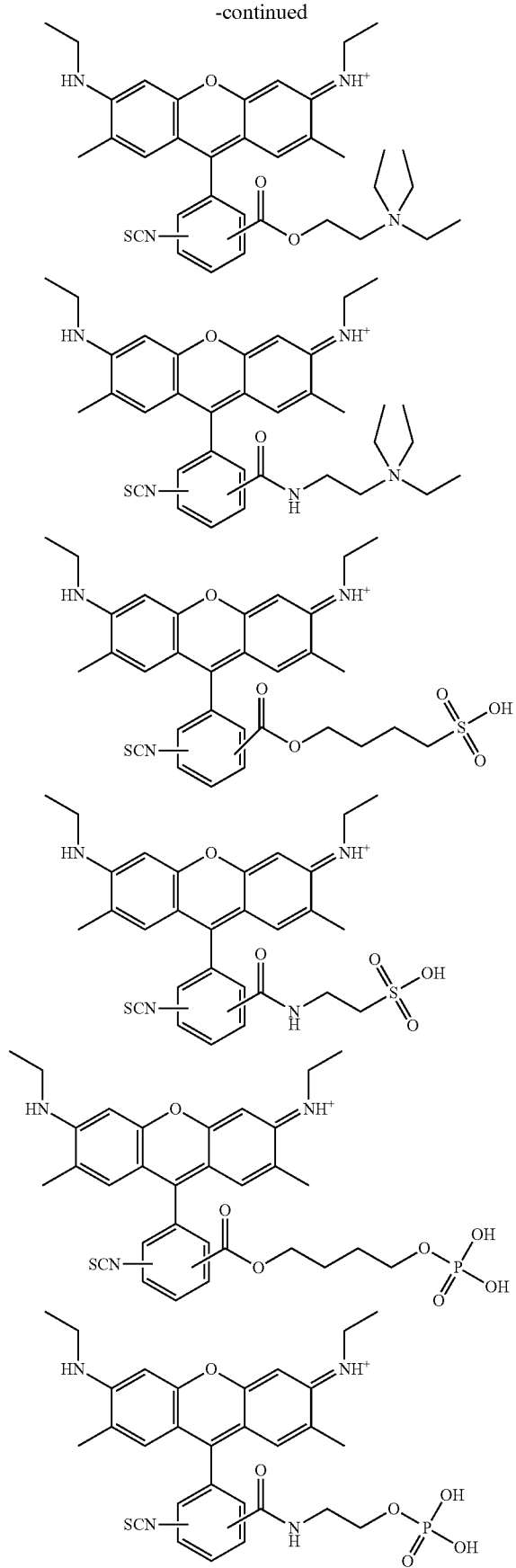
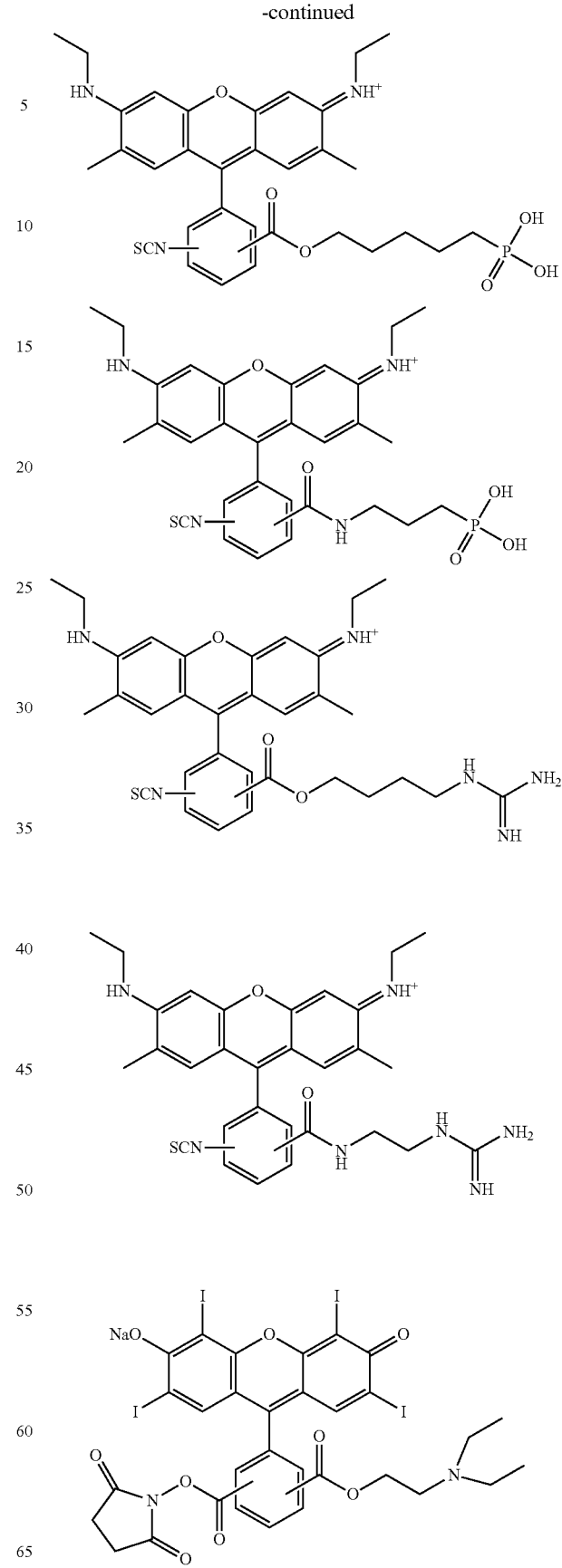

239
-continued
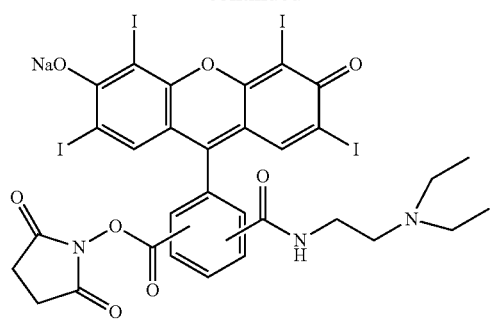
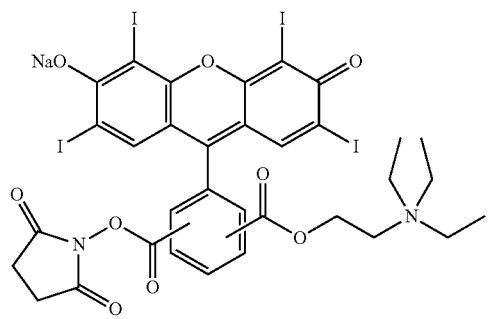
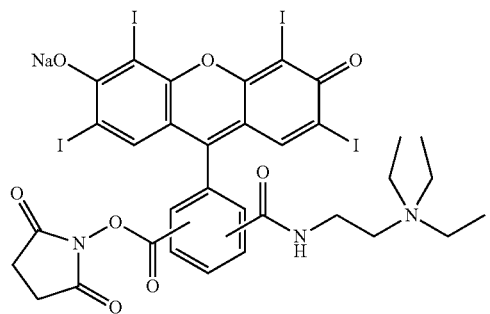
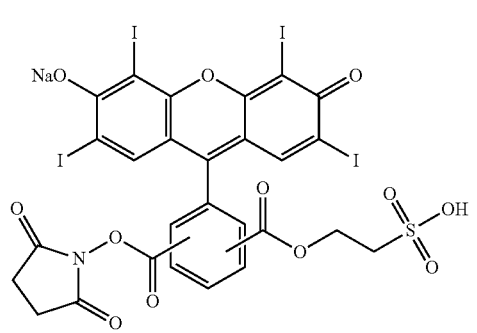
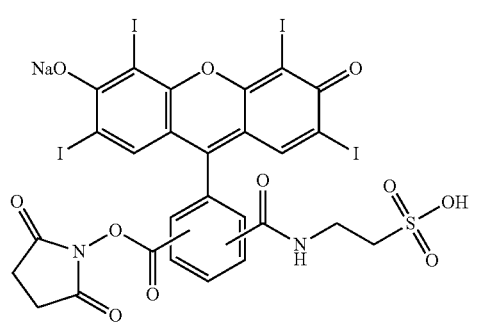
240
-continued
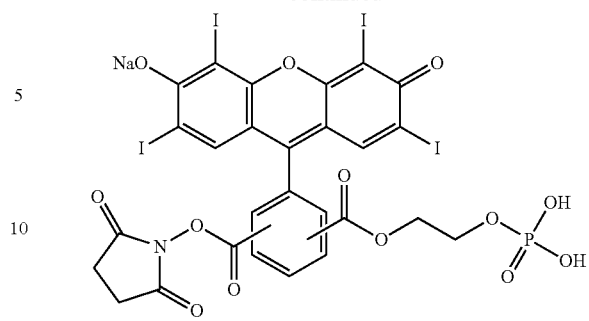
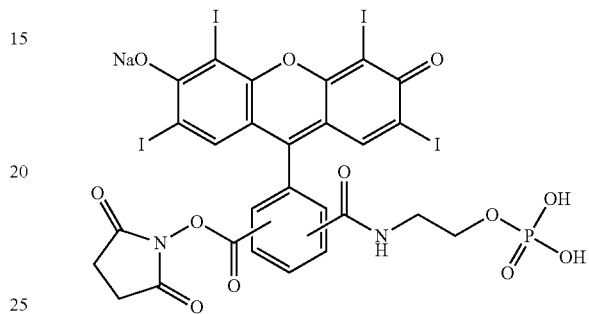
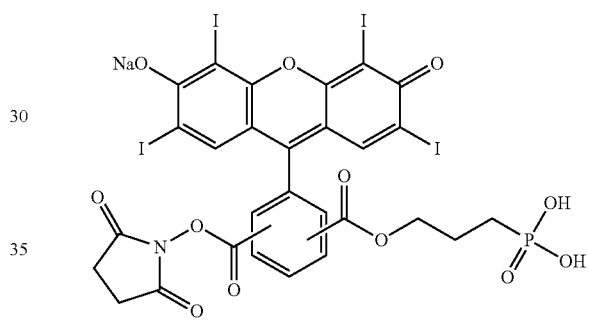
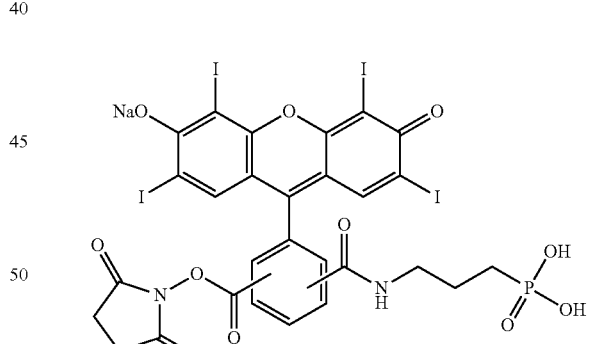
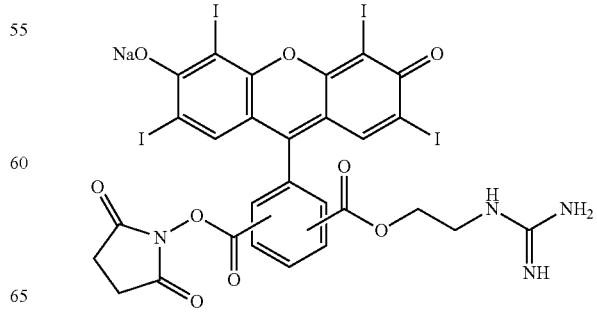

241
-continued
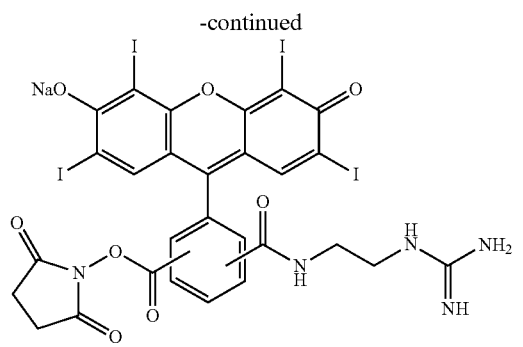
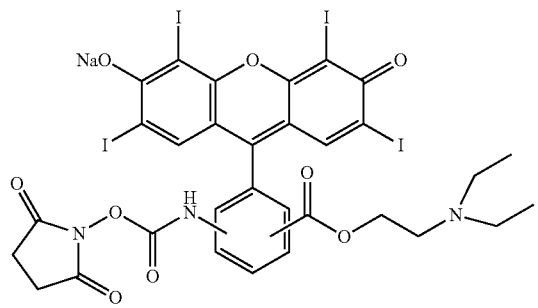
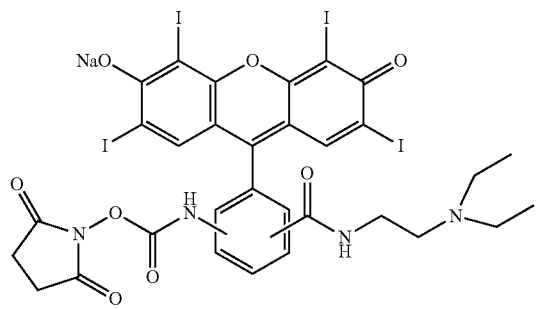
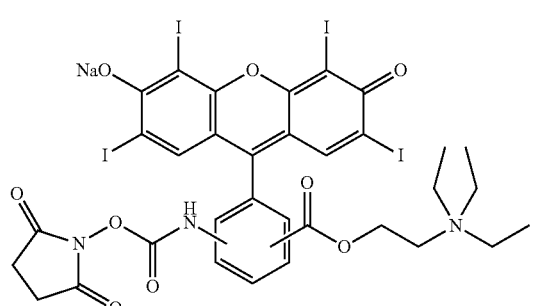
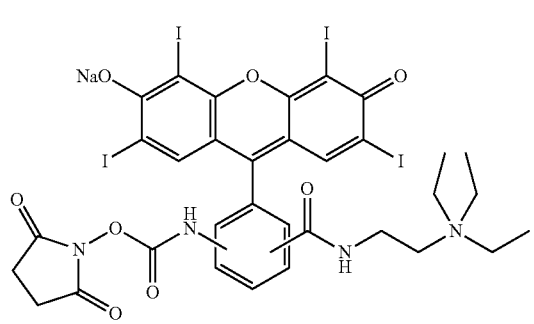
242
-continued
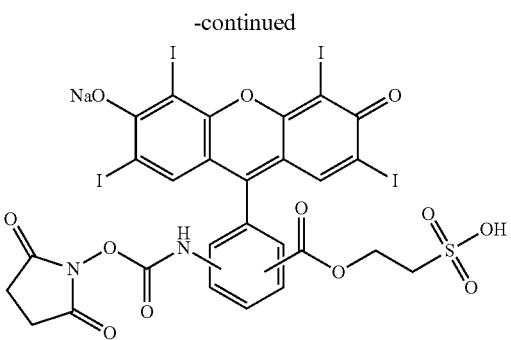
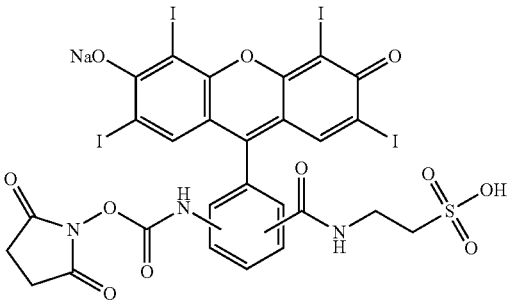
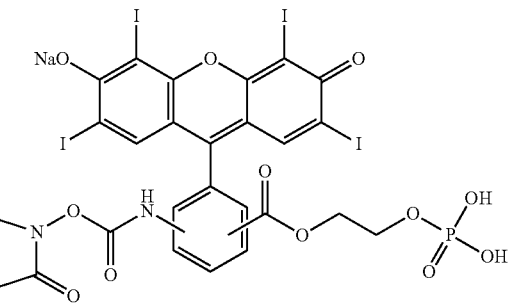
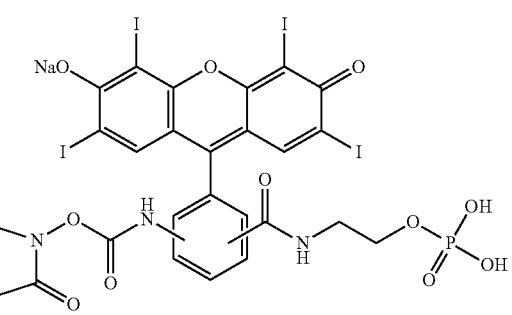
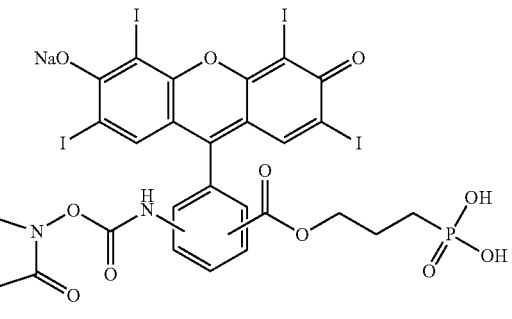

-continued
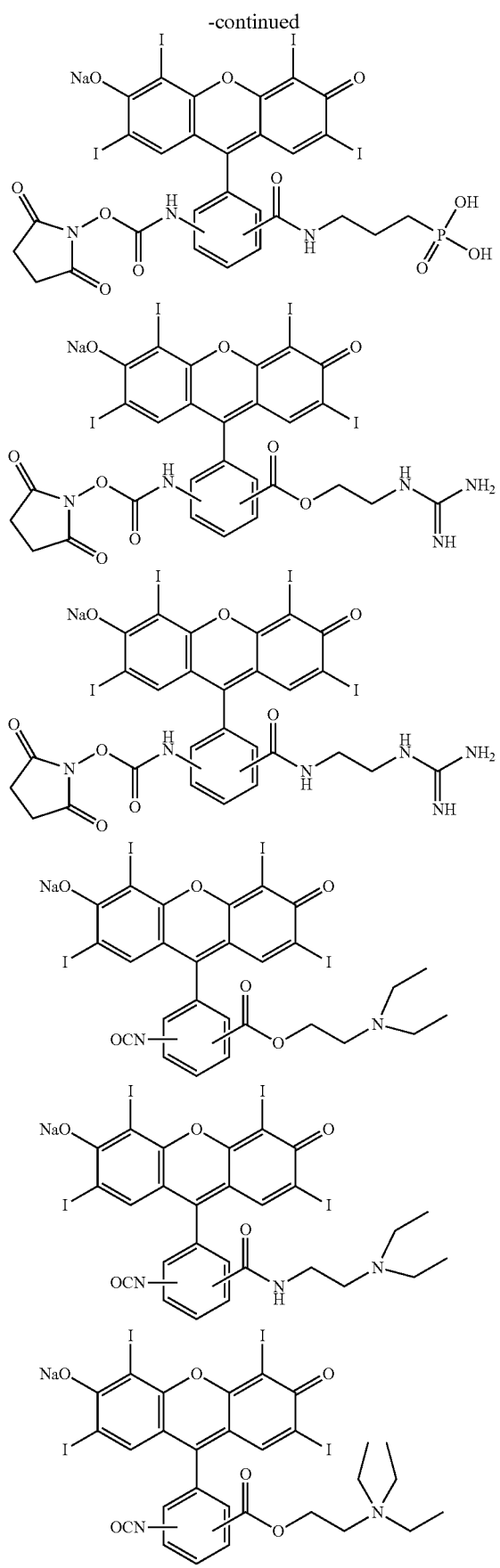
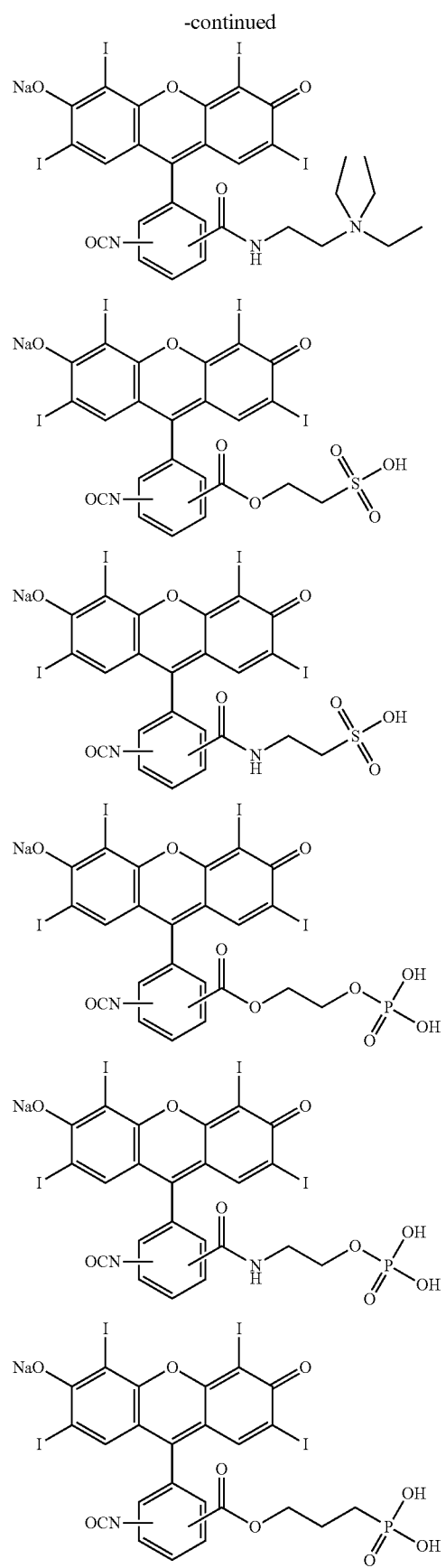

245
-continued
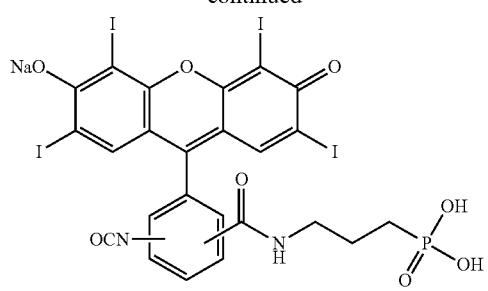
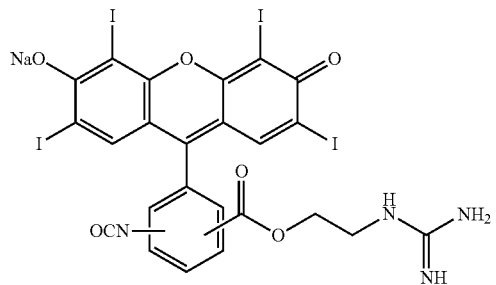
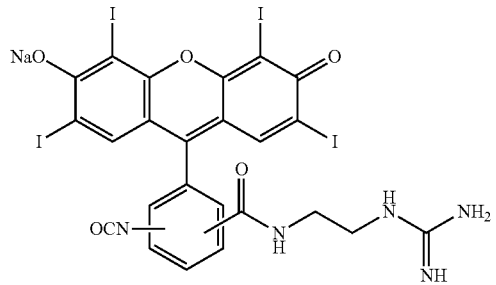
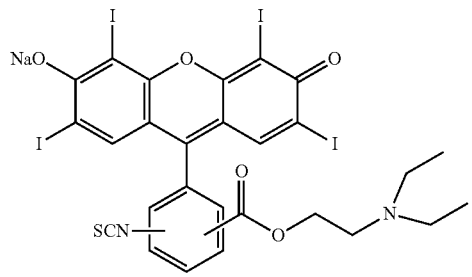
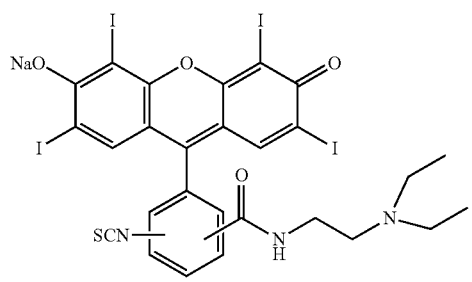
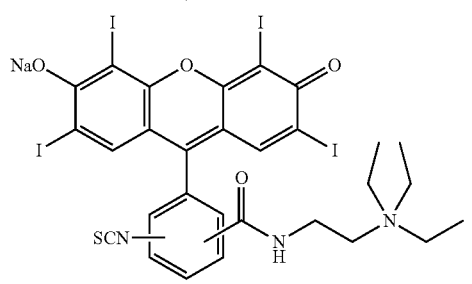
246
-continued
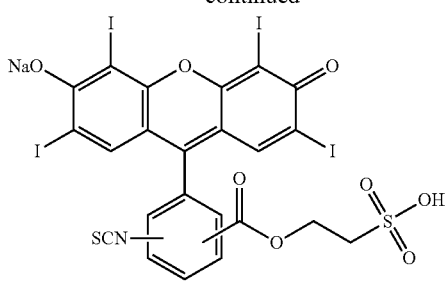
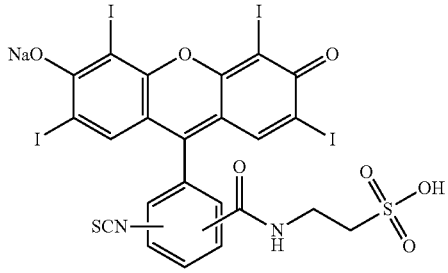
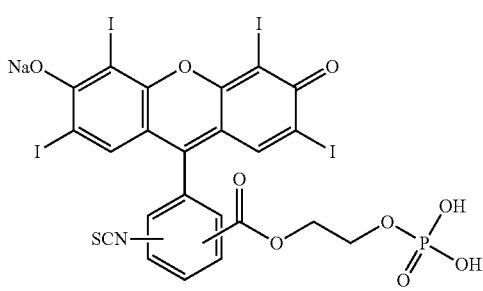
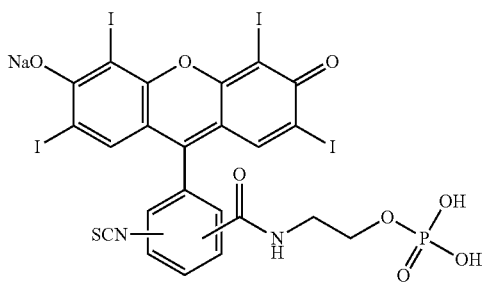
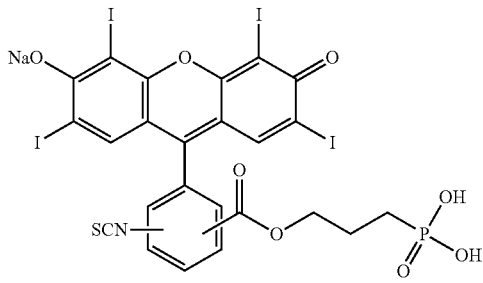
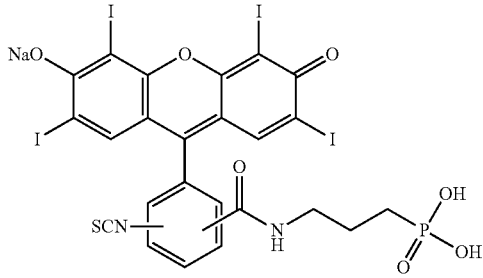

247
-continued
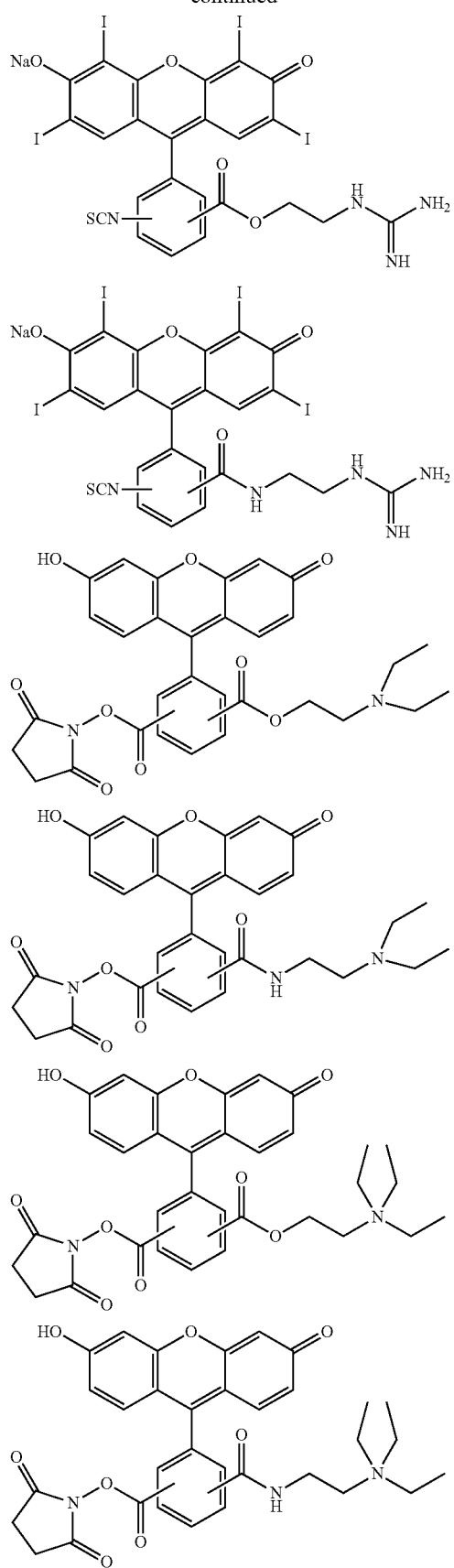
248
-continued
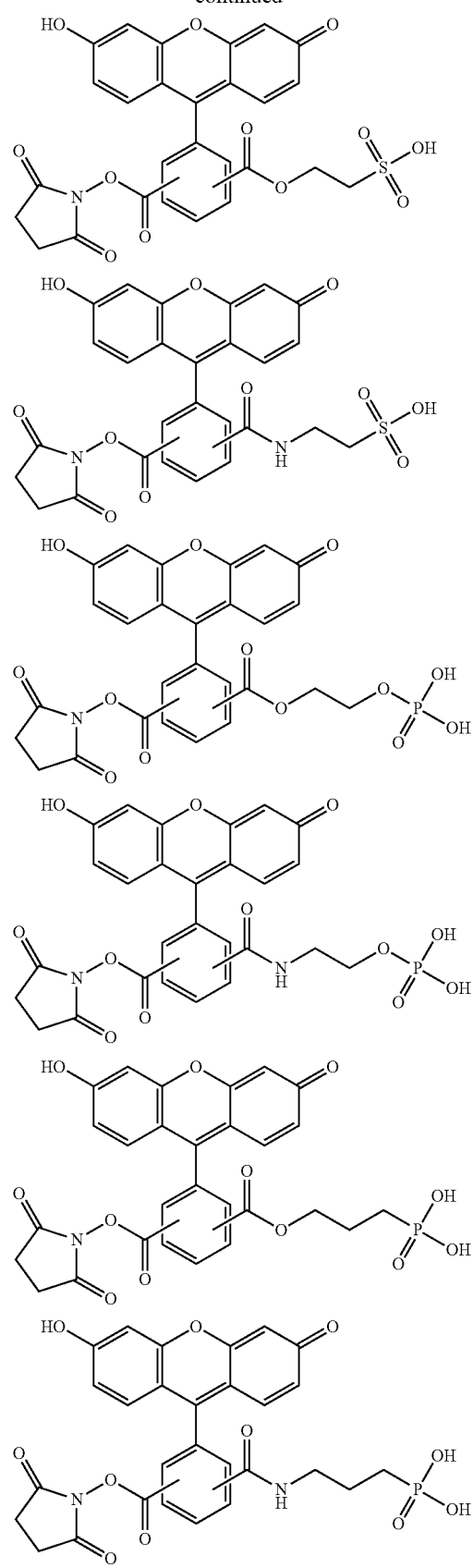

249
-continued
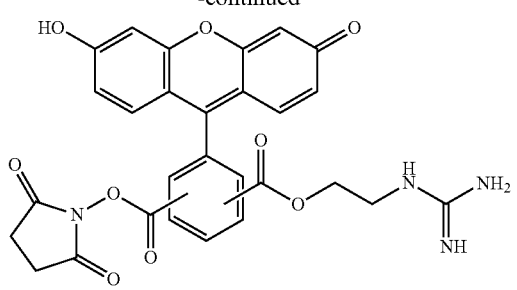
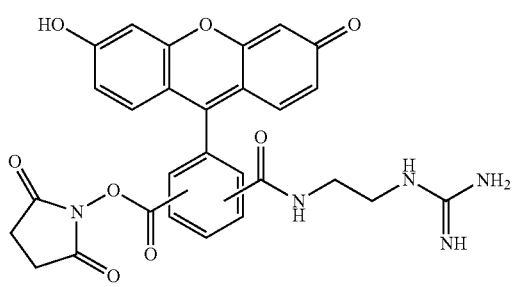
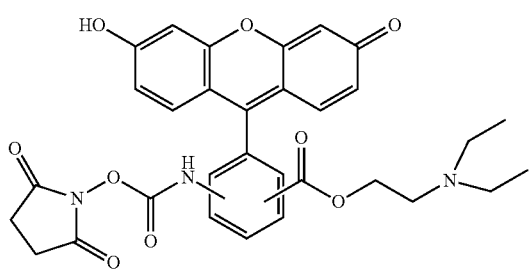
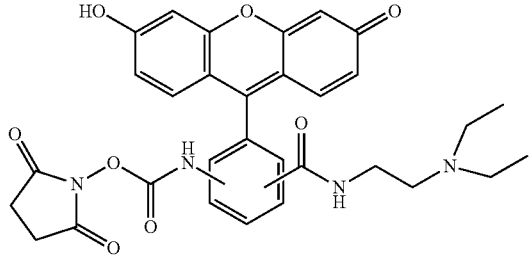
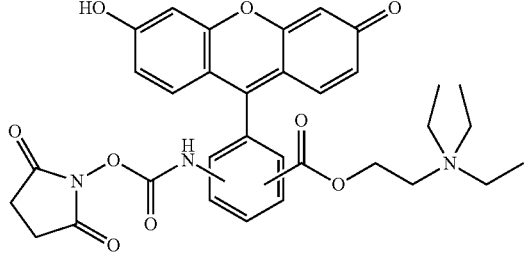
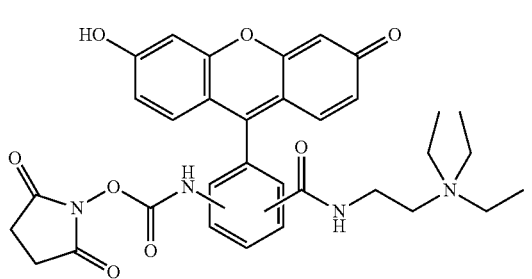
250
-continued
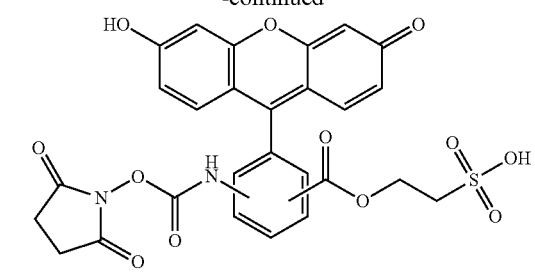
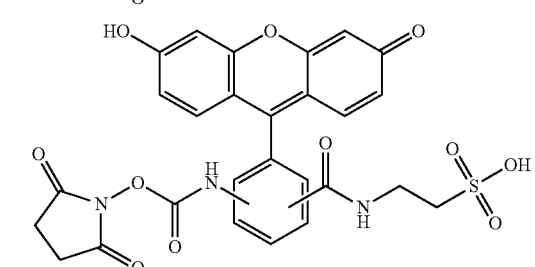
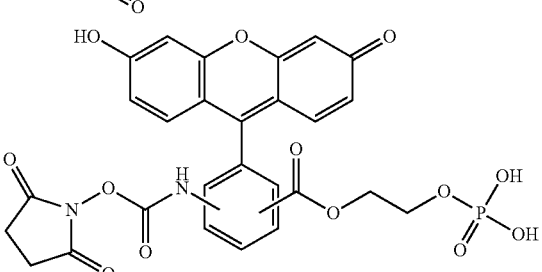
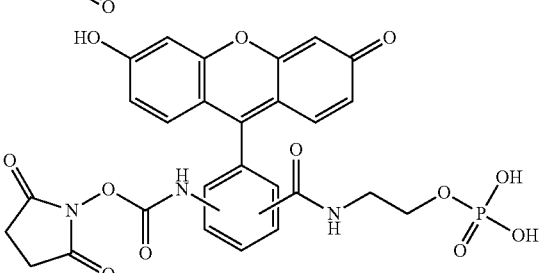
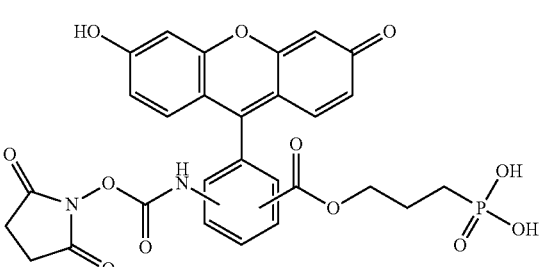
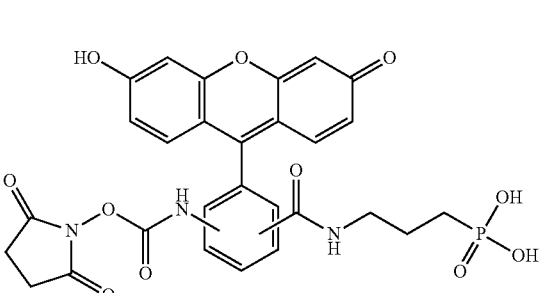

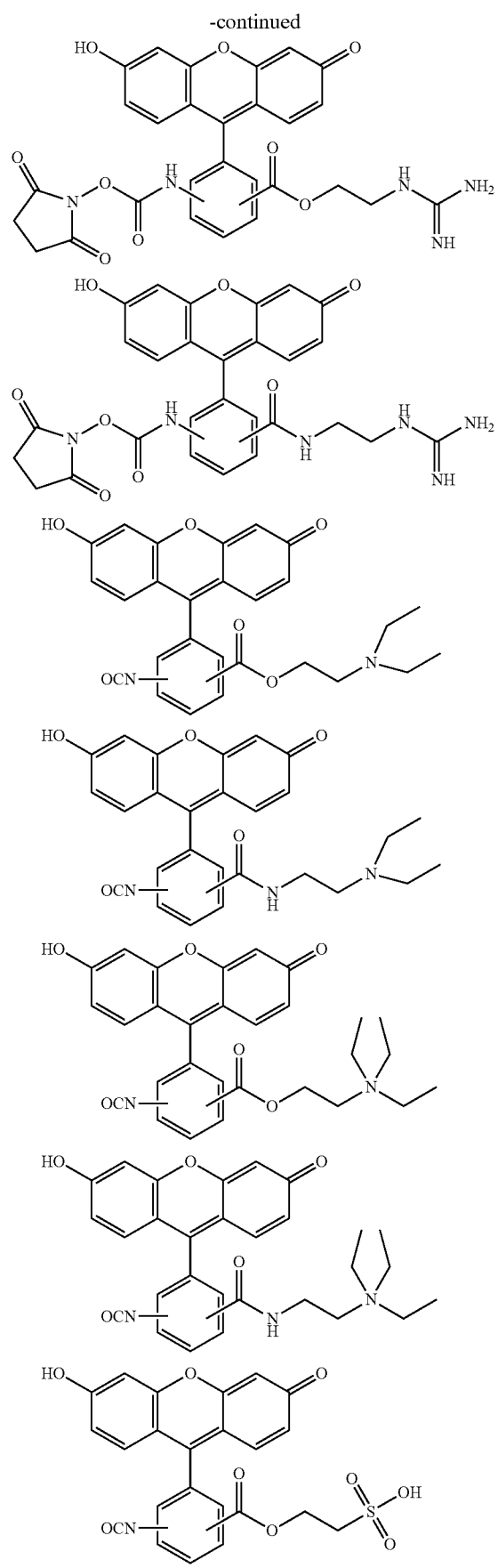
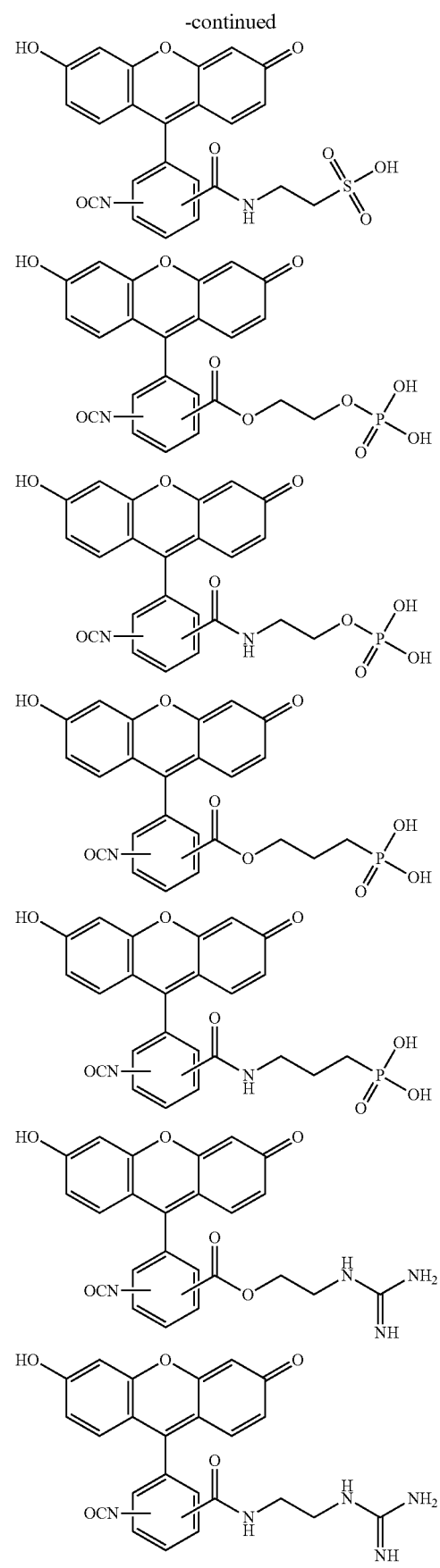

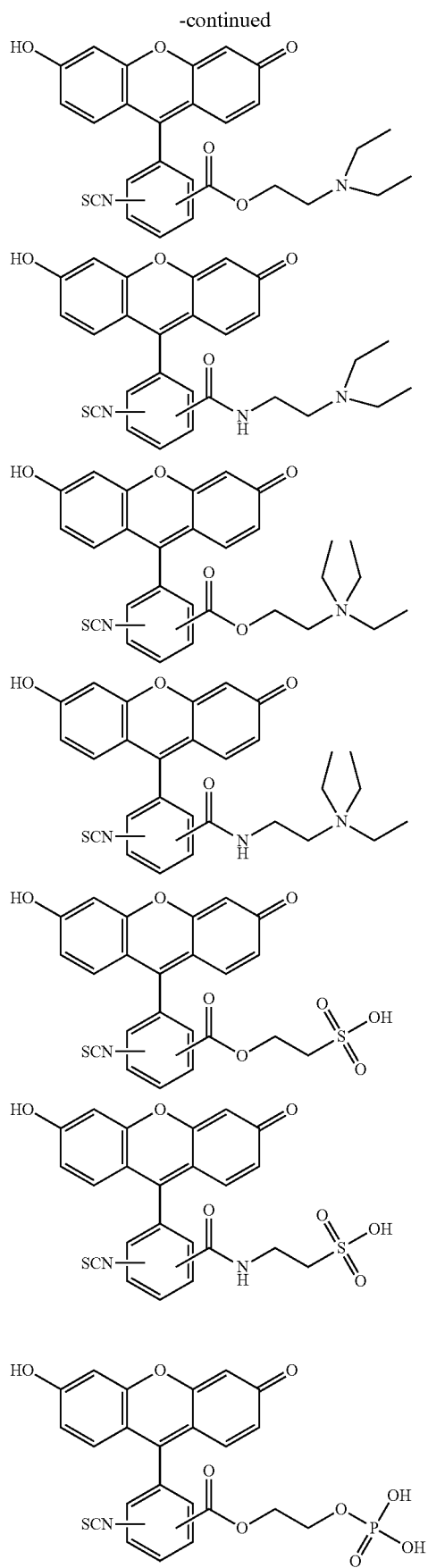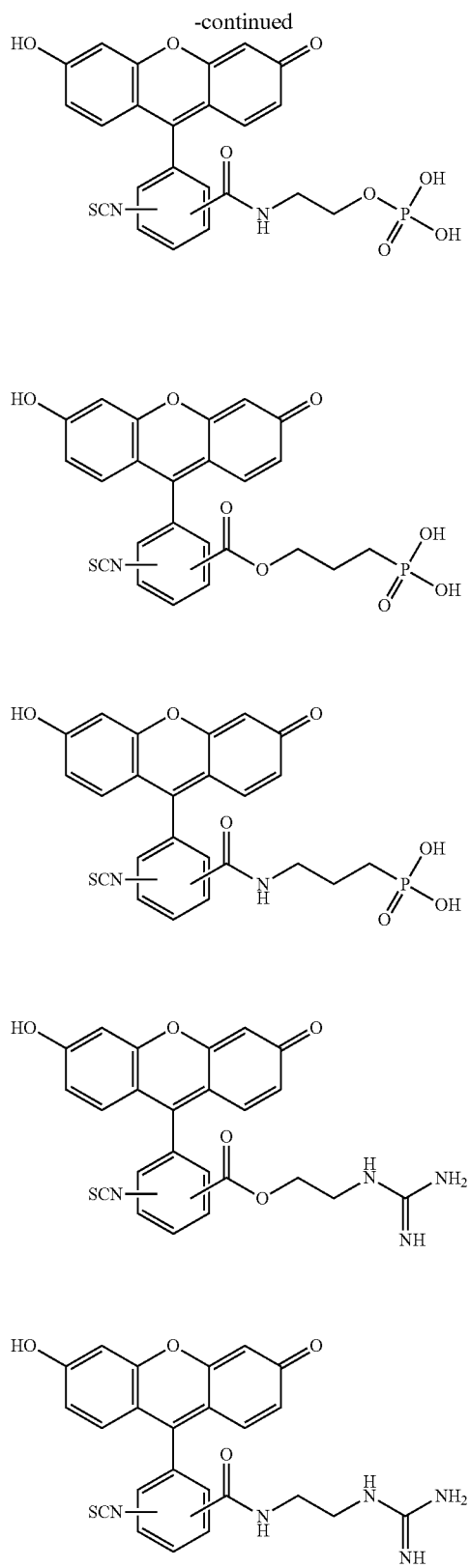
The following schemes I, II, III and IV can be used to practice the invention and make the compounds described herein.

Scheme I

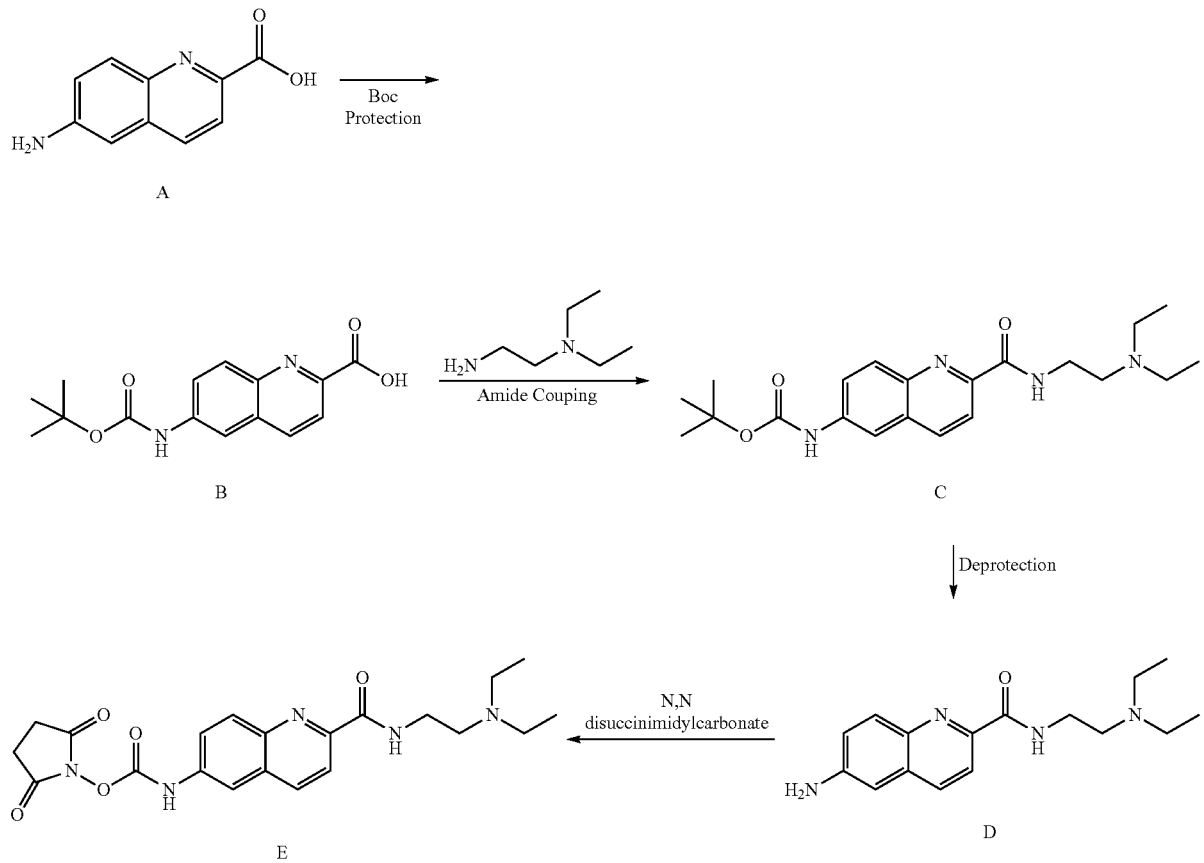

Preparation of 2,5-dioxopyrrolidin-1-yl(2-((2-(diethylamino)ethyl)carbamoyl)quinolin-6-yl)carbamate 40 mg of B was dissolved in 2.5 mL of a 1:4 mixture of dimethylformamide:dichloromethane in a 10 mL flask equipped with a stir bar and purged with $N_2$. 1.7 mg of dimethylaminopyridine and 181 µL of dicyclohexylcarbodiimide were then added to the flask. After stirring for 10 min, 2-(diethylamino)ethylamine (57 mg) in 3 mL of dichloromethane was added to the flask. This was then stirred at room temperature for 20 hours. After this time, 3 mL of water was added to the reaction flask. The organic layer was separated and the aqueous layer was extracted with 2 mL of dichloromethane. The organic phases were combined, dried, and then evaporated to dryness to provide the crude material. This was subjected to standard organic chemistry purification techniques to provide the desired material C in >95% purity.

1.8 g of C was dissolved in a mixture of 5.3 g of trifluoracetic acid in 30 mL of dichloromethane. The reaction mixture was stirred at room temperature for 48 hours. After removal of the solvent under reduced pressure, the crude material was dissolved in 30 mL of 0.5 N HCl. This mixture was then extracted with 50 mL aliquots of ethyl acetate. The organic phases were combined, dried, and then evaporated to dryness to yield 1.2 gram of the crude product. This was subjected to standard organic chemistry purification techniques to provide the desired material D in >98% purity.

425 mg of D was added to 6 mL of dry acetonitrile in a dry 10 mL Erlenmeyer flask equipped with a stir bar, and allowed to dissolve. In a separate 25 mL flask equipped with a 10 mL dropping funnel and a stir bar, 380 mg of N,N-disuccinimidylcarbonate (DSC) was dissolved in 6 mL of dry acetonitrile, and the system was purged with $N_2$. The solution of D was then transferred to the dropping funnel, and added dropwise to the DSC solution over the course of 10 min. The solution was then allowed to stir for 4 hours. At this point, the solvent was removed, and the desired product E was dried at room temperature under high vacuum.

Scheme II

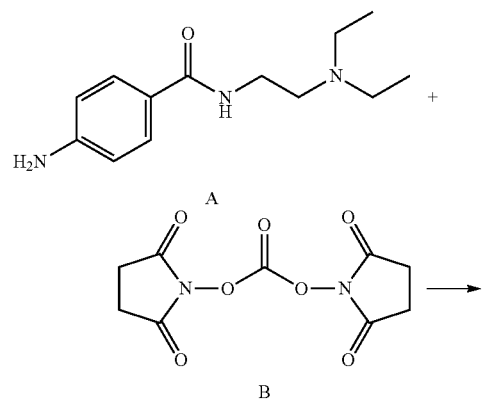

-continued

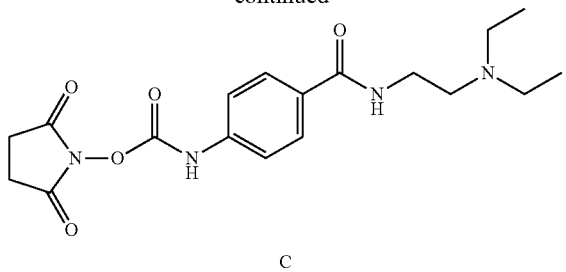

C

Preparation of 2,5-dioxopyrrolidin-1-yl (4-((2-(diethylamino)ethyl)carbamoyl)phenyl)carbamate In a first method, 2.6 g of procainamide A was added to 47 g of dry acetonitrile in a dry 100 mL Erlenmeyer flask equipped with a stir bar, and allowed to dissolve. In a separate 1 L flask equipped with a dropping funnel and a stir bar, 3.2 g of N,N-disuccinimidylcarbonate (DSC) B was dissolved in 417 g of dry acetonitrile, and the system was purged with $N_2$. The solution of procainamide was then transferred to the dropping funnel, and added dropwise to the DSC solution over the course of 1 hour. The solution was then allowed to stir for 4 hours. At this point, the solvent was removed, and 2,5-dioxopyrrolidin-1-yl (4-((2-(diethylamino)ethyl)carbamoyl)phenyl)carbamate C was dried at room temperature under high vacuum.

In a second method, 8.2 g of procainamide was added to 50 mL of dry dichloromethane in a dry 100 mL Erlenmeyer flask equipped with a stir bar, and allowed to dissolve. In a separate 1 L flask equipped with a dropping funnel and a stir bar, 10.1 g of N,N-disuccinimidylcarbonate (DSC) was mixed with 400 mL of dry dichloromethane, and the system was purged with $N_2$. The solution of procainamide was then transferred to the dropping funnel, and added dropwise to the DSC solution over the course of 1 hour. The solution was then allowed to stir for 4 hours. At this point, the desired product was removed from the mother liquor by filtration, then dried at room temperature under high vacuum.

Scheme III

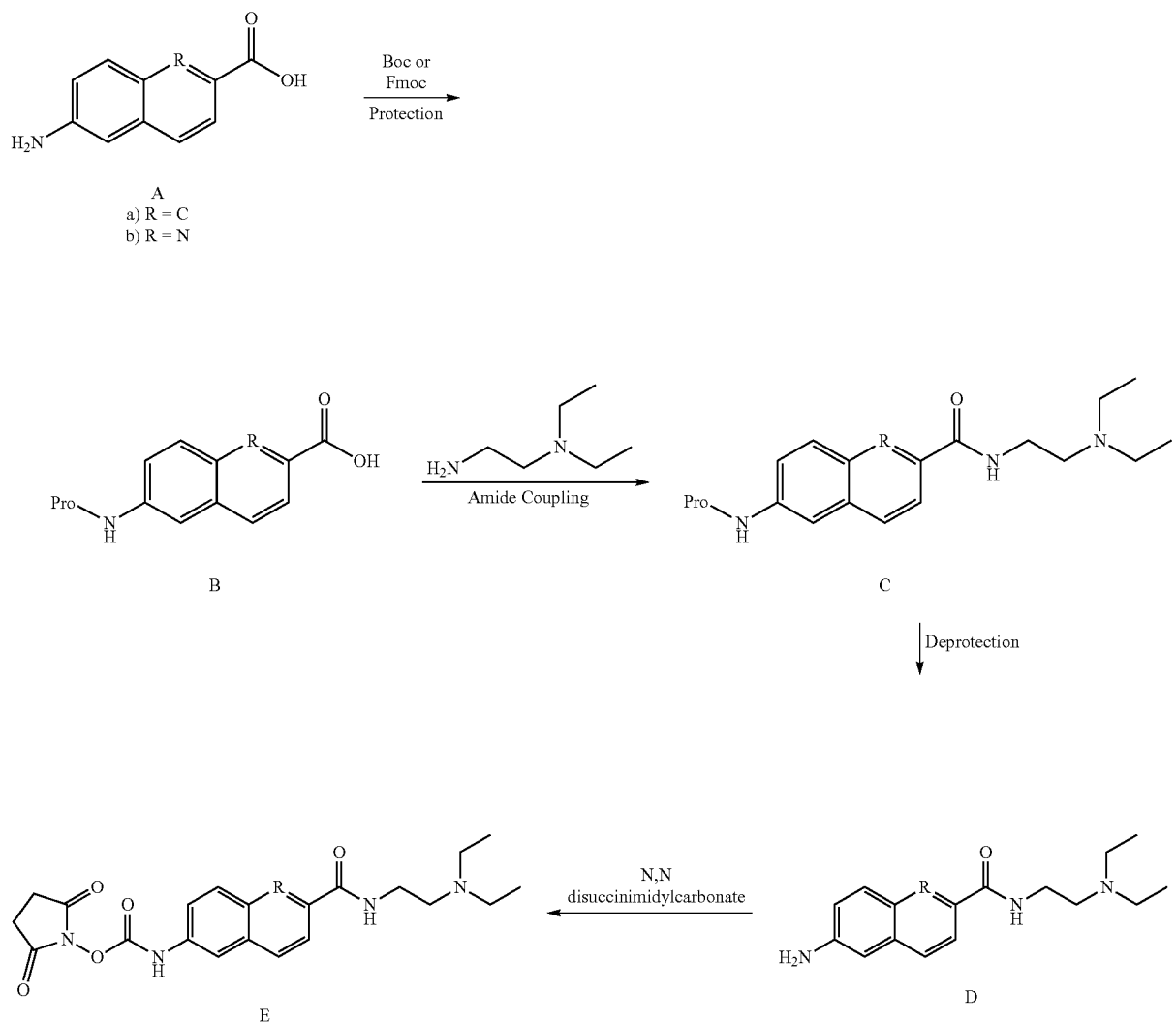

Methods used for Scheme I and Scheme II are applicable to Scheme III for making the compounds presented herein.

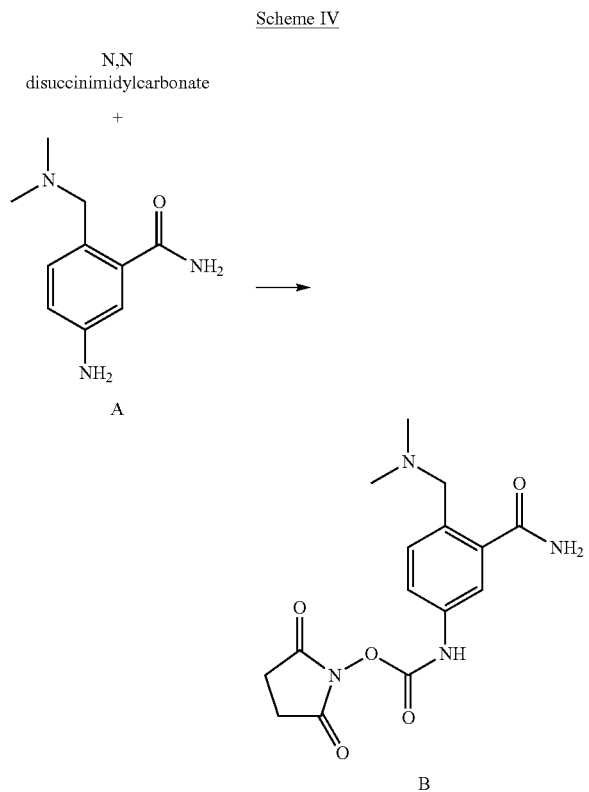

Scheme IV

A

B

Methods used for Scheme I and Scheme II are applicable to Scheme IV for making the compounds presented herein.

N-linked and O-linked glycans are common glycans from recombinant biotherapeutic proteins, N-glycans being the more prominent. N-linked glycans are attached to asparagines via an N-acetylglucosamine ("GlcNAc") residue in an Asn-Xxx-(Ser, Thr) motif where Xxx can be any amino acid except proline. O-linked glycans are attached to either Serine or Threnine. N-linked glycans can be removed from the glycoprotein chemically or enzymatically. Analytical methods of analyzing N-linked glycans have become considerably sophisticated. CE-, HPAEC-PAD, HILIC-LC/FLR, RPLC/MS, MALDI-MS are the most common analytical instrumentations. Liquid chromatography ("LC") separation with fluorescence detection is widely used in the pharmaceutical industry for the characterization of enzymatically/chemically released glycan, typically tagged with a fluorescent dye at the reducing end of a glycan. Kalyan R. Anumula & Shirish T. Dhume, *High Resolution and High Sensitivity Methods for Oligosaccharide Mapping and Characterization by Normal Phase High Performance Liquid Chromatography Following Derivatization with Highly Fluorescent Anthranilic Acid,* 8 GLYCOBIOLOGY 685 (1998); Karina Mariño et al., *A Systematic Approach to Protein Glycosylation Analysis: A Path Through the Maze,* 6 NATURE CHEMICAL BIOLOGY 713 (2010). Fluorescent measurements are sensitive and quantitative; the low detection limit is in the low femtomoles. With recent advancements in mass spectrometry instrumentation, the combination of liquid chromatography, fluorescence and MS has gained more popularity as an analytical instrument platform for routine characterization of fluorescently labeled N-linked glycans. Therefore, relative quantitation and molecular weight measurements can be done in a single analysis. Shigeo Suzuki et al., *Comparison of the Sensitivities of Various Derivatives of Oligosaccharides in LC/MS with Fast Atom Bombardment and Electrospray Ionization Interfaces,* 1006 ANAL CHEM 2073 (1996). However, another challenge is that glycans do not ionize efficiently via electro-spray-ionization ("ESI"). Therefore, in general, tagging with an MS active moiety is required.

The sample preparation step can be very time consuming as it requires enzymatic digestion on the protein to release N-linked glycans followed by fluorescence tagging reaction. For example, the derivatization with a fluorescence moiety accomplished by reductive amination can require up to 4 hours. Derivatization using the aromatic amine, 2-aminobenzamide (2AB), is the most established method and requires this reductive amination. The 2AB tag improves the MS sensitivity compared to the non-labeled glycan and is fluorescently active.

Provided herein is a rapid method for fluorescent tagging N-linked glycans using novel chemical reagents. These tags are designed to enhance the analyte mass spectrometry response. This same chemical tag maybe used for amino acid and peptide labeling. The reaction mechanism may be the same for all three types of molecules, whereby the derivatization occurs at the amine moiety. Amino acid analysis, peptide mapping and glycan profiling are each an integral part of the overall biotherapeutic protein characterization. Therefore, it is advantageous to have rapid universal fluorescent derivatization methods which improve detection of the MS instrumentation.

New molecules (also referred herein to as "reagents") specific for N-linked glycans amino acids and peptides, are provided for enhanced MS detection and rapid fluorescence tagging of glycans and other biomolecules with enhanced MS signals. Through the use of these reagents, the reaction times necessary to carry out the tagging process (or otherwise sometimes referred to herein as "labeling") is measured in seconds, rather than minutes or hours. The described molecules are useful in a wide variety of processes that rely on glycan and amino acid/peptide analysis for essential information of a product, process, or protein. As such, the molecules described herein may be used in processes such as protein characterization, cell culture monitoring, synthetic peptide manufacturing, and food analysis.

The reagents provided herein can consist of three functional components a) a tertiary amino group or other MS active atom, b) a highly fluorescent moiety, and c) a functional group that rapidly reacts with amines (such as an isocyanate, or succidimidylcarbamate). Other reagents can consist of two functional components a) a tertiary amino group or other MS active atom, and b) a functional group that rapidly reacts with amines (such as an isocyanate, or succidimidylcarbamate). The components serve the following purposes: (1) the amino group or MS active group gives good MS signal; (2) the fluorescent moiety provides a good fluorescence signal; and (3) the reactive functional group gives rapid tagging of desired biomolecules.

The enhanced MS signal observed upon utilization of a 2AB tagging reagent (slow reaction-hours), for example, is a function of the amino or amine group present in the system following tagging. Currently available rapid tagging agents contain no amino functionality following tagging of the desired biomolecule. Rather, these compounds have functionalities which do not provide the same electron density for mass spectrometry applications (e.g., urea or carbamate) and tie up the electron density resulting in low MS signal.

Biomolecules are organic compounds that are involved in the maintenance and metabolic processes of living organisms. Many disease conditions are due to impaired amino acid metabolism (e.g. phenylketonuria). As noted above, a biomolecule can also be a therapeutic agent such as peptide based pharmaceuticals that have been used to treat the disease. Glycans, amino acids, peptides and proteins are closely monitored during protein drug development and production. Many biomolecules can be detected by tagging them with a fluorescent label. The resulting conjugate or complex will show fluorescence, thereby facilitating their detection. There is recent movement in the industry towards using MS for detection and quantitation of biomolecules. Fluorescent detection is still widely used for its sensitivity and quantitative analysis. Therefore, the combination of liquid chromatography, mass spectrometry and fluorescent detection is an analytical platform that can be used for a comprehensive protein analysis. Notwithstanding, there is no single technique that is capable of providing a complete structural analysis of N-linked glycans.

Mammalian and plant glycoproteins are biomolecules that commonly contain any one or more three types of constituent glycans, oligo- and polysaccharides. Glycans are important for protein folding and any alteration thereof may eliminate or alter activity. Often an immune response is triggered by an unrecognized glycan. Of the three types of glycans, analytical methods of analyzing N-linked glycans have become considerably sophisticated.

Structurally, N-linked glycans are attached to asparagines via an N-acetylglucosamine (GlcNAc) residue in an Asn-Xxx-(Ser, Thr) motif where Xxx can be any amino acid except proline. The N-glycan can be removed from the glycoprotein with hydrazine whether manually or with the aid of automated hydrazinolysis equipment. The reagent cleaves peptide bonds between the N-linked glycan and asparagines to produce the glycan biomolecule. Several enzymes are available for releasing N-glycans. N-glycosidase F (PNGase-F), a commonly used enzyme, cleaves the intact glycan as the glycosylamine leaving aspartic acid in place of the asparagine at the N-linked site of the protein. Harvey, D. J., *Identification of Protein-Bound Carbohydrates by Mass Spectrometry,* 1 PROTEOMICS 311 at 311-312, 317 (2001), incorporated herein by reference.

Detection of Molecules by MS and Fluorescence

Most amino acids and/or glycans are not readily detectable due to the absence of a strong chromophore or fluorophore or MS active moiety. The absorbance and fluorescence response are quite weak. A commonly used tactic to maximize the sensitivity of an assay is to convert the compound of interest into a derivative that exhibits a better response for the particular detection method being utilized. The selection of a derivatizing agent is a critical choice in the development of an analytical procedure. The derivatizing agent affects the ultimate sensitivity and accuracy of the analysis by maximizing the sensitivity, yield and stability of the derivatized molecules.

Basically, the following determinations must be performed separately: (1) the glycosylated sites; (2) the glycosylated site occupancy; (3) the structure and amount of each glycan at each site: and (4) the number of glycoforms. Id at 312, incorporated herein by reference. In most situations, MS can provide the answers to each of these steps. Hence the need for enhanced MS signals. Because of the branched nature of the glycan, however, structural determination of the glycan is complicated. Here, the monosaccharide unit, the anomericity and ring size of each monosaccharide, the monosaccharide sequence and ring conformation together with identification of other groups must be determined. With the exception of ring conformation, MS can be used directly or indirectly to make these determinations using MALDI and/or ESI as the preferred MS technique. Id. at 313-316, incorporated herein by reference.

Currently, for N-glycans, derivatives are most commonly added to the reducing terminus of the glycan by reductive amination reaction with an aromatic amine. Id. at 318-319. Reducing-Terminal Derivatization, incorporated herein by reference. Reductive amination, while producing an MS active compound, is a very slow process and can take four (4) hours to tag the reagent to the compound. Reducing-terminal derivatives may also be prepared by reactions other than reductive amination. Id. at 319, incorporated herein by reference.

Most glycans are not readily detectable due to the absence of a strong chromophore or fluorophore. Free glycans released from glycoproteins enzymatically or chemically can be analyzed directly via MALDI MS or ESI/MS/MS directly without any chemical tagging. Ying Qing Yu et al., *A Rapid Sample Preparation Method for Mass Spectrometric Characterization of N-linked Glycans,* 19 RAPID COMM. MASS SPECTROMETRY 2331 (2005). This label-free approach is suitable for qualitative analysis for glycans. However, this approach is not as well suited for relative quantitation due to the fact that glycans from a single protein sample can be very heterogeneous in that the ionization efficiency is not the same among them. Therefore, a single analysis platform that can perform both quantitive and qualitative analysis is desirable. Since a fluorescent detector only detects the dye itself, the fluorescent response from various glycans can be used for relative quantitation. The selection of a derivatizing agent is a critical choice in the development of an analytical procedure. For N-glycans, derivatives are often added to the reducing terminus of the glycan by reductive amination reaction with an aromatic amine. Reductive amination, while producing an MS active compound, is a very slow process and can take up to four hours to complete. There are many aromatic amine compounds that are used for reductive amination for glycans, most of them giving a low to moderate MS response. Recently, it was reported that procainamide can be used to enhance glycan MS response. Song Klapoetke et al., *The Evaluation of a Novel Approach for the Profiling and Identification of N-linked Glycans With a Procainamide Tag by HPLC With Fluorescent and Mass Spectrometric Detection,* 53 J. PHARMACEUTICAL AND BIOMEDICAL ANAL. 315 (2010). A significant increase of glycan ionization was observed when compared with 2AB-labeled glycans. Id. However, procainamide labeling procedure is similar to other commonly used reductive amination reagents, and therefore, it still takes a half day for the labeling step.

As such, fluorogenic derivatization prior to an HPLC analysis of amino acids currently serves as an efficient tool in the analysis of these systems. For example, phanquinones and benzooxadiazoles are nitrogen containing fluorophores that can be used as pre-column derivatization agents. These compounds are devoid of intrinsic fluorescence. However, on conjugation with amino acids, they form the corresponding fluorescent conjugates.

Uses of the Reagent Compounds Presented Herein

The present compounds are particularly useful for derivatizing glycans and also amino acids and proteins because they react quickly with the molecules and form a stable, highly fluorescent MS derivative. The general methodology for an analysis of a glycan or amino acid using the compounds of the subject invention consists of three closely related processes: (1) formation of derivatives in the sample; (2) separation of the derivatives; and (3) detection of the separated derivatives. The first step is generally performed by reacting a mixture with one of the present reagents to yield a distinct compound. These derivatives provide a fluorescent signal which can then be detected in the detection stage of the analysis.

The separation step is based upon the differences in the chemical structure of the derivatives. The derivatized amino acids differ from each other in the same way that the chemical structures of the precursor amino acids differ. The derivatives must be separated so that the detector signal can be correctly related to the concentration of each derivative. The derivatized amino acids can be separated and detected by chromatography, e.g., by high performance liquid chromatography (HPLC) or capillary zone electrophoresis (CZE). HPLC is particularly useful for this purpose. These technologies are well suited for this purpose because they are selective and can be used with very small samples. It is also possible to carry out the separation step by separating the amino acids prior to their derivatization.

The detection step is generally carried out using either an absorbance or fluorescence detector. As each derivative is eluted from the chromatographic column after separation, its presence and quantity is detected by a mass spectrometer and/or by the aborbance or emission of light. The sensitivity of the assay depends upon the strength of the signal produced.

In the case of peptide analysis, reverse phase HPLC can be also used to analyze the peptide digests. In a given peptide digest there may be from 20 to 150 different peptides, each of which must be resolved and quantified. In many instances, the available sample is very small. For example, the analyst may be determining the structure of a protein that is isolated from an organism or one that has been synthesized by recombinant DNA technologies. Typically, nanomole quantities of a protein digest are studied. Due to the scarcity and cost of many proteins, it is very desirable to use as small a sample as possible.

Figure 2:
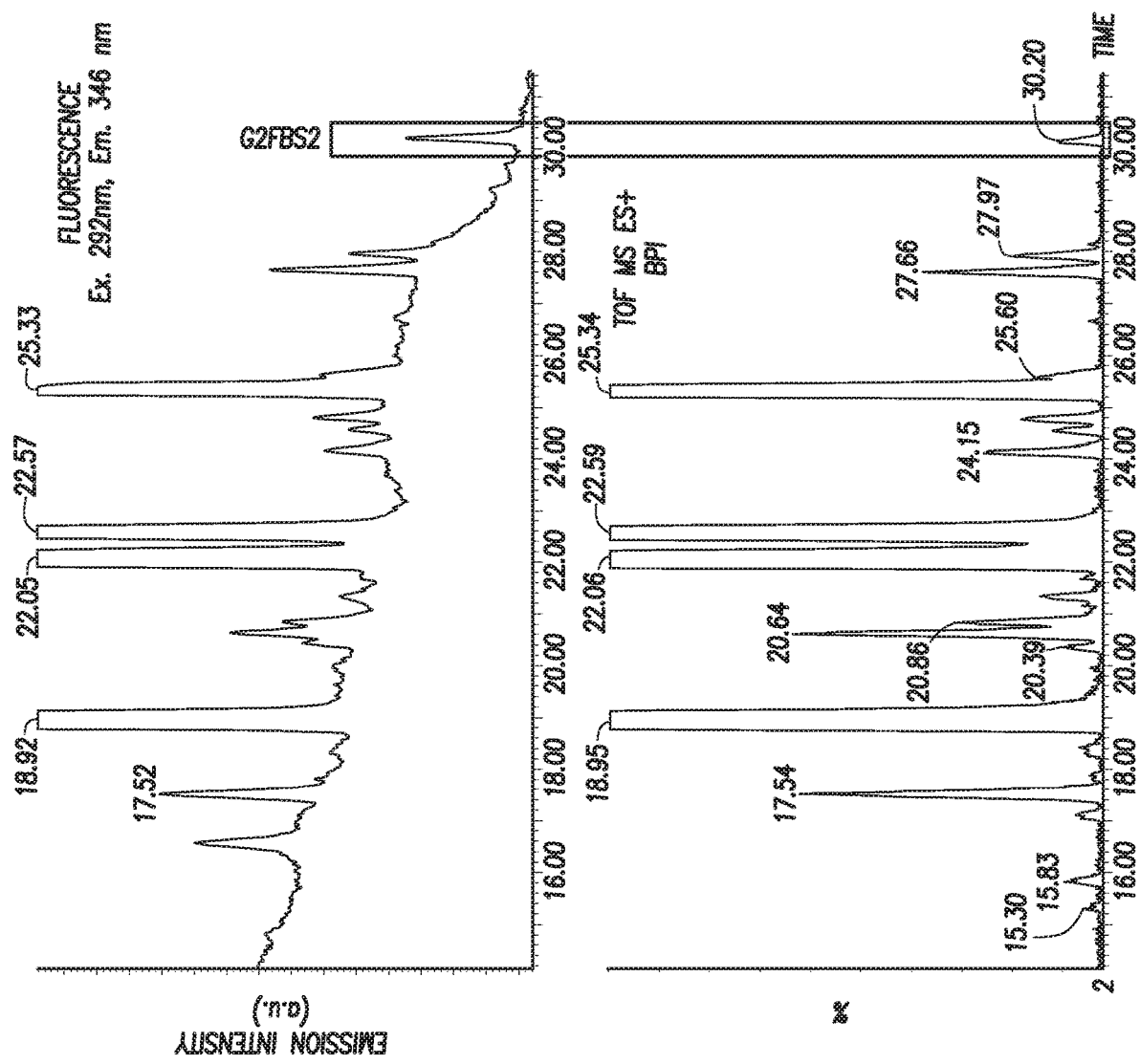
FIG. 2 shows the fluorescence and MS detection of the glycan G2FBS2 released from 0.8 µg Herceptin IgG labeled with 2,5-dioxopyrrolidin-1-yl (4-((2-(diethylamino)ethyl)carbamoyl)phenyl)carbamate.

As described in Example I below, we tested the labeling of N-linked glycans with 2,5-dioxopyrrolidin-1-yl (4-((2-(diethylamino)ethyl)carbamoyl)phenyl)carbamate. Here, N-linked glycans were released from a glycoprotein (Herceptin) using PNGase F prior to labeling with 2,5-dioxopyrrolidin-1-yl (4-((2-(diethylamino)ethyl)carbamoyl)phenyl) carbamate. The 2,5-dioxopyrrolidin-1-yl (4-((2-(diethylamino)ethyl)carbamoyl)phenyl)carbamate was solubilized in water free acetonitrile to a final concentration of 45 µg/µl. 100 µl of 2,5-dioxopyrrolidin-1-yl (4-((2-(diethylamino)ethyl)carbamoyl)phenyl)carbamate solution was added to the released glycan sample and left at room temperature for 5 minutes, during which time the labeling reaction finished. The labeled sample was lyophilized using a speed vac. The lyophilized sample was reconstituted in 60% acetonitrile/water solution prior to chromatographic separation using HILIC LC method. As shown in FIGS. 1 and 2, the samples were analyzed using fluorescence and MS detection.

Additional Uses for the Molecules Presented Herein

Absorbance detection is generally used in protein mapping work. Two different detection processes which are often used for this purpose are: a) detection at 210-215 nm using a single wavelength detector; and b) broadband spectral detection using a photodiode array (PDA) detector. In the first method, all peptides absorb at that wavelength, thus the user can ensure that all peptides eluted from the column are detected. One difficulty with this technique is that a wide variety of compounds absorb in this region of the spectrum, and extreme care must be taken to ensure that all reagents, eluents, glassware, etc. are scrupulously clean to ensure that the observed signal is solely from the peptides. In the second method, the PDA detector collects the spectra of the eluent at specific time intervals (e.g. a spectrum between 200 and 350 nm is collected every second). This provides more information than a single wavelength and thus can assist in distinguishing between peptides which may elute with similar retention times.

Peptide mapping often involves the qualitative and quantitative analysis of trace levels of peptides in the digested protein. The identification and quantitation of peptides in complex mixtures in the present method is effected by a three stage process: a) tagging the peptides of interest with the heterocyclic aromatic carbamates or other reactive groups, which exhibit a stronger absorbance or fluorescence signal than the original compound; b) separating the derivatized samples; and c) detecting the derivatized peptides by absorbance or fluorescence techniques. The separation conditions for a derivative are frequently drastically different from the separation of the starting compounds. Likewise, the efficiency of a separation has a serious impact on the detection process. Use of the present heterocyclic aromatic carbamates and/or similar reactive groups provides a mapping method adaptable for use with nanogram quantities of protein. Further, the methods described herein provide a means for enhancing the sensitivity of known methodologies for detecting peptides in biological samples, such as tissue, urine, blood and saliva.

Derivatization Agent Selection

There are several criteria important for the utility of a derivatization method. The analytical procedure must provide accurate quantitation of each component present in a complex mixture. To accomplish this, it is necessary to resolve the components of interest, not only from each other, but from components generated by the derivatization procedure. Quantitative conversion of all underivatized glycans and amino acids, including secondary amino acids, to single products is highly desirable, and facilitates good quantitation.

Detection selectivity is another advantageous feature for amino acid derivatives. Underivatized amino acids all absorb weakly in the low UV (200-220 nm) range, but detection at such wavelengths is subject to interference by many compounds present in sample mixtures or chromatographic mobile phases. Derivatization with reagents absorbing at approximately 254 nm provides a measure of selectivity, but any aromatic organic compounds, frequently present in biological samples, can interfere at this wavelength. Reagents that enable detection via fluorescence, electrochemical response or visible-range absorbance would be desirable for superior detection selectivity.

Finally, it is necessary for derivatives to be sufficiently stable to allow separation and detection without significant degradation. Highly stable derivatives are also favorable as they allow a sample to be reanalyzed, if so desired, without assaying another sample.

In the past, a number of derivatization procedures have been developed to permit the assay of amino acids by high performance liquid chromatographic and electrophoretic separations. Five such procedures commonly utilized for this purpose include:

(1) The o-phthalaldehyde (OPA)/mercaptan method. The OPA procedure can detect amino acids with a typical detectable level in the order of about 100 femtomole (fmol). The formation of the derivatives is rapid. A significant difficulty with this method is the adduct is fairly unstable, and must be prepared very shortly before the detection step. An additional problem is that this reagent will not form a derivative with secondary amino acids.

(2) The 9-fluorenylmethylchloroformate (FMOC method). The FMOC procedure provides for stable derivatives, with a minimum detectable level in the order of a few hundred fmol. There are a number of disadvantages with the FMOC procedure. Free tryptophan and cystine cannot be quantitated easily. The derivatizing reagent must be removed from the reaction mixture by an extraction step because it is itself fluorescent. The reagent has also been reported to form multiple derivatives with histidine. The reagent is also hazardous to work with, because it is corrosive and is a lachrymator.

(3) The phenylisothiocyanate method (PITC). The PITC procedure yields stable derivatives which are formed rapidly. It can be used for both primary and secondary amino acids, as well as cystine. The method uses absorbance as the detection procedure, and can provide a minimum detection limit of 1 pmol. However, the derivatives are not fluorescent and detection must be performed at 254 nm, which does not allow for good detection selectivity.

(4) The dansyl chloride method. The dansyl chloride method provides stable derivatives with a minimum detectability in the order of about 1.5 pmol. It is able to detect secondary amines and cysteine, but it results in multiple derivatives.

(5) Fluorescent succinimidocarbamates have been used as derivatizing agents for amines, amino acids, peptides, phosphates and other classes of compounds. When the succinimidocarbamate reagent is used to tag a compound with a fluorescent group, a detection limit of about 1 pmol can be achieved. These reagents are used in conjunction with modern separation techniques such as high performance liquid chromatography, thin layer chromatography or capillary electrophoresis. Nimura et al., 58 ANAL. CHEM. 2372 (1986). Succinimidyl activated carbamates have been prepared by reacting carbocyclic aromatic amines with di-(N-succinimidyl) carbonate. Takeda et al., 24 TETRAHEDRON LETT., 4569 (1983).

Current derivatization chemistry for HPLC analysis of a broad range of samples includes Waters' AccQTag Amino Acid Analysis System. Waters AccQTag method is a pre-column derivatization technique for peptide and protein hydrolysate amino acids. The AccQTag methodology is based on a derivatizing reagent developed specifically for amino acid analysis. Waters AccQFluor reagent (6-amino-quinolyl-N-hydrozysuccinimidyl carbamate, or ACQ) is an N-hydroxysuccinimide-activated heterocyclic carbamate, a known class of amine-derivatizing compounds. See, EP0533200 B1.

This reagent converts both primary and secondary amino acids to stable, fluorescent derivatives and hydrolyzes to yield 6-aminoquinoline, a non-interfering byproduct. The AccQFluor reagent reacts rapidly with primary and secondary amino acids to yield highly stable ureas that fluoresce strongly at 395 nm. The resulting derivatives are stable at room temperature for up to one (1) week.

The key to the rapid and simple Waters AccQTag Amino Acid Analysis method is the derivatizing reagent and a simple, pre-column derivatization protocol. Waters AccQFluor Reagent is a highly reactive compound, 6-aminoquinolyl-N-hydroxysuccinimidyl carbamate (AQC), which forms stable derivatives with primary and secondary amino acids in a matter of seconds. The derivatives are easily separated by reversed phase HPLC using Waters AccQTag Amino Acid Analysis System in less than 35 minutes.

Excess reagent is consumed during the reaction to form aminoquinoline (AMQ). AMQ has significantly different spectral properties than any of the derivatized amino acids. This allows for the programming of a detector wavelength that maximizes the spectral emission response of the derivatives while minimizing the response of the AMQ. The derivatization protocol—adding reagent to and heating a properly buffered sample—is simple and straight forward. The amino acid derivatives can be injected directly without further sample preparation. Common buffer salts and detergents have little effect on reaction yield or on the reproducibility of results.

Another example of derivatization chemistry for HPLC analysis of a broad range of samples is the InstantAB™ kit from Prozyme which is used to tag N-linked glycans, for example, the Glyko® InstantAB™ kit (available from Prozyme, Inc., Hayward, Calif.). InstantAB™ provides rapid tagging and strong fluorescence but produces a weak MS signal. In fact, the MS signal of this molecule is significantly reduced when compared to the standard 2-AB reagent.

Presented herein are molecules that contain a tertiary amine, a fluorescent moiety and a reactive functional group. Certain other molecules may simply contain the tertiary amine and reactive functional groups. All molecules, however, undergo rapid functionalization. Through the use of a tertiary amine, all of the molecules are MS active (active in mass spectrometry), while others may also be fluorescent.

As noted above, the current state of the art utilizes tagging molecules that either 1) react very slowly and give good MS/fluorescence signals or 2) react quickly and have good fluorescence signal, but have poor MS signal. The lack of MS signal in the currently rapid reacting molecules is believed to arise from the lack of an electron rich amine—any nitrogen present loses electron density as part of urea or carbamate functionality. Herein, we provide the addition of an amino group or other MS active atom to the fluorescent moiety of the rapidly reacting systems, or alternatively, adding a reactive functional group to the slow reacting (high fluorescence and MS signal) system in order to decrease reactivity time (from hours to seconds).

The present molecules can have heterocyclic aromatic groups that exhibit a higher fluorescence quantum yield that that of carbocyclic aromatics used as tags. Nimura et al Anal. Chem. 58, 2372 (1986). This increase in the fluorescence quantum yield of the tag provides an increase in the sensitivity of the tagged amine. For some of the heterocyclic molecules, the emission maximum of an amine compound derivatized with the reactive group is at a significantly different wavelength than the emission maximum of the free heterocyclic amine. The wavelength shift has very significant implications for fluorescence detection of tagged amines. Furthermore, since the observed fluorescence is predominantly from the derivative, background noise is eliminated or reduced and a more sensitive assay obtained.

Sample Preparation

The molecules provided herein do not provide a work-around for proper sample preparation. To obtain high quality mass spectra, the condition of the sample is of critical importance. Compounds other than the analyte will generally have an adverse effect on ion yield and must be removed. Indeed, while small amounts of sodium are essential for ionization by MALDI, carbohydrates are particularly susceptible to the effects of salts. Moreover, many carbohydrates occur as mixtures. Therefore it is important to ensure that isolation and purification techniques do not cause fractionation of the sample with a loss of quantitative information. Exemplary is sialic acids which often are lost from glycoproteins when pH is too low or sample temperature too high.

Example I

Tagging of N-Linked Glycans Released from Herceptin

N-linked glycans were released from 0.8 µg of Herceptin using standard PNGase F protocols prior to labeling with 2,5-dioxopyrrolidin-1-yl (4-((2-(diethylamino)ethyl)carbamoyl)phenyl)carbamate. 2,5-dioxopyrrolidin-1-yl (4-((2-(diethylamino)ethyl)carbamoyl)phenyl)carbamate was solubilized in dry (water free) acetonitrile to a final concentration of 45 µg/µl. 10 µl of this solution was then added to the to the released glycan sample. This mixture was left at room temperature for 5 minutes. The labeled sample was then lyophilized using a speed vac and reconstituted in 60% acetonitrile/water solution prior to chromatographic separation using a HILIC LC method and analysis by fluorescence and MS detection, as shown in FIGS. 1 and 2.

We claim:
1. A compound of the structural Formula III:

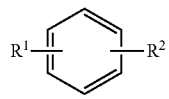

wherein
  $R^1$ is

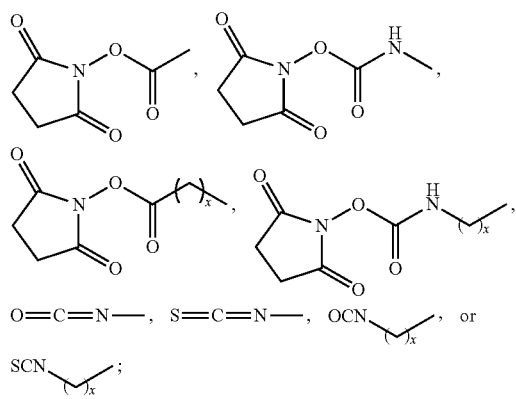

$R^2$ is

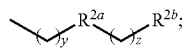

$R^{2a}$ is selected from ester, amide, amine, ether, urea, carbamate, carbonate, thiol, thiourea, thiocarbamate, alkyl or carbonyl;

$R^{2b}$ is

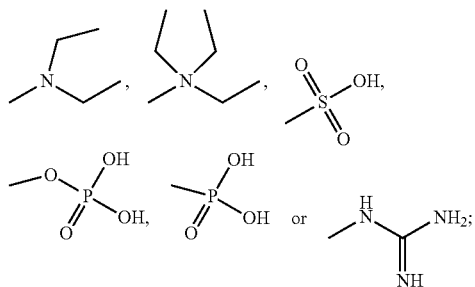

x=0-12;
y=0-12;
z=1-12; and
salts or solvates thereof, wherein said compound is a mass spectrometry (MS) active, fluorescent compound.

2. A method for analyzing a glycan in a sample containing at least one glycan by means of liquid chromatography and mass spectrometry comprising labeling the glycan in the sample by reacting the glycan with the compound according to claim 1 for a time and under conditions suitable to facilitate the labeling; providing a sample containing the glycan labeled with the compound; and subjecting the labeled compound to liquid chromatograph and mass spectrometry.

3. A compound of the structural Formula IV:

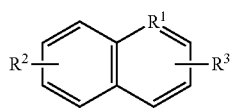

wherein
  $R^1$ is O or N;
  $R^2$ is

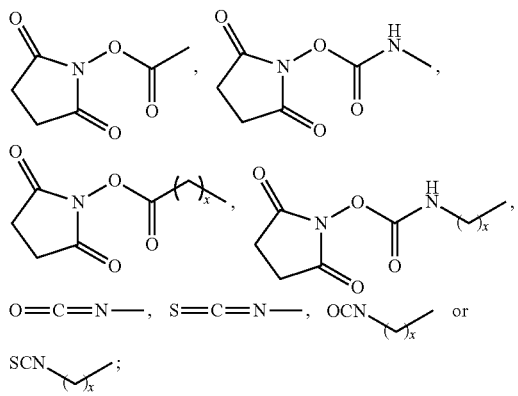

$R^3$ is

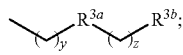

$R^{3a}$ is selected from ester, amide, amine, ether, urea, carbamate, carbonate, thiol, thiourea, thiocarbamate, alkyl or carbonyl;

$R^{3b}$ is

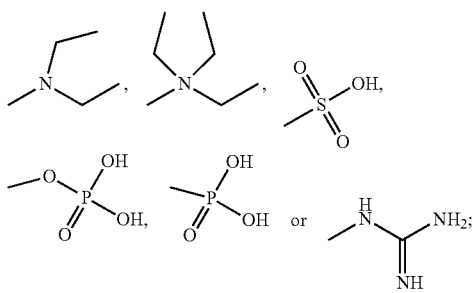

x=0-12;
y=0-12;
z=1-12; and
salts or solvates thereof.

4. A method for analyzing a glycan in a sample containing at least one glycan by means of liquid chromatography and mass spectrometry comprising labeling the glycan in the sample by reacting the glycan with the compound according to claim 3 for a time and under conditions suitable to facilitate the labeling; providing a sample containing the glycan labeled with the compound; and subjecting the labeled compound to liquid chromatograph and mass spectrometry.

5. A compound of Formula IV:

wherein
FL is

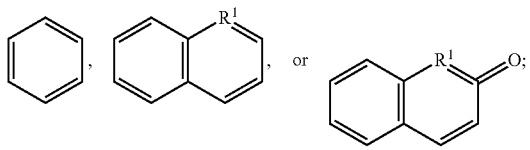

$R^1$ is O or N;
$R^2$ is

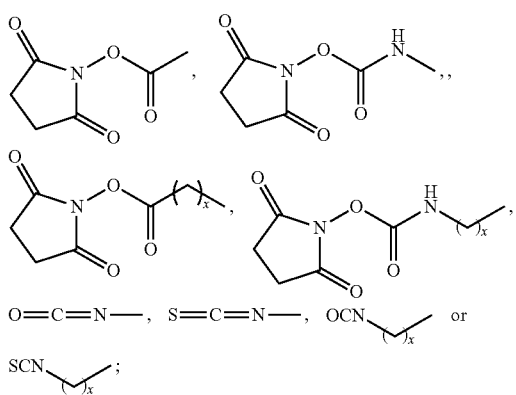

$R^3$ is

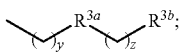

$R^{3a}$ is selected from ester, amide, amine, ether, urea, carbamate, carbonate, thiol, thiourea, thiocarbamate, alkyl or carbonyl;
$R^{3b}$ is

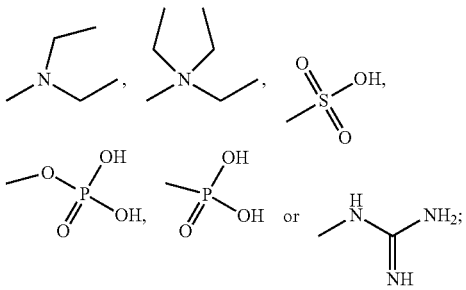

x=0-12;
y=0-12;
z=1-12;

and salts or solvates thereof, wherein said compound is a mass spectrometry (MS) active, fluorescent compound.

6. A method for analyzing a glycan in a sample containing at least one glycan by means of liquid chromatography and mass spectrometry comprising labeling the glycan in the sample by reacting the glycan with the compound according to claim 5 for a time and under conditions suitable to facilitate the labeling; providing a sample containing the glycan labeled with the compound; and subjecting the labeled compound to liquid chromatograph and mass spectrometry.

7. A method for analyzing a glycan in a sample containing at least one glycan by means of liquid chromatography and mass spectrometry comprising labeling the glycan in the sample by reacting the glycan with a compound according to Formula III for a time and under conditions suitable to facilitate the labeling; providing a sample containing the glycan labeled with the compound; and subjecting the labeled compound to liquid chromatograph and mass spectrometry wherein the compound of Formula III is:

wherein
$R^1$ is

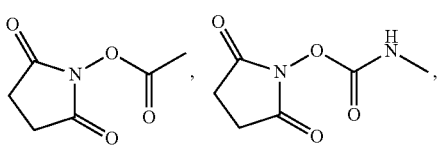

-continued
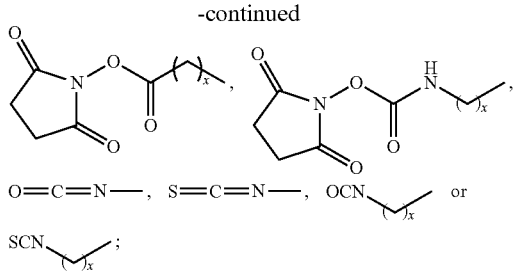
R² is
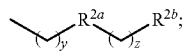
R²ᵃ is selected from ester, amide, amine, ether, urea, carbamate, carbonate, thiol, thiourea, thiocarbamate, alkyl or carbonyl;
R²ᵇ is
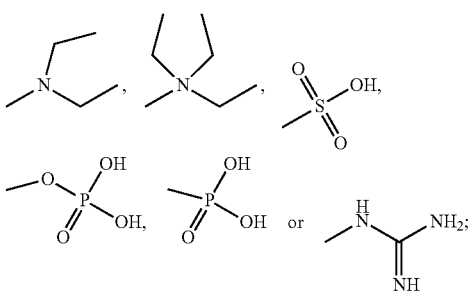
x=0-12;
y=0-12;
z=1-12;
salts or solvates thereof.
* * * * *